(12) United States Patent
Chou et al.

(10) Patent No.: US 11,147,699 B2
(45) Date of Patent: *Oct. 19, 2021

(54) METHODS OF INTRACEREBRAL IMPLANT DELIVERY

(71) Applicant: Route 92 Medical, Inc., San Mateo, CA (US)

(72) Inventors: Tony M. Chou, San Mateo, CA (US); Joey English, San Mateo, CA (US)

(73) Assignee: Route 92 Medical, Inc., San Mateo, CA (US)

( * ) Notice: Subject to any disclaimer, the term of this patent is extended or adjusted under 35 U.S.C. 154(b) by 501 days.

This patent is subject to a terminal disclaimer.

(21) Appl. No.: 15/747,089

(22) PCT Filed: Jul. 22, 2016

(86) PCT No.: PCT/US2016/043742
§ 371 (c)(1),
(2) Date: Jan. 23, 2018

(87) PCT Pub. No.: WO2017/019564
PCT Pub. Date: Feb. 2, 2017

(65) Prior Publication Data
US 2018/0242978 A1    Aug. 30, 2018

Related U.S. Application Data

(60) Provisional application No. 62/301,857, filed on Mar. 1, 2016, provisional application No. 62/275,963, filed (Continued)

(51) Int. Cl.
*A61F 2/966* (2013.01)
*A61F 2/95* (2013.01)
(Continued)

(52) U.S. Cl.
CPC .......... *A61F 2/966* (2013.01); *A61B 17/1214* (2013.01); *A61B 17/12109* (2013.01);
(Continued)

(58) Field of Classification Search
CPC ...... A61B 2017/1205; A61B 17/12118; A61B 17/12109; A61B 17/1214;
(Continued)

(56) References Cited

U.S. PATENT DOCUMENTS 2,623,520 A    12/1952   Bamford, Jr. et al.
2,730,101 A    1/1956    Hoffman
(Continued)

FOREIGN PATENT DOCUMENTS

EP    1639951 A1    3/2006
EP    2684545 A1    1/2014
(Continued)

OTHER PUBLICATIONS

"Twin-Pass Dual Access Catheter" Brochure. Vascular Solutions (2009) 4 pages. Web. Accessed Sep. 25, 2018.
(Continued)

*Primary Examiner* — Jing Rui Ou
(74) *Attorney, Agent, or Firm* — Mintz Levin Cohn Ferris Glovsky and Popeo, P.C.

(57) ABSTRACT

The method of delivering an implant in an intracranial vessel includes deploying an anchor of a tethering device in an anchoring vessel forming a first fixation point and advancing a guide-sheath to a location near the anchoring vessel. The tethering device has a tether extending proximally from the anchor and the guide-sheath has at least one lumen. The method includes attaching the guide-sheath to the tether of the tethering device forming a second fixation point proximal to the first fixation point, delivering an implant through the lumen of the guide-sheath towards a treatment site distal (Continued)

to the first fixation point and located within an intracranial vessel, and deploying the implant at the treatment site. Related devices, systems, and methods are also provided.

27 Claims, 65 Drawing Sheets

Related U.S. Application Data on Jan. 7, 2016, provisional application No. 62/275,939, filed on Jan. 7, 2016, provisional application No. 62/196,613, filed on Jul. 24, 2015.

(51) Int. Cl.
| | | |
|---|---|---|
| A61B 17/12 | (2006.01) | |
| A61F 2/07 | (2013.01) | |
| A61F 2/915 | (2013.01) | |
| A61F 2/06 | (2013.01) | |

(52) U.S. Cl.
CPC .......... *A61B 17/12118* (2013.01); *A61F 2/95* (2013.01); *A61B 17/12113* (2013.01); *A61B 2017/1205* (2013.01); *A61F 2/07* (2013.01); *A61F 2/915* (2013.01); *A61F 2002/068* (2013.01); *A61F 2002/91558* (2013.01); *A61F 2002/91566* (2013.01); *A61F 2002/91575* (2013.01); *A61F 2220/0016* (2013.01); *A61F 2230/0091* (2013.01)

(58) Field of Classification Search
CPC ...... A61B 17/12113; A61F 2/07; A61F 2/915; A61F 2002/068; A61F 2002/91558; A61F 2002/91566; A61F 2002/91575; A61F 2220/0016; A61F 2230/0091; A61F 2/966; A61F 2/95
See application file for complete search history.

(56) References Cited

U.S. PATENT DOCUMENTS

| | | |
|---|---|---|
| 3,612,050 A | 10/1971 | Sheridan |
| 3,631,848 A | 1/1972 | Muller |
| 3,949,757 A | 4/1976 | Sabel |
| 3,996,938 A | 12/1976 | Clark, III |
| 4,013,080 A | 3/1977 | Froning |
| 4,406,656 A | 9/1983 | Hattler et al. |
| 4,844,092 A * | 7/1989 | Rydell .................. A61M 25/01 600/585 |
| 4,946,443 A | 8/1990 | Hauser et al. |
| 5,207,648 A | 5/1993 | Gross |
| 5,263,938 A * | 11/1993 | Orr .................. A61M 25/09041 604/171 |
| 5,267,960 A | 12/1993 | Hayman et al. |
| 5,338,300 A | 8/1994 | Cox |
| 5,370,623 A | 12/1994 | Kreamer |
| 5,385,562 A | 1/1995 | Adams et al. |
| 5,464,023 A | 11/1995 | Viera |
| 5,484,407 A | 1/1996 | Osypka |
| 5,527,292 A | 6/1996 | Adams et al. |
| 5,591,194 A | 1/1997 | Berthiaume |
| 5,658,309 A | 8/1997 | Berthiaume et al. |
| 5,776,141 A | 7/1998 | Klein et al. |
| 5,997,523 A | 12/1999 | Jang |
| 6,120,480 A | 9/2000 | Zhang et al. |
| 6,238,430 B1 | 5/2001 | Klumb et al. |
| 6,368,355 B1 | 4/2002 | Uflacker |
| 6,475,195 B1 | 11/2002 | Voda |
| 6,554,849 B1 | 4/2003 | Jones et al. |
| 6,595,989 B1 * | 7/2003 | Schaer ............... A61B 18/1492 606/41 |
| 6,676,637 B1 | 1/2004 | Bonnette et al. |
| 6,692,473 B2 | 2/2004 | St. Cyr et al. |
| 6,740,104 B1 | 5/2004 | Solar et al. |
| 6,755,803 B1 | 6/2004 | Le et al. |
| 7,033,325 B1 | 4/2006 | Sullivan |
| 7,232,452 B2 | 6/2007 | Adams et al. |
| 7,316,678 B2 | 1/2008 | Nash et al. |
| 7,374,560 B2 | 5/2008 | Ressemann et al. |
| 7,604,612 B2 | 10/2009 | Ressemann et al. |
| 7,736,355 B2 | 6/2010 | Itou et al. |
| 7,850,654 B2 | 12/2010 | Belhe et al. |
| 7,854,746 B2 | 12/2010 | Dorn et al. |
| 7,967,789 B2 | 6/2011 | Solar et al. |
| 7,972,294 B2 | 7/2011 | Nash et al. |
| 8,021,351 B2 | 9/2011 | Boldenow et al. |
| 8,048,032 B2 | 11/2011 | Root et al. |
| 8,142,413 B2 | 3/2012 | Root et al. |
| 8,157,760 B2 | 4/2012 | Criado et al. |
| 8,172,831 B2 | 5/2012 | Webler, Jr. |
| 8,251,978 B2 | 8/2012 | Nash et al. |
| 8,292,850 B2 | 10/2012 | Root et al. |
| 8,425,549 B2 | 4/2013 | Lenker et al. |
| 8,465,456 B2 | 6/2013 | Stivland |
| 8,523,801 B2 | 9/2013 | Nash et al. |
| 8,708,954 B2 | 4/2014 | Webler |
| 8,758,325 B2 | 6/2014 | Webster et al. |
| 8,795,288 B2 * | 8/2014 | Melsheimer ........ A61B 17/3415 604/523 |
| 8,840,568 B2 * | 9/2014 | Kimura ........... A61M 25/09041 206/364 |
| RE45,380 E | 2/2015 | Root et al. |
| 8,996,095 B2 | 3/2015 | Anderson et al. |
| 9,034,007 B2 | 5/2015 | Janardhan |
| 9,144,662 B2 | 9/2015 | Di Caprio et al. |
| RE45,760 E | 10/2015 | Root et al. |
| RE45,776 E | 10/2015 | Root et al. |
| 9,241,699 B1 | 1/2016 | Kume et al. |
| 9,265,512 B2 | 2/2016 | Garrison et al. |
| 9,561,345 B2 | 2/2017 | Garrison et al. |
| 9,681,882 B2 | 6/2017 | Garrison et al. |
| 9,820,761 B2 | 11/2017 | Garrison et al. |
| 2001/0020175 A1 * | 9/2001 | Yassour .................. A61F 2/01 606/200 |
| 2001/0044598 A1 * | 11/2001 | Parodi ............... A61M 25/1027 604/104 |
| 2002/0016597 A1 | 2/2002 | Dwyer et al. |
| 2002/0035391 A1 | 3/2002 | Mikus et al. |
| 2002/0091407 A1 | 7/2002 | Zadno-Azizi et al. |
| 2002/0111666 A1 | 8/2002 | Hart et al. |
| 2002/0165573 A1 * | 11/2002 | Barbut .................. A61F 2/013 606/194 |
| 2002/0173785 A1 | 11/2002 | Spear et al. |
| 2003/0050600 A1 | 3/2003 | Ressemann et al. |
| 2003/0233038 A1 | 12/2003 | Hassett |
| 2004/0030290 A1 * | 2/2004 | Mangano ............... A61M 25/01 604/164.04 |
| 2004/0073158 A1 * | 4/2004 | Shah .................. A61M 25/0662 604/19 |
| 2004/0098081 A1 * | 5/2004 | Landreville ............... A61F 2/95 623/1.11 |
| 2004/0106852 A1 * | 6/2004 | Windheuser .... A61M 25/09041 600/125 |
| 2005/0251206 A1 | 11/2005 | Maahs et al. |
| 2005/0273147 A1 * | 12/2005 | Israel ................ A61F 2/95 623/1.11 |
| 2006/0009830 A1 * | 1/2006 | Atkinson .................. A61F 2/86 607/126 |
| 2006/0129091 A1 * | 6/2006 | Bonnette ............... A61B 17/22 604/93.01 |
| 2006/0259063 A1 | 11/2006 | Bates et al. |
| 2007/0198075 A1 | 8/2007 | Levy |
| 2007/0208302 A1 | 9/2007 | Webster et al. |
| 2008/0200946 A1 * | 8/2008 | Braun ............... A61M 25/0054 606/198 |
| 2009/0264865 A1 | 10/2009 | Kawai |
| 2009/0281379 A1 | 11/2009 | Binmoeller et al. |
| 2010/0056910 A1 * | 3/2010 | Yanuma .......... A61M 25/09041 600/434 |
| 2010/0217276 A1 | 8/2010 | Garrison et al. |
| 2010/0268029 A1 | 10/2010 | Phan et al. |

(56) References Cited

U.S. PATENT DOCUMENTS

| | | |
|---|---|---|
| 2011/0264133 A1 | 10/2011 | Hanlon et al. |
| 2012/0065660 A1 | 3/2012 | Ferrera et al. |
| 2012/0095485 A1 | 4/2012 | Cully et al. |
| 2012/0116350 A1 | 5/2012 | Strauss et al. |
| 2013/0035628 A1 | 2/2013 | Garrison et al. |
| 2013/0116701 A1 | 5/2013 | Wang et al. |
| 2013/0281788 A1 | 10/2013 | Garrison |
| 2014/0025043 A1 | 1/2014 | Wang et al. |
| 2014/0128901 A1 | 5/2014 | Kang et al. |
| 2014/0296868 A1 | 10/2014 | Garrison et al. |
| 2014/0358178 A1 | 12/2014 | Hewitt et al. |
| 2014/0371709 A1 | 12/2014 | Allen et al. |
| 2015/0173782 A1 | 6/2015 | Garrison et al. |
| 2015/0174368 A1 | 6/2015 | Garrison et al. |
| 2015/0190615 A1* | 7/2015 | Shaltis ............... A61M 25/0147 604/510 |
| 2015/0238334 A1 | 8/2015 | Kang et al. |
| 2016/0220741 A1 | 8/2016 | Garrison et al. |
| 2016/0367272 A1 | 12/2016 | Garrison et al. |
| 2017/0020540 A1 | 1/2017 | Chou et al. |
| 2017/0274180 A1 | 9/2017 | Garrison et al. |
| 2017/0281204 A1 | 10/2017 | Garrison et al. |
| 2017/0368309 A1 | 12/2017 | Garrison et al. |
| 2018/0028205 A1 | 2/2018 | Chou et al. |
| 2018/0064453 A1 | 3/2018 | Garrison et al. |
| 2018/0116684 A1 | 5/2018 | Garrison et al. |
| 2018/0133436 A1 | 5/2018 | Garrison et al. |
| 2018/0193042 A1 | 7/2018 | Wilson et al. |
| 2018/0207399 A1 | 7/2018 | Chou et al. |
| 2018/0361114 A1 | 12/2018 | Chou et al. |
| 2019/0008534 A1 | 1/2019 | Garrison et al. |
| 2019/0046218 A1 | 2/2019 | Garrison et al. |
| 2019/0366042 A1 | 12/2019 | Garrison et al. |
| 2019/0366043 A1 | 12/2019 | Garrison et al. |
| 2020/0016369 A1 | 1/2020 | Garrison et al. |
| 2020/0038628 A1 | 2/2020 | Chou et al. |
| 2020/0046939 A1 | 2/2020 | Garrison et al. |
| 2020/0046940 A1 | 2/2020 | Garrison et al. |

FOREIGN PATENT DOCUMENTS

| | | |
|---|---|---|
| WO | WO-95/06487 A2 | 3/1995 |
| WO | WO-2005/084130 A2 | 9/2005 |
| WO | WO-2014/008489 A1 | 1/2014 |
| WO | WO-2015/100178 A1 | 7/2015 |
| WO | WO-2015/157330 A1 | 10/2015 |

OTHER PUBLICATIONS

Aboodi, Michael S., et al. (2014) "Long-Term Impact of Balloon Postdilatation on Neointimal Formation: An Experimental Comparative Study Between Second-Generation Self-Expanding Versus Balloon-Expandable Stent Technologies." *Catheterization and Cardiovascular Interventions* 2014, 83:397-404.

Bates, Eric R., et al. (2007) "ACCF/SCAVSIVIB/SIR/ASITN 2007 Clinical Expert Consensus Document on Carotid Stenting." *JACC*, vol. 49, No. 1, 2007 Jan. 2/9, 2007:126-70.

Bodily, K.D. et al. (2011) "Stent-Assisted Coiling in Acutely Ruptured Intracranial Aneurysms: A Qualitative, Systematic Review of the Literature." *AJNR Am J Neuroradiol*, 2011, 32:1232-36.

Brott, Thomas G., et al. (2011), "2011 ASA/ACCF/AHA/AANN/AANS/ACR/ASNR/CNS/SAIP/SCAI/SIR/SNIS/SVM/SVS Guideline on the Management of Patients With Extracranial Carotid and Vertebral Artery DiseaseECVD Guideline: Full Text." J Am Coll Cardiol. 57(8):e16-e94.

Cho, Leslie and Debabrata Mukherjee (2006) "Basic Cerebral Anatomy for the Carotid Interventionalist: The Intracranial and Extracranial Vessels." *Catheterization and Cardiovascular Interventions* 2006, 68:104-111.

Cook, Stephane, et al. (2007) "Incomplete Stent Apposition and Very Late Stent Thrombosis After Drug-Eluting Stent Implantation." Circulation. 2007;115:2426-2434.

Dyet, John F., et al. (2000) "Mechanical properties of Metallic Stents: How Do These Properties Influence the Choice of Stent for Specific Lesions?" Cardiovasc Intervent Radiol (2000) 23:47-54.

Faggioli, GianLuca, et al., 2009, "Atherosclerotic aortic lesions increase the risk of cerebral embolism during carotid stenting in patient with the complex aortic arch anatomy." *J Vasc Surg*, 2009, 49:80-85.

Farooq, Vasim et al. (2011) "The Use of a Guide Catheter Extension System as an Aid During Transradial Percutaneous Coronary Intervention of Coronary Artery Bypass Grafts." *Catheterization and Cardiovascular Interventions*, vol. 78, No. 6, 2011, pp. 847-863.

Farooq, Vasim, et al. (2016) "Forward and Back Aspiration during ST-Elevation Myocardial Infarction: a Feasibility Study." EuroIntervention, vol. 11, No. 14, 2016, pp. 1639-1648.

Fiorella, David and Henry H. Woo (2007). "Emerging Endovascular Therapies for Symptomatic Intracranial Atherosclerotic Disease." *Stroke* 2007.38:2391-2396. Web. Accessed Sep. 20, 2018.

Flores, A., et al. "Endovascular treatment for M2 occlusions in the era of stentrievers: a descriptive multicenter experience." J NeuroIntervent Surg 2015;7:234-237. Web. Accessed Dec. 17, 2018.

Gavrilidou P., et al. (2013) "Morphological characteristics of the external carotid artery." *ARS Medica Tomitana*, 2013; 2(73): 74-78.

Grenacher, Lars, et al. (2006) "In Vitro Comparison of Self-Expanding Versus Balloon-Expandable Stents in a Human Ex Vivo Model." *Cardiovasc Intervent Radiol* 2006, 29:249-254. Springer Science+Business Media, Inc., Published Online: Nov. 22, 2005.

Henkes, H., et al. (2002) Endovascular Coil Occlusion of Intracranial Aneurysms Assisted by a Novel Self-Expandable Nitinol Microstent (Neuroform). *Interventional Neuroradiology* 2002, 8:107-119.

Henkes, H., et al. (2005) "Treatment of intracranial atherosclerotic stenoses with balloon dilatation and self-expanding stent deployment (WingSpan)." Neuroradiology (2005) 47: 222-228. https://doi.org/10.1007/s00234-005-1351-2.

Jankowitz, Brian, et al. (2012) "Manual Aspiration Thrombectomy Adjunctive Endovascular Recanalization Technique in Acute Stroke Interventions." *Stroke*. 2012;43:1408-1411. Web. Accessed Sep. 26, 2018.

Jankowitz, Brian et al. (2015) "Primary manual aspiration thrombectomy (MAT) for acute ischemic stroke: safety, feasibility and outcomes in 112 consecutive patients." *J NeuroIntervent Surg* 2015; 7:27-31. Web. Accessed Sep. 20, 2018.

Jiang, Wei-Jian, et al. (2004), "Stenting of symptomatic M1 Stenosis of Middle Cerebral Artery: An Initial Experience of 40 Patients." *Stroke* 2004; 35:1375-1380. Web. Accessed Sep. 20, 2018.

Kim, JK, et al. (2004) "Elective stenting for symptomatic middle cerebral artery stenosis presenting as transient ischaemic deficits or stroke attacks: Short term arteriographical and clinical outcome."*J Neurol Neurosurg Psychiatry* 2004, 75: 847-851.Web. Accessed Sep. 20, 2018.

Kocak, Burak, et al. (2012) "Endovascular treatment of extracranial vertebral artery stenosis." *World J Radiol* Sep. 28, 2012; 4(9): 391-400.

Krejza, Jaroslaw, et al. (2006) "Carotid Artery Diameter in Men and Women and the Relation to Body and Neck Size." *Stroke*. 2006, 37:1103-1105. Web. Accessed Sep. 20, 2018.

Lam, Russell C. (2007) "The impact of increasing age on anatomic factors affecting carotid angioplasty and stenting." *J Vasc Surg* 2007, 45:875-80.

Layton, K.F., et al. (2006) "Bovine Aortic Arch Variant in Humans: Clarification of a Common Misnomer." *AJNR AM J Neuroradiol*. 27, 2006: 1541-1542.

Liang, Guobiao, Xu Gao, Zhiqing Li, Xuezhong Wei & Hongli Xue (2010) "Neuroform stent-assisted coiling of intracranial aneurysms: a 5 year single-center experience and follow-up." Neurological Research, 32:7, 721-727, DOI: 10.1179/016164109X12445616596409.

Lin, Ning, et al. (2015) "Utilization of Pipeline embolization device for treatment of ruptured intracranial aneurysms: US multicenter experience." *Journal of NeuroInterventional Surgery* 2015; 7:808-815. Published Online First Sep. 17, 2017. Web. Date Accessed Dec. 17, 2018. https://jnis.bmj.com/content/7/11/808.

(56) References Cited

OTHER PUBLICATIONS

Meerkin, David, et al. (2010) "The Twin-Pass Dual Access Catheter for Assessment of the No-Reflow Phenomenon." J Invasive Cardiol. Mar. 2010; D11822 (3) 22:125-9.
Mega, Jessica L, et al. (2011) "Dosing Clopidogrel Based on CYP2C19 Genotype and the Effect on Platelet Reactivity in Patients With Stable Cardiovascular Disease." *JAMA*, 2011, 306, (20):2221-2228. Web. Accessed Sep. 20, 2018.
Mehran, Roxana, et al. (2003) "Safety of an Aspirin-Alone Regimen After Intracoronary Stenting With a Heparin-Coated Stent Final Results of the HOPE (HEPACOAT and an Antithrombotic Regimen of Aspirin Alone) Study." *Circulation* 2003,108:1078-1083. Web. Accessed Sep. 25, 2018.
Migliavacca, Francesco, et al.(2004) "Stainless and shape memory alloy coronary stents: a computational study on the interaction with the vascular wall." *Biomech Model Mechanobiol* 2:205-217.
Min, Sang-Hyuk, Sung-Hyun Yoon and Joon-Yeul Lee (2013) "Intervertebral Foraminal Widening Caused by the Tortuous Cervical Vertebral Artery." *The Journal of the Korean Orthopaedic Association*, vol. 48 No. 3 2013: 246-250.
Mocco, J., Ziad Darkhabani and Elad I. Levy (2009) "Pharos Neurovascular Intracranial Stent: Elective Use for a Symptomatic Stenosis Refractory to Medical Therapy." Catheterization & Cardiovascular Intervention, 2009, vol. 74, Issue 4:642-646.
Nohara, Alison M. and David F. Kallmes (2003) "Transradial Cerebral Angiography: Technique and Outcomes." *AJNR Am J Neuroradiol* 2003, 24:1247-50.
Perez-Arjona, EA, DelPresto Z, Fessler RD. (2004) "Direct percutaneous carotid artery stenting with distal protection: technical case report." *Neurol Res* 2004, 26:338-41.
Piotin, Michel, et al. (2010) Stent-Assisted Coiling of Intracranial Aneurysms: Clinical and Angiographic Results in 216 Consecutive Aneurysms. *Stroke*.2010, 41:110-115. Web. Accessed Sep. 20, 2018.
Raja, Vijay N., Subhash Banerjee, and Emmanouil S., Brilakis (2010) "Use of the Twin-Pass Catheter for Wiring a Jailed Side Branch." Hellenic J Cardiol 2010; 51: 267-270.
Sambu, N., et al. (2011) "Prevalence of hyporesponsiveness to aspirin and clopidogrel in patients with stent thrombosis: is it time for tailored therapy?" *PCR Online*. Archives, vol. 7, Supplement M, 2 pages. http://www.pcronline.com/eurointervention/M_issue/volume-7/supplement-m/70/prevalence-of-hyporesponsiveness-to-aspirin-and-clopidogrel-in-patients-with-stent-thrombosis-is-it-time-for-tailored-therapy.htm.
Stys, Adam T. et al. "A Novel Application of GuideLiner Catheter for Thrombectomy in Acute Myocardial Infarction: A Case Series." *Journal of Invasive Cardiology*, vol. 25, No. 11, 2013, pp. E254-E259. 6 pages. (http://www.invasivecardiology.com/issue/4284).
Turk, Aquilla S, et al. (2014) "Initial clinical experience with the ADAPT technique: A direct aspiration first pass technique for stroke thrombectomy." *J NeuroIntervent Surg* 2014;6:231-237. doi:10.1136/neurintsurg-2013-010713. Web. Accessed Sep. 26, 2018.
United States. Food and Drug Administration. Boxed Warning on Plavix. Press Announcement. "*FDA Announces New Boxed Warning on Plavix.*" (2010). 1 page. Web. Wayback Machine. Accessed Sep. 25, 2018. (http://www.fda.gov/NewsEvents/Newsroom/PressAnnouncements/ucm204253.htm).
Vitek, Jiri J, et al., (2000) "Carotid Artery Stenting: Technical Considerations." *AJNR AM J Neuroradiol* 21:1736-1743.
Wang, Huan et al. (2005) Transaxillary Carotid Stenting: Technical Case Report, Neurosurgery, vol. 56, Operative Neurosurgery 2, Apr. 2005, ONS—E441, 4 pages.
Wanke, Isabel, et al. (2003) "Treatment of Wide-Necked Intracranial Aneurysms with a Self-Expanding Stent System: Initial Clinical Experience." *AJNR Am J Neuroradiol* 24:1192-1199, Jun./Jul. 2003.
White, C.J. et al. "Peripheral Vascular Intervention" (2001) Physicians' Press, The Manual of Interventional Cardiology 3rd edition. Chapter 36. Royal Oak, MI. 2001:831-901.
Yang, Pengfei, et al. (2015) "stent-assisted Coil Placement for the Treatment of 211 Acutely Ruptured Wide-necked intracranial Aneurysms: A Single-Center 11-Year Experience." *Radiology*. vol. 276: No. 2, Aug. 2015; 545-552, 619.
U.S. Appl. No. 13/921,165, filed Jun. 18, 2013, US 2013-0281788.
U.S. Appl. No. 15/699,401, filed Sep. 8, 2017, US 2017-0368309.
U.S. Appl. No. 15/727,373, filed Oct. 6, 2017, US 2018-0028205.
U.S. Appl. No. 15/866,012, filed Jan. 9, 2018, US 2018-0193042.
U.S. Appl. No. 15/875,214, filed Jan. 19, 2018, US 2018-0361114.
U.S. Appl. No. 15/875,342, filed Jan. 19, 2018, US 2018-0207399.
U.S. Appl. No. 16/117,741, filed Aug. 30, 2018, US 2019-0008534.
U.S. Appl. No. 16/117,753, filed Aug. 30, 2018, US 2019-0046218.
U.S. Appl. No. 16/414,532, filed May 16, 2019, US 2019-0351182.
U.S. Appl. No. 16/530,845, filed Aug. 2, 2019, US 2020-0023160.
U.S. Appl. No. 16/543,215, filed Aug. 16, 2019, US 2019-0366042.
U.S. Appl. No. 16/543,226, filed Aug. 16, 2019, US 2019-0366043.
U.S. Appl. No. 16/584,220, filed Sep. 26, 2019, US 2020-0016369.
U.S. Appl. No. 16/584,351, filed Sep. 26, 2019, US 2020-0038628.
U.S. Appl. No. 16/596,531, filed Oct. 8, 2019, US 2020-0046939.
U.S. Appl. No. 16/596,535, filed Oct. 8, 2019, US 2020-0046940.
PCT/US2019/032694, filed May 16, 2019, WO 2019/222518.

\* cited by examiner

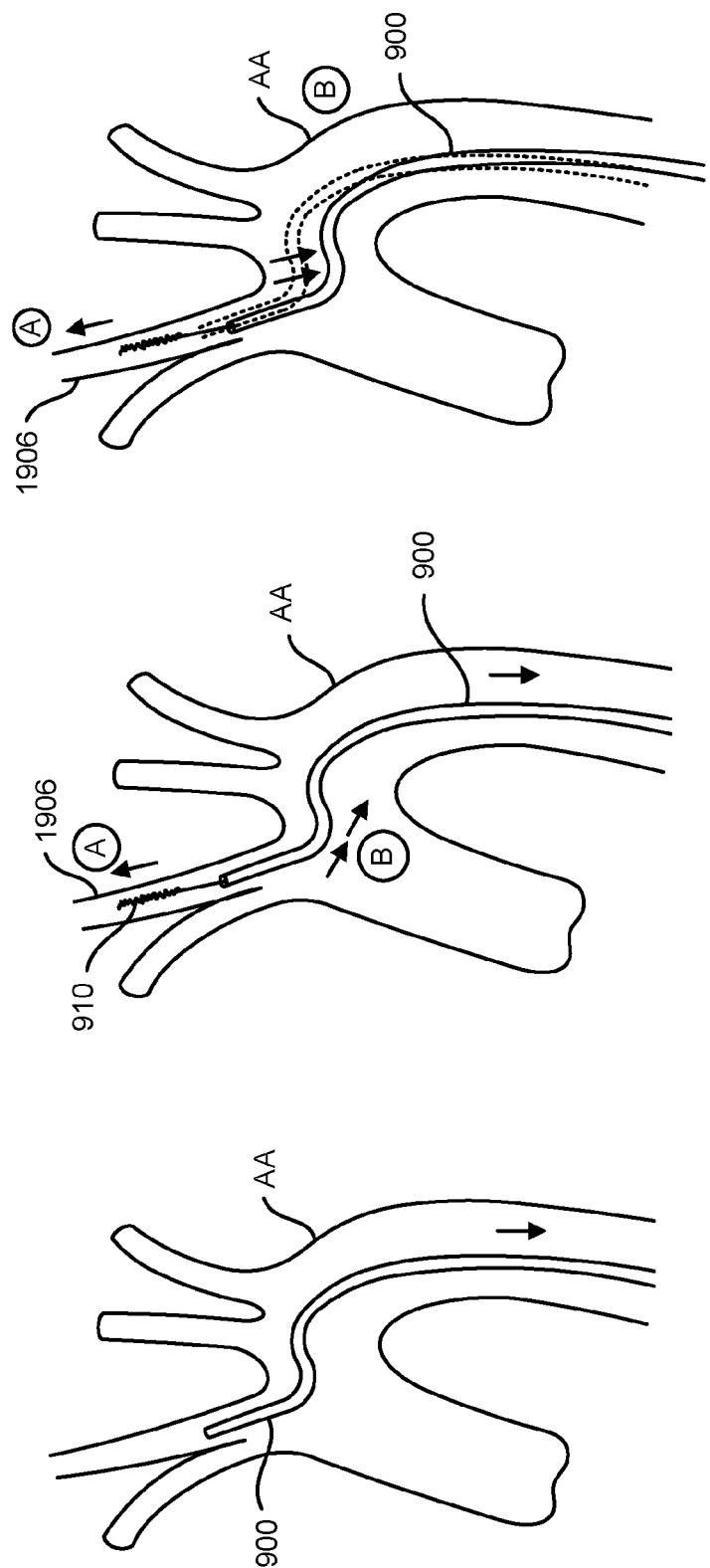

Detail A

A-A

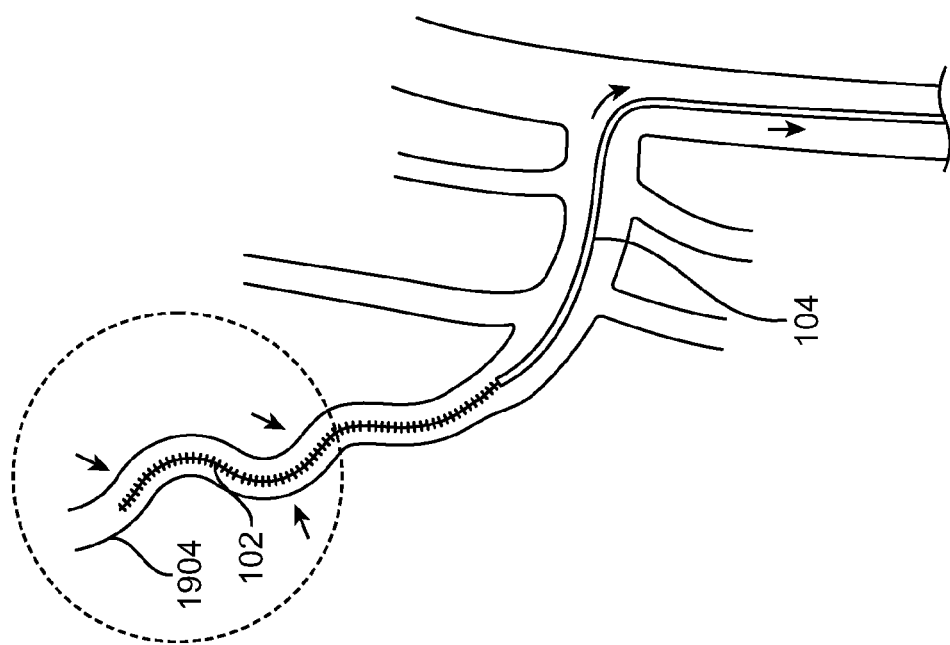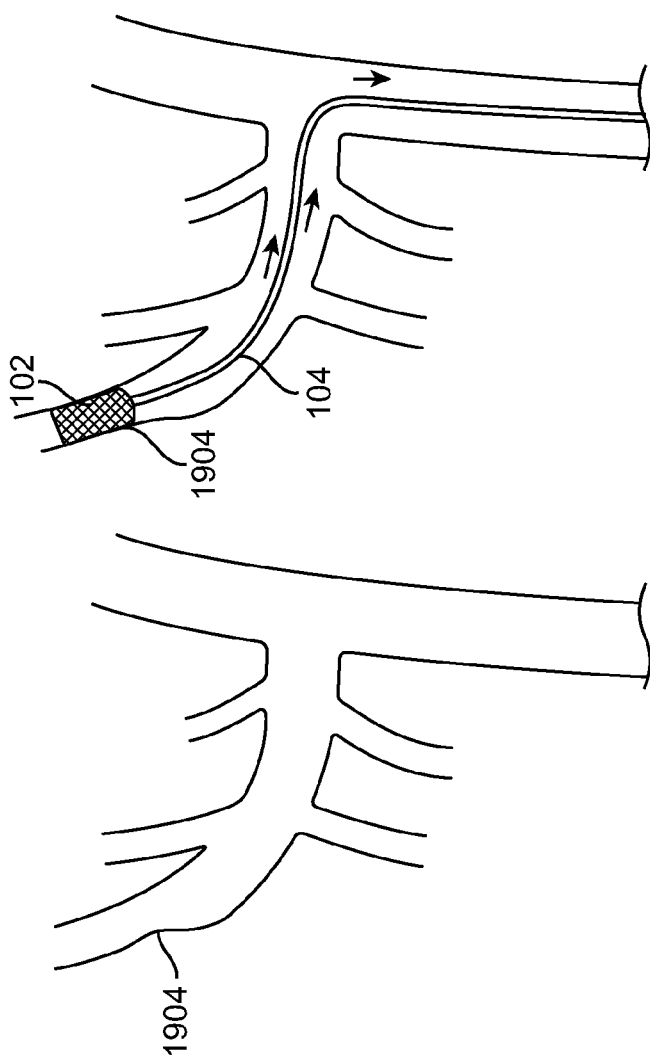

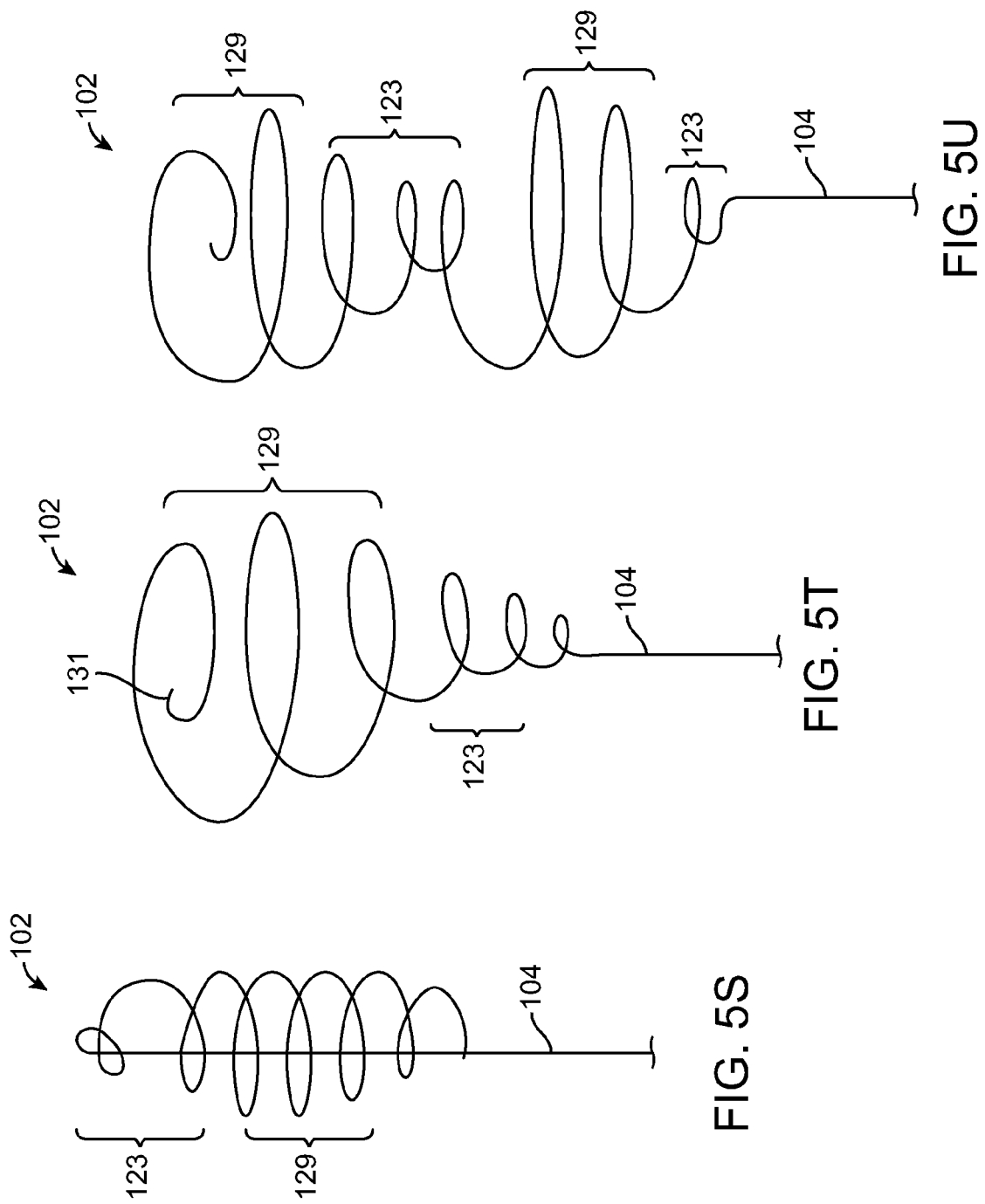

Detail B

Detail B

Detail B

Detail B

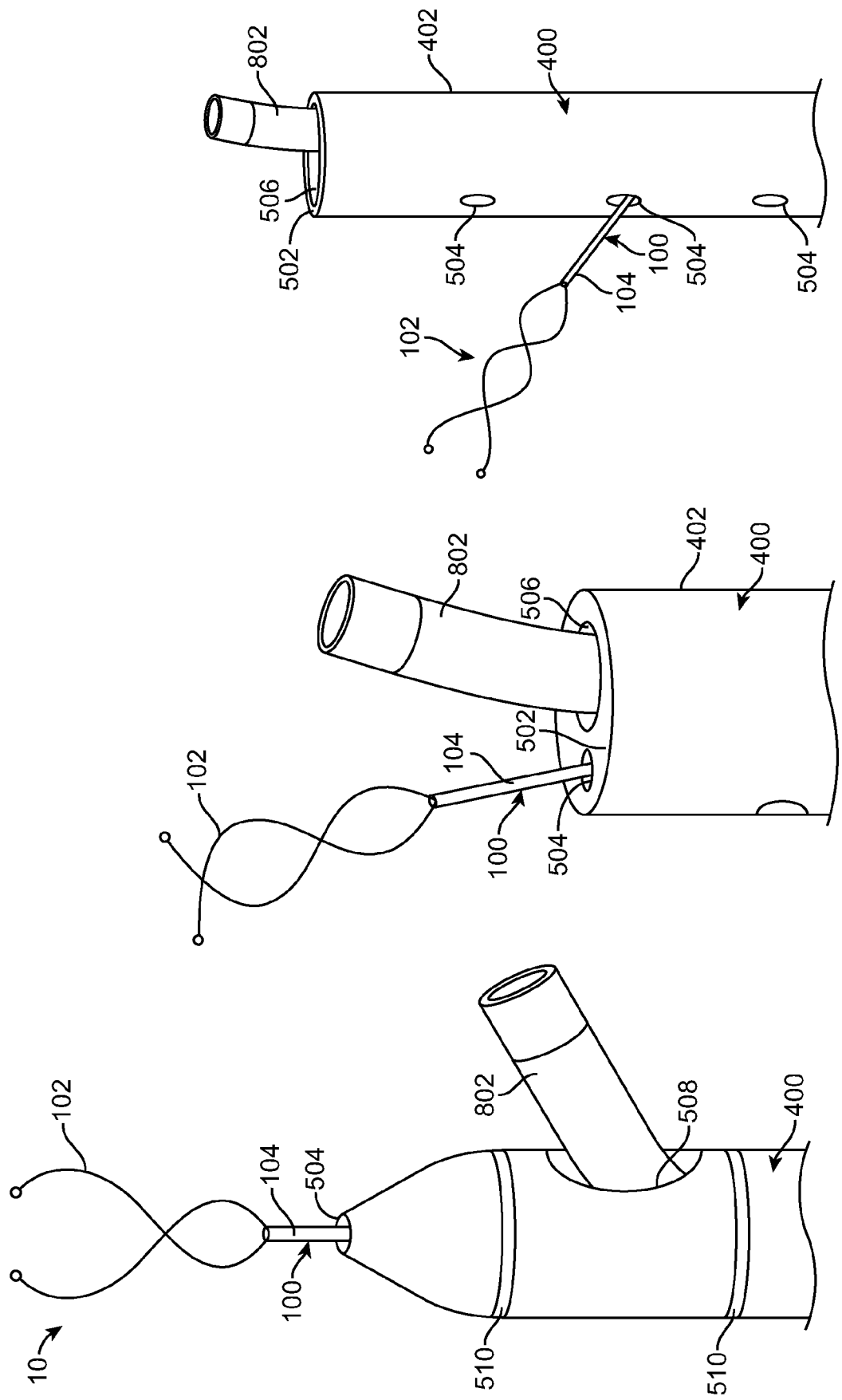

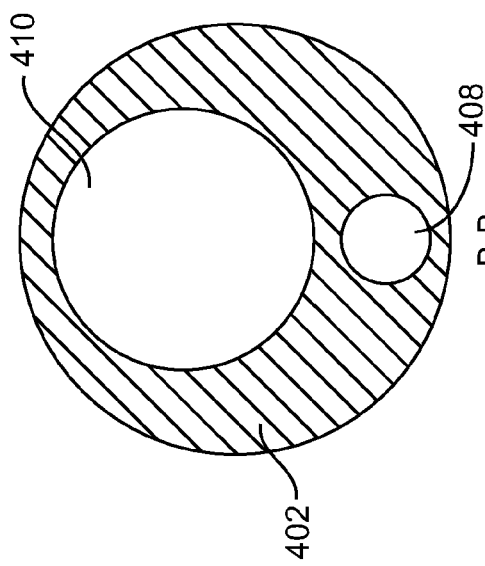
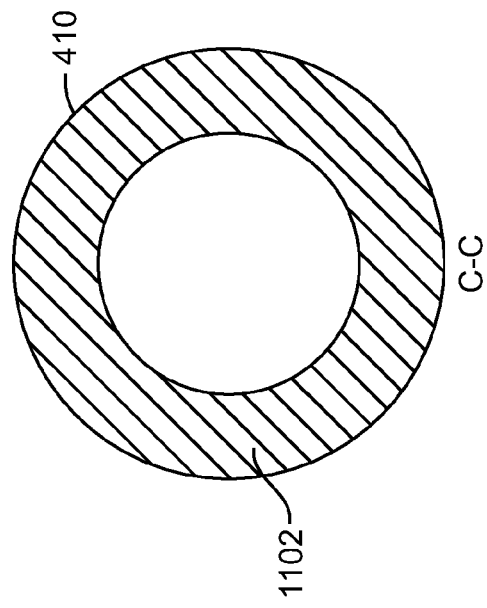
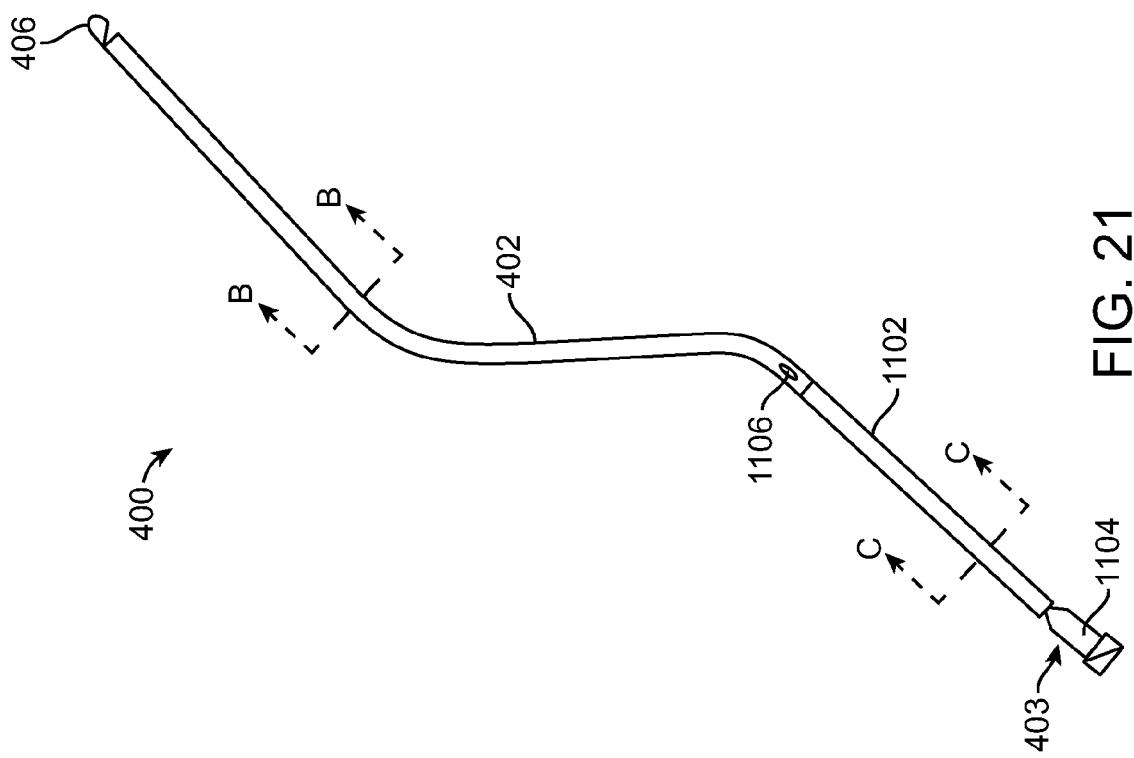

METHODS OF INTRACEREBRAL IMPLANT DELIVERY

CROSS-REFERENCE TO RELATED APPLICATIONS

This application is a National Stage entry, filed under 35 U.S.C. § 371, of International Application No. PCT/US2016/043742, filed on Jul. 22, 2016, and claims priority to U.S. Provisional Application Nos. 62/196,613, filed Jul. 24, 2015, entitled "Anchoring Guide System;" and 62/275,963, filed Jan. 7, 2016, entitled "Method of Intracerebral Implant Delivery;" and 62/275,939, filed Jan. 7, 2016, entitled "Anchoring Delivery system;" and 62/301,857, filed Mar. 1, 2016, entitled "Anchoring Delivery System." Priority to the aforementioned filing date is claimed and the entire contents of each are hereby incorporated by reference herein in their entireties and for all purposes.

FIELD

The present technology relates generally to medical devices and methods, and more particularly, to delivery systems and methods for delivering implant devices to a target anatomy.

BACKGROUND INFORMATION

Vascular disease caused by stenosis or narrowing of a vessel is commonly treated by endovascular implantation of scaffolding devices such as stents, often in combination with balloon angioplasty, to increase the inner diameter or cross-sectional area of the vessel lumen. Other serious vascular defects include aneurysm in which a bulge or bubble protrudes out in a radial direction from the vessel that, if left untreated, may continue expanding until it bursts thereby causing hemorrhaging from the vessel. Endovascular implantation of scaffolding devices or stents can also be used to treat aneurysms to occlude, partially occlude, and/or assist in the implantation of a coil into the aneurysm.

Treating arteriosclerosis and aneurysms in vessels of the brain by endovascular implantation of stents and stent-like devices is particularly challenging due, in part, to the tortuosity of the vasculature and the small size of the vessels. Further, the risk of stroke and thromboembolic complications is high due to the release of thromboembolic material during delivery of the stent and, in the case of flow diverters for treatment of aneurysm, can block blood flow to branch vessels. Stent length also poses a risk for further thromboembolic complications.

SUMMARY

It would be advantageous, in particular, in cases where it might be impossible to advance a catheter deep into the vasculature, to provide an anchoring delivery system to provide support during delivery of an implant (or during any other procedures employing the advancement of sheaths or catheters) to provide a faster, easier and more efficient endovascular implantation of stents and other implantable devices in the treatment of cerebrovascular diseases. For example, an anchoring delivery system may be beneficial during interventions within the cerebral vasculature involving the delivery of implants such as stents, flow diverters and coils, through tortuous or complex target anatomy.

In an aspect, described is a method of delivering an implant in an intracranial vessel. The method includes deploying an anchor of a tethering device in an anchoring vessel forming a first fixation point. The tethering device has a tether extending proximally from the anchor. The method includes advancing a guide-sheath to a location near the anchoring vessel. The guide-sheath has at least one lumen. The method includes attaching the guide-sheath to the tether of the tethering device forming a second fixation point proximal to the first fixation point, delivering an implant through the lumen of the guide-sheath towards a treatment site distal to the first fixation point and located within an intracranial vessel, and deploying the implant at the treatment site.

The implant can be a balloon-expandable stent, a self-expanding stent, or a flow diverter. The treatment site can be an aneurysm or a stenosis or other treatment site within a vessel. The first fixation point can be formed in the anchoring vessel near a bifurcation between the anchoring vessel and a vessel leading to the treatment site. Delivering the implant through the lumen can tension the tether between the first fixation point and the second fixation point. Deploying the anchor can include deploying the anchor from a low profile configuration to a higher profile configuration. Advancing the guide-sheath can include advancing the guide-sheath over the tether such that the tether extends at least in part through the at least one lumen of the guide-sheath. The guide-sheath can include at least a second lumen, and the tether can extend through at least a portion of the second lumen. Attaching the guide-sheath to the tether can include using a tether gripper at the second point of fixation to attach the guide-sheath to the tether of the tethering device. The tether gripper can be on one or both of the tethering device and the guide-sheath. The method can further include preventing prolapse of the guide-sheath during delivery of the implant. The method can further include resisting tension stored in the guide-sheath during delivery of the implant. The implant can be a self-expanding stent and deploying the implant at the treatment site can include unsheathing the self-expanding stent by withdrawing proximally a constraint. The method can further include preventing the self-expanding stent from missing the treatment site during unsheathing. The method can further include removing the anchor from the anchoring vessel, and removing the guide-sheath.

In an interrelated aspect, provided is a method of delivering an implant in an intracranial vessel including delivering a tethering device to an anchoring vessel. The tethering device includes a tether extending proximally from an anchor. The method includes deploying the anchor of the tethering device in the anchoring vessel, advancing a guide-sheath over the tether of the tethering device to position an opening from the guide-sheath near an entrance of a target vessel bifurcating from the anchoring vessel, and delivering an implant through the guide-sheath to a treatment site distal to the anchoring vessel.

The method can further include attaching the guide-sheath to the tether of the tethering device. The tethering device can fix and support the guide-sheath for delivering the implant through the guide-sheath. The anchor can be deployed at an anchoring site in the anchoring vessel. The guide-sheath can include a lumen to receive at least a portion of the tether. The guide-sheath can be attached to the tether at a point of fixation proximal to the anchoring vessel. Delivering the implant through the guide-sheath can tension the tether between the anchor deployed in the anchoring vessel and the point of fixation. The implant can be delivered through a first lumen of the guide-sheath and the tether can extend at least in part through the first lumen. The implant can be delivered through a first lumen of the guide-sheath and the tether can extend at least in part through a second lumen separate from the first lumen. The implant can be a balloon-expandable stent, a self-expanding stent, or a flow diverter. The treatment site can be an aneurysm or a stenosis or other treatment site within a vessel. The method can further include preventing prolapse of the guide-sheath during delivery of the implant. The method can further include resisting tension stored in the guide-sheath during delivery of the implant. The implant can be a self-expanding stent and deploying the implant at the treatment site can include unsheathing the self-expanding stent by withdrawing proximally a constraint. The method can further include preventing the self-expanding stent from missing the treatment site during unsheathing. The method can further include removing the anchor from the anchoring vessel, and removing the guide-sheath.

In an interrelated aspect, provided is a method of delivering an implant in an intracranial vessel that includes advancing a guidewire near an anchoring vessel and exchanging the guidewire for a tethering device. The tethering device includes a tether extending proximally from an anchor. The method includes deploying the anchor of the tethering device in the anchoring vessel, advancing a guide-sheath over the tether of the tethering device to position an opening from the guide-sheath near an entrance of a target vessel bifurcating from the anchoring vessel, attaching the guide-sheath to the tether of the tethering device, and delivering an implant through the guide-sheath to a treatment site.

The anchor can be deployed at an anchoring site in the anchoring vessel distal to the entrance of the target vessel. The guide-sheath can include a lumen to receive at least a portion of the tether. The lumen can be different or the same as the lumen through which the implant is delivered. The guide-sheath can be attached to the tether at a point of fixation proximal to the anchoring vessel. Delivering the implant through the guide-sheath can tension the tether anchor deployed in the anchoring vessel and the point of fixation. The implant can be a balloon-expandable stent, a self-expanding stent, or a flow diverter. The treatment site can be an aneurysm or a stenosis or another treatment site in the vessel. The method can further include preventing prolapse of the guide-sheath during delivery of the implant. The method can further include resisting tension stored in the guide-sheath during delivery of the implant. The implant can be a self-expanding stent and deploying the implant at the treatment site can include unsheathing the self-expanding stent by withdrawing proximally a constraint. The method can further include preventing the self-expanding stent from missing the treatment site during unsheathing. The method can further include removing the anchor from the anchoring vessel, and removing the guide-sheath.

In some variations, one or more of the following can optionally be included in any feasible combination in the above methods, apparatus, devices, and systems. More details of the devices, systems, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking the figures are not to scale in absolute terms or com-paratively, but are intended to be illustrative. Also, relative placement of features and elements may be modified for the purpose of illustrative clarity FIGS. 1A-1C illustrate prolapse of a catheter within the aorta near the takeoff of the great vessels;

FIGS. 5M-5O illustrate schematic views of an anchoring vessel and an anchor;

FIGS. 5S-5U illustrate schematic views of further implementations of a distal portion of a tethering device, in accordance with an interrelated implementation;

FIG. 18 illustrates a distal end of an anchoring delivery system having a tethering device in a tether lumen of a tetherable guide-sheath and a working device in a working lumen of the tetherable guide-sheath, in accordance with an implementation;

FIG. 19 illustrates a distal end of an anchoring delivery system having a tethering device in a tether lumen of a tetherable guide-sheath and a working device in a working lumen of the tetherable guide-sheath, in accordance with an implementation;

FIG. 20 illustrates a distal end of an anchoring delivery system having a tethering device and a working device in a same lumen of a tetherable guide-sheath, in accordance with an implementation;

FIG. 21 illustrates a perspective view of a tetherable guide-sheath, in accordance with an implementation;

FIG. 22 illustrates a sectional view, taken about line B-B of FIG. 21, of a tetherable guide-sheath, in accordance with an implementation;

FIG. 23 illustrates a sectional view, taken about line C-C of FIG. 21, of a tetherable guide-sheath, in accordance with an implementation;

Figure 1D:
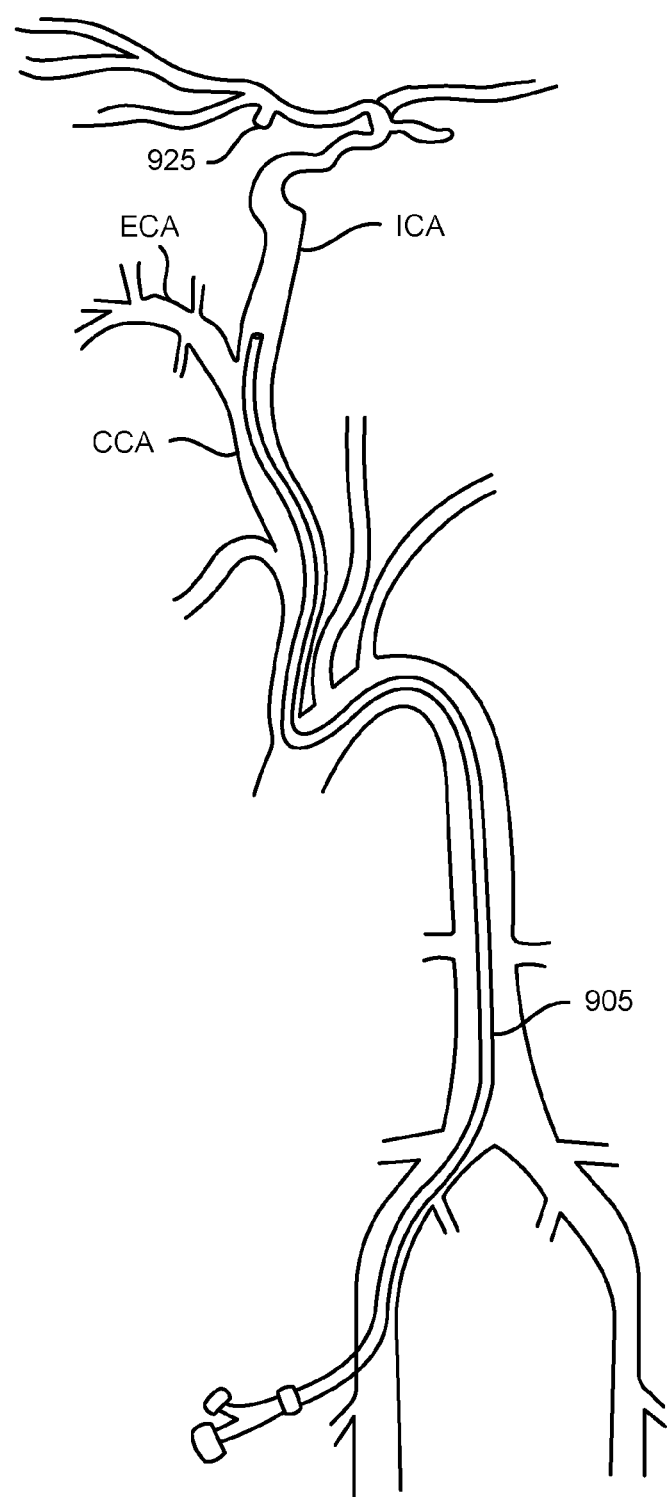
FIGS. 1D-1F illustrate advancement of implant delivery systems through a typical sheath system.

It should be appreciated that the drawings are for example only and are not meant to be to scale. It is to be understood that devices described herein may include features not necessarily depicted in each figure.

DETAILED DESCRIPTION

Endovascular access of the neurovasculature requires navigation of vessels, often tortuous and diseased, which can complicate delivery of devices such as intracerebral stents and their delivery systems. Resistance points during advancement of various implantable devices through the vessel can lead to a chain reaction of events involving the buckling and storage of tension within the catheter length. Further, many cases involve a trial and error iterative process of different constructs of supporting catheters and stiff wires to build a "tower" into the intracerebral vasculature—each iteration involving further guidance and support. This can be traumatic to the vessel through which the devices are passed and ultimately, the entire system can lose column strength and such that the devices fail to traverse to the desired location.

To access the cerebral anatomy, guide catheters and guide sheaths are used to direct interventional devices, such as stents, coils, and flow diverters, to a target site, such as an embolism, stenosis, or an intracranial aneurysm, from the access site. It can be challenging to establish guide or sheath position in a fashion that is stable and provides support for the device delivery. To maneuver the catheters into position, coaxial, triaxial, or quadraxial systems are often used in which a guidewire/microcatheter system is first deployed and coaxial larger catheters are subsequently delivered. The clinical challenge, especially in the octogenarian population, is the elongation of the aortic arch against the fixed thoracic descending aorta, leading to a shifting of all great vessels, especially the brachiocephalic takeoff. Such shifting makes it more challenging to access the anatomy during treatment of, e.g., stroke, aneurysm, and other distally located vascular diseases. As catheters, wires, balloons, stents, or retrievable structures are advanced through the great vessels, they have a tendency to prolapse into the ascending aorta when pushed into a highly angulated and/or tortuous anatomy.

Described herein are methods that include delivering an implant and/or an implant delivery system to a target vessel of a neurovascular anatomy. The methods can include delivering the implant through a working lumen of a guide-sheath. More particularly, the guide-sheath can be fixed to a tether of a tethering device, and the tether can be attached to an anchor expanded within an anchoring vessel. Thus, the anchored tethering device and tetherable guide-sheath system, i.e., the anchoring delivery system, may support the implant delivery system during delivery to the target vessel. The methods described herein leverage the support provided by the anchoring delivery system, either from a transfemoral or transcervical route, to deliver implants within the cerebral vasculature with a very precise and accurate delivery with "one-to-one" tactile feedback and control. Precision and accuracy in delivery allows for the use of shorter devices that are better matched to the target site, e.g. a stent that is as long as the stenosis or a flow diverter that covers only the neck of an aneurysm. This also can reduce the risk of poor apposition of these stent products to the vessel wall, easing the concern for stent thrombosis. The stent delivery system can include a balloon expandable implant, e.g., a non-shape memory stent or flow diverter as well as self-expanding implants.

The Challenge of Intracerebral Implant Placement

Referring now to the figures, when advancing a catheter 900, such as a catheter of an implant delivery system, in tortuous anatomy or against resistance at a tip of the catheter 900, such as shown in FIGS. 1A-1B, resistance to movement may be felt by an operator. For example, as tip point A encounters a vessel wall, e.g., within a tortuous anatomy, a counter force is directed through the catheter 900 at point B. Particular to the involvement of access to the great vessels, e.g., the brachiocephalic, common carotid, or subclavian takeoffs from an aorta at the aortic arch AA, there is a dramatic transition from the "free space" of the aorta arch AA to the great vessels, and to the target vessel (e.g. a 2-3 mm intracerebral artery). Referring to FIG. 1C, the catheter 900 body in the aorta arch AA is "free" and buckles into the arch AA, which offers no resistance and can be a potential space for "storage" of catheter length and tension. The buckling at the level of the aorta/great vessel takeoff into the free space of the aorta can lead to withdrawal of the catheter 900 tip at tip point A, as well as a guidewire (910) that the catheter 900 is being delivered over. The anchoring delivery systems described herein provide guide support by "fastening" and supporting the body of the catheter 900 at a point to overcome the resistance at tip point A to advance the catheter 900 toward a target site 925 in the target vessel 1906.

Figure 1E:
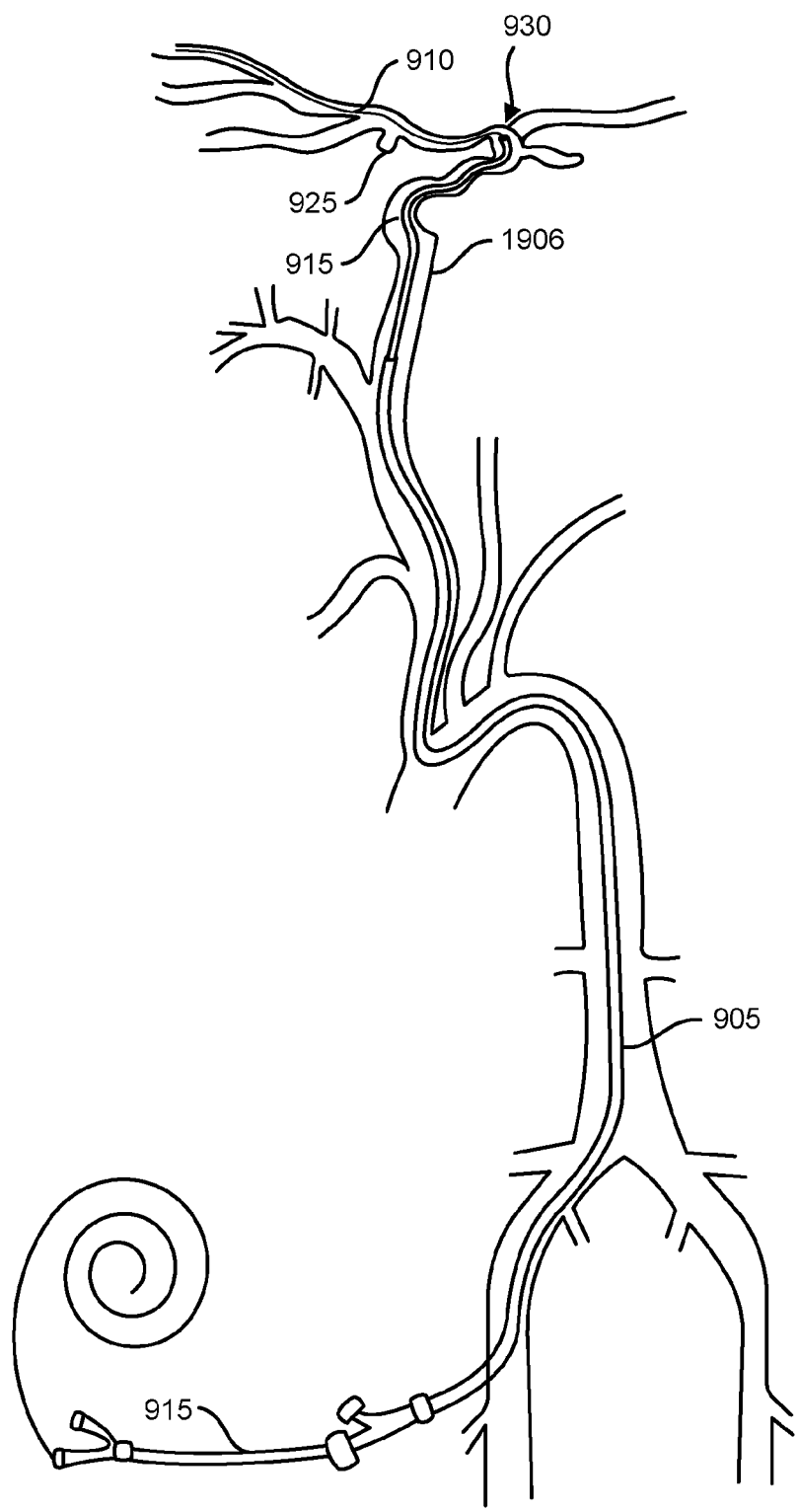
Figure 1F:
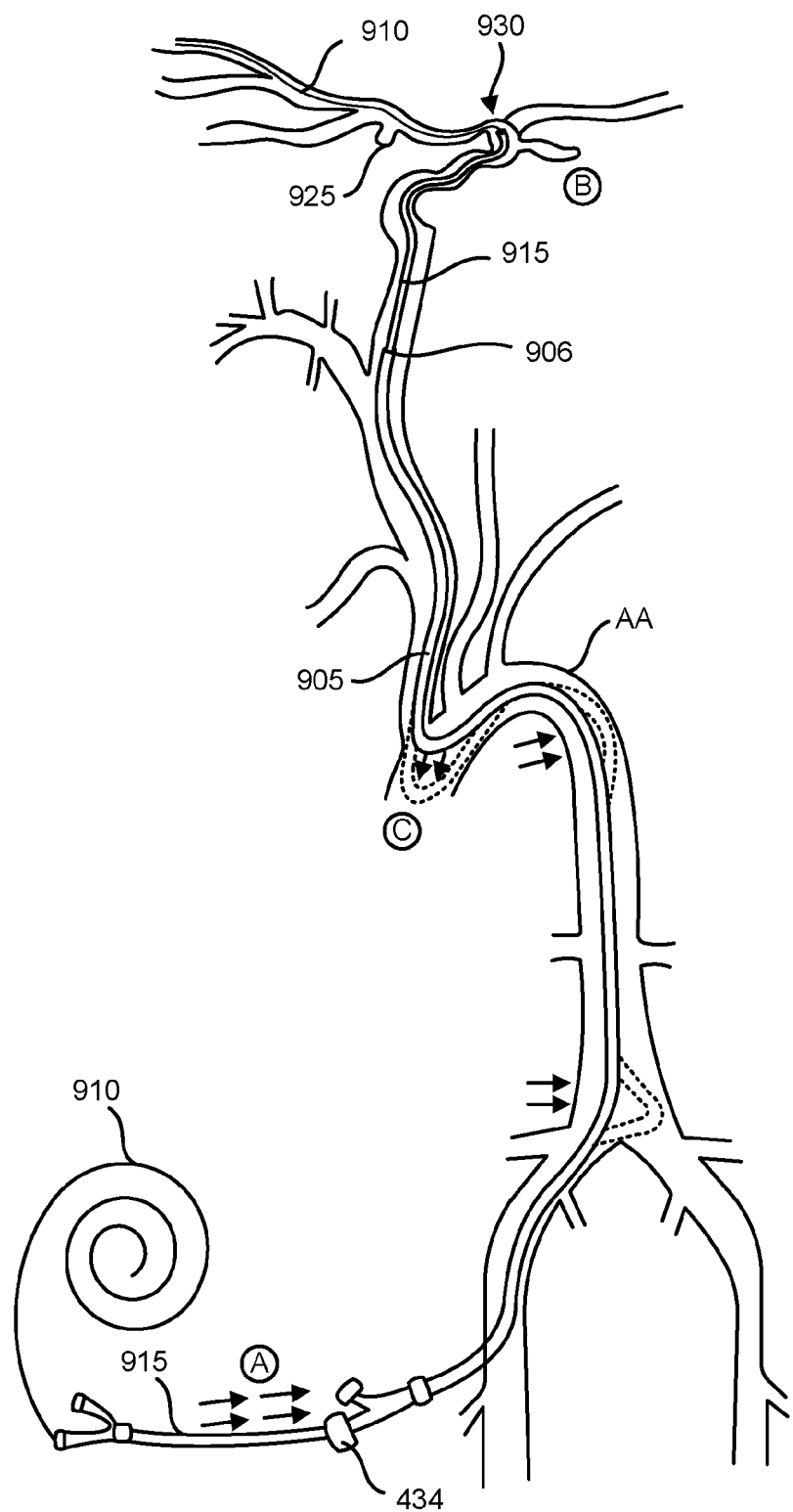

FIGS. 1D-1F show traditional sheath and support systems that can provide "support from below." FIG. 1D shows a sheath 905 used in neuro-intervention that either inserts through a short sheath at the groin or are themselves advanced to the level of the CCA or ICA. A guide catheter 900 is often advanced through the sheath 905 to gain a higher level of support to the petrous or bony ICA. Referring to FIG. 1E, a procedural guidewire 910 and a stent delivery system 915 for delivery of an implant may then be advanced through the sheath 905 or through a coaxial system including the sheath 905 and the guide catheter 900.

It should be appreciated that phrases like "working device," "stent delivery system," or "implant delivery system" may be used interchangeably herein and are not intended to be limiting. For example, when referring to "stent delivery system", the implant payload may be a "stent" in the traditional sense, but may also be a flow diverter having a scaffold configured to divert blood flow around an aneurysm sac, or an embolic coil configured to fill the aneurysm sac, or a combination thereof. Further, the implant may be a self-expanding implant or stent that is contained within a delivery system sheath, or an implant on a balloon that is actively expanded. Thus, as used herein "implant delivery system" or "stent delivery system" incorporates both self-expanding (SE) systems and balloon-expandable (BE) systems and is not intended to be limiting. An SE stent system is illustrated in the figure, and thus, the catheter 900 can represent the outer sheath of the SE stent system surrounding the stent in the undeployed/unexpanded state. In the example, there is an aneurysm shown as the target site 925 in the target vessel 1906 for implant placement. It should be appreciated that the target site 925 for implant placement can vary and need not include an aneurysm. For example, the target site 925 can be an occluded, partially occluded, or otherwise narrowed or stenotic region of a vessel.

Referring to FIG. 1F, the stent delivery system 915 can meet an obstruction or, as in the case shown, an extreme tortuosity 930 such as the carotid siphon or other tortuous locations common in the intracerebral anatomy. These resistance points are often met with stent advancement and can lead to a chain reaction of events in typical cases. This can also occur with inflation balloon systems, simple microcatheter advancement or even guidewire advancement depending on how "tenuous" the purchase of the sheath and guide systems is. As mentioned above, many cases involve a trial and error iterative process of different constructs of supporting catheters and stiff wires to build the "tower" to the intracerebral vasculature that can be traumatic to the vasculature and to the patient and prolong procedure times.

Still with respect to FIG. 1F, the standard sheath system placed in the ICA is shown with advancement of a stent delivery system 915 targeting the distal target site 925. Advancement of the stent delivery system 915 with forward push at the rotating hemostatic valve (RHV) 434 at point A of FIG. 1F can lead to advancement of the stent delivery system 915 through the sheath 905, out of the sheath tip 906 and into the tortuous distal carotid and cerebral anatomy. The tip of the stent delivery system 915 can be guided by the course of a previously positioned procedural guidewire 910 and may encounter an area of tortuosity 930 where it meets resistance in taking that curve (near point B of FIG. 1F). Further advancement of the stent delivery system 915 can lead to downward force that can buckle the stent delivery system 915 and the sheath 905 (point C in FIG. 1F).

The sum effect of forward pressure in such systems can be stent advancement to a point of ultimate resistance and stoppage. At this point, continued advancement can create a downward and lateral force on the catheter systems below (point B in FIG. 1F). The chain reaction that can follow uncovers a series of buckling and prolapse points along the system course, for example, from the femoral anatomy to the stent tip as shown in dotted lines. A common buckle point is at the transition from the aorta AA to the target great vessel (point C in this case, the ascending aorta and the brachiocephalic artery). Because of the bending and the downward force, this buckle point often pulls the entire guidewire/stent delivery system/sheath system downwards with continued forward stent delivery system 915 advancement. The casual observer can see a resulting appearance of the stent delivery system 915 moving "backwards" on fluoroscopic imaging with advancement, all the advancement of force leading to catheter prolapse into the aorta AA and erosion of the support to advance wires or stent systems northward. The course of the coaxial stent delivery system 915 and sheath 905 may lead to further buckling and prolapse throughout the aorta AA, which can force the course of the coaxial system to "take the greatest curve" up to the stent tip. Prolapse and loss of length can cause more and more withdrawal of the stent delivery system 915 tip, frustrating the operator and leading to prolonged procedure times and complications from the back and forth movement required to advance systems in this "slippery slope" situation. The entire system may lose column strength as the downward and lateral pressures create awkward turns and "corkscrew" paths through which guidewire and stent fail to traverse. This can lead to complete displacement of the system and loss of purchase in the great vessel.

The Anchoring Delivery System

The anchoring delivery systems described herein can rapidly, consistently and easily create a transfemoral guide-catheter position with "100% support" by creating a tension between an insertion site, such as a femoral insertion site, and an anchoring vessel, such as the right or left subclavian (RSA or LSA) or external carotid artery (ECA). Additionally, and as will be described in more detail below, a secondary anchoring may use the junction of a tether of a tethering device and a tetherable guide-sheath as a capture point for the carina of a bifurcation between ECA and CCA (for LSA/RSA, between the bifurcation of the innominate or brachiocephalic artery and subclavian). It should be appreciated that although much of the description refers to the implantation of a sheath using a transfemoral route of insertion, other routes are considered herein. For example, a transcervical route in which a sheath enters the vascular space at the level of the common carotid artery (CCA) or internal carotid artery (ICA) is also considered herein. Where the method involves using an anchoring delivery system that includes a tethering device and a tetherable guide-sheath inserted transfemorally, methods are also considered herein where a sewn-in sheath entering the vascular space from a transcervical route that could be fastened or sutured in place to mitigate any backing-out or pulling-in of the sheath tip relative to the push-and-pull of typical catheter interventions as described in more detail herein.

The following discussion of the anchoring delivery system incorporates the right ECA as the anchoring vessel, as this is will commonly be used in more challenging anatomy. The anchoring vessel, however, may be any vessel or anatomy that an anchor of the tethering device may be secured within. Typically, an operator will go straight for the ipsilateral ECA or ICA above (the bifurcation of the CCA) as this is the target of stiff wire placement for delivery of standard sheaths. An anchoring artery will preferentially not be in the path to the cerebral target, thus, anchoring target arteries will be the external carotid artery (ECA) or subclavian artery (SA) to access the internal carotid artery (ICA) or common carotid artery (CCA), respectively. The choice of ipsilateral SA or ECA as the anchoring target can depend on anatomy and clinical indication. For instance—it may be more challenging for certain anatomies to easily reach the ECA; as well, if carotid stenting is being contemplated—anchoring in the SA will give the operator guide support to access most any ICA through the generally non-tortuous thoracic CCA.

Described herein are anchoring delivery systems for providing fixation and support for the advancement of one or more working devices. The anchoring delivery systems described herein can include one or more tethering devices and a guide-sheath tethered by the one or more tethering devices and configured to receive and support the advancement of an implant delivery system therethrough. Each of the components of the anchoring delivery system and methods of using the anchoring delivery system for implant delivery will be described in more detail below.

It should be appreciated that the configuration of the tethering devices described herein can vary. The tethering device can be used with various guide-sheaths as described herein, including the tetherable guide-sheath described in more detail below as well as any of a variety of comparable commercially available guide-sheaths to form an anchoring delivery system 10. For example, the tethering devices described herein can be used with guiding sheaths having an ID between 0.087"-0.089" such as the Cook SHUTTLE 6F (Cook Medical, Inc., Bloomington, Ind.), Terumo DESTINATION 6F (Terumo Europe NV), Cordis VISTA BRITE TIP (Cordis Corp., Hialeah, Fla.), and Penumbra NEURON MAX 088 (Penumbra, Inc., Alameda, Calif.), or comparable commercially available guiding sheath. Further, it should be appreciated that the working devices for advancing through the guiding sheath can vary and need not be limited to the implementations shown in the figures. The guiding sheath, whether the tetherable guide sheath 400 or another commercially-available guiding sheath, can be used to deliver any of a variety of working devices configured to provide treatments such as large-bore catheters, aspiration thrombectomy, advanced catheters, wires, balloons, retrievable structures such as coil-tipped retrievable stents "Stentriever," stents, flow diverters, and a variety of other implantable devices.

Tethering Devices

Figure 2A:
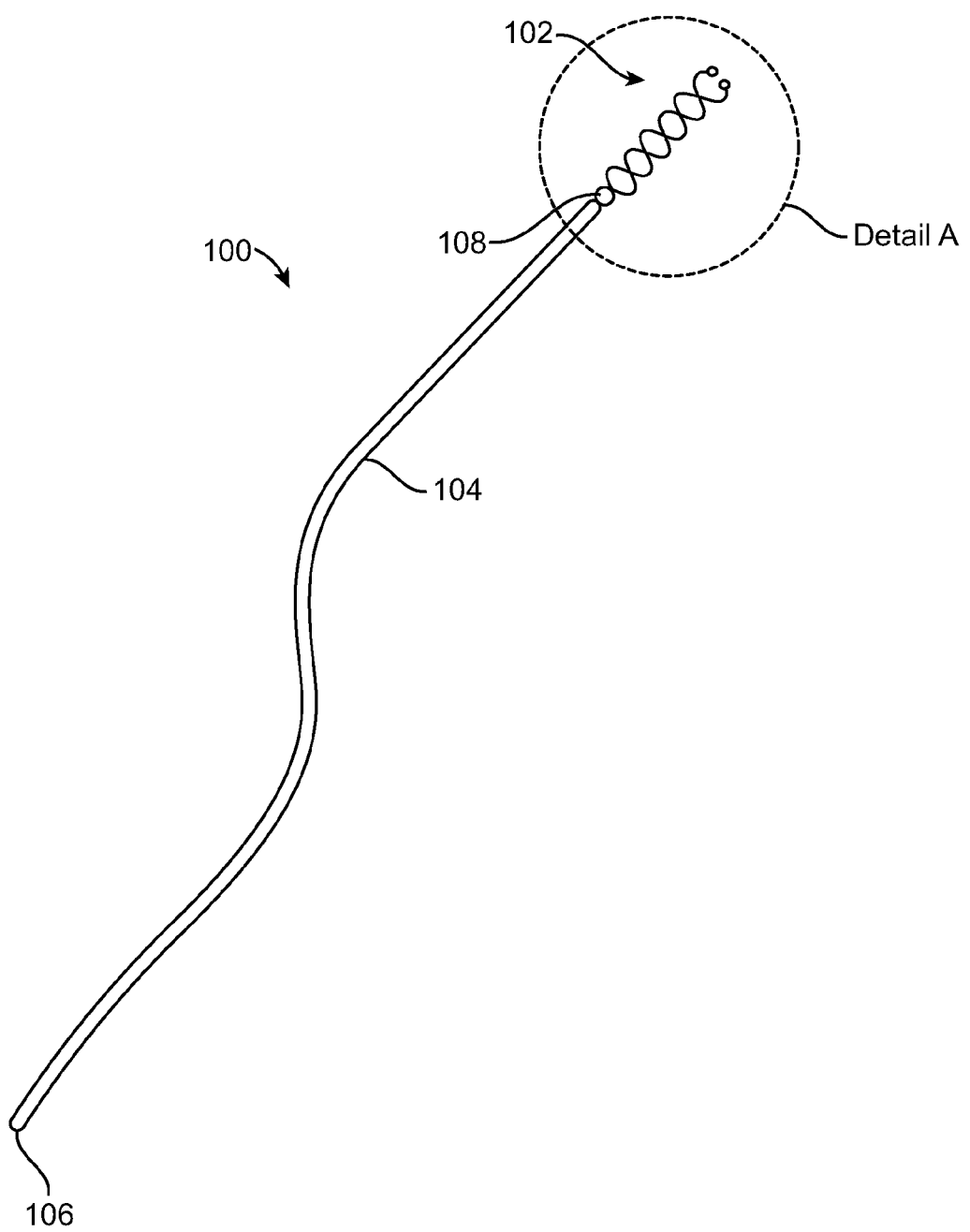
FIG. 2A illustrates a perspective view of a tethering device, in accordance with an implementation.

The anchoring delivery system 10 can include a tethering device 100. FIG. 2A shows a perspective view of a tethering device 100 in accordance with an implementation. The tethering device 100 can include a distal anchor 102 coupled to a proximal tether 104, for example, by a distal and/or a proximal joint 108. The tether 104 can be an elongate element extending proximally from the distal anchor 102 such as a filamentous element having an outer diameter that is small and flexible enough to curve through the tortuous vessels of the cerebral vasculature without kinking. Keeping the tether 104 to a small diameter allows the diameter of a tethered guide-sheath sized to receive the tether 104 to be as small as possible minimizing the access arteriotomy size. In at least some implementations, the tether 104 has a relatively low "pushability" such that it is generally not useful for advancing the anchor 102 through the vasculature without the assistance of a delivery tool. However, upon application of a proximal pulling force on the tether 104, for example when the tethering device 100 is anchored in a vessel by the anchor 102, the tether 104 is strong enough to maintain the tethering device 100 in a tensioned or taut state, as will be described in more detail below. The anchor 102 can have any of a variety of configurations as will be described in more detail below. Generally, the anchor 102 has a first, low-profile (unexpanded or constrained) configuration such that the anchor 102 may be delivered to the anchoring anatomy. The anchor 102 also has a second, higher-profile (expanded or unconstrained) configuration after delivery to and deployment within the target location such that the anchor 102 anchors (itself and the tethering device 100) within the target anatomy. It should be appreciated that use of the terms "expanded" and "unexpanded" as used herein with regard to the anchor 102 of the tethering device 100 refer generally to an overall shape or profile of the anchor 102 that is, in the case of an "expanded" anchor, greater than the overall shape or profile of the anchor 102 during delivery to the target anatomy or, in the case of an "unexpanded" anchor, less than the overall shape or profile of the anchor 102 during anchoring in the target anatomy, respectively. "Expanded" and "unexpanded" as used herein are not intended to require any particular type of change in profile of the anchor 102.

The anchor 102 can be deployable from the unexpanded state to the expanded state to fix a distal end of the tether 104 at an anchoring site in an anchoring vessel of a target anatomy, as described below. Thus, the anchor 102 may have enough radial strength in the expanded configuration to grip the anchoring anatomy and resist a proximal pull on the tether 104. The anchor 102 is generally configured to anchor within the anchoring vessel, as opposed to dilating a stenosis or scaffold the vessel such as with stents. However, it should be appreciated that the anchors 102 described herein can anchor in a manner that also dilates, scaffolds, embeds, and/or distorts the anchoring vessel within which the anchor 102 is anchored. The anchors 102 described herein can also facilitate anchoring of the tethering device 100 by other features that do not necessarily involve a change in shape, such as by externalizing a portion of the wire and/or incorporating superficial magnetic features in order to clamp outside the body, as will be described in more detail below.

Still with respect to FIG. 2A, the tether 104 of the tethering device 100 can be an elongated member extending from a proximal end 106 of the tethering device 100 to a distal joint 108 and having an outer surface extending along a longitudinal axis. The tether 104 can be stiffer and/or less prone to bending than the wires typically attached to retrievable structures, such as a Merci retriever or a Stentriever device, such that upon anchoring of the distal anchor 102 into a vessel the tether 104 can serve a supportive function to support a guide-sheath against buckling or prolapse, which will be described in more detail below. The tether 104 can also be formed by a combination of elements providing the proper supportive function. The tether 104 can have various dimensions and/or material configurations. The dimensions and/or material configurations of the tether 104 can be selected to achieve a desired tensile strength, flexibility, and trackability. In some implementations, a diameter of the tether 104 ranges from 0.005 inches to 0.025 inches, e.g., 0.008 inches, or 0.009 inches, or 0.010 inches, or 0.035 inches, depending on the degree of support that the tether 104 provides. The tether 104 can be a solid wire rod, a ribbon, or a hypotube of stainless steel or NiTi. In some implementations, the tether 104 can be a stainless steel rod, ribbon or hypotube. In other implementations, the tether 104 can be Drawn Filled Tubing (DFT) with a radiopaque core, such as an outer sheath of a composite to provide strength and a core material to provide superelasticity, conductivity, radiopacity, resiliency, etc. In some implementations, the tether 104 can be DFT of Nickel titanium with a radiopaque core such as platinum or tantalum.

The tether 104 can have several different cross-sectional areas at locations along its longitudinal axis between the proximal end 106 of the tether 104 to where it couples with the anchor 102. For example, a proximal section near the proximal end 106 of the tether 104 can have a first cross-sectional diameter. The first cross-sectional diameter may be sized, for example, to favor support over trackability. Similarly, the tether 104 can include a distal section distal to the proximal section that has a different cross-sectional diameter compared to the first cross-sectional diameter. For example, the distal section can include a second cross-sectional diameter that is smaller than the first cross-sectional diameter of the proximal section. As such, the distal section of the tether 104 can be configured to favor trackability over support.

The anchor 102 of the tethering device 100 can be sized to engage a range of vessel diameters, i.e., covering the lumen diameters to provide solid apposition against target anchor 102 sites such as the proximal CCA, proximal and mid-subclavian, and the external carotid artery (ECA). For example, the anchor 102 of the tethering device 100 can engage arteries of about 1 mm inside diameter to arteries with 40 mm inside diameters. For some procedures, it may be more common to anchor in arteries ranging from 2 mm inside diameter to 10 mm inside diameter. In other implementations, the anchor 102 of the tethering device 100 may be sized to be able to engage smaller arteries such as side branches. In comparison to conventional retrievable structures used in SMAT procedures, which are typically rather flimsy and unable to anchor against an artery wall, the anchors described herein are specifically designed to anchor within a target anatomy. For example, the anchors described herein can be sized to anchor within internal carotid artery (ICA), middle cerebral arteries at the M1 segment, Vertebral, Basilar vessels, or vessels generally larger than 3 mm. The anchors described herein can also be sized to anchor within vessels in the insular segment arteries at the M2 segment, P1 or vessels which are generally within the 2 mm-3 mm range. The anchors described herein can also be sized to anchor within vessels that are at the M3 segments or within vessels that are generally less than 2 mm.

The anchor 102 of the tethering device 100 can have any of a variety of configurations as described herein. For example, the anchor 102 can include an expandable structure configured to self-expand upon release of a constraint and/or expand when a force is applied. In some implementations (e.g., FIGS. 2B and 2D), the anchor 102 of the tethering device 100 can include a self-expanding material, such as nitinol, to expand to an understood diameter in the air and exert a controllable and consistent radial outward pressure when expanded and constrained within a vessel. In an implementation, the anchor 102 can include a closed-cell stent like structure, e.g., made of self-expanding material like nitinol that may be set to a desired shape, for example, by a heat set process. In other implementations, the anchor 102 of the tethering device 100 can include a non-self-expanding material (e.g., FIG. 2C) such that the anchor 102 expands when a force is applied.

The anchor 102 can be collapsed to a first configuration for delivery into the target vessel, expanded to a second configuration upon deployment in the target vessel and subsequently collapsed to or towards the first configuration for removal from the vessel. The anchor 102 of the tethering device 100 can collapse or be constrained to a small dimension such that it can be delivered through the lumen of a delivery catheter, e.g., a microcatheter or finder catheter as described below. In some implementations, the anchor 102 of the tethering device 100 can be actively collapsed using one or more additional features or components. The anchor 102 can additionally or optionally be malleable such that it can be pulled into the small dimension. The anchor 102 of the tethering device 100 can be deployed by unsleeving the anchor 102, e.g., advancing the anchor 102 from the lumen of the delivery catheter, retracting the delivery catheter to expose the anchor 102 from the lumen, or a combination or the two.

Figure 2B:
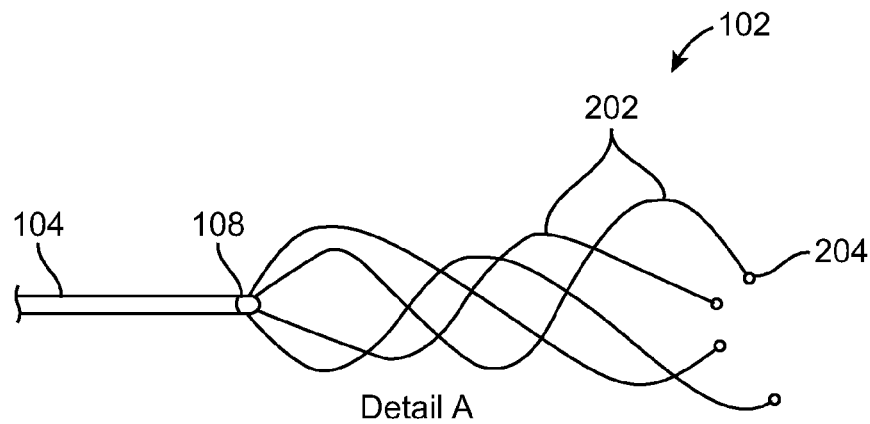
FIGS. 2B-2D illustrate detail views, taken from Detail A of FIG. 2A, of an anchor coupled to a tether of a tethering device.

FIG. 2B is a detail view taken from Detail A of FIG. 2A of an anchor 102 coupled to a tether 104 of a tethering device 100. As described above, the tether 104 can terminate at a distal joint 108 between the proximal end 106 and the anchor 102. The anchor 102 can be physically connected or attached to the tether 104 by one or more joints. The joint 108 may be a permanent attachment between the tether 104 and the anchor 102, such as a welding joint or other attachment joint. Alternatively, the anchor 102 can be detachably connected to the tether 104 at the joint 108. For example, the tether 104 can terminate at the distal joint 108, and the distal joint 108 may be severable at the discretion of an operator to decouple the anchor 102 from the tether 104. The decoupling between the anchor 102 and the tether 104 can be a permanent or reversible decoupling. For example, the distal joint 108 between the tether 104 and the anchor 102 may be an adhesive joint having a predetermined breaking stress, such that when sufficient pulling force is applied to the tether 104, the distal joint 108 breaks to detach the tether 104 from the anchor 102. In another implementation, the distal joint 108 can be a threaded joint. For example, the tether 104 can include an external thread at the distal joint 108 that engages with an internal thread of a tube section located at a proximal end or a distal joint 108 of the anchor 102. Thus, the operator can rotate the tether 104 around the longitudinal axis of the tethering device 100 when the anchor 102 is anchored in the anchoring anatomy to unscrew the tether 104 from the anchor 102. It should be appreciated that other mechanisms of detachment between the tether 104 and the anchor 102 are considered herein. Detachment of the anchor 102 from the tether 104 can be useful where re-sheathing of the anchor 102 by a delivery catheter or a tetherable guide-sheath, which will be described in more detail below, is not possible or may cause rupture or damage to a vessel. Thus, the anchor 102 can be left behind in the vessel and the tether 104 may be safely removed from a patient.

Figure 5A:
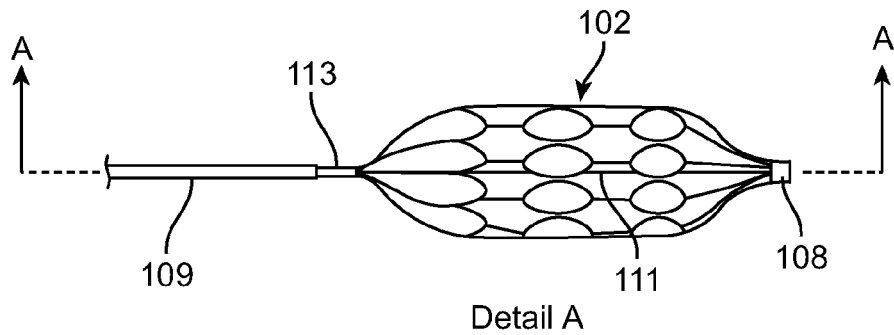
FIG. 5A illustrates a detail view, taken from Detail A of FIG. 4, of a distal portion of a tethering device.

As shown in FIG. 2B, the anchor 102 can include several convoluted struts 202 extending from the distal joint 108 to respective distal strut ends 204. The convoluted struts 202 can follow any path from the distal joint 108 to the distal strut ends 204. In an implementation, the convoluted struts 202 can extend in a generally longitudinal direction when the anchor 102 is in the unexpanded or constrained state, and the convoluted struts 202 can expand to extend in a generally spiral direction when the anchor 102 is in the expanded state. Thus, a transverse dimension of the convoluted struts 202 can be less in the unexpanded state than in the expanded state, and a longitudinal length of the convoluted struts 202 can be greater in the unexpanded, constrained state than in the expanded state. As shown in FIG. 2B, when the convoluted struts 202 expand together they can form a weaved structure that can engage an inner surface of the anchoring vessel. The respective proximal ends of the convoluted struts 202 can be attached to the distal joint 108 and the distal strut ends 204 can be freely suspended. More particularly, the distal strut ends 204 may not be attached to each other such that the struts 202 are individually cantilevered from the distal joint 108. However, the distal strut ends 204 can be coupled to each other, e.g., by being commonly connected to a second joint of the anchor 102, for example as shown in FIG. 5A, which will be described in more detail below. The struts 202 can also incorporate one or more barbs or cleats to improve their anchoring strength within the vessel and prevent slippage of the anchor 102 in a proximal direction, for example, upon a pulling force being applied during use.

Figure 2C:
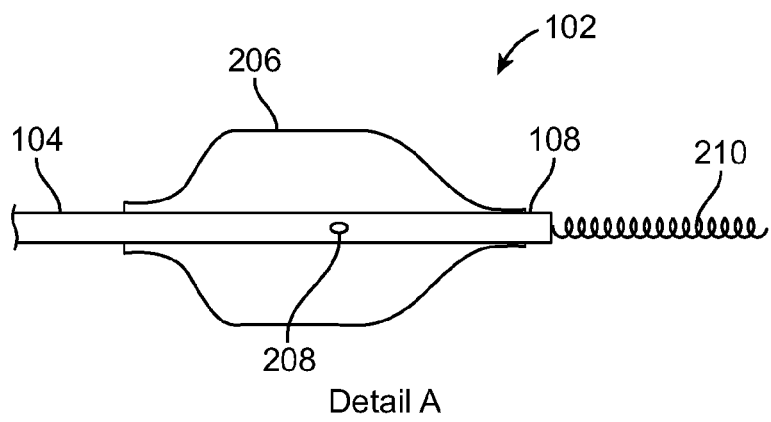

FIG. 2C is a detail view taken from Detail A of FIG. 2A of an additional implementation of an anchor 102 coupled to a tether 104 of a tethering device 100. The anchor 102 can include a balloon 206 having an outer surface containing an internal volume. The tether 104 can include a tubular structure, such as a hypotube, extending from the proximal end 106 to a distal joint 108. An inner lumen of the tether 104 can be in fluid communication with the internal volume of the balloon 206 through an inflation port 208 formed in a sidewall of the tether 104 hypotube. To facilitate tracking of the anchor 102, the distal joint 108 of the tether 104 can be connected to a soft, distal tip 210. The distal tip 210 can be a spiral wire coil or other configuration tip that is flexible and atraumatic to the anchoring anatomy.

Figure 2D:
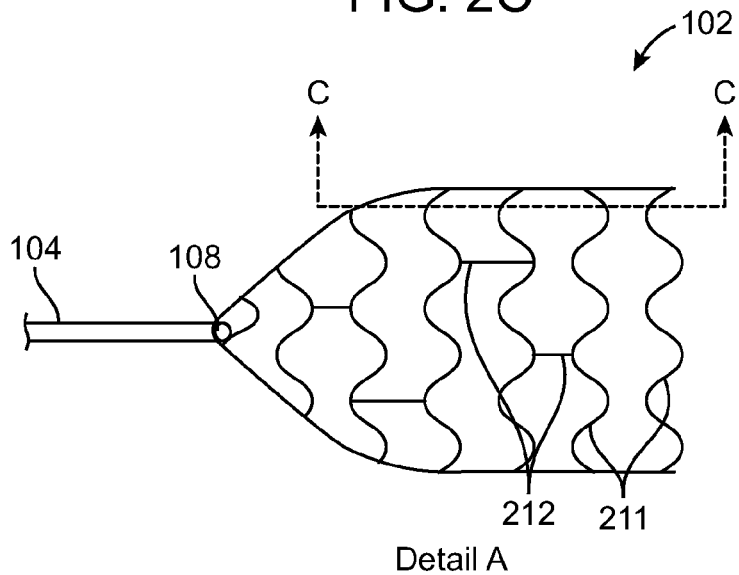

FIG. 2D is a detail view taken from Detail A of FIG. 2A of an additional implementation of an anchor 102 coupled to a tether 104 of a tethering device 100. The anchor 102 can include a self-expandable structure capable of self-expanding from a first, collapsed state to a second, expanded state. The tether 104 can connect to the anchor 102 at a distal joint 108 and an outer diameter of the anchor 102 can enlarge from the distal joint 108 towards the distal-most terminus of the anchor 102. Thus, when the self-expandable structure is expanded, an outer dimension of the structure from the distal joint 108 towards a distal-most terminus of the anchor can gradually widen to a maximum dimension. The self-expandable structure of the anchor 102 can include a sequence of anchor rings 211 disposed longitudinally relative to each other. The anchor rings 211 can be connected by one or more ring connectors 212, such that the anchor rings 211 transmit longitudinal force between each other. The self-expandable structure can have an open cell or a closed cell configuration, as is known in the art, depending on the number of ring connectors 212 used between adjacent anchor rings 211.

Figure 3:
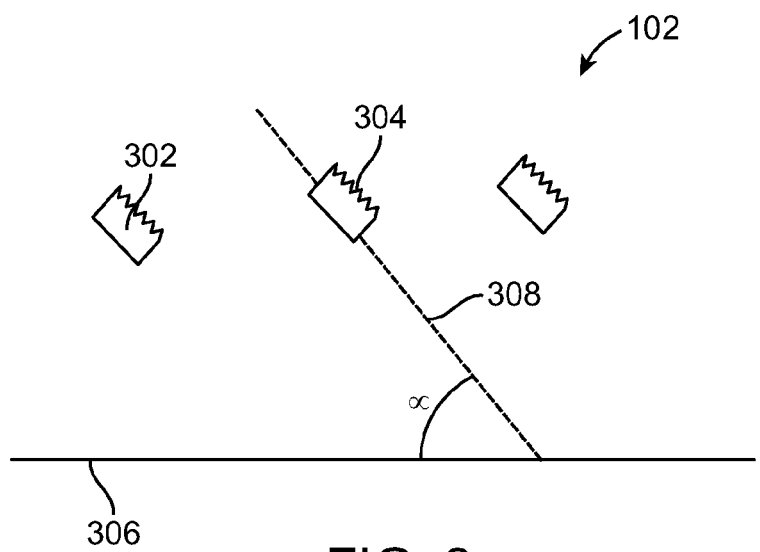
FIG. 3 illustrates a detail view of an anchor of a tethering device.

As mentioned above, the anchor 102 may have enough radial strength in the expanded configuration to grip the anchoring anatomy and resist a proximal pull on the tether 104. FIG. 3 is a detail view of an implementation of an anchor 102 of a tethering device 100 that includes one or more ribs or struts 302 making up the expandable anchor 102. The configuration of the struts 302, for example, their orientation and/or how they provide a shape to the anchor 102 as a whole, as well as by incorporating features such as barbs, hooks, cleats, surface textures, etc. can be designed such that they aid to resist longitudinal movement of the anchor 102 once engaged with the anchoring anatomy. For example, the struts 302 can be configured to resist being pulled proximally when the strut 302 is engaged with tissue. In some implementations, the strut 302 can be specifically designed to resist proximal movement within the anchoring anatomy, but may still be pushed in a distal direction through the anchoring anatomy. Thus, the anchor 102 can provide directionally biased resistance to movement within the anchoring anatomy. As shown in FIG. 3, the struts 302 can include respective strut surfaces 304, which may face generally outward relative to a longitudinal axis 306 passing through the tether 104. The struts 302 can be oriented, e.g., by design or shape setting, such that a strut plane 308 passing through the strut 302 parallel to the strut surface 304 is directed at an angle α to the longitudinal axis 306. This may be referred to as "fish scaling". More particularly, the struts 302 or the cells of the anchor 102 can bend outward during deployment such that a longitudinal plane passing through the struts 302 becomes angled relative to the longitudinal direction. For example, the angle can be proximally directed such that the strut 302 will tend to dig into a tissue at the anchoring anatomy when the anchor 102 is pulled proximally. Thus, the "fish-scaled" struts 302 can resist a proximal pull applied to the tether 104. By contrast, the angle of the strut plane 308 can allow the struts 302 to be pushed distally without the struts 302 digging into the tissue. Thus, the anchor 102 can be configured to grip the anchoring anatomy in one direction (e.g. proximally) but not in another direction (e.g. distally). "Fish-scaling" in stent design is often deemed to be undesirable for certain indications. However, "fish-scaling" of the anchor 102 in this context can be beneficial.

In addition to shaping the anchor 102 as a whole in a manner that facilitates gripping of the anchoring anatomy by the struts 302 can be individually modified to facilitate such gripping. For example, the strut surface 304 can be ribbed or roughened, e.g., by bead blasting or chemical etching, to increase friction between the tissue at the anchoring anatomy and the anchor 102. In an implementation, rather than roughening the strut surface 304 by a secondary manufacturing process, the strut surface 304 can be manufactured by a process that does not include a polishing process that is otherwise applied to the remainder of the anchor 102. For example, the anchor 102 may be electropolished during manufacturing, but strut surface 304 may be masked during the electropolishing process to avoid smoothing the strut surface 304. In another implementation, surface treatments such as applying an adhesive to the outer surface of the struts 302 (or any other structural feature of the anchor 102) can be used to permanently or temporarily bond the anchor 102 with the tissue at the anchoring anatomy. The adhesive can be activated upon contact with the tissue such that it does not cause the anchor 102 to stick to an inner surface of the tetherable guide-sheath or another catheter, e.g., a finder catheter, that the tethering device 100 is delivered through.

As mentioned above, the anchor 102 of the tethering device 100 can also be designed to enhance anchoring by providing traction due to incorporation of one or more features that protrude from the anchor 102 to anchor to the surrounding anatomy. For example, the anchor 102 can include features having a predetermined shape and size, such as one or more barbs or hooks, that protrude from the sides of the anchor 102 to imbed into surrounding vascular tissue and grip the vessel when a proximal pull force is exerted on the tether 104. These gripping features of the anchor 102, however, can be configured to collapse such that the anchor 102 can be removed from the vessel. In some implementations, the features can be configured to yield and/or collapsed when a distal tip of guide-sheath is advanced over them, as will be described in more detail below. For example, the struts 202 shown in FIG. 2B can incorporate one or more cleats or barbs on their distal ends to improve their grip within the anatomy. The cleats can protrude outward toward the vessel wall such that upon expansion or release of the struts 202 from their constrained configuration the pointed ends of the cleats engage with the vessel wall. The cleats can be configured to undergo flexure upon re-sheathing such that they can be removed from the anatomy. For example, the cleats in the unconstrained configuration can bend outward such that their pointed ends extend towards the vessel wall and/or bend back towards the proximal direction to improve engagement with the vessel wall, for example, upon proximal pull force on the tethering device. Their pointed ends can be urged away from the vessel wall during re-sheathing, for example, such that they flex back in the distal direction upon distal advancement of a sheath or tubular structure to once again constrain the struts 202 in a low profile configuration.

It should be appreciated that reference to one implementation of an anchor as having a particular feature, such as a surface treatment, anchoring feature, cleat, barb, etc., may be incorporated into any of the various anchors described herein.

Figure 4:
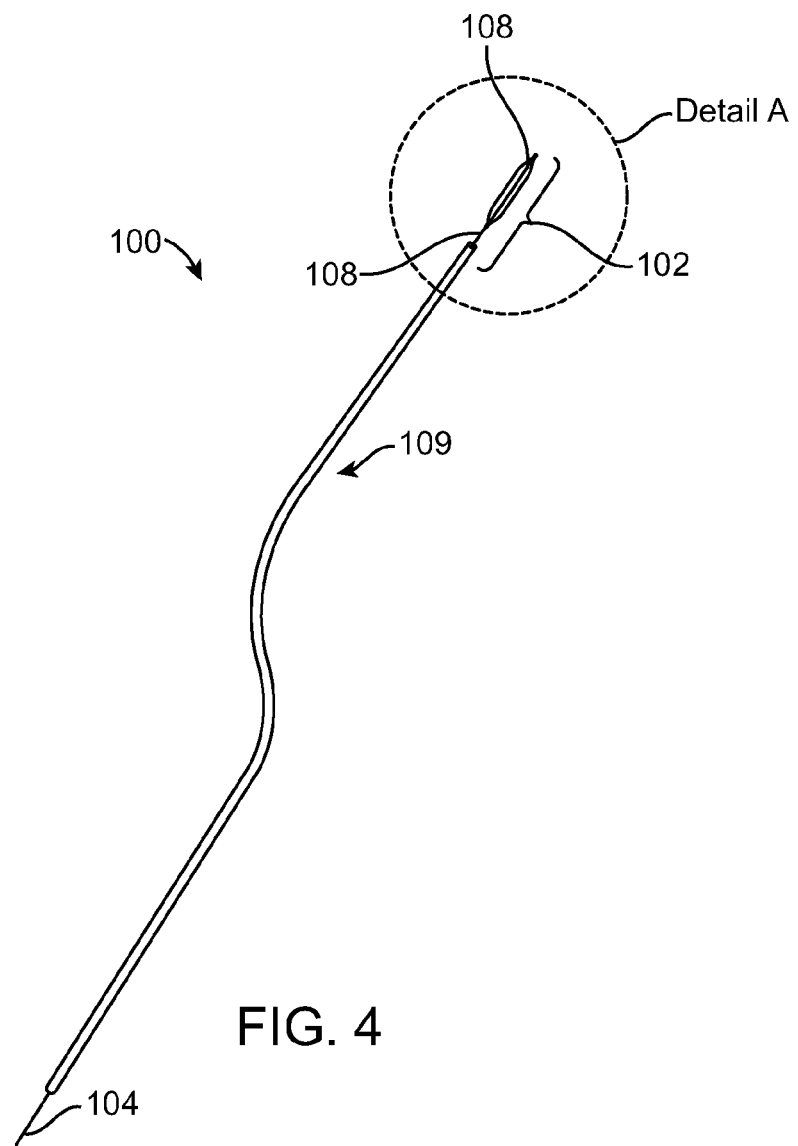
FIG. 4 illustrates a perspective view of a tethering device, in accordance with an interrelated implementation.

FIG. 4 shows a perspective view of another tethering device in accordance with an implementation having an anchor 102 physically connected to a tether 104 and further including a pusher tube 109. The tether 104 can be attached to the anchor 102 at one or more joints 108, such as a first joint 108 distal to the anchor 102 and/or a second joint 108 proximal to the anchor 102. The pusher tube 109 can slide distally and proximally relative to the tether 104, and may be removed prior to delivery of a guide-sheath over the tether 104. The tether 104 and/or pusher tube 109 can be gripped and advanced to push the anchor 102 forward for delivery to an anchoring site in a target anatomy. Similarly, the pusher tube 109 can be retracted over the tether 104 to remove the pusher tube 109 from the target anatomy, while keeping the anchor 102 and the tether 104 in place to receive a tetherable guide-sheath, as will be described in more detail below. In some implementations, the anchor 102 is collapsed or constrained inside the pusher tube 109 and the pusher tube 109 is used to provide some heft and pushability such that the pusher tube 109 is used to advance an otherwise flexible wire of the tether 104, for example through a microcatheter, finder catheter, or diagnostic catheter. The size of the pusher tube 109 can remain small enough such that a guide-sheath can be thread onto it, as will be discussed in more detail below.

Referring to FIG. 5A, a detail view, taken from Detail A of FIG. 4, of a distal portion of a tethering device is illustrated in accordance with an implementation. The anchor 102 can be configured to expand when a force is applied. The anchor 102 can include a closed-cell stent like structure, e.g., made of self-expanding material like nitinol. The anchor 102 can include a slit tube structure, for example, a structure that includes a tube made of a self-expanding material like nitinol, and having several longitudinal slits or slots that allow the tube to be expanded from an unexpanded, tubular shape, to an expanded shape. Accordingly, the anchor 102 may be set to a desired shape, for example, by a heat set process. Alternatively, the anchor 102 can be formed from spring steel, alloys, or even polymeric material. Furthermore, the tether 104 can include an anchor wire 111 extending through a runner tube 113. The anchor wire 111 can be seen in FIG. 5A although is hidden behind a middle rib 115 of the slit tube in FIG. 5D. The anchor wire 111 can connect to the anchor 102 at the distal joint 108. Similarly, the runner tube 113 may be connected to the anchor 102 at the proximal joint 108. Thus, a withdrawal or pulling load applied to the anchor wire 111 can lead to compression of the anchor 102 between the distal joint 108 and the proximal joint 108. The compression may cause outward bowing and expansion of the ribs 115 of the anchor 102. Accordingly, when actuated within an anchoring vessel, the anchor 102 may secure the tethering device 100 within the target anatomy.

Figure 5B:
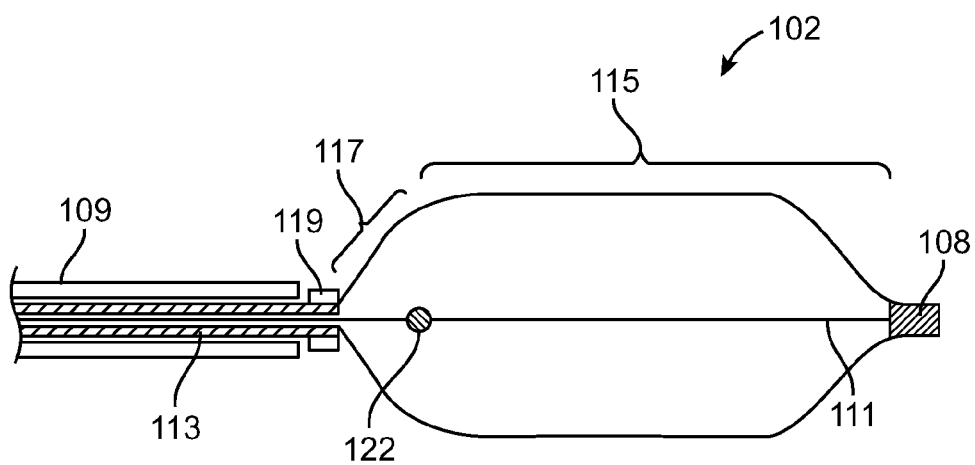
FIG. 5B illustrates a sectional view, taken about line A-A of FIG. 5A, of a distal portion of a tethering device.

FIG. 5B is a sectional view of FIG. 5A taken about line A-A, of a distal portion of the tethering device 100 shown in FIG. 4. The anchor 102 can be a self-expanding structure having one or more rib segments 115 interconnected with one or more spreader segments 117. The anchor 102 can also include a slit tube structure having one or more rib segments 115 extending longitudinally between a proximal joint 108 and a distal joint 108 as shown in FIGS. 5D-5G. Each rib segment 115 can have a distal end attached to the distal joint 108 and a proximal end attached to a distal end of a corresponding spreader segment 117. Similarly, each spreader segment 117 can have a proximal end connected to the proximal joint 108 of the anchor 102. In an implementation, the proximal joint 108 includes a tether collar 119, such as a band that is swaged, glued, or otherwise affixed to one or more of the anchor 102 or the runner tube 113 of the tether 104.

Still with respect to FIGS. 5A-5B, the anchor wire 111 can include a rigid member designed to transmit longitudinal force to the distal joint 108. Thus, the anchor wire 111 can be fixed to the distal joint 108, and can impart an expansion force to the anchor 102 when pulled. More particularly, when a compressive load is applied to the anchor 102 between the distal joint 108 and the tether collar 119, the rib segments 115 may tend to bow outward, and the spreader segments 117 may maintain a lateral separation between the proximal ends of the rib segments 115 and the anchor wire 111. Accordingly, the anchor 102 may expand from an unexpanded state, e.g. a tubular shape, to an expanded state, e.g. a bulbous shape. The anchor wire 111 may have an outer diameter of 0.006 inch, the runner tube 113 may have an outer diameter of 0.011 inch, and the pusher tube 109 may have an outer diameter of 0.020 inch. The wall thicknesses of the runner tube 113 and the pusher tube 109 may be minimized for their respective materials, which may be a medically acceptable material such as nitinol or stainless steel.

Figure 5C:
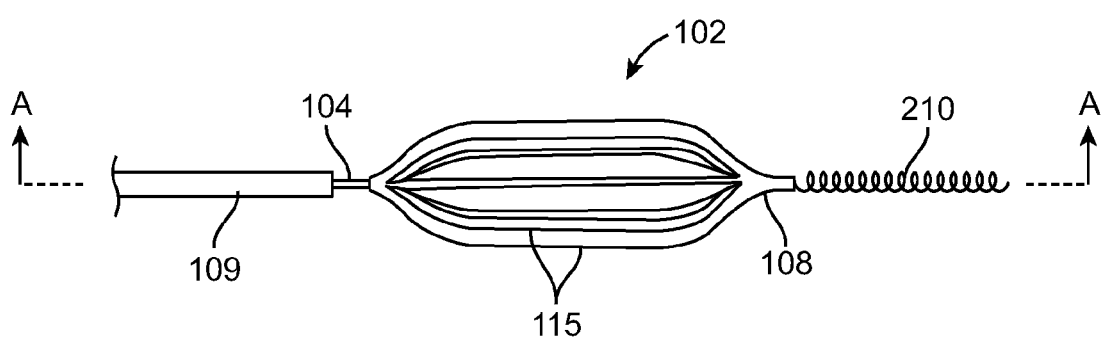
FIG. 5C illustrates a detail view, taken from Detail A of FIG. 4, of a distal portion of a tethering device.

FIG. 5C is a detail view of a distal portion of a tethering device. As with other implementations, the anchor 102 can be configured to self-expand and/or expand when a force is applied to it. The anchor 102 can include a slit tube structure, for example a tube made of a self-expanding material like nitinol, and the tube can include several longitudinal slits or slots that allow the tube to be expanded from an unexpanded, tubular shape, to an expanded shape as shown. Accordingly, the slit tube structure can be set to a desired shape, for example the illustrated expanded shape, by a heat set process. Alternatively the anchor can be formed from spring steel, alloys, or polymeric materials as described elsewhere herein. The tether 104 can include an anchor wire 111 (hidden behind a middle rib of the slit tube structure in FIG. 5C) extending through a runner tube 113. The anchor wire 111 can connect to the anchor 102 at the distal joint 108. Similarly, the runner tube 113 can connect to the anchor 102 at the proximal joint 108. Thus, a withdrawal or pulling load applied to the anchor wire 111 can lead to compression of the anchor 102 between the distal joint 108 and the proximal joint 108. The compression can cause outward bowing and expansion of the ribs 115 of the anchor 102. Accordingly, when actuated within the anchoring vessel, the anchor 102 can secure the tethering device 100 within the target anatomy.

Figure 5D:
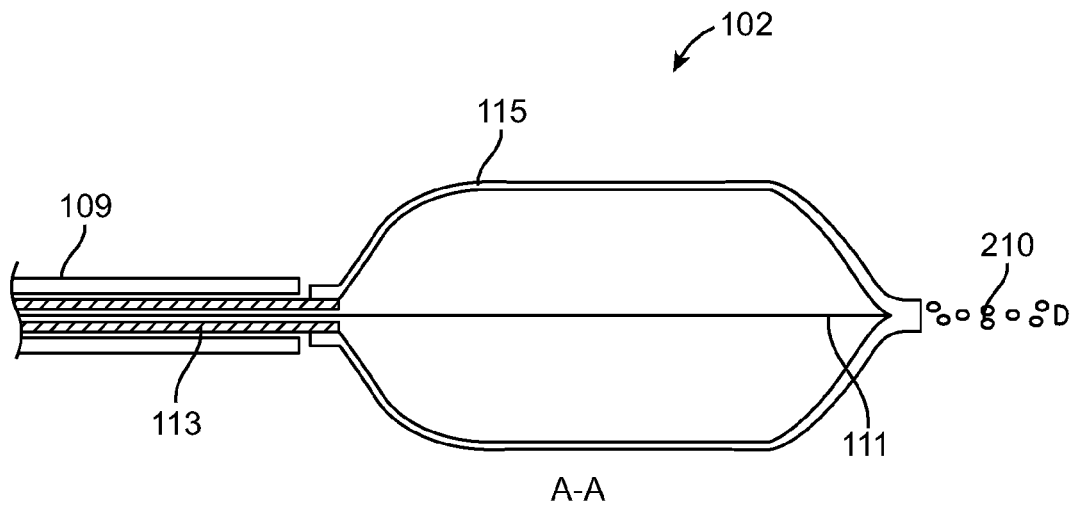
FIG. 5D illustrates a sectional view, taken about line A-A of FIG. 5C, of a distal portion of a tethering device.

FIG. 5D is a sectional view taken about line A-A of FIG. 5C of a distal portion of a tethering device. The anchor 102 can be a slit tube structure having one or more rib segments extending longitudinally between the proximal joint 108 and the distal point 108. Each rib segment 115 may have a distal end attached to the distal joint 108 and a proximal end attached to the proximal joint 108. In an implementation, the proximal joint 108 includes a tether collar 119, such as a band that is swaged, glued, or otherwise affixed to one or more of the anchor 102 or the runner tube 113 of the tether 104. The distal end of the anchor 102 in any of the various implementations described herein can include an atraumatic distal tip 210 (see FIGS. 5C-5E).

Figure 5E:
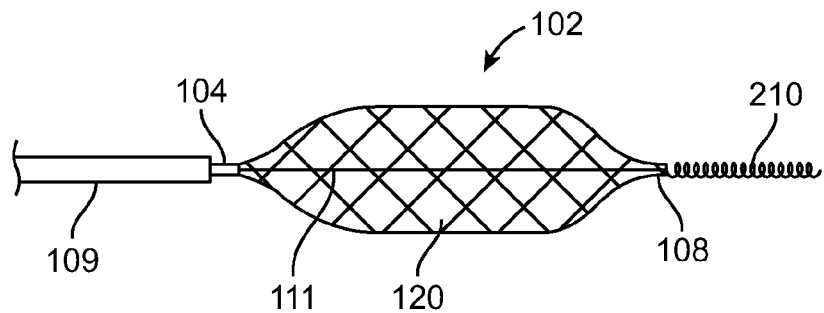
FIG. 5E illustrates a detail view, taken from Detail A of FIG. 4, of a distal portion of a tethering device.

FIG. 5E illustrates an interrelated implementation in which the anchor 102 includes a braid or overlapping wire structure. The anchor 102 can include a braided mesh 120 made of self-expanding material such as nitinol such that the mesh structure can be set to a desired shape by, for example, a heat set process. As with other implementations, the tether 104 can include an anchor wire 111 extending through a runner tube 113 such that a withdrawal or pulling load applied to the anchor wire 111 can lead to compression of the anchor 102 between the distal joint 108 and the proximal joint 108. The compression can cause outward bowing and expansion of the braided mesh 120 to secure the tethering device in the target anatomy.

The runner tube 113 can be large enough to provide a slip fit with the anchor wire 111, such that the anchor wire 111 is able to easily slide along an entire length of the runner tube 113. Nonetheless, the runner tube 113 may be small enough to minimize a diameter of a tether lumen in the guide-sheath, as will be described below. The runner tube 113 can be fixed to the proximal joint 108 of the anchor 102, and can be longer than a distance between the anchoring site and an exit port in the tetherable guide-sheath, but shorter than an overall length of the anchor wire 111 and the anchor lengths. Accordingly, the anchor wire 111 can exit a proximal end of the runner tube 113. The runner tube 113 can have a similar length to the pusher tube 109, or the runner tube 113 can be shorter than the pusher tube 109, for example, to minimize an overall length of the anchoring delivery system 10.

The pusher tube 109 can be large enough to provide a slip fit with the runner tube 113, such that the runner tube 113 is able to easily slide along a length of the pusher tube 109. The pusher tube 109, however, may be small enough to abut the tether collar 119 or a proximal end of the anchor 102. Accordingly, the pusher tube 109 can be pressed forward (and/or the anchor 102 withdrawn) such that a distal face of the pusher tube 109 presses against the tether collar 119 (or proximal end of the anchor 102) to exert a forward load on the anchor 102. The pusher tube 109 can be longer than an overall length of a delivery catheter, which may typically be 100 cm in length. Accordingly, the pusher tube 109 can be grasped and pulled back after delivery of the anchor 102 to the anchoring site to remove the pusher tube 109 from the anchor 102, the tether 104 and the patient anatomy.

Figure 5F:
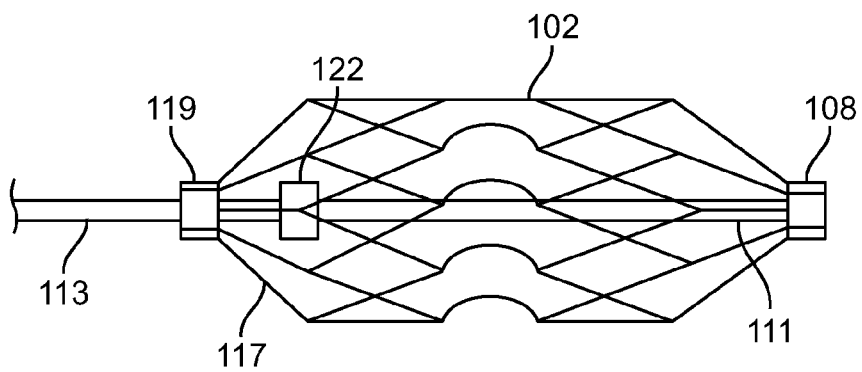
FIG. 5F illustrates a detail view, taken from Detail A of FIG. 4, of a distal portion of a tethering device.
Figure 5G:
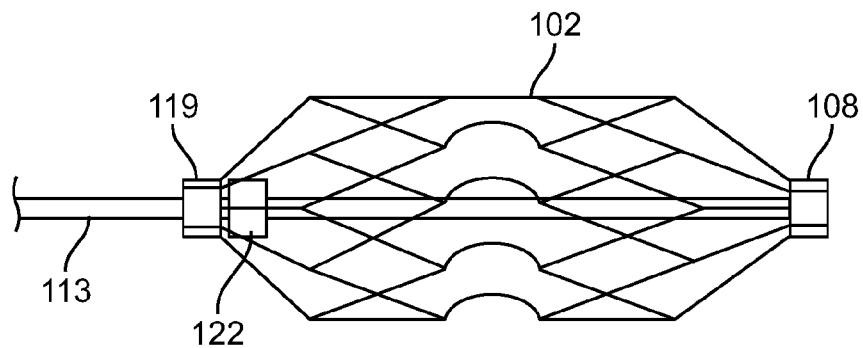
FIG. 5G illustrates the tethering device of FIG. 5F after further expansion of the anchor.

FIGS. 5F-5G illustrate a distal portion of an implementation of the tethering device 100. As previously described, a distal end of an elongated member such as the anchor wire 111 may be connected to a distal end of the anchor 102 at a distal joint 108. The connection can be either permanent or temporary, e.g., like the transition described above. For example, the anchor wire 111 can be threaded into the distal joint 108 of the anchor 102 such that it may be rotated to detach from the anchor 102. The anchor wire 111 can also be connected permanently to the anchor 102 such as by soldering, welding, gluing, crimping or other fasteners. The anchor 102 can be preloaded into a pusher tube 109 or constricting sheath. The anchor 102 can be loaded during the procedure into a catheter, which might have already been placed into the vasculature of a patient. The distal attachment point or joint 108 between the anchor wire 111 allows the push force to be transmitted to the distal portion of the anchor 102 such that the anchor 102 can be "pulled" into the pusher tube 109, which can significantly simplify loading. When the anchor 102 is constricted by the pusher tube 109, or is inside a catheter, the distal end of the pusher tube 109 or the distal end of the catheter can be positioned at the location where the anchor 102 is to be deployed. During deployment, the pusher tube 109 or the catheter can remain stable and the anchor 102 can be pushed out, e.g. by applying a distal load to the runner tube 113. After the distal part of the anchor 102 is in contact with an inner surface of the anchoring anatomy, the pusher tube 109 may be pulled back to allow the anchor 102 to expand into contact with the anchoring anatomy. In some implementations, the anchor 102 has a closed cell structure and the anchoring structure will be constricted in its diameter as long as the anchor 102 is not fully released. This feature can significantly simplify the release of the anchor 102 into the target anatomy.

As best shown in FIGS. 5F and 5G, the tethering device 100 can include a stopper 122 attached to the anchor wire 111. The stopper 122 can limit an amount of expansion of the anchor 102. For example, when the anchor wire 111 is pulled back within the runner tube 113, the stopper 122 may eventually contact a proximal end of the anchor 102 and/or the tether collar 119, to prevent additional bowing of the rib segments 115. At that point, the anchor 102 can grip the anchoring vessel with sufficient friction to resist being pulled proximally by the tether 104. Accordingly, the expansion of the anchor 102 may stop. A distance between the stopper 122 and the proximal end of the anchor 102 can define the maximum expansion dimension of the anchor 102. Furthermore, the distance can correlate with a radial force applied to the anchoring anatomy by the anchor 102. Thus, the stopper 122 can be located to tune the radial force and the corresponding fictional force applied to the tissue by the anchor 102. More particularly, the anchor 102 can be configured to apply sufficient frictional force to the tissue to resist a pull force applied by an operator to the tether 104, or a reaction load applied to the tether 104 by a working device being advanced to a target anatomy, as described below.

The anchors described herein are designed to stay fixed in a vessel when deployed, but may slide through a catheter for delivery to the anchoring site by pushing on the tether 104 and/or pusher tube 109 of the system. Additionally, the anchor 102 may be withdrawn into a capturing element, such as a tetherable guide-sheath 400, a micro catheter, etc., for removal from the anatomy. Accordingly, pulling the anchor 102 into the capturing element may retract and collapse the expandable structure rather than expand the expandable structure. Furthermore, the elongated section of the tethering device 100, i.e., the combination of the tether 104 and the pusher tube 109, may be larger during delivery of the anchor 102 to the anchoring site than after delivery. More particularly, after delivering the anchor 102, the pusher tube 109 may be removed from the anatomy to make the remaining portion of the elongated section, i.e., the tether 104, as thin as possible such that the tetherable guide-sheath may be advanced over the tether 104 and fixed to the tether 104 while maintaining a sufficiently large working lumen to advance a working device through the tetherable guide-sheath to a target vessel.

The anchors described herein can include a structure configured to anchor within an anchoring vessel that relies upon apposition of a plurality of struts or rings with the underlying vessel. The anchors described herein can also include a structure configured to anchor within an anchoring vessel without relying upon apposition. For example, the anchors can incorporate a coiled wire having one or more loops configured to be constrained to a straighter, low profile configuration during delivery and upon release of the constraint take on a higher profile configuration that is helical, spiral, twisted, bent, curved, or double-curved etc. such that the anchor anchors within the vessel, for example, as shown in FIGS. 5H-5L, and as will be described in more detail below.

Figure 5H:
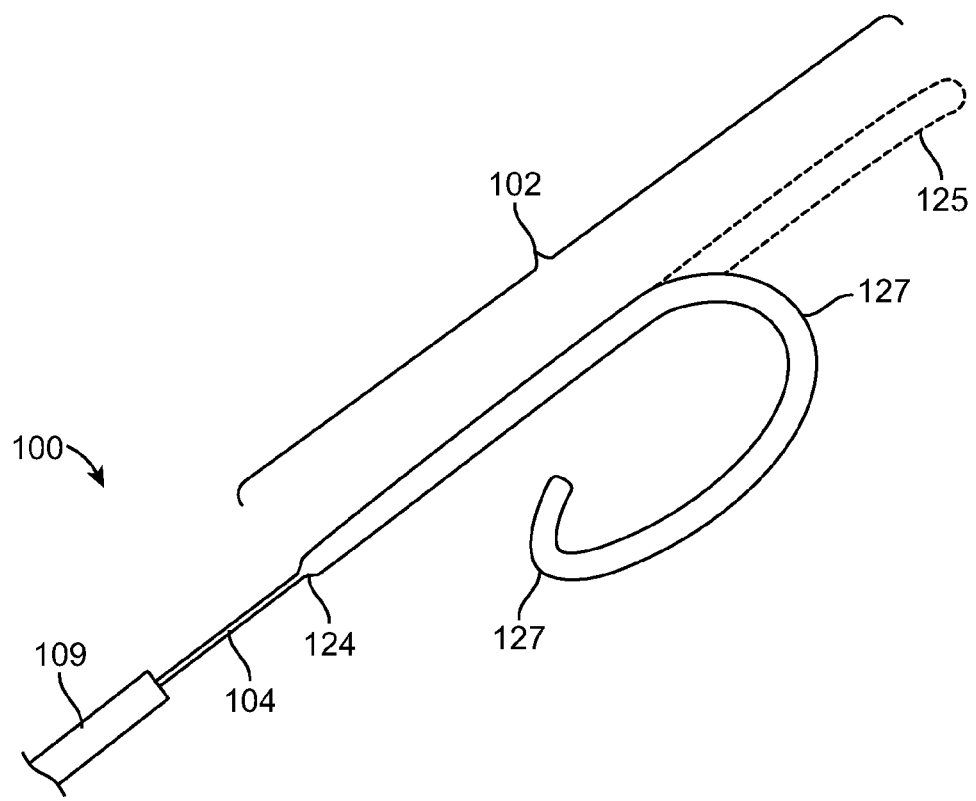
FIG. 5H illustrates a detail view, taken from Detail A of FIG. 4, of a distal portion of a tethering device, in accordance with an interrelated implementation.

FIG. 5H shows a detail view of a distal portion of a tethering device in accordance with an implementation. The tethering device 100 can include an anchor 102 configured to deform or distort the vessel as opposed to vessel apposition devices, such as a stent-type anchor, which rely upon high radial force. Such anchors provide excellent holding force even if deployed in straight vessels. The anchor 102 provides simplicity in manufacture, deliverability, anchoring even in relatively straight vessels, and speed of execution that is appealing from a clinical standpoint. The tethering device 100 can include an anchor 102 having a shape memory wire that passively changes (e.g. self-expands) from a smaller profile configuration to a larger profile configuration. The tethering device 100 including the anchor 102 can be configured to be inserted into a vessel through a diagnostic catheter that accepts 0.038-inch (0.97 mm) guide wires. As such, the anchor 102 may include a wire segment, e.g., a segment of wire having a diameter of, e.g., 0.038-inch, that is formed from a shape memory wire, e.g., nitinol wire. The shape memory wire may be pre-formed into a heat set shape having one or more primary and/or secondary curves, bends, coils, or turns. The shape memory wire can include a heat set shape that includes, but is not limited to, a J-shape, a hook-shape or other profile having one or more bends, curves, coils, etc. Furthermore, the shape memory wire may be elastically deflected into a substantially straightened or elongated shape for delivery through a lumen of a catheter. Thus, the anchor 102 may be delivered in the smaller profile configuration when the shape memory wire is straightened (as shown by dotted lines 125 in FIG. 5H), and the anchor 102 may change into the larger profile configuration when the wire returns towards the pre-set hook-shape 127 within the anchoring vessel. When the anchor 102 returns towards the resting shape inside the vessel, the vessel itself can undergo an amount of distortion and in turn engage the anatomy surrounding the vessel. Thus, the vessel distortion and resistance provided by the anatomy adjacent the vessel can contribute to the level of holding force provided by the anchor 102 upon deployment in the anchoring vessel, as is described in more detail below.

Figure 5I:
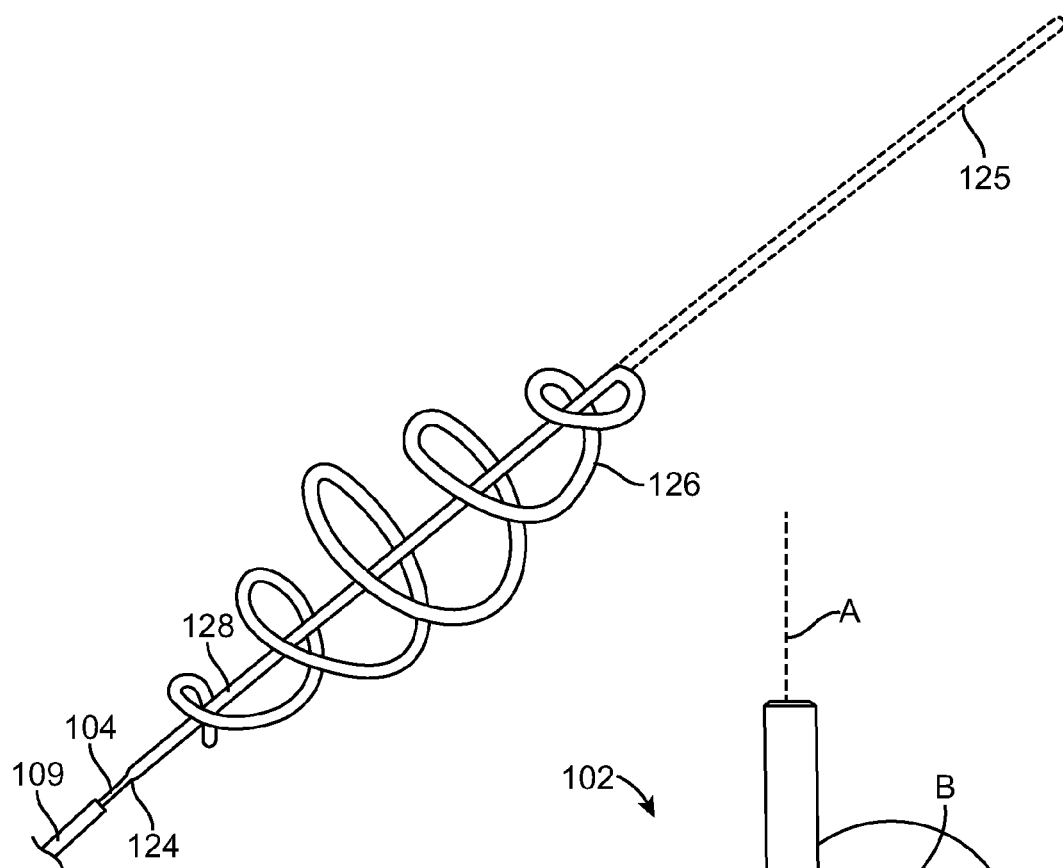
FIG. 5I illustrates a detail view, taken from Detail A of FIG. 4, of a distal portion of a tethering device, in accordance with an interrelated implementation.

FIG. 5I, a detail view of a distal portion of a tethering device, is shown in accordance with an implementation. As described above, the tethering device 100 having a self-expanding shape memory wire design may include a pre-formed shape that incorporates one or more loops or coils 126. More particularly, the anchor 102 can include a coil 126 having one or more turns about an axis. For example, a longitudinal segment 128 of the anchor 102 may be along the central axis and the turn(s) of the coil segment 126 may extend proximally from a distal end of the longitudinal segment 128 toward a proximal end of the longitudinal segment 128. The proximal end of the longitudinal segment 128 may, for example, be at the transition point 124 between the anchor 102 and the anchor wire 111. The coil 126 can be a single loop, 1.5 loop, or a 2 loop anchor 102. Each loop of the coil 126 can be a 6 mm loop.

Figure 5J:
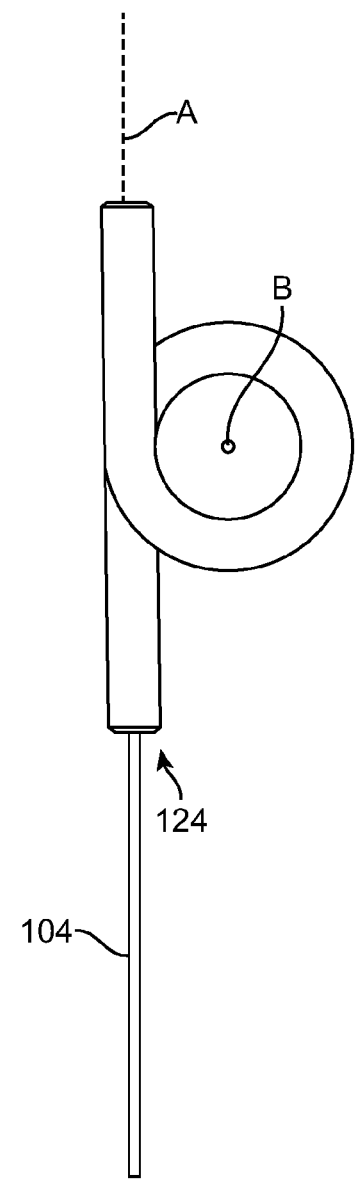
FIGS. 5J-5L illustrate detail views, taken from Detail A of FIG. 4, of a distal portion of a tethering device, in accordance with an interrelated implementation.
Figures 5K, 5L:
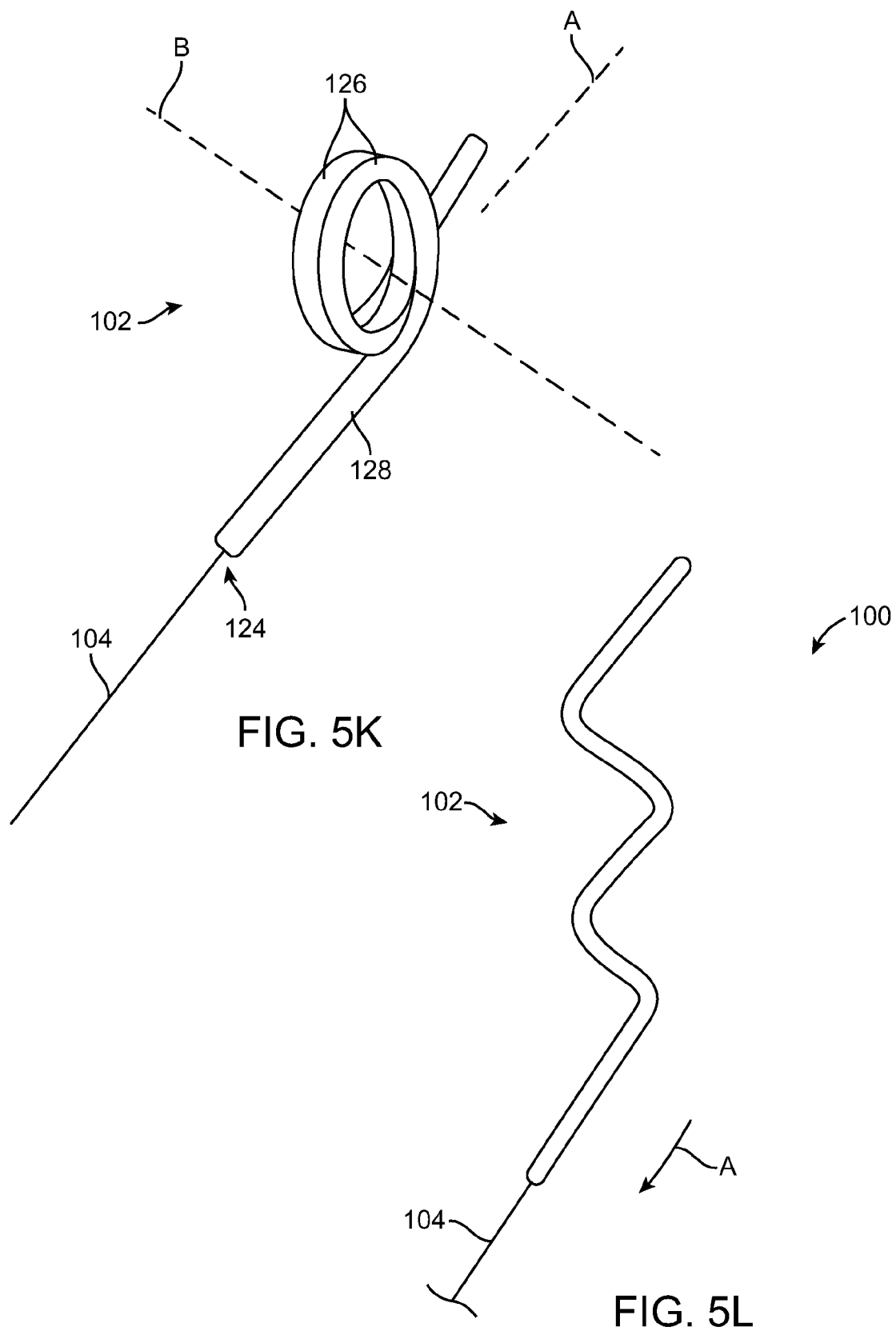

The coil segment 126 may extend out of plane with a direction of insertion or in plane with a direction of insertion. FIGS. 5J-5L show another implementation of an anchor 102 formed by an extension spring configured to coil in plane with a direction of insertion. The longitudinal segment 128 of the anchor 102 can be along the central axis A. The coil(s) 126 can loop back toward a proximal end of the longitudinal segment 128 and then back toward a distal end of the longitudinal segment 128. Rather than the coil(s) 126 being about the central axis A, the coil(s) 126 can loop around an axis B that is at an angle to, such as perpendicular or orthogonal to, the central axis A forming a pigtail type coil or spiral wire. The coils 126 in a resting state, unconstrained by either a tubular element or vessel (i.e. in the air), can touch each other or align side-by-side (see FIG. 5K). During delivery towards a vessel, the coils 126 are constrained in a substantially straightened configuration, for example, within a tubular delivery element. Withdrawal of the tubular delivery element in a proximal direction (arrow A in FIG. 5L), unsheathes the coils 126 and deploys the anchor 102 in the vessel. When deployed within a vessel, the coils 126 take on a helical, semi-helical, curved, or "wiggle" shape that can distort the vessel and fix the anchor 102 to the deployed location. As described above, the return of the coils 126 towards this shape following removal of a straightening constraint (e.g. lumen of a finder catheter through which the anchor 102 is delivered) can distort the vessel from its natural path to a path that is dictated in part by the shape the coils 126 take on upon unsheathing. For example, FIG. 5M illustrates an anchoring vessel 1904 following its natural path within the cerebral anatomy. FIG. 5N illustrates a tethering device 100 deployed within the anchoring vessel 1904 where the anchor 102 of the tethering device 100 is a stent-like vessel apposition device. The anchoring vessel 1904 generally maintains its natural path and anchoring is provided by the apposition of the anchor 102 against the vessel wall with or without the presence of additional barbs or cleats or other feature to improve fixation of the anchor 102. FIG. 5O illustrates another implementation of a tethering device 100 deployed within the anchoring vessel 1904. In this implementation, the anchor 102 takes on a substantially helical shape within the anchoring vessel 1904, which in turn, causes the anchoring vessel 1904 to distort away from its natural path and instead follow the directional turns of the anchor 102. In this implementation, engagement between the distorted vessel 1904 and the tissues of the adjacent anatomy assist in the holding force provided by the anchor 102. The distortion within the surrounding tissue allows the resistance of the surrounding tissue to these distortions to increase the hold of the anchor 102 such that the anchor 102 now engages an entire "block" of tissue rather than just the vessel wall. The holding force provided can be sufficient to prevent the anchor 102 from being dislodged from the anchoring vessel 1904 upon application of a pulling force on the tether 104 in a proximal direction even when tightly drawn and coupled to the proximal end of the guiding sheath 400 such that advancement of a working device causes a downward pulling force on the sheath 400.

The wire composition and size, as well as the coil diameter, the number of coils, and the amount of expected external force on the anchor 102 can all be considered in the design of the anchor 102. FIG. 5K shows two coil segments 126 to the anchor 102, however, the anchor 102 can include one, two, three, four, five, six, or more coil segments 126. The diameter of the coils 126 can vary depending on the vessel within which the anchor device is intended to be used. The diameter of the coils 126 can affect the holding force as the smaller the coil loop, generally the stiffer the anchor.

The tethering device 100 can include the tether 104 extending proximally from the anchor 102. In an implementation, the tether 104 may have a smaller diameter than the shape memory wire used to form the anchor 102. In some implementations, the tether 104 can be formed from a shape memory wire having a diameter between about 0.005-inch to about 0.014-inch, e.g., 0.006-inch, 0.007 inch, 0.008 inch, or 0.009-inch up to 0.016-inch. In other implementations, the tether 104 can have a diameter from about 0.005 inches to 0.025 inches, e.g., 0.008 inches, or 0.009 inches, or 0.010 inches, or 0.035 inches, depending on the degree of support that the tether 104 provides. The tether 104 can be a solid wire rod, a ribbon, or a hypotube. In some implementations, the tether 104 can be a stainless steel rod, ribbon or hypotube. In other implementations, the tether 104 can be Drawn Filled Tubing (DFT) with a radiopaque core, such as an outer sheath of a composite to provide strength and a core material to provide superelasticity, conductivity, radiopacity, resiliency, etc. In some implementations, the tether 104 can be DFT of Nickel titanium with a radiopaque core such as platinum or tantalum.

Figure 5P:
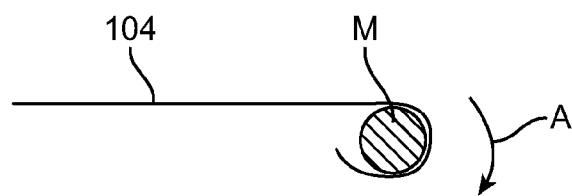
FIGS. 5P-5R illustrate schematic views of a method of manufacturing an anchor of a tethering device, in accordance with an implementation.
Figure 5Q:
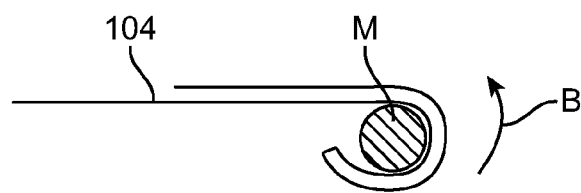
Figure 5R:
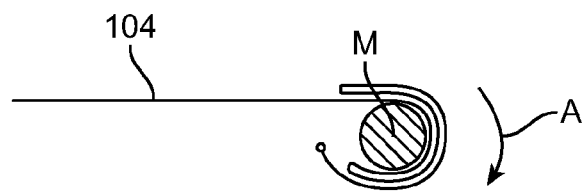

The tether 104 may be integrally formed with the anchor 102, e.g., the anchor 102 and the tether 104 may be segments of a same wire. Alternatively, the anchor 102 and the tether 104 may be different wires that are connected at a transition point 124 via a mechanical, adhesive, or welded bond. In some implementations, the wire of the tether 104 is integral with the wire of the anchor 102 and the anchor 102 created by coiling over a mandrel and/or via grinding. For example, in some implementations the anchor 102 can be formed by winding the wire around a shaft such as a mandrel. The ends of the anchor 102 can be bent into a desired shape, whether that is straight or otherwise looped, hooked, or bent. The anchor 102 can be formed by cold winding or hot winding and then hardened to relieve stress and allow resilience in the spring. The anchor 102 can be formed by coiling a length of wire around a mandrel M in a first direction (arrow A in FIG. 5P) and doubling back around the mandrel M in a second opposition direction (arrow B in FIG. 5Q) to create a first overlap section. More overlap sections can be created by once again coiling the wire about the mandrel M in the first direction (arrow A in FIG. 5R) until a coil having a particular holding strength is formed. More coils can be formed in the length of wire in a similar manner until an anchor 102 is formed having the desired number of coils having a desired overall diameter and a desired holding force. The anchor 102 can also be formed by grinding a round or flat wire using a coiling lathe to create single diameter coils or tapered coils. The anchor 102 can be formed of a plurality of materials including a core wire and an external coil laser welded to the core wire. The anchor 102 can be formed of stainless steel wire, nitinol wire, drawn filled tube (DFT) with a radiopaque core, hypotube.

One skilled in the art will appreciate that a shape memory wire may be pre-formed to have numerous larger profile configuration shapes. For example, the coil segment 126 of the anchor 102 may extend distally from the longitudinal segment 128 of the anchor 102 with turns having increasing diameters such that a conical coil shape is formed. Alternatively, the turn diameters may increase and decrease in a longitudinal direction of the coil segment 126 such that a barbell shaped coil segment is formed. Still further, the coil segments 126 may each have a diameter that are substantially the same and sized to engage the vessel within which the anchor 102 is implanted upon release from the catheter lumen. Thus, the anchor 102 may include a shape memory wire segment that may be deformed or deflected to the smaller profile configuration and then released into a heat set shape of the larger profile configuration to create friction against a vessel wall. The larger profile configuration of the anchor 102 may be wider in a transverse dimension than the smaller profile, and thus, the anchor 102 may press against a vessel wall to anchor the tethering device 100 when it emerges from the lumen of the catheter.

FIGS. 5S-5U illustrate various implementations of a distal end of a tethering device 100. The anchor 102 can include one or more shock absorber regions 123 and one or more anchoring loop regions 129. FIG. 5S illustrates an anchor 102 having a wire coiled into a distal shock absorber region 123 adjacent a central anchoring loop region 129 whereas FIG. 5T illustrates a distal anchoring loop region 129 having a floppy J-tip 131. FIG. 5U illustrates an anchor 102 having a wire coiled into a distal anchoring loop region 129 and a proximal anchoring loop region 129 interspersed with a first shock absorber region 123 and a second shock absorber region 123, thus creating two sets of anchoring loops 129 and two sets of absorbent loops 123.

The anchor 102, with or without additional barbed or cleat elements, can embed within the wall of the vessel and optionally can cause the vessel within which it is deployed to undergo a degree of distortion, particularly if a proximal tugging force is applied on the tether 104. Thus, the friction between the anchor 102 and the vessel aids in the retention of the tethering device in the vessel as does the distortion of the vessel within which the tethering device is anchored, and optionally engagement between barbs of the anchor and the vessel. The vessel can deform into a single or double curve under the distortion force of the anchors 102 described herein further improving their anchoring function while maintaining flow through the anchor 102 with little disturbances due to the presence of the anchor 102. Thus, a combination of forces provides an anchoring function. The combination of proficient anchoring for the delivery of implant delivery systems and maintenance of blood flow in and around the anchor are beneficial to successful interventions within the neurovasculature and consistent access catheter delivery to the skull base.

It should be appreciated that the anchor itself need not embed within the wall of the vessel due to a shape change upon deployment. In some implementations, the anchor 102 is deployed in a more superficial anatomic location, such as within a facial artery, that allows for fixation of the anchor 102 from outside the body anatomy. For example, the tethering device 100 can include a proximal tether 104 and a distal anchor 102 deployed within a superficial vessel. The distal anchor 102 can be fastened within the superficial vessel by magnetic attraction between the distal anchor 102, formed of a magnetic material such as stainless or incorporating magnetic elements, and one or more magnets placed on a skin surface near the superficial vessel, such as on the cheek or the neck near the ear. In other implementations, at least a portion of the anchor 102 can be externalized and clamped outside the body.

It should be appreciated that various anchor implementations are described herein and the term anchor is used generally herein to refer to an element used for anchoring of the tethering device within a target anatomy. Anchors can include any of a variety of configurations as described herein including, but not limited to self-expanding or non-self-expanding devices, braids, mesh, wires, stents, coils, or other particular implementation described herein. Any of a variety of combinations of features of the anchors are considered herein. Further, although a particular anchor implementation may be shown in a particular figure for purposes of illustration, it is not intended to be limiting or to suggest that the anchor implementation shown would be the only anchor implementation useful for that particular feature.

The deployment of the various anchoring devices described herein will now be described. It should be appreciated that the anchor shown in the figure is represented in schematic for illustration purposes only to represent a change from a low profile configuration to a higher profile configuration. The actual configuration of the anchor can vary as described herein.

Figure 6A:
FIGS. 6A-6B illustrate schematic views of a tethering device deployment, in accordance with an implementation.
Figure 6B:
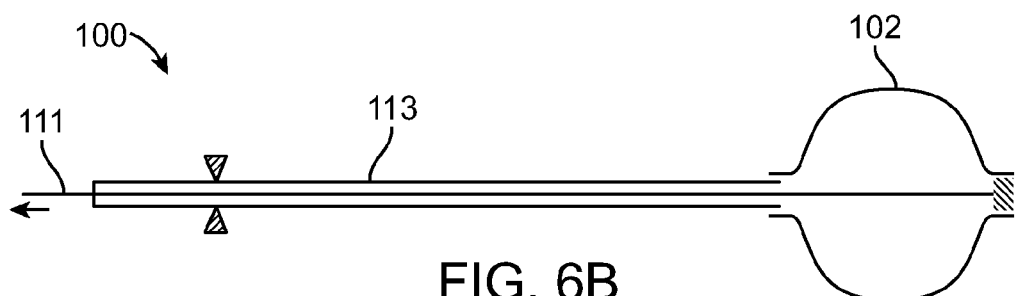

Referring to FIGS. 6A-6B, a schematic view of a tethering device deployment is illustrated in accordance with an implementation. The tethering device 100 can include a distal anchor 102, a proximal tether 104 having an inner anchor wire 111 and an outer runner tube 113. When deploying the tethering device 100, the operator may fix the runner tube 113 in place and adjust the placement of the anchor 102 in the vessel. The anchor 102 can be expanded and the anchoring can be tested by pulling the anchor wire 111 relative to the runner tube 113 and then fixing the two in relative position to each other (see FIG. 6B). The tethering device 100 can be adjustable, for example, if there is slip or an "extreme" moment during the procedure extra anchoring can be transiently applied to the anchoring vessel and released when the distension applied to the vessel is not desired. The expansion applied by pulling the anchor wire 111 can be in addition to expansion provided by self-expansion of the anchor 102 to a preformed expanded shape, for example as shown in FIGS. 2B-2D or FIGS. 5A-5B. If the runner tube 113 and anchor wire 111 interaction provides some friction the expansion of the anchor 102 can be retained from the friction between the two systems. It can provide anchoring that allows the deployment of the guide-sheath over the tether 104, i.e., the runner tube 113/anchor wire 111 combination, as will be described in more detail below.

Figure 7A:
FIGS. 7A-7B illustrate schematic views of a tethering device deployment, in accordance with an implementation.
Figure 7B:
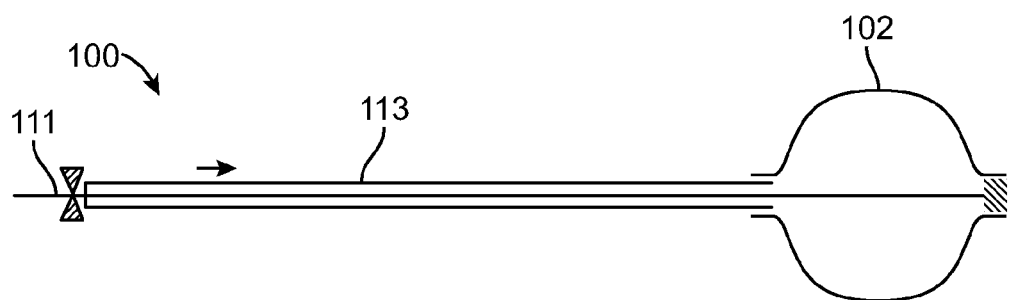

Referring to FIG. 7A, a schematic view of a tethering device deployment is illustrated in accordance with an implementation. Once tetherable guide-sheath 400 is positioned, another adjustment of the runner tube 113 relative to the anchor wire 111 can be done, and then the anchor wire 111 can be locked in place relative to the tetherable guide-sheath 400. Referring to FIG. 7B, a schematic view of a tethering device deployment is illustrated in accordance with an implementation. In an implementation, when the fixation point is applied to the anchor wire 111, downward forces on the tetherable guide-sheath will transmit directly to the anchor wire 111 and in return will expand the anchor 102 as the distal tip is pulled downward with downward force—further anchoring the system in response to downward force. It is expected that during the procedure, as long as the anchor wire 111 fixation relative to the tetherable guide-sheath 400 is constant, the anchor 102 will expand and anchor in accordance with the forces that are transmitted downward on the tetherable guide-sheath 400. Increasing or decreasing "baseline anchoring" can be dialed into the system in accordance with operator preferences and the needs of the procedure. The baseline anchoring may also be applied by self-expansion of the anchor 102 to a preformed expanded shape as shown in FIGS. 5D-5F.

Figure 8A:
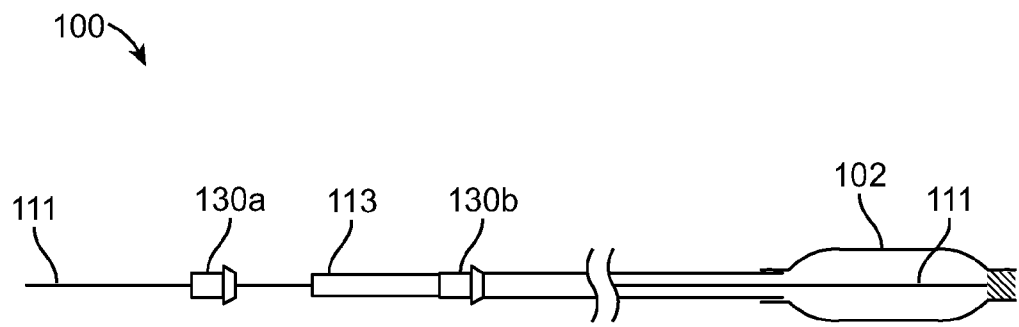
FIG. 8A illustrates a schematic view of a tethering device in an unexpanded state, in accordance with an implementation.

Referring to FIG. 8A, a schematic view of a tethering device in an unexpanded state is illustrated in accordance with an implementation. Taking this to a more mechanical level, one or more locking elements 130 may be used to "open and close" the anchor 102 at different diameters (and corresponding tensions against the vessel wall). The anchor 102 is shown in a low-profile configuration with the anchor 102 cut away so that the anchor wire 111 traversing the entire length of the assembly is visible within the anchor 102 and exiting the proximal end of the runner tube 113. Specialized locking elements 130 can be applied individually to the portions of the anchor wire 111 and the runner tube 113 that are exposed, e.g., that are situated outside of a patient anatomy and/or a rotating hemostatic valve (RHV) coupled with the tetherable guide-sheath, as described below. For example, a first locking element 130a can be coupled to the anchor wire 111 and a second locking element 130b can be coupled to runner tube 113.

Figure 8B:
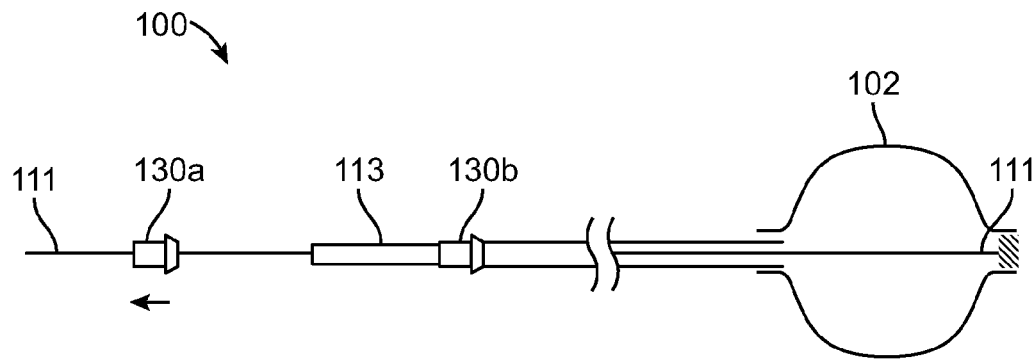
FIG. 8B illustrates a schematic view of the tethering device of FIG. 8A in an expanded state.

Referring to FIG. 8B, a schematic view of a tethering device in an expanded state is illustrated in accordance with an implementation. With tightened down locking elements 130a, 130b, the relationship of the anchor wire 111 to the runner tube 113 can be adjusted—either adjusted to tactile feedback or perhaps to fluoroscopic visualization of the expansion and contraction of the anchor. Tension can be applied by pulling the two locking elements 130a, 130b apart to expand the anchor 102. The reverse can be used to contract the anchor 102 and may even be held contracted to withdraw the device into a catheter or sheath.

Figure 8C:
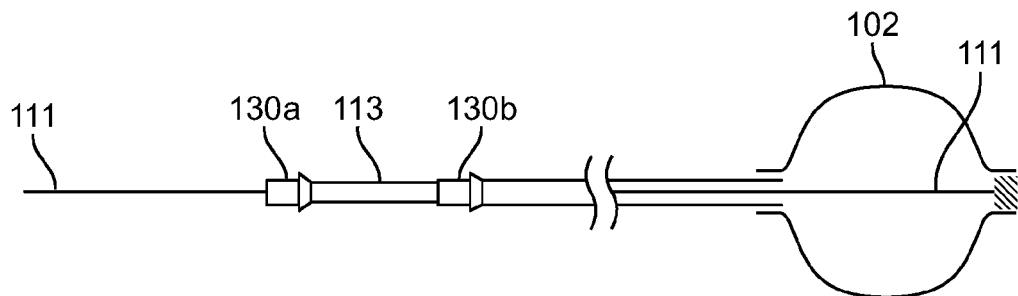
FIG. 8C illustrates a schematic view of the tethering device in an expanded state of FIG. 8B and a locked state.

Referring to FIG. 8C, a schematic view of a tethering device in an expanded state and locked state is illustrated in accordance with an implementation. Once the desired tension is applied to expand the anchor 102 to a target dimension for anchoring at an anchoring site in an anchoring vessel, the anchor wire locking element 130a can be advanced forward to abut a proximal end of the runner tube 113. Holding the anchor wire locking element 130a firm against the runner tube 113 at the anchor wire/runner tube transition and locking the anchor wire locking element 130a down at that position can lock the relationship of the anchor wire 111 and the runner tube 113 relative to each other (and lock the anchor 102 under a fixed tension). This is "locking open" the anchor 102. For added security, the runner tube locking element 130b can be loosened and advanced to the face of the RHV and/or the tetherable guide sheath, and locked down to prevent movement of the runner tube 113 relative to the RHV/tetherable guide-sheath assembly. If the RHV being used is not "specialized" to hold the runner tube 113 firmly, there can be a risk of slippage. If the runner tube 113 is of a stainless steel or nitinol or hardened material, when the operator encounters resistance on advancing interventional tools and anchoring is called for a downward force can be transmitted from the tetherable guide-sheath down the column of the tether 104, for example, formed by the anchor wire 111 extending through the runner tube 113. A standard commercial RHV can slip, and thus, a tether gripper such as a specialized RHV may be used to reinforce the relationship of the tether 104 relative to the sheath assembly and is described in more detail below (see FIGS. 25-27).

Figure 9A:
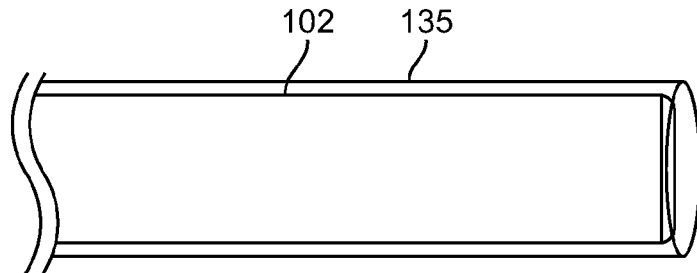
FIGS. 9A-9C illustrate schematic views of a tethering device deployment, in accordance with an implementation.
Figure 9B:
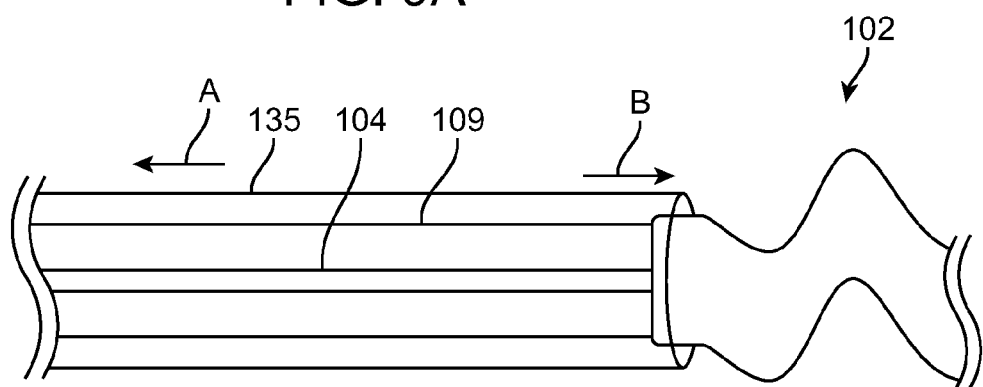
Figure 9C:
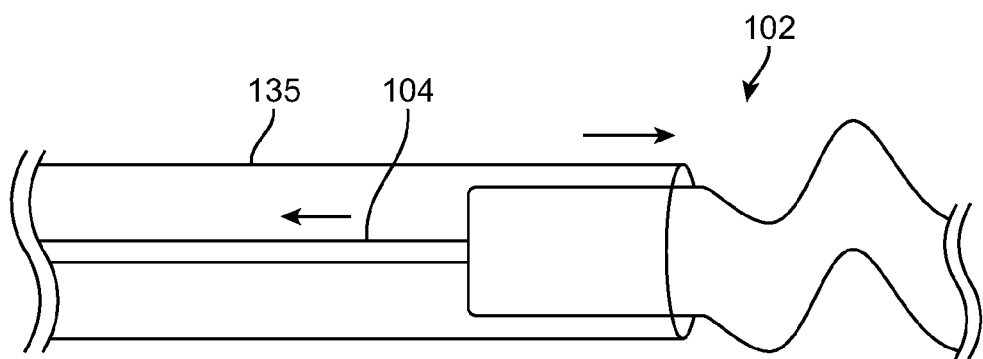

As described herein the tethering device can vary in its pushability, steerability, torque and opacity. Thus, in some implementations the tethering device 100 can have a relatively pushable tether 104 such that the tethering device 100 can be advanced through a guide catheter. In other implementations, the tethering device has a tether 104 that is less pushable to advance and steer the anchor 102 into place. Thus, a pusher tube 109 or other tubular element 135 configured to receive the tether 104 may be incorporated to aid in the delivery of the anchor 102 to the target site through a catheter lumen. FIGS. 9A-9B illustrate a schematic view of a tethering device 100 having an anchor 102 configured to be elastically deformed into a low profile configuration. In the low-profile configuration, the coil segments 126 of the anchor 102 coupled at a distal end region of the tether 104 are extended or substantially straightened into a smaller profile configuration such as those shown by dotted lines in FIGS. 5H-5I such that the anchor 102 can be positioned within a tubular element 135 (see FIG. 9A). A pusher tube 109 can be positioned over the tether 104 and within the tubular element 135 such that a distal end of the pusher tube 109 abuts a proximal end of the anchor 102 to aid in the delivery of the anchor 102 at the target location. In order to release the anchor 102 into the higher-profile configuration, the tubular element 135 can be withdrawn in a proximal direction (arrow A) and/or the pusher tube 109 advanced in a distal direction (arrow B) urging at least a portion of the anchor 102 to exit the tubular element 135 prior to unsheathing the anchor 102 from the tubular element 135 such that the anchor 102 emerges from the lumen of the tubular element 135 and self-expand or otherwise return to a larger profile configuration to anchor within a vessel (see FIG. 9B). The pusher tube 109 can have an outer diameter between that of the tether 104 and the anchor 102, for example an outer diameter of 0.006-inch to 0.038 inch, e.g. 0.021-inch. As described elsewhere herein, one or more locking elements 130 can be coupled to the tether 104, the tubular element 135, and/or a portion of the pusher tube 109 and situated outside of a patient anatomy and/or a rotating hemostatic valve (RHV) coupled with a proximal end of the tetherable guide-sheath. Further, as described elsewhere herein, the anchor 102 can be re-sheathed such as by advancing the tubular element 135 in a distal direction, pulling the tether 104 in a proximal direction, or both such that the anchor 102 abuts a distal end of the tubular element 135 and gradually straightens as the anchor 102 is pulled into the tubular element 135 (FIG. 9C).

Figure 10A:
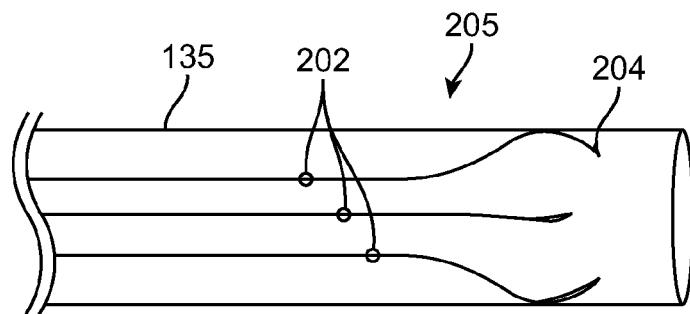
FIGS. 10A-10C illustrate schematic views of a tethering device deployment, in accordance with an implementation.
Figure 10B:
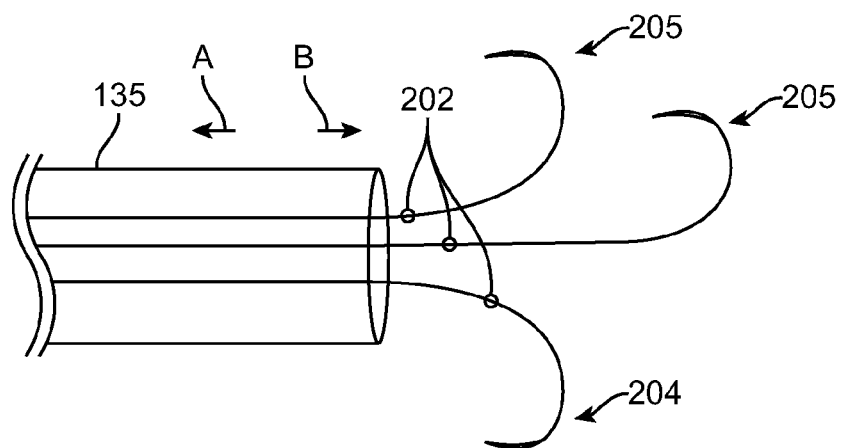
Figure 10C:
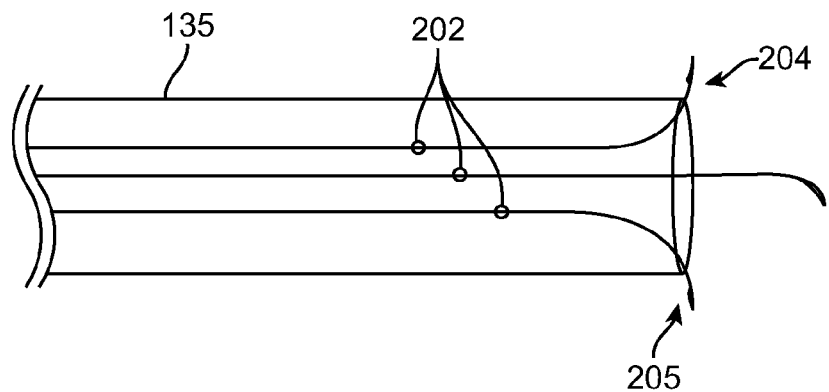

As described above, the anchor 102 can incorporate one or more struts 202 having free, distal strut ends 204. As shown in FIGS. 10A-10C, the strut ends 204 can form cleats 205 that protrude outwards upon expansion or release of the struts 202 form their constrained configuration such that the pointed ends 204 of the cleats 205 can engage with the vessel wall. The cleats 205 can undergo flexure upon sheathing and re-sheathing such that they can be removable from the vessel. FIG. 10A shows the struts 202 in a constrained configuration such that the cleats 205 and their pointed ends 204 are contained within a tubular element 135. Upon retraction of the tubular element 135 in a proximal direction (arrow A) and/or extension of the struts 202 in a distal direction (arrow B), the struts 202 and associate cleats 205 are released from constraining forces (FIG. 10B). The struts 202 can flex in a direction away from the longitudinal axis of the tubular element 135 and the associated cleats 205 can flex or bend such that their pointed ends 204 extend towards the vessel wall. In some implementations, the cleats 205 upon release from the constraint of the tubular element 135 can take on a curved shape such that their pointed ends 204 are oriented in a direction back toward a proximal direction (see FIG. 10B). As such, the cleats 205 can allow for distal movement within the vessel, but are prevented from moving proximally within the vessel due to the pointed ends 204 of the cleats 205 snagging on the vessel wall. The pointed ends 204 of the cleats 205 can be urged away from the vessel wall during re-sheathing, for example by advancing the tubular element 135 in a distal direction such that the pointed ends 204 of the cleats 205 flex back towards the longitudinal axis and the struts 202 are constrained in the lower profile configuration within the tubular element 135 (see FIG. 10C).

Figure 10D:
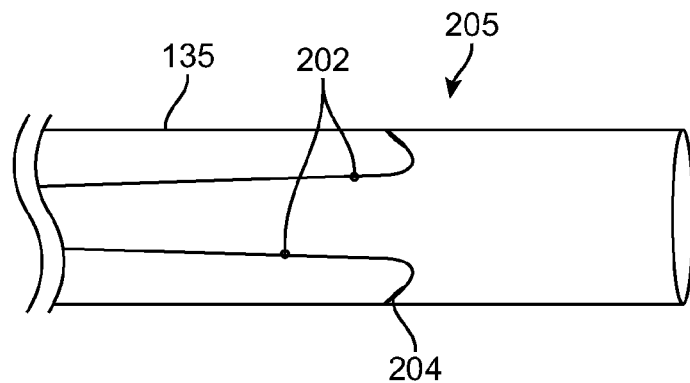
FIGS. 10D-10E illustrate schematic views of a further implementation of a tethering device deployment, in accordance with an implementation.
Figure 10E:
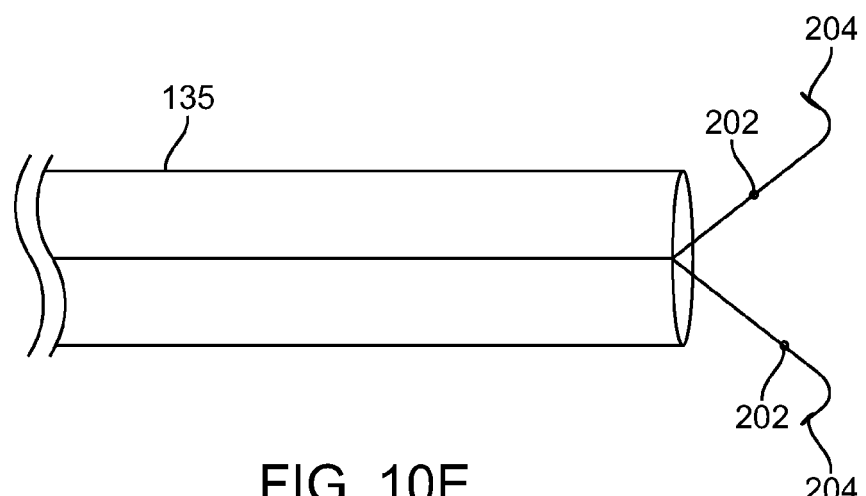

FIGS. 10D-10E illustrate another implementation of cleats 205 that can spring out upon withdrawal of or advancement from a tubular element 135.

Tetherable Guide-Sheath

Figure 11:
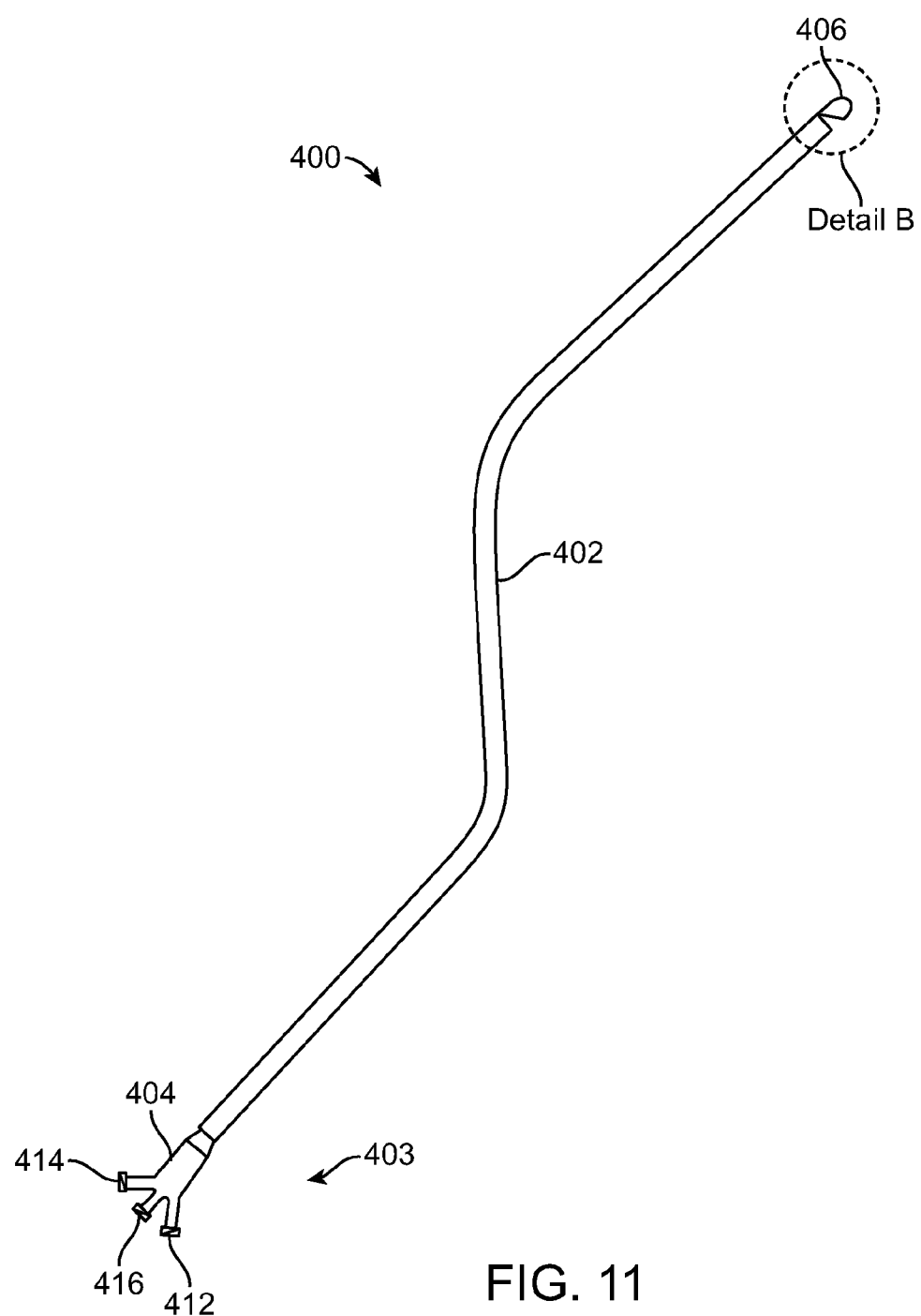
FIG. 11 illustrates a perspective view of a tetherable guide-sheath, in accordance with an implementation.

As mentioned above, the anchoring delivery system 10 can include a tethering device 100 configured to be used with a guide-sheath to support and guide working devices such as implant delivery systems to a target anatomy. FIG. 11 shows a perspective view of an implementation of a tetherable guide-sheath 400. The tetherable guide-sheath 400 can be an over-the-wire (OTW) type device and include an elongated body 402 extending from a proximal furcation 404 at a proximal end region 403 to a tip 406 at a distal end configured to bluntly dissect through and dilate narrowed sections of a diseased vessel as it is advanced. The proximal furcation 404 may include several lumens molded into a connector body to connect to corresponding lumens of the body 402 of the tetherable guide-sheath 400. For example, the body 402 and the proximal furcation 404 may include a respective tether lumen 408 and a respective working lumen 410. The proximal furcation 404 may also include additional lumens, e.g., an optional lumen 412, that can be connected to a corresponding lumen of the body 402 to serve a purpose other than receiving the tether 104 of the tethering device 100 or receiving a working device 802 to be delivered to a target anatomy. For example, the optional lumen 412 may be connected with a syringe to deliver contrast through a contrast lumen in the body 402 toward the tip 406 and into the target anatomy. A segment of the tether lumen 408 can bifurcate away from a segment of the working lumen 410. More particularly, the segment of the tether lumen 408 may extend at an angle from the segment of the working lumen 410 to create a separation between the tether proximal port 414 and the working proximal port 416. The tether lumen 408 can extend from the tether distal port 504 at a distal end to a tether proximal port 414 of the proximal portion 403 of the elongated body 402. Similarly, the working lumen 410 can extend from a distal end to a working proximal port 416 of the proximal portion 403 of the elongated body 402.

The furcation 404 can be coupled to a rotating hemostatic valve (RHV) 434. As mention above, the furcation 404 can include an optional lumen 412 that may be connected with a syringe via a connector 432 to deliver a forward drip, a flush line for contrast or saline injections through a line in the body 402 toward the tip 406 and into the target anatomy. The optional lumen 412 can also connect to a large-bore aspiration line and an aspiration source (not shown) such as a syringe or pump to draw suction through the working lumen 410, as described in the U.S. Patent Application, filed Jul. 22, 2016, which is incorporated herein by reference. The furcation 404 can be constructed of thick-walled polymer tubing or reinforced polymer tubing. The RHV 434 allows for the introduction of devices through the guide-sheath 400 into the vasculature, while preventing or minimizing blood loss and preventing air introduction into the guide-sheath 400. The RHV 434 can include a flush line or connection to a flush line so that the guide-sheath 400 can be flushed with saline or radiopaque contrast during a procedure. The flush line can also be used as a second point of aspiration. The RHV 434 can be integral to the guide-sheath 400 or the guide-sheath 400 can terminate on a proximal end in a female Luer adaptor to which a separate hemostasis valve component, such as a passive seal valve, a Tuohy-Borst valve or rotating hemostasis valve may be attached. The valve 434 can have an adjustable opening that is open large enough to allow removal of devices that have adherent clot on the tip without causing the clot to dislodge at the valve 434 during removal. Alternately, the valve 434 can be removable and is removed when a device is being removed from the sheath 400 to prevent clot dislodgement at the valve 434. The furcation 404 can include various features of the proximal components described, for example, in U.S. application Ser. No. 15/015,799, filed Feb. 4, 2016, which is incorporated herein in its entirety. The systems described herein can provide advantages from a user-standpoint over tri-axial systems in that they can be safely used by a single user. Common tri-axial systems have multiple RHV—one for each component inserted. The positional location of the various components on the table, from left to right, inform users of which component it is. For example, components positioned to a right side of the table are inserted more distally and components positioned to the left side of the operating table are inserted more proximally. The space on the table must be quite large (e.g. up to 210 cm-220 cm long). Generally all the components are arranged in this way and require an additional technician to organize and arrange the various components. The systems described herein incorporate components inserted through a single RHV. As such, rather than relying on a positional organization spread out across a table over 6 feet long, multiple components of the systems described herein extend through the same RHV such that a single user can control delivery, all the components can be shorter, and can be used with less risk of sterile field contamination.

The length of the elongated body 402 is configured to allow the distal tip 406 of the body 402 to be positioned as far distal as the bifurcation between the external carotid artery (ECA) and the internal carotid artery (ICA), for example, from a transfemoral approach with additional length providing for adjustments if needed. In some implementations, the length of the body 402 can be in the range of 80 to 90 cm or up to about 100 cm or up to about 105 cm. In implementations, the body 402 length is suitable for a transcarotid approach to the bifurcation of the carotid artery, in the range of 20-25 cm. In further implementations, the body 402 length is suitable for a transcarotid approach to the CCA or proximal ICA, in the range of 10-15 cm. The body 402 is configured to assume and navigate the bends of the vasculature without kinking, collapsing, or causing vascular trauma, even, for example, when subjected to high aspiration forces.

Figure 12A:
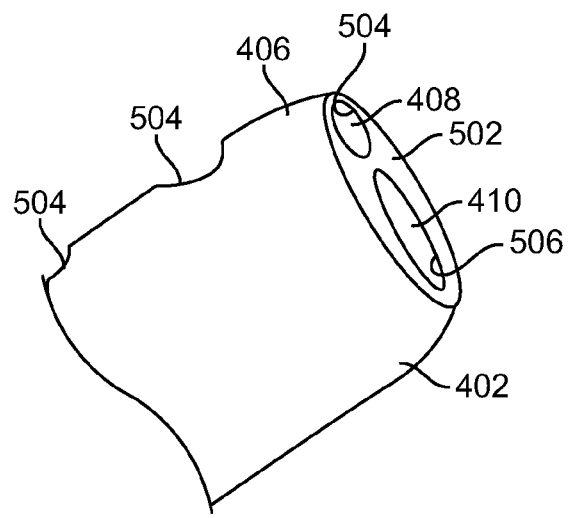
FIGS. 12A-12B illustrate detail views, taken from Detail B of FIG. 11, of a distal end of a tetherable guide-sheath.

Referring to FIG. 12A, a detail view, taken from Detail B of FIG. 11, of a distal end of a tetherable guide-sheath is illustrated in accordance with an implementation. The tip 406 of the tetherable guide-sheath 400 can have a same or similar outer diameter as a section of the body 402 leading up to the distal end. Accordingly, the tip 406 may have a distal face 502 orthogonal to a longitudinal axis passing through the body 402 and the distal face 502 may have an outer diameter substantially equal to a cross-sectional outer dimension of the body 402. In an implementation, the tip 406 includes a chamfer, fillet, or taper, making the distal face 502 diameter slightly less than the cross-sectional dimension of the body 402. In a further implementation, the tip 406 may be an elongated tubular portion extending distal to a region of the body 402 having a uniform outer diameter such that the elongated tubular portion has a reduced diameter compared to the uniform outer diameter of the body 402 (see FIGS. 12C-12E). Thus, the tip 406 can be elongated or can be more bluntly shaped. Accordingly, the tip 406 may be configured to smoothly track through a vasculature and/or to dilate vascular restrictions as it tracks through the vasculature. In an implementation, the tether lumen 408 may have a distal end forming a tether distal port 504 in the distal face

502. Similarly, the working lumen 410 may have a distal end forming a working port 506 in the distal face 502. As will be described below, the tetherable guide-sheath 400 may also include one or more tether entry ports 504 along a side of the body 402.

Figure 12B:
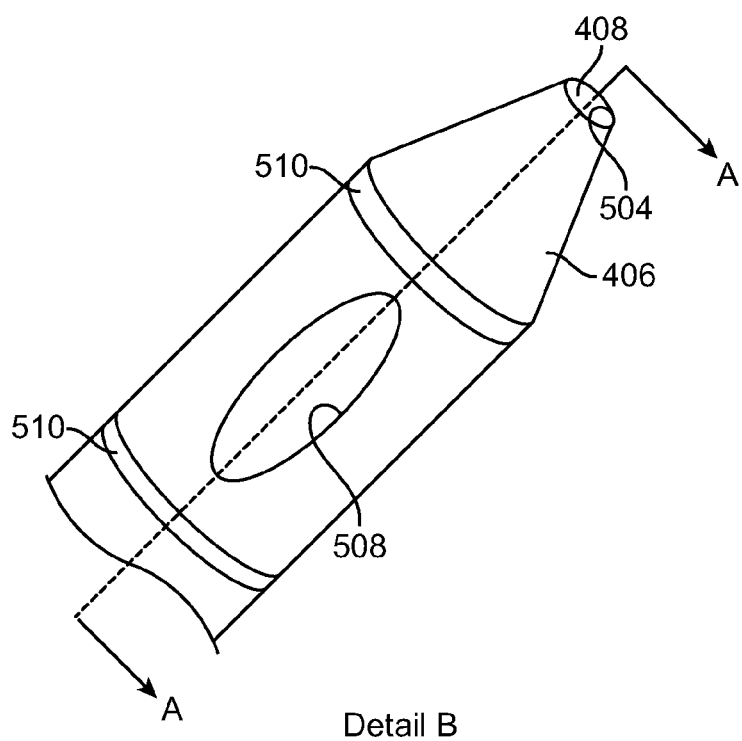

Referring to FIG. 12B, a detail view, taken from Detail B of FIG. 11, of a distal end of a tetherable guide-sheath is illustrated in accordance with an implementation. The tetherable guide-sheath 400 may include a tip 406 that tapers from a section of the body 402 leading up to the distal end. That is, an outer surface of the body 402 may have a diameter that reduces from a larger dimension to a smaller dimension at a distal end of the tether lumen 408, i.e., at the tether distal port 504. For example, the tip 406 can taper from an outer diameter of approximately 0.114" to about 0.035". The angle of the taper of the tip 406 can vary depending on the length of the tapered tip 406. For example, in some implementations, the tip 406 tapers from 0.110" to 0.035" over a length of approximately 50 mm. In an implementation, the tether distal port 504 is centered along a longitudinal axis passing through the body 402. Thus, the tapered tip 406 may be concentrically disposed around the tether distal port 504. Accordingly, the tapered tip 406 may track smoothly around bends within the targeted anatomy to avoid causing trauma to the tissue. The working lumen 410 may extend parallel to the tether lumen 408 through the body 402 to a mouth 508 located proximal to the tether distal port 504 near the distal end of the tetherable guide-sheath 400. More particularly, the working port 506 may be an elongated mouth 508 disposed in a side surface of the body 402, for example proximal to the tip taper. The mouth 508 may be formed in the side surface using manufacturing techniques such as skiving and/or drilling. Thus, the mouth 508 may have a dimension in at least one direction that is larger than a diameter of the working lumen 410. For example, the mouth 508 may have a longitudinal dimension that is larger than a cross-sectional diameter of the working lumen 410. The diameter of the mouth 508 can be at least 1.5×, 2×, 2.5×, or 3× as large as an outer diameter of a working device 802 extending therethrough. The mouth 508 can be skived such that it has a length from a proximal end to a distal end that allows for a working device 802 to exit at a range of angles, for example, very nearly parallel to the body 402 to a position that is at an angle to the body 402, for example substantially perpendicular as well as greater than a right angle to the body 402. This arrangement allows for ease of delivery of a working device 802 through the mouth 508 even in the presence of a severe angulation within the vessel being traversed or where a bifurcation is present. Often, tortuous segments in vessels and bifurcations have severe angulations to 90° or greater angle up to 180°. Classic severe angulation points in the vasculature can include the aortoiliac junction, the left subclavian artery takeoff from the aorta, the brachiocephalic (innominate) artery takeoff from the ascending aorta as well as many other peripheral locations. A distal tip 406 can extend well beyond a distal end of the mouth 508 such that the tip 406 forms an elongate, soft tip for maneuvering through the turns of the vasculature (see, e.g., FIGS. 12C-12D). In some implementations, the mouth 508 can be located just proximal to the tip 406 or can be located at least 0.25 mm or more away from the tip 406.

In an implementation, the tetherable guide-sheath 400 includes one or more radiopaque markers 510. The radiopaque markers 510 can be disposed near the mouth 508. For example, a pair of radiopaque bands may be swaged, painted, embedded, or otherwise disposed in or on the body 402, for example on either side of the mouth 508.

In some implementations, the radiopaque markers 510 include a barium polymer, tungsten polymer blend, tungsten-filled or platinum-filled marker that maintains flexibility of the distal end of the device and improves transition along the length of the guide-sheath 400 and its resistance to kinking. In some implementations, the radiopaque marker 510 is a tungsten-loaded PEBAX or polyurethane that is heat welded to the body 402. The markers 510 are shown in the figures as rings around a circumference of one or more regions of the body 402. However, the markers 510 can have other shapes or create a variety of patterns that provide orientation to an operator regarding the position of the mouth 508 within the vessel. Accordingly, an operator may visualize a location of the mouth 508 under fluoroscopy to confirm that the mouth 508 is directed toward a target anatomy where a working device 802 is to be delivered. For example, radiopaque marker(s) 510 allow an operator to rotate the body 402 of the tetherable guide-sheath 400 at an anatomical access point, e.g., a groin of a patient, such that the mouth 508 provides access to an ICA by subsequent working device(s), e.g., catheters and wires advanced to the ICA. In some implementations, the radiopaque marker(s) 510 include platinum, gold, tantalum, tungsten or any other substance visible under an x-ray fluoroscope. In various implementations, the distance from the tether distal port 504 to the mouth 508 should be in a range that facilitates maneuvering of subsequent devices advanced through mouth 508. It should be appreciated that any of the various components of the systems described herein can incorporate radiopaque markers as described above.

Figures 12C, 12D:
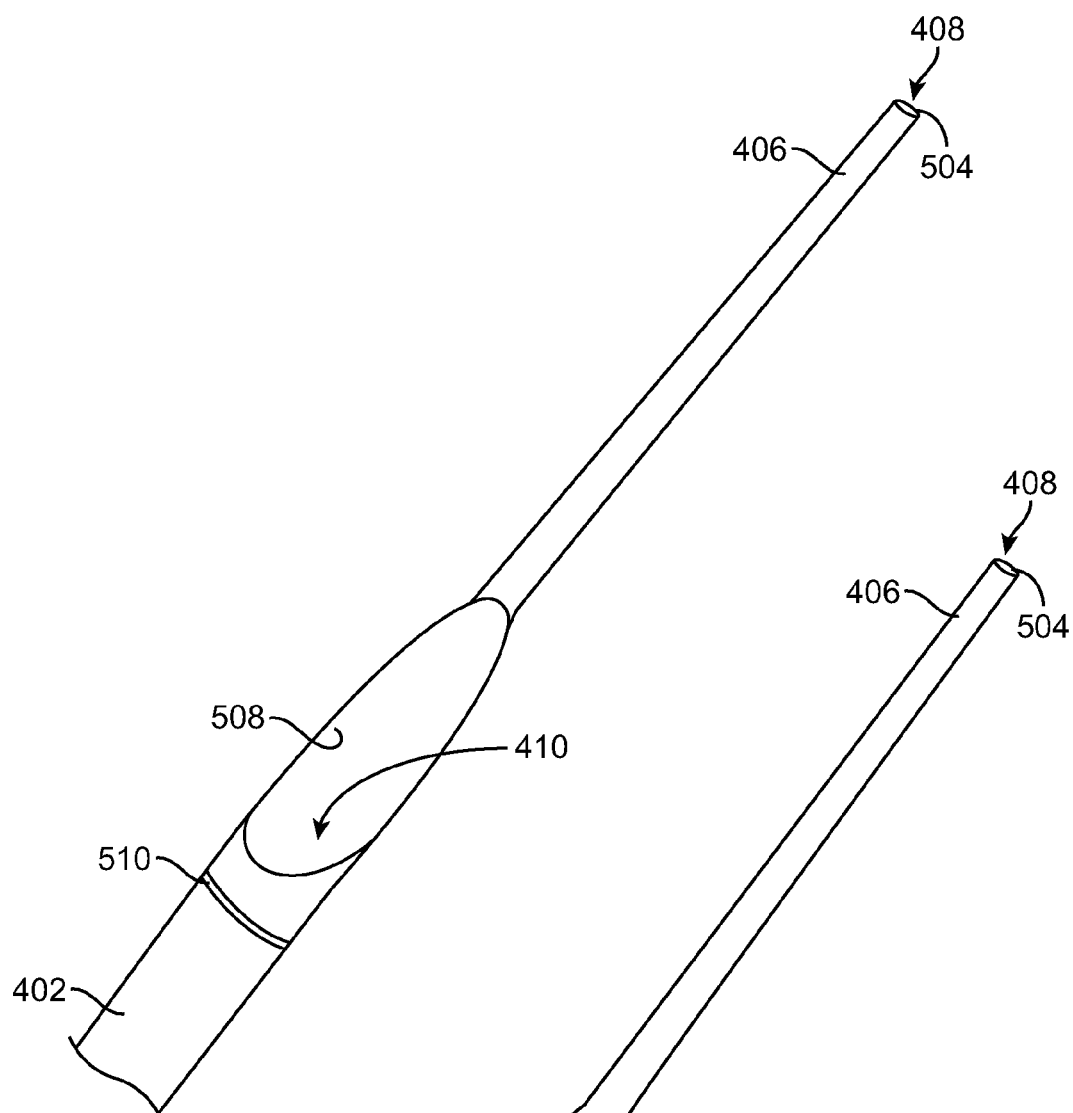
FIGS. 12C-12D illustrate detail views, taken from Detail B of FIG. 11, of a distal end of a tetherable guide-sheath.
Figure 12E:
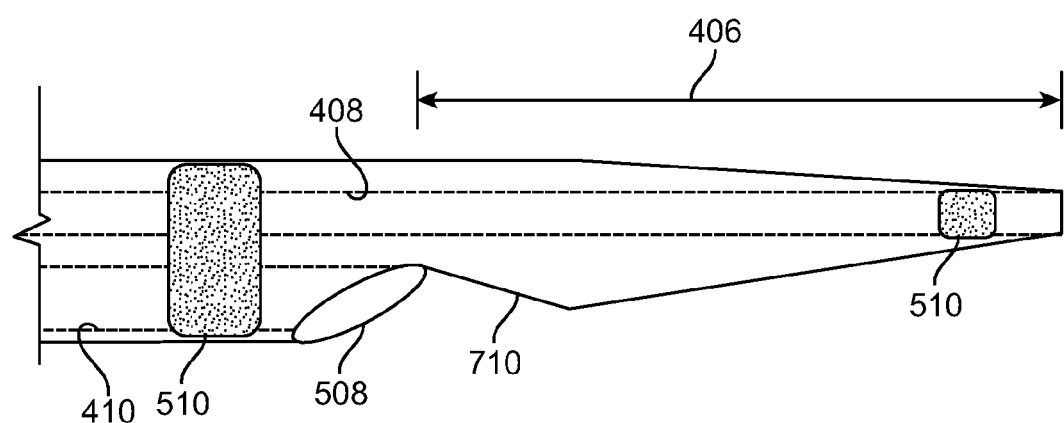
FIG. 12E illustrates a detail view of another implementation of a distal end of a tetherable guide-sheath.
Figure 13:
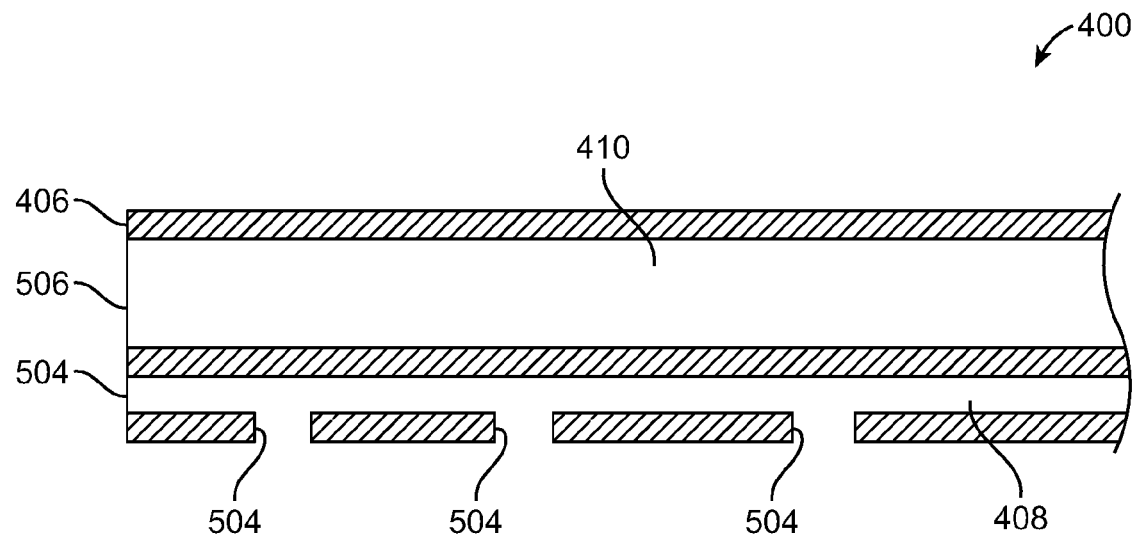
FIG. 13 illustrates a sectional view of a distal end of a tetherable guide-sheath, in accordance with an implementation.

Referring to FIG. 13, a sectional view of a distal end of a tetherable guide-sheath is illustrated in accordance with an implementation. In an implementation, the tetherable guide-sheath 400 includes the tip 406 at the distal face 502 of the body 402. Thus, FIG. 13 may be a cross-sectional view of the distal end of the tetherable guide-sheath 400 illustrated in FIG. 12A and described above. The working lumen 410 and the tether lumen 408 can extend longitudinally along respective axes between the proximal end 403 of the tetherable guide-sheath 400 and the distal tip 406. Furthermore, the tether lumen 408 may include more than one tether distal port 504. For example, a tether distal port 504 may optionally be disposed in the distal face 502 of the body 402, and one or more additional tether entry ports 504 may be disposed in a side surface of the body 402, such that the ports are in fluid communication with the tether lumen 408. More particularly, several tether entry ports 504 may be disposed in the side surface at regularly spaced intervals. The tether 104 may be inserted through any of the tether entry ports 504 into the tether lumen 408 to allow the tip 406 of the tetherable guide-sheath 400 to be advanced into a same or a different anatomy than the anatomy that the anchor 102 is deployed within. For example, the tether 104 may be disposed in an anchoring vessel and the tip 406 of the tetherable guide-sheath 400 may be advanced into a target vessel that bifurcates away from the anchoring vessel. As such, it will be recognized that depending on the tether distal port 504 through which the tether 104 is placed, a different length of the tetherable guide-sheath 400 may be advanced into the target anatomy. For example, when the tether 104 is placed in the most distal tether distal port 504 in the side surface, a distal segment of the tetherable guide-sheath 400 between the utilized tether distal port 504 and the tip 406 may be advanced into the target anatomy. When the tether 104 is placed in the most proximal port in the side surface, however, the distal segment of the tetherable guide-sheath 400 between the utilized tether distal port 504 and the tip 406 may be longer. Accordingly, a stump tip of the tetherable guide-sheath 400 as that shown in FIG. 12A or a long tip of the tetherable guide-sheath 400 as shown in FIGS. 12C-12D may be advanced into the target anatomy.

Figure 14:
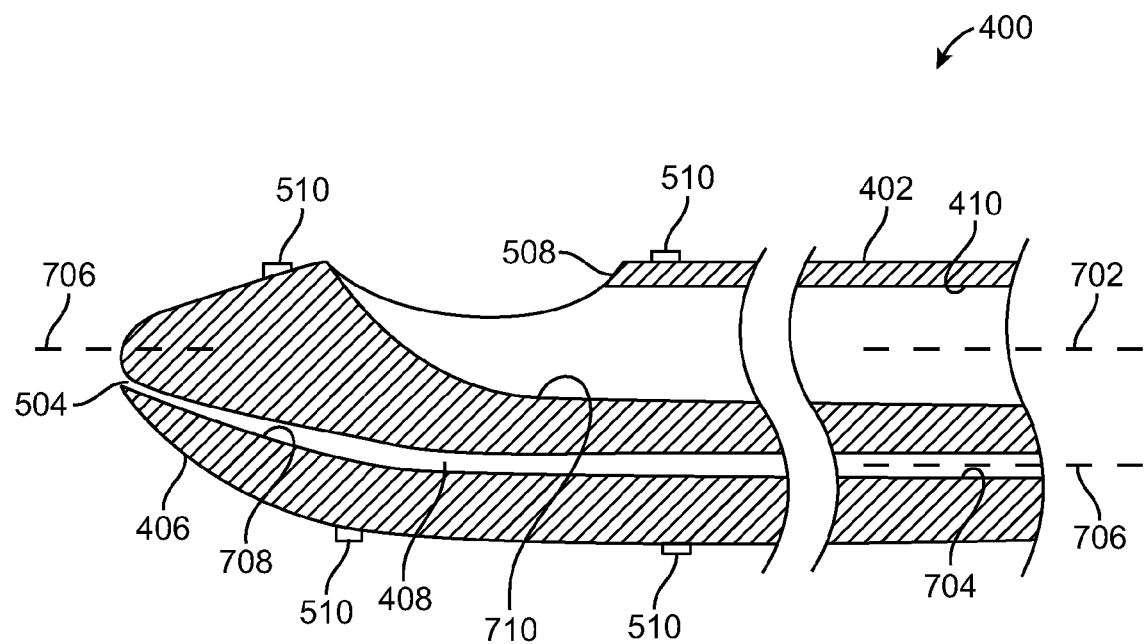
FIG. 14 illustrates a sectional view, taken about line A-A of FIG. 12B, of a distal end of a tetherable guide-sheath.

Referring to FIG. 14, a sectional view, taken about line A-A of FIG. 12B, of a distal end of a tetherable guide-sheath is illustrated in accordance with an implementation. In an implementation, the tetherable guide-sheath 400 includes the mouth 508 on a side surface of the body 402. The working lumen 410 and the tether lumen 408 may extend in a longitudinal direction through at least a portion of the tetherable guide-sheath 400. For example, the working lumen 410 may extend along a longitudinal working axis 702 between the proximal furcation 404 and the mouth 508. Similarly, a proximal tether lumen 704 having a segment extending proximal to the mouth 508 may extend along a longitudinal tether axis 706 from the proximal furcation 404 (in the case of an OTW tetherable guide-sheath 400) and/or an exit port (in the case of a rapid-exchange (RX) type of tetherable guide-sheath 400 as described below). The lumens need not, however, extend longitudinally over the entire length of the tetherable guide-sheath 400. For example, a distal tether lumen 708 segment may be directed radially inward from the proximal tether lumen 704 over a portion of the tetherable guide-sheath 400 distal to the mouth 508. More particularly, the tether lumen 408 may diverge from the longitudinal direction toward the tether distal port 504, which may be centrally located relative to a cross-section of the body 402. Thus, the tether axis 706 passing through the tether distal port 504 may be radially offset from the tether axis 706 passing through the proximal tether lumen 704. The tether axis 706 passing through the tether distal port 504 may pass through the working lumen 410 at a location proximal to the mouth 508, i.e., the tether distal port 504 may be longitudinally aligned with the working lumen 410. In an implementation, the tether axis 706 passing through the tether distal port 504 may be coaxial with the working axis 702, or may be closer to the working axis 702 than to the tether axis 706 extending through the proximal tether lumen 704.

In an implementation, the working lumen 410 extends along a deflecting surface 710 that directs a working device 802 passing distally through the body 402 outward through the mouth 508. More particularly, the working lumen 410 may extend from the mouth 508 at the tip 406 of the tetherable guide-sheath 400 to a proximal end 403 of the tetherable guide-sheath 400, and the tetherable guide-sheath 400 may include a deflecting surface 710 between the working lumen 410 and the tether lumen 408. The deflecting surface 710 may be oblique to the working lumen 410. That is, the deflecting surface 710 may include a ramp having a radius that provides a smooth distal transition from the working axis 702 to an exit axis extending radially outward through the mouth 508. The exit axis may be at an angle to the working axis 702, for example, a 10, 15, 20, 25, 30, 35, 40, or 45 degree angle. In some implementations the exit axis is at a 30° angle.

As described above, the body 402 of the tetherable guide-sheath 400 may include at least one lumen, and may include several lumens. More particularly, the implementations depicted in FIGS. 12-14 are dual-lumen catheters having a working lumen 410 accompanied by a tether lumen 408 along a majority of a length of tetherable guide-sheath 400. A diameter of tether lumen 408 may be less than a diameter of working lumen 410. Furthermore, the diameter of tether lumen 408 may vary. For example, the tether lumen 408 may have a diameter large enough to receive the tether 104, but not large enough to receive the anchor 102 of the tethering device 100. Alternatively, the tether lumen 408 may have a diameter large enough to receive the anchor 102 over at least a portion of a length of the tether lumen 408, e.g., to allow the anchor 102 to be pushed or pulled through the tether lumen 408. The tether lumen 408 may also have a diameter large enough to receive the anchor 102 when the anchor 102 is urged into a lower profile configuration such that it can be received within at least a portion of the tether lumen 408.

According to some implementations, the tether lumen 408 is independent of the working lumen 410, and the working lumen 410 runs the entire length of tetherable guide-sheath 400. In some implementations, the tetherable guide-sheath 400 will have performance characteristics similar to other sheaths used in carotid access and AIS procedures in terms of kinkability, radiopacity, column strength, and flexibility. The working lumen 410 may deliver a working device toward the anchor 102, and the working device may be directed to the deflecting surface 710 to smoothly exit at an angle to the longitudinal axis of the working lumen 410. Furthermore, the mouth 508 of the tetherable guide-sheath 400 may be wider than the internal diameter of the working lumen 410 so as to allow a wide range of exit angles of a working device exiting the tetherable guide-sheath 400. According to some implementations, the exiting working device can run almost parallel with the tetherable guide-sheath 400 to greater than 90 degrees, which severely angulated arteries may require. Exit angles from the mouth 508 of the tetherable guide-sheath 400 should consider the variety of angles that the anatomy may require.

Figure 15A:
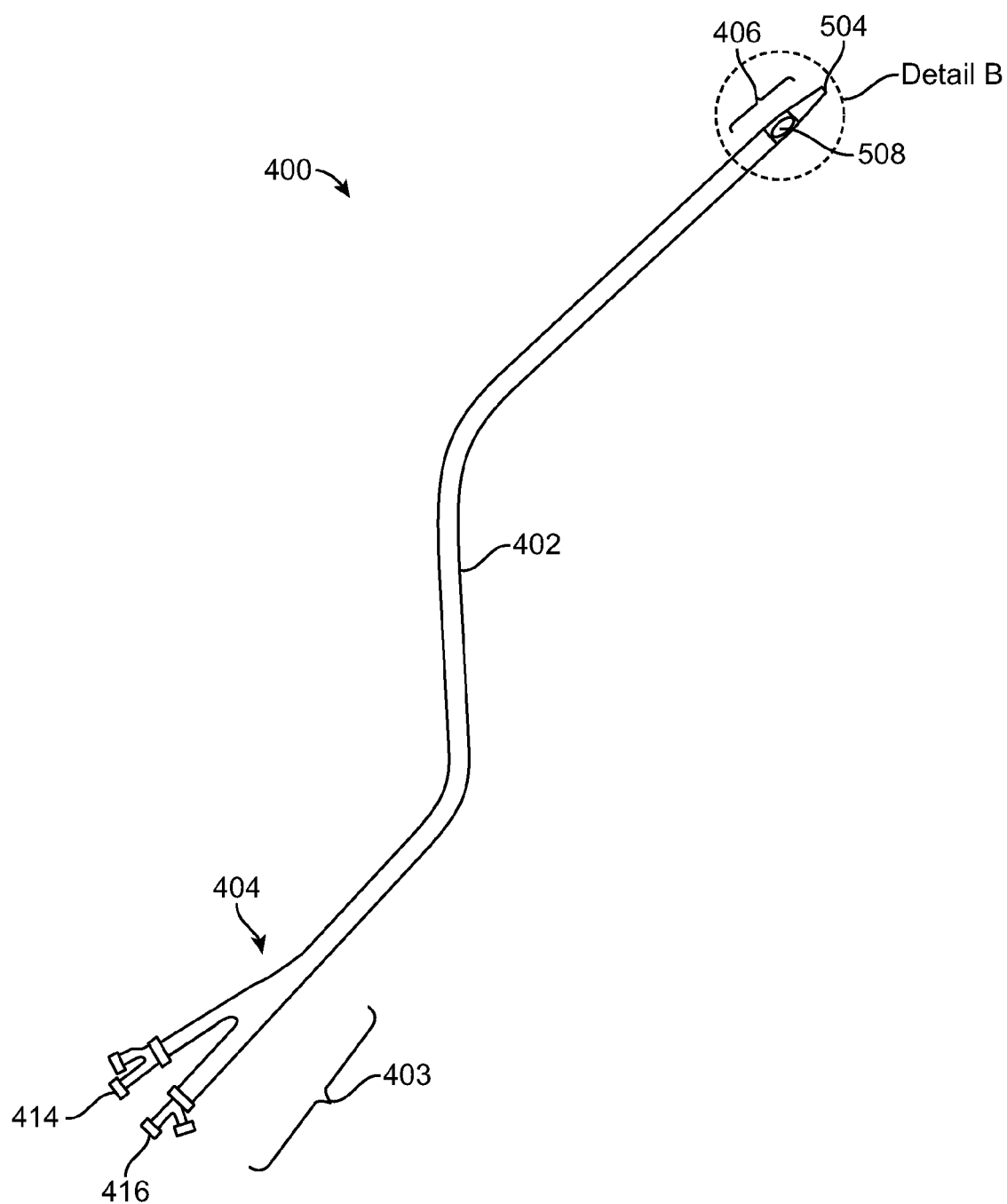
FIG. 15A illustrates a perspective view of a tetherable guide-sheath, in accordance with an implementation.

FIG. 15A illustrates a perspective view of an implementation of a tetherable guide-sheath 400. As with other implementations, the tetherable guide-sheath 400 can include an elongated body 402 containing one or more lumens extending from a distal end to a proximal portion. For example, a tether lumen 408 may extend from a tether distal port 504 at a tip 406 of the tetherable guide-sheath 400 to a tether proximal port 414 of the proximal portion 403. Similarly, a working lumen 410 may extend from a mouth 508 of the tip 406 to a working proximal port 416 of the proximal portion 403. The tetherable guide-sheath 400 may include a proximal furcation 404 in the proximal portion 403 where a segment of the tether lumen 408 bifurcates away from a segment of the working lumen 410. More particularly, the segment of the tether lumen 408 may extend at an angle from the segment of the working lumen 410 to create a separation between the tether proximal port 414 and the working proximal port 416. One or more of the tether proximal port 414 or the working proximal port 416 may incorporate a tether gripper 1502 (see FIGS. 25-27).

Figure 15B:
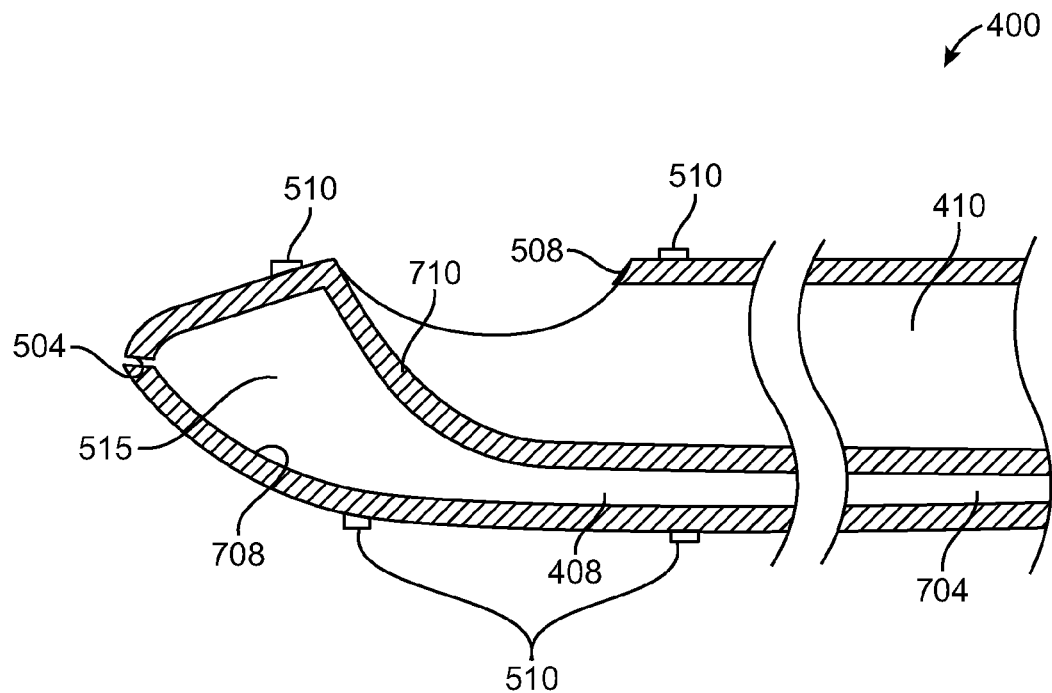
FIG. 15B illustrates a detailed sectional view, taken from Detail B of FIG. 15A, of a distal portion of a tetherable guide-sheath, in accordance with an implementation.

Referring to FIG. 15B, a detailed sectional view taken from Detail B of FIG. 15A, of a distal portion of a tetherable guide-sheath is illustrated in accordance with an implementation. In an implementation, the tetherable guide-sheath 400 may include a chamber 515 located proximal to the tether distal port 504 in the tip 406. The chamber 515 may be sized to receive the anchor 102 of the tethering device 100. For example, the tether distal port 504 may be chamfered, i.e., having a distal port diameter that is larger than a proximal port diameter, such that the proximal joint 108 of the tethering device 100 moves smoothly into the tether distal port 504 when the tetherable guide-sheath 400 is advanced over the anchor 102. The tether distal port 504 may expand slightly to receive the anchor 102. Furthermore, the anchor 102 may be retracted into the chamber 515 to store the anchor 102. Thus, in an implementation, the chamber 515 within the tip 406 of the tetherable guide-sheath 400 may have a chamber volume that is at least as large as a volume occupied by the anchor 102 when the anchor 102 is in the unexpanded, lower profile state. The chamber 515 may also have a variable chamber volume as described in more detail below with respect to FIGS. 17A-17B.

Figure 15C:
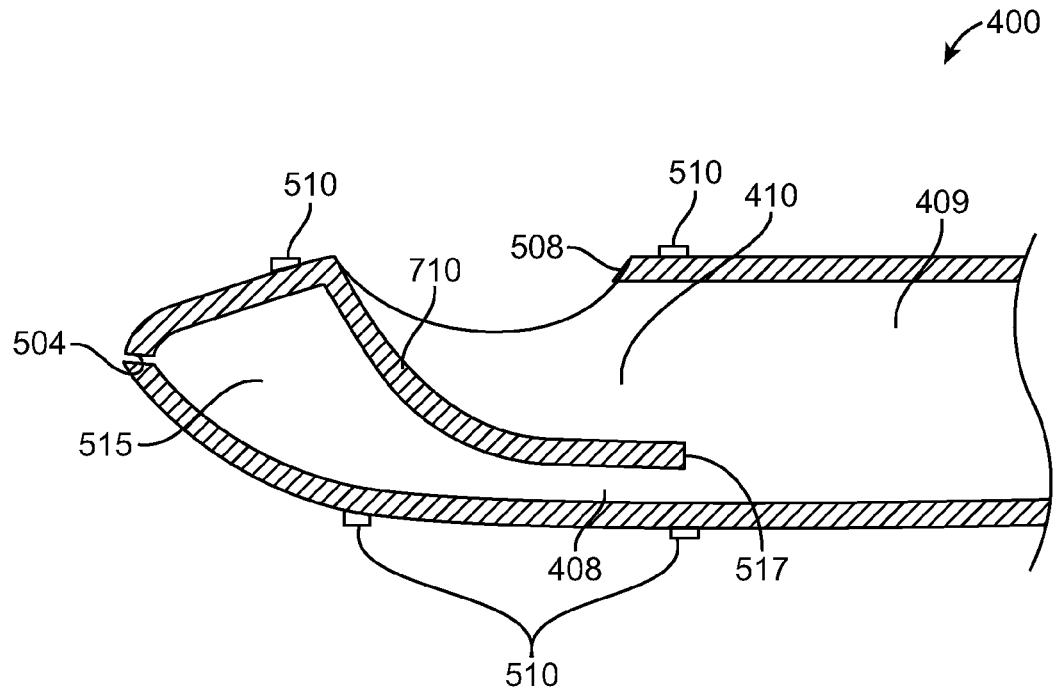
FIG. 15C illustrates a detailed sectional view, taken from Detail B of FIG. 15A, of a distal portion of a tetherable guide-sheath, in accordance with an implementation.

Referring to FIG. 15C, a detailed sectional view, taken from Detail B of FIG. 15A, of a distal portion of a tetherable guide-sheath is illustrated in accordance with an implementation. In an implementation, the separation between the working lumen 410 and the tether lumen 408 proximal to the mouth 508 may have a termination point distal to the tether gripper and/or the exit port of the tetherable guide-sheath 400. For example, the wall 517 dividing the working lumen 410 and the tether lumen 408, which the ramp 710 makes up a portion of, may end proximal to the mouth 508. This may allow the anchor 102 to remain separated from a working device in the working lumen 410 in the distal region of the tetherable guide-sheath 400. However, separation between the tether 104 and the working device at a location proximal to the mouth 508 may be less critical, and thus, the separating barrier or wall 517 may terminate near this region in order to maximize the cross-sectional area of a proximal portion of the tetherable guide-sheath 400. It will be appreciated that when there is no separating barrier between the working lumen 410 and the tether lumen 408 the lumens merge into a common lumen 409 and the tether 104 and the working device exit through a single proximal port, e.g., in the tether gripper 1502. Furthermore, it will be appreciated that a proximal edge of the separating barrier 517 may include a tapered wall thickness to ease the distal joint 108 of the working device as it is advanced from the common lumen 409 into the working lumen 410 and through the mouth 508.

Figure 16A:
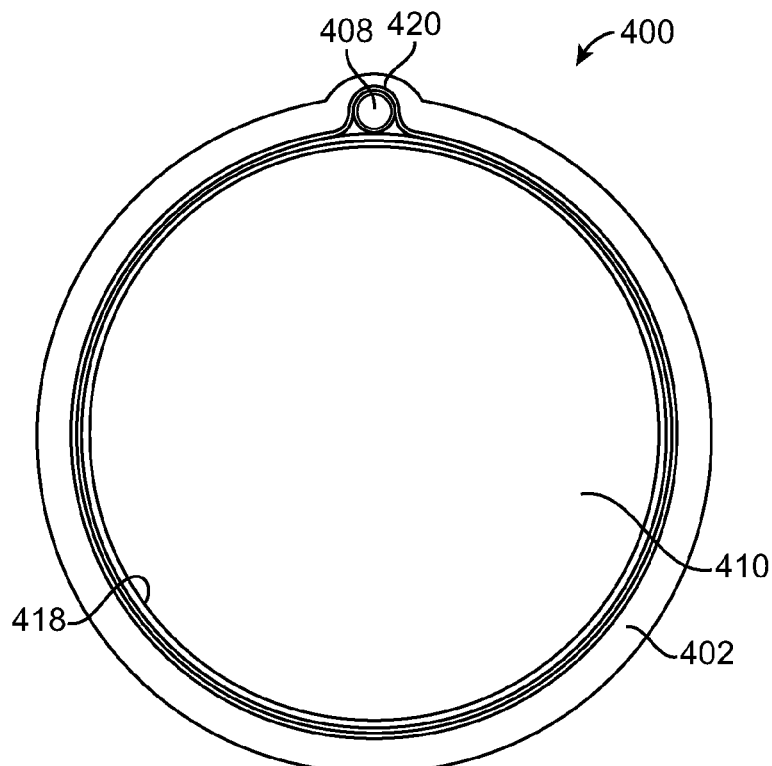
FIGS. 16A-16B illustrate sectional views of a tetherable guide-sheath, in accordance with an implementation.

Referring to FIG. 16A, a sectional view of a tetherable guide-sheath is illustrated in accordance with an implementation. The available cross-sectional area of the tetherable guide-sheath 400 may be used to maximize the working lumen 410 and to minimize the tether lumen 408. For example, the body 402 of the tetherable guide-sheath 400 may surround the working lumen 410 defined by an inner diameter of a working lumen liner 418, and the tether lumen 408 may be defined by an inner diameter of a tether lumen liner 420. The lumen liners 418, 420 may be, for example, non-concentric tubes that are laterally spaced and positioned adjacent to one another. In an implementation, a dimension of the tether lumen 408 is large enough to allow a slip fit between the tether lumen liner 420 of the tetherable guide-sheath 400 and the runner tube 113 of the tethering device 100. The dimension, however, may not be large enough to allow a slip fit between the tether lumen liner 420 and the pusher tube 109 of the tethering device 100. More particularly, the tether lumen 408 may be configured to advance over the tether 104 only after the pusher tube 109 has been removed. Accordingly, cross-sectional area that would otherwise be required to receive the runner tube 113 may instead be dedicated to the working lumen 410, and thus, the working lumen 410 may be maximized within the available cross-sectional area of the tetherable guide-sheath 400.

The inner liners can be constructed from a low friction polymer such as PTFE (polytetrafluoroethylene) or FEP (fluorinated ethylene propylene) to provide a smooth surface for the advancement of devices through the inner lumen. An outer jacket material can provide mechanical integrity to the inner liners and can be constructed from materials such as PEBAX, thermoplastic polyurethane, polyethylene, nylon, or the like. A third layer can be incorporated that can provide reinforcement between the inner liner and the outer jacket. The reinforcement layer can prevent flattening or kinking of the inner lumens of the body 402 to allow unimpeded device navigation through bends in the vasculature as well as aspiration or reverse flow. The body 402 can be circumferentially reinforced. The reinforcement layer can be made from metal such as stainless steel, Nitinol, Nitinol braid, helical ribbon, helical wire, cut stainless steel, or the like, or stiff polymer such as PEEK. The reinforcement layer can be a structure such as a coil or braid, or tubing that has been laser-cut or machine-cut so as to be flexible. In another implementation, the reinforcement layer can be a cut hypotube such as a Nitinol hypotube or cut rigid polymer, or the like. The outer jacket of the body 402 can be formed of increasingly softer materials towards the distal end. For example, proximal region of the body 402 can be formed of a material such as Nylon, a region of the body 402 distal to the proximal region of the body 402 can have a hardness of 72 D whereas areas more distal can be increasingly more flexible and formed of materials having a hardness of 55 D, 45 D, 35 D extending towards the distal tip 406, which can be formed of a material having a hardness of 35 D, for example. The body 402 can include a hydrophilic coating.

Figure 16B:
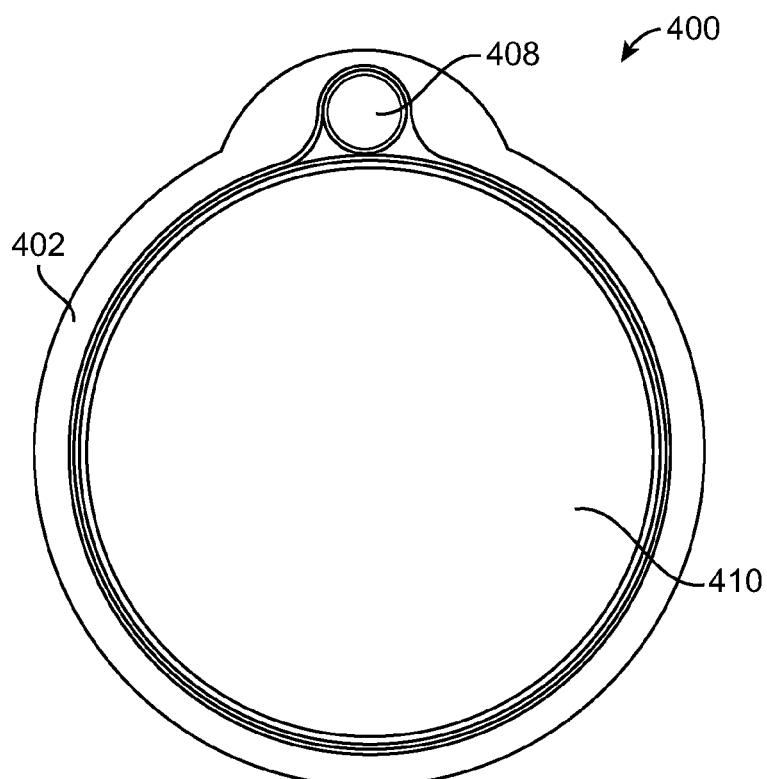

Referring to FIG. 16B, a sectional view of a tetherable guide-sheath is illustrated in accordance with an implementation. Dimensions of the tether lumen 408 and a working lumen 410 of the tetherable guide-sheath 400 may be varied in accordance with the principle described above. More particularly, although the size of the tetherable guide-sheath 400 may be changed to accommodate a particular anatomy and/or intended working device, the tether lumen 408 may be sized to receive the runner tube 113 of a corresponding tethering device 100 in the anchoring delivery system, but may not be large enough to receive the pusher tube 113 of the corresponding tethering device 100.

The flexibility of the body 402 can vary over its length, with increasing flexibility towards the distal portion of the body 402. The variability in flexibility may be achieved in various ways. For example, the outer jacket may change in durometer and/or material at various sections. A lower durometer outer jacket material can be used in a distal section of the guide-sheath compared to other sections of the guide-sheath. Alternately, the wall thickness of the jacket material may be reduced, and/or the density of the reinforcement layer may be varied to increase the flexibility. For example, the pitch of the coil or braid may be stretched out, or the cut pattern in the tubing may be varied to be more flexible. Alternately, the reinforcement structure or the materials may change over the length of the elongate body 402. In another implementation, there is a transition section between the distal-most flexible section and the proximal section, with one or more sections of varying flexibilities between the distal-most section and the remainder of the elongate body 402. In this implementation, the distal-most section is about 2 cm to about 5 cm, the transition section is about 2 cm to about 10 cm and the proximal section takes up the remainder of the sheath length.

Figure 17A:
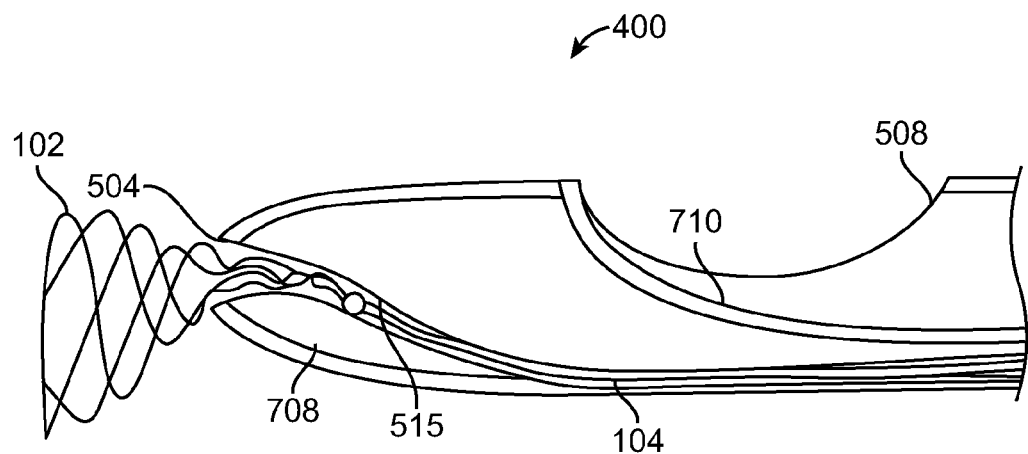
FIG. 17A illustrates a support guide during retrieval of an anchoring structure.
Figure 17B:
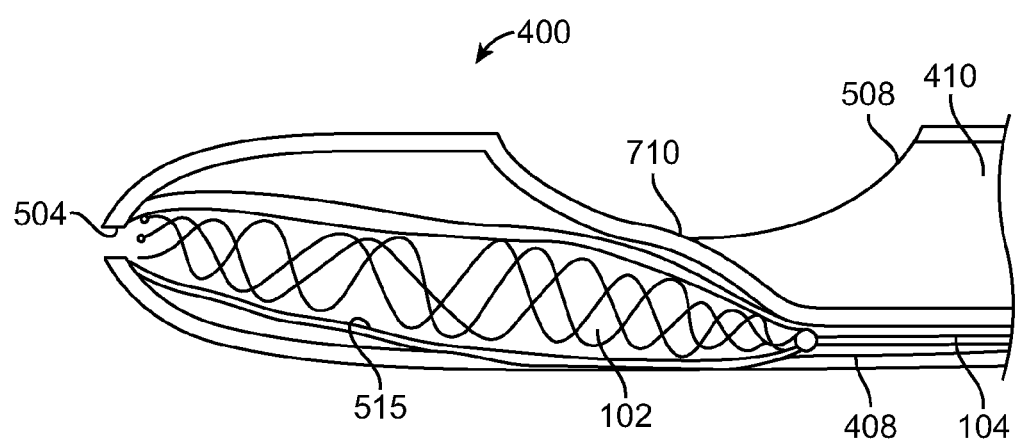
FIG. 17B illustrates the retrieved anchoring structure in a tip of the support guide of FIG. 17A.

FIGS. 17A-17B illustrate an implementation of a distal end of a tetherable guide-sheath 400 including a variable volume chamber 515. As mentioned above, the ramped deflecting surface 710 can deflect working devices from the working lumen 410 out through the mouth 508 as the working device exits the guide-sheath 400. The ramped deflecting surface 710 may be formed from a flexible membrane that is able to move, for example, toward the mouth 508 or toward an interior of the chamber 515. Thus, the ramp 710 may flex toward the chamber when a working device is being delivered through the mouth 508 of the working lumen 410. Similarly, after the working device is removed from the working lumen 410, the ramp 710 may flex toward the mouth 508 to capture the anchor 102 within the chamber 515.

As mentioned, the tetherable guide-sheath 400 may capture the anchor 102 of the tethering device 100 in one of the lumens of the tetherable guide-sheath 400. The ramp 710 not only can deflect working devices as the devices exit the tetherable guide-sheath 400, but also can deflect the anchor 102 of the tethering device 100 as it is withdrawn into the chamber 515. As an anchor 102 of a tethering device 100 is withdrawn in a proximal direction through the tether distal port 504 into chamber 515, the anchor 102 can be deflected from the expanded state towards the unexpanded state as a reaction to a relative lack of expansion of the tether distal port 504 as compared to the anchor 102 of the tethering device 100 (see FIG. 17A) as the anchor 102 is withdrawn into the tether lumen 408. More particularly, as described below, the distal tip of the tetherable guide-sheath 400 may be advanced over the tether 104 to the anchor 102 of the tethering device 100 in the anchoring vessel, and the design of the anchor 102 may allow the anchor 102 to collapse as the distal tip of the tetherable guide-sheath 400 swallows the anchor 102 and the anchor 102 is pulled into the distal tether lumen 708 segment. In some implementations, the tether distal port 504 can have a large diameter at the tip where the anchor 102 is withdrawn to avoid additional friction. The retrieval of the anchor 102 of tethering device 100 may therefore be a smooth interaction having a reduced likelihood that the anchor 102 will catch on the distal tip or fracture on an edge of the distal tip of the tetherable guide-sheath 400. Traction can be applied to the tether 104 simultaneously as the tetherable guide-sheath 400 is advanced forward so that the tethering device 100 causes minimal trauma to the vessel. Once the tip of the tetherable-guide sheath 400 is advanced over guide tether 104 and reaching the anchor 102 in the ECA, the design of the tethering device 100 can allow the anchor 102 to collapse as the distal tip of the guide-sheath 400 swallows the anchor 102. In some implementations, the withdrawal of the anchor 102 can cause expansion of deflecting surface into the working lumen 410. At the end of the procedure, such reduction in working lumen diameter 410 can be acceptable. In some implementations, an outer diameter of the tetherable guide-sheath 400 minimally increases with the capture of the anchor 102 of the tethering device 100. For example, the distal region of the tetherable guide-sheath 400 can have an inner diameter of about 0.087" to 0.088" and can be enlarged to a diameter of about 0.100" to 0.120" although the size can vary and/or can be flared.

FIGS. 18-20 illustrate different configurations of an anchoring delivery system 10 having a tethering device 100 and a tetherable guide-sheath 400 configured to receive a working device 802 therethrough. FIG. 18 shows a tethering device 100 extending through a tether lumen 408 of a tetherable guide-sheath 400 and a working device 802 extending through a working lumen 410 of the tetherable guide-sheath 400. The anchoring delivery system 10 may include a combination of the tethering device 100 and the tetherable guide-sheath 400. For example, the anchoring delivery system 10 may be manufactured as a kit including at least the tethering device 100 and the tetherable guide-sheath 400. The kit can include one or more tethering devices 100 and one or more tetherable guide-sheaths 400, such as a first tetherable guide-sheath 400 having a first inner diameter and a second tetherable guide-sheath 400 having a second, larger inner diameter. In some implementations, the kit can include the tethering device 100 pre-assembled with one or more of a hypotube positioned over the tether 104 and the anchor 102 in a low profile configuration within a delivery tool. It should be appreciated that the tethering device 100 can be provided separately from the tetherable guide-sheath 400 such that it can be used with another appropriately sized commercial guiding sheath as described elsewhere herein. The different inner diameters of the tetherable guide-sheaths 400 can be used to receive different outer diameter working devices 802. In some implementations, the working lumen 410 of a first tetherable guide-sheath 400 can have an inner diameter that is 6 F and the working lumen 410 of a second tetherable guide-sheath 400 can have an inner diameter that is 8 F. The 6 F has an inner diameter of 0.071" and the 8 F has an inner diameter of 0.088". Thus, the tetherable guide-sheaths 400 can receive working devices having an outer diameter that is snug to these dimensions. It should be appreciated that the tetherable guide-sheath 400 can be OTW or RX, which will be described in more detail below.

During use, the tethering device 100 may be physically coupled with the tetherable guide-sheath 400, e.g., by tracking the tetherable guide-sheath 400 over the tethering device 100 and/or by locking the components together, as described below. When the tetherable guide-sheath 400 includes a centrally located tether distal port 504 distal to the mouth 508, the tether 104 of the tethering device 100 may extend distally from the tether distal port 504 to the deployed anchor 102 along the longitudinal axis passing through the body 402 of the tetherable guide-sheath 400. Furthermore, the anchoring delivery system 10 can include a working device 802, which may be packaged as part of the same kit or provided separately as its own kit, to be delivered to a target anatomy. During use, the working device 802 can be tracked through the tetherable guide-sheath 400 to exit the tetherable guide-sheath 400 through the mouth 508, the mouth 508 optionally located between the radiopaque markers 510, into the target anatomy. The target anatomy can bifurcate away from the anchoring anatomy. It should be appreciated that the anchoring delivery system 10 shown in FIG. 18 can include any of a variety of tethering devices described herein including a tethering device 100 incorporating an anchor 102 configured to take on a higher profile configuration.

Referring to FIG. 19, a distal end of an anchoring delivery system having a tethering device 100 in a tether lumen 408 of a tetherable guide-sheath 400 and a working device 802 in a working lumen 410 of the tetherable guide-sheath 400 is illustrated in accordance with an implementation. The tethering device 100 can include an anchor 102 configured to be released from constraint and expanded in the anchoring anatomy at a location distal to the tetherable guide-sheath 400. More particularly, the tether 104 can extend proximally from the deployed anchor 102 through the tether distal port 504 and within the tether lumen 408 to an exit port in the tetherable guide-sheath 400. Similarly, the working device 802 being delivered to the target anatomy can pass through the working port 506 and the working lumen 410 to a proximal exit point, e.g., at the proximal furcation 404. As shown, when the tether distal port 504 and the working port 506 are formed in a distal face 502 of the body 402, the tether 104 and the working device 802 can exit the tetherable guide-sheath 400 generally parallel to each other. The components may, however, diverge along different paths. For example, the tether 104 may extend distally into the anchoring anatomy and the working device 802 may extend distally into the target anatomy, which may bifurcate away from the anchoring anatomy. It should be appreciated that the anchoring delivery system shown in FIG. 19 can include any of a variety of tethering devices described herein including a tethering device incorporating an anchor configured to take on a higher profile configuration.

Referring to FIG. 20, a distal end of an anchoring delivery system having a tethering device 100 and a working device 802 in a same lumen of a tetherable guide-sheath 400 is illustrated in accordance with an implementation. When the tetherable guide-sheath 400 includes a working port 506 in the distal face 502 of the body 402 and one or more tether entry ports 504 in the side surface of the body 402, the tethering device 100 may extend laterally through the tether entry ports 504 into the anchoring anatomy and the working device 802 to be delivered to the target anatomy can extend distally from the distal face 502 along a longitudinal axis of the body 402. As described above, depending upon the tether distal port 504 through which the tether 104 is inserted, a different length of the tetherable guide-sheath 400 may be tracked into the target anatomy. For example, a segment of the tetherable guide-sheath 400 distal to the tether distal port 504 holding the tether 104 may be advanced into the target anatomy that bifurcates from the anchoring anatomy. Accordingly, the tether 104 and the segment of the tetherable guide-sheath 400 distal to the utilized tether distal port 504 may be pressed against the carina at which the anchoring anatomy and the target anatomy bifurcate. It should be appreciated that the anchoring delivery system shown in FIG. 20 can include any of a variety of tethering devices described herein including a tethering device incorporating an anchor configured to take on a higher profile configuration.

As shown in FIG. 20, tetherable guide-sheath 400 can include a single lumen in which at least one elongated structure can be received. For example, the tether lumen 408 and the working lumen 410 can be a same lumen running longitudinally through tetherable guide-sheath 400 from proximal furcation 404 to tether distal port 504 and working port 506. Thus, the tether 104 may enter a same lumen of tetherable guide-sheath 400 through the tether distal port 504 as the working device 802 enters through the working port 506, rather than being received by separate lumens of tetherable guide-sheath 400. Thus, working port 506 shown in FIG. 20 can also be the tether distal port 504.

According to some implementations, the length of the tetherable guide-sheath 400 is long enough to access the target anatomy and exit the arterial access site with extra length outside of a patient's body for adjustments. For example, the tetherable guide-sheath 400 can be long enough to access the petrous ICA from the femoral artery such that an extra length is still available for adjustment. The tetherable guide-sheath 400 can be a variety of sizes to accept various working devices 802 and can be accommodated to the operator's preference. For example, current MAT and SMAT techniques describe delivering aspiration catheters having inside diameters of 0.071-0.072 inches to an embolus during AIS. Accordingly, the working lumen 410 of the tetherable guide-sheath 400 can be configured to receive such aspiration catheters as the working device 802. It should be appreciated that the guide-sheaths described herein can be sized to receive other types of working devices besides aspiration catheters, such as stent delivery catheters. For example, the working lumen 410 can have an inner diameter of at least 6 French, or preferably at least 6.3 French to accommodate such working devices 802. The inner diameter of the tetherable guide-sheath 400, however, may be smaller or larger. In some implementations, the working lumen 410 can have an inner diameter of 7 French or 8 French to accommodate even larger working devices 802. In some implementations, the working lumen 410 can having inner diameter of 0.088" or 0.071" and thus, are configured to receive a working device 802 having an outer diameter that fits snug with these dimensions. Regardless of the length and inner diameter, the tetherable guide-sheath 400 is resistant to kinking during distal advancement through the vasculature.

Referring to FIG. 21, a perspective view of a tetherable guide-sheath is illustrated in accordance with an implementation. The tetherable guide-sheath 400 can be a rapid exchange (RX) type device. Accordingly, the tetherable guide-sheath 400 can include a hypotube 1102 extending distally from a connector 1104 at a proximal end 403. The hypotube 1102 can be coupled with the body 402 of the tetherable guide-sheath 400 at a joint between the connector 1104 and the tip 406. Furthermore, an exit port 1106 can be positioned distal from the joint. The exit port 1106 can connect with the tether lumen 408 in the body 402. Furthermore, the connector 1104 can connect with the working lumen 410 in the body 402.

Referring to FIG. 22, a sectional view, taken about line B-B of FIG. 20, of a tetherable guide-sheath is illustrated in accordance with an implementation. The body 402 of the tetherable guide-sheath 400 can include one or more lumens extending longitudinally toward the tip 406. For example, the body 402 can include the tether lumen 408 to receive the tether 104 of the tethering device 100. Furthermore, the body 402 can include the working lumen 410 to receive the working device 802 to be delivered through tetherable guide-sheath 400 to a target anatomy. The lumens 408, 410 can be sized to receive their respective working devices in a sliding fit. For example, the tether 104 can have an outer diameter of 0.014 inch and the tether lumen 408 can have an inner diameter in a range of 0.015-0.020 inch sufficient to receive the outer diameter of the tether 104. Similarly, the tether 104 can have an outer diameter of 0.035 inch and the tether lumen 408 can have an inner diameter in a range of 0.036-0.041 inch. The working lumen 410 may be similarly sized according to the working device 802 that will be delivered through it to the target anatomy.

Referring to FIG. 23, a sectional view, taken about line C-C of FIG. 20, of a tetherable guide-sheath is illustrated in accordance with an implementation. When tetherable guide-sheath 400 is an RX-type working device, the hypotube 1102 may have an inner diameter that is at least as large as the working lumen 410 in the body 402. For example, the working lumen 410 in the hypotube 1102 may have a diameter that is at least 0.001 inch larger than any working device 802 that it is intended to receive.

Figure 24:
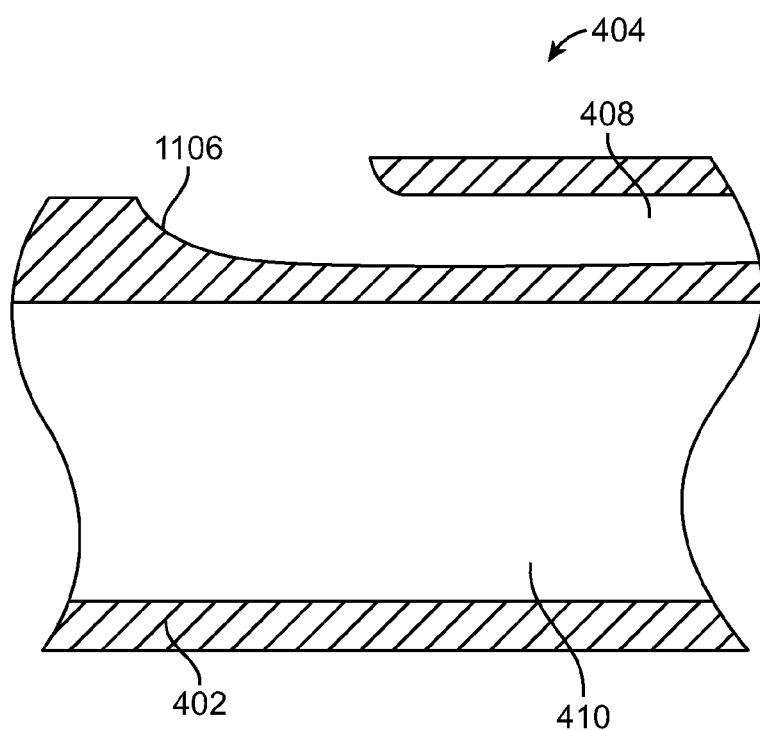
FIG. 24 illustrates a sectional view of a proximal end of the tether lumen of a tetherable guide-sheath, in accordance with an implementation.

Referring to FIG. 24, a sectional view of a proximal end of the tether lumen of a tetherable guide-sheath is illustrated in accordance with an implementation. When the tetherable guide-sheath 400 is an RX type device, the tether 104 of the tethering device 100 can exit the exit port 1106 in the body 402 distal to the hypotube 1102, which contains the working lumen 410 of the tetherable guide-sheath 400. Accordingly, the exit port 1106 may be considered to be the proximal furcation 404 in the tetherable guide-sheath 400, as it represents a location where the tether 104 and the working device 802 diverge from each other at a proximal location in the system. In practice, the exit port 1106 can be located within the patient, and thus, the tether 104 and the hypotube 1102 can emerge from the access site in a side-by-side manner. The tether lumen 408 and the working lumen 410 can extend along respective longitudinal axes that are parallel to each other near the exit port 1106. However, like the mouth 508 of the tetherable guide-sheath 400, the tether lumen 408 may be directed toward the exit port 1106 formed in the side surface of the body 402 such that the tether 104 exits the body 402 at an angle to the longitudinal axis of the tether lumen 408. This exit angle may be controlled by a radius used to form the exit port 1106.

Figure 25:
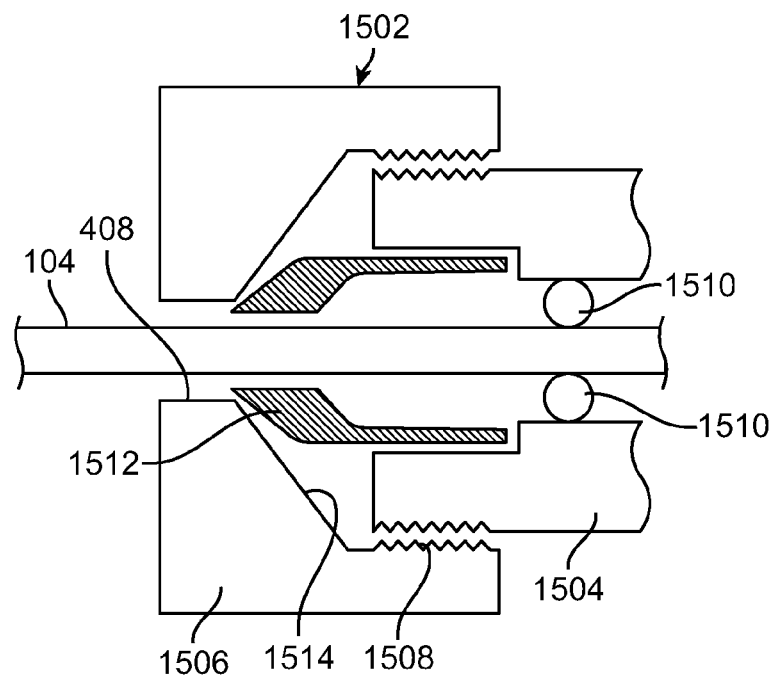
FIG. 25 illustrates a tether gripper of a tetherable guide-sheath, in accordance with an implementation.

As mentioned above, the anchoring delivery systems described herein can include a tether gripper 1502 to fasten the tether 104 of the tethering device 100 to the tetherable guide-sheath 400. FIG. 25 shows a tether gripper 1502 in accordance with an implementation. More particularly, one or more of the tethering device 100 or the tetherable guide-sheath 400 can include the tether gripper 1502 at a point of fixation between the components to attach the tetherable guide-sheath 400 to the tether 104 of the tethering device 100. Thus, the tetherable guide-sheath 400 can be reversibly attachable to the tether 104 at the point of fixation, which can be located proximal to the anchoring site at which the anchor 102 of the tethering device 100 is deployed within the anchoring anatomy. Accordingly, when the anchor 102 is deployed at the anchoring site and the tetherable guide-sheath 400 is attached to the tether 104 at the point of fixation, any proximal loading applied to the tetherable guide-sheath 400 distal to the fixation point can tension the tether 104 between the anchoring site and the point of fixation. Furthermore, this tension can have a straightening effect on the tetherable guide-sheath 400 to increase the column strength of the tetherable guide-sheath 400 and buttress the tetherable guide-sheath 400 against buckling or prolapse. Proximal loading on the tetherable guide-sheath 400 may result from, e.g., delivery or advancement of the working device 802 through the working lumen 410 of the tetherable guide-sheath 400 toward the target anatomy. Thus, the support provided by fixing the tether 104 to the tetherable guide-sheath 400 in combination with anchoring within the anatomy by the anchor 102 can prevent buckling of the tetherable guide-sheath 400 during working device 802 delivery, which can improve the ease and success of any interventional procedure performed through the tetherable guide-sheath 300.

In an implementation, the tether gripper 1502 is incorporated in the tetherable guide-sheath 400. One or both of the tether proximal port 414 or the working proximal port 416 can incorporate a tether gripper 1502. The tether gripper 1502 can include a clamping or clipping mechanism, such as a cleat, clamp, clip, etc., to fix the respective proximal port to a separate device passing through the port. The tether gripper 1502 can also include tape or suture to fix the respective proximal port to a separate device passing through the port. By way of example, the tether proximal port 414 can include an RHV capable of being tightened onto the runner tube 113 of the tethering device 100 when the runner tube 113 extends through the tether lumen 408 of the tetherable guide-sheath 400. As such, a fixation point may be formed between the tethering device 100 and the tetherable guide-sheath 400 at the tether gripper 1502 at some point proximal to the tether distal port 504. Again with respect to FIG. 25, the tether gripper 1502 can include a fixation mechanism having a gripper body 1504 that includes the tether lumen 408 and a cap 1506 that screws onto the gripper body 1504 via fastening threads 1508. Furthermore, the tether gripper 1502 can include one or more seals 1510 that surround the tether 104 when it is passed through the gripper body 1504, and thus, prevents fluid leakage through the tether gripper 1502. It will be appreciated that the seal 1510 is illustrated here without a backing surface, but in an implementation, the tether gripper 1502 can be designed such that the seal 1510 is squeezed when the cap 1506 is screwed onto the gripper body 1504. The seal 1510 can squeeze the tether 104 with enough force to fasten the tether 104 within the tether gripper 1502. In an implementation, the tether gripper 1502 can include a rotating hemostatic valve (RHV) that is configured to fix the tether 104 to the tetherable guide-sheath 400 without additional clamping features. For example, the RHV can be connected to the proximal furcation 404 and can be actuated to compress the seal 1510 that grips the tether 104.

In an implementation, the tether gripper 1502 can incorporate additional clamping features to grip the tether 104. For example, a collet 1512 component can be incorporated in the tether gripper 1502 such that the tether 104 passes through a central opening of the collet 1512 between the collet 1512 teeth. When the cap 1506 is screwed onto the gripper body 1504, a taper 1514 in the cap 1506 can press against the collet 1512 teeth forcing them against the tether 104. Accordingly, the tether 104 can be gripped with greater force than can be achieved using, e.g., an elastomeric seal 1510, and the tether gripper 1502 of the tetherable guide-sheath 400 can be used to fix the tetherable guide-sheath 400 to the tether 104.

Figure 26:
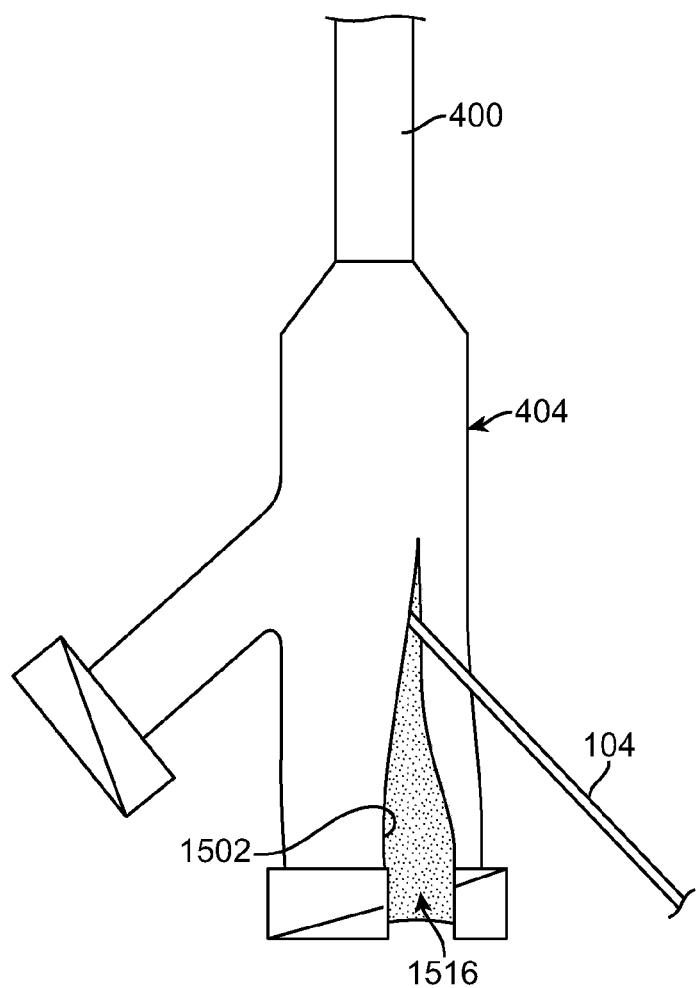
FIG. 26 illustrates a tether gripper of a tetherable guide-sheath, in accordance with an implementation.

FIG. 26 shows a further implementation of a tether gripper of a tetherable guide-sheath. The tether gripper 1502 of the tetherable guide-sheath 400 can be incorporated in the proximal furcation 404 of the tetherable guide-sheath 400. For example, the proximal furcation 404 can include a gripping feature to clamp the tether 104. For example, the tether gripper 1502 can include a slot 1516 formed through a sidewall of the proximal furcation 404 such that the tether 104 can be pulled laterally outward through the proximal furcation 404. Furthermore, by pulling the tether 104 out and upward through the slot 1516 with sufficient force, the tether 104 can be wedged toward a distal portion of the slot 1516. Accordingly, the tether gripper 1502 can pinch the tether 104 and prevent movement between the tether 104 and the tether gripper 1502. More particularly, the tether gripper 1502 can fix the tether 104 to the tetherable guide-sheath 400.

In the tether gripper 1502 implementations described above with respect to FIGS. 25-26, the tether lumen 408 may extend from the tether distal port 504 at the tip 406 of the tetherable guide-sheath 400 to the tether gripper 1502 connected to or incorporated in the tetherable guide-sheath 400.

Figure 27:
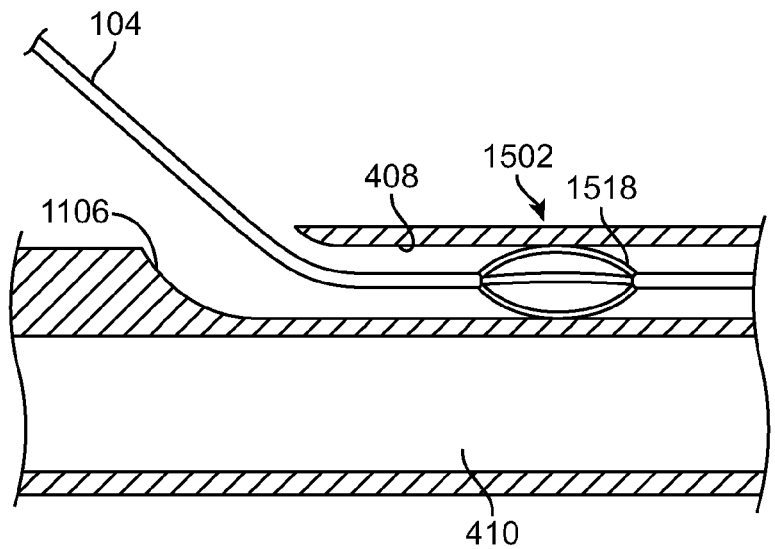
FIG. 27 illustrates a tether gripper of a tethering device, in accordance with an implementation.

As described above, the tetherable guide-sheath 400 can also be an RX type device such that the tether 104 can exit the tetherable guide-sheath 400 through the exit port 1106 within the patient anatomy as shown in FIG. 21. Thus, the exit port 1106 may not be reachable to fix the tether 104 to the tetherable guide-sheath 400 at the exit port 1106. FIG. 27 shows an implementation of a tether gripper 1502 of a tethering device 100 for use with an RX type guide-sheath. The tether 104 can be attached to the tetherable guide-sheath 400 proximal to the exit port 1106, e.g., using a clamp, clip, etc., to fasten the tether 104 to the body 402 of the tetherable guide-sheath 400. The distance between the fixation point and the exit port 1106 in such a case, however, may allow the tether 104 to bend relative to the tetherable guide-sheath 400 such that the tetherable guide-sheath 400 is not adequately buttressed against buckling. Accordingly, the tether gripper 1502 can be incorporated in the tether 104 to fix the tether 104 to the tetherable guide-sheath 400 within the tether lumen 408. For example, the tether gripper 1502 can be integrated in the tether 104 at a location distal to the exit port 1106. In an implementation, the tether gripper 1502 can include an expandable structure 1518 that can expand radially within the tether lumen 408 to press against an inner surface of the tether lumen 408 and lock the tether 104 to the tetherable guide-sheath 400 from moving slideably within the lumen 408. The expandable structure 1518 can be a self-expanding structure that is captured by a thin tubular sheath disposed over a proximal segment of the tether 104. More particularly, the thin tubular sheath can be retracted to expose the expandable structure 1518 and allow it to expand against the tether lumen 408 surface to lock the tether 104 to the tetherable guide-sheath 400. Furthermore, the thin tubular sheath can be advanced to capture the expandable structure 1518 and allow the tetherable guide-sheath 400 to be tracked over the tether 104 again.

The expandable structure 1518 of the tether gripper 1502 can be an inflatable member, such as a balloon, that is not self-expandable so-to-speak. More particularly, the tether 104 can have a tubular structure along a proximal segment. The tubular structure can have a proximal end 106 in fluid communication with the tether gripper 1502. The tether gripper 1502 can be connected to a syringe for inserting an inflation fluid into the tubular structure. Thus, the inflation fluid can be delivered into an inner volume of the expandable structure 1518 located at a distal joint of the tubular structure, causing the balloon to be inflated to press against the tether lumen 408 surface. The tubular structure can have a distal joint connected with a proximal end of a core wire. More particularly, the tether 104 can include a distal segment having a core wire extending from the distal joint of the tubular structure to the anchor 102. Accordingly, the tethering device 100 can include an anchor 102 at a distal joint 108, a core wire portion of the tether 104 extending proximally from the anchor 102, and a tether gripper 1502 portion extending proximally from the core wire portion. The tether gripper 1502 implementations described above are not intended to be limiting, but rather, illustrate that the tether gripper 1502 can be incorporated in one or both of the tethering device 100 or the tetherable guide-sheath 400 to fix the components of the anchoring delivery system 10 to each other during use.

Methods of Using an Anchoring Delivery System to Deploy a Working Device

As described above, advancement of a working tool such as a stent delivery system over a guidewire through an access sheath can create back and forth motion exacerbated by a laxity present in typical sheath systems. Upon meeting resistance, the stent delivery system can create tension that forces the entire delivery system downward (e.g. into the aorta) and laterally (e.g. against the vessel wall). Depending on the size of the vessel, there may be a greater or lesser effect than the prolapse or buckling into the aorta. The anchoring delivery systems described herein can address many of the issues that standard neurovascular delivery systems can create.

Figure 28:
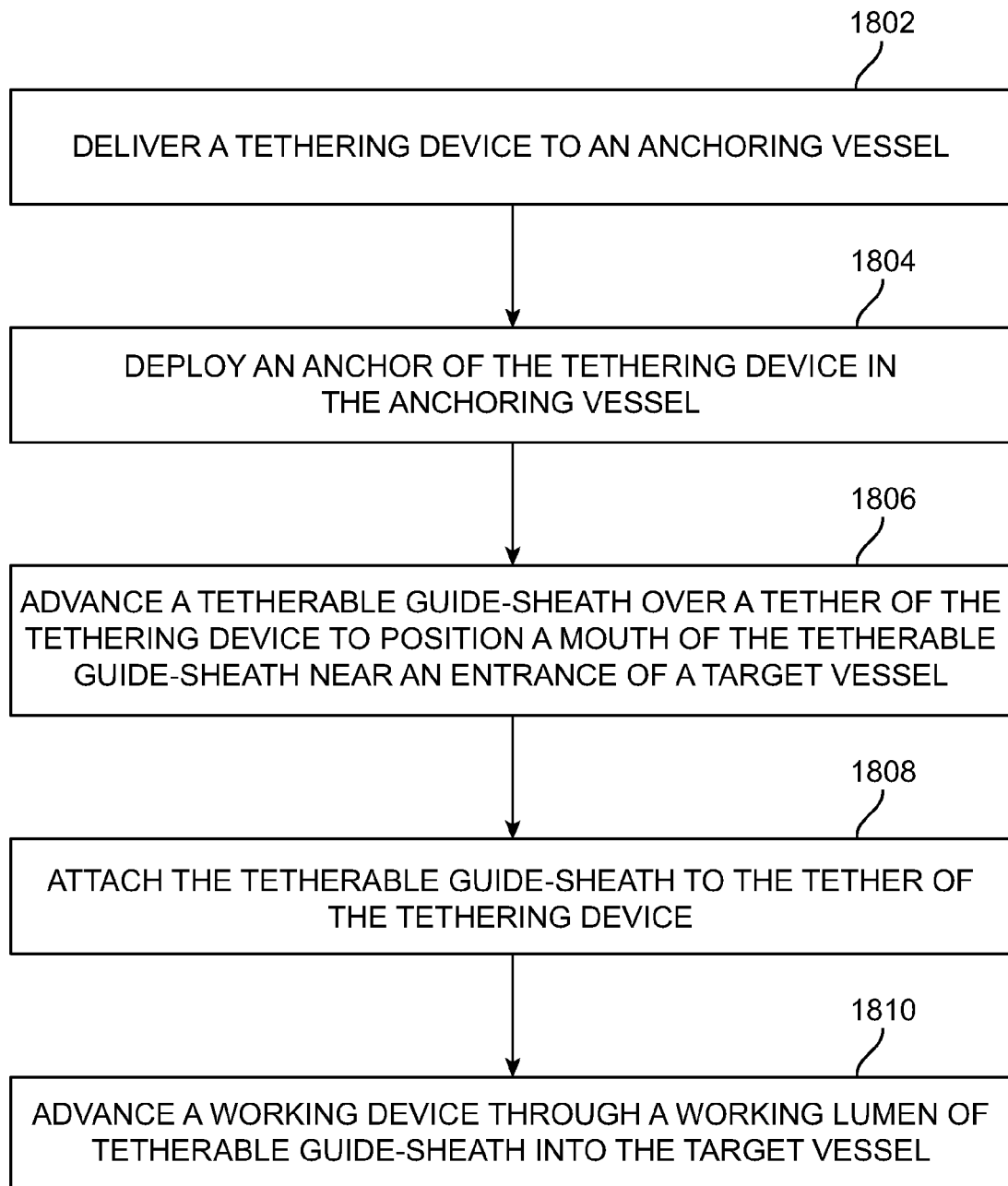
FIG. 28 illustrates a method of using an anchoring delivery system to deliver a working device.

Referring to FIG. 28, a method of using an anchoring delivery system to deliver a working device that is an implant delivery system is illustrated in accordance with an implementation. FIGS. 29A-29F illustrate operations of the method illustrated in FIG. 28. Accordingly, FIGS. 28-29 are described in combination below. It should be appreciated that the implant delivery system can vary and includes a standard neurovascular delivery system having a flow diverter or a stent implant.

An arterial access device 1902, such as a standard transfemoral sheath, can be inserted into an arterial access point such as the femoral artery. Referring to FIG. 29, the arterial access device 1902 is shown inserted via a percutaneous puncture into the common femoral artery (CFA), such as near the groin. In alternate implementations, other access points can be used such as radial artery access, brachial artery access, transcervical or transcarotid access to the CCA or proximal internal carotid artery (ICA), or any other access point. In some implementations, arterial access device 1902 has an inside diameter range of 3 to 10 French. For example, the transfemoral sheath illustrated in FIG. 21A can be a standard 7 French sheath size.

After inserting the arterial access device 1902, a finder tool set, which can include a guidewire (not shown), a microcatheter 1910, and/or a finder catheter 1908, can be inserted individually or in combination into the transfemoral sheath and advanced to an anchoring vessel 1904, e.g., an ECA, ICA, CCA, etc. For example, a guidewire can be advanced to the distal ECA, ipsilateral to a target vessel 1906, which may be the ICA, using conventional techniques known to persons having ordinary skill in the art. For example, the guidewire can be preloaded into a finder catheter 1908 and advanced to the aortic arch (AA). In some implementations, the finder catheter 1908 includes a hook-shaped distal section, such as in the case of a Vertebral, Hockey Stick, VTK shape, or LIMA pre-shaped catheter or the like. A distal end of the finder catheter 1908 can be manipulated and positioned at the brachiocephalic artery or right CCA. The guidewire can then be pushed up as far as possible to the anchoring vessel 1904, e.g., the distal ipsilateral ECA. A microcatheter 1910 can be advanced over the guidewire. Optionally, the finder catheter 1908 can be advanced over the guidewire and the microcatheter 1910 to an anchoring site of the anchoring vessel 1904, e.g., the ECA distal to a takeoff of the target vessel 1906.

At operation 1802, the tethering device 100 can be delivered to the anchoring vessel 1904. For example, still referring to FIG. 29A, the guidewire can be removed from the microcatheter 1910 and the tethering device 100 can be inserted into and advanced through a lumen of the microcatheter 1910 and the finder catheter 1908 until the anchor 102 is near the anchoring vessel 1904. As described above, the tethering device 100 can include an anchor 102, such as an expandable element that can anchor and/or fix into an artery with or without scaffolding the artery, and the anchor 102 can be connected to the tether 104, which includes an elongated member. The anchor 102 is not shown in FIG. 29A, since it is hidden within a distal region of the microcatheter 1910 placed in the anchoring vessel 1904. Thus, delivery of the tethering device 100 to the anchoring vessel 1904 can include advancement of the anchor 102 connected to the distal end of the tether 104 through the vasculature, and not necessarily deployment of the anchor 102 from the unexpanded state to the expanded state. Depending on the implementation, the tethering device 100 can include a pusher tube, such as a hypotube, extending over the tether 104 such that a distal end of the pusher tube is positioned adjacent a proximal end of the anchor 102, such as an anchor shown in FIGS. 5H-5K. The pusher tube can provide "pushability" to an otherwise floppy tether 104 such that the anchor 102 can be advanced through the microcatheter 1910 positioned within the vessel. A distal end of the pusher tube 109 can abut against the anchor 102 and urge it forward through a lumen of the microcatheter 1910. The tethering device 100 and the pusher tube 109 can be preloaded or otherwise assembled with a delivery tool configured to maintain the anchor 102 in a low profile configuration such that the anchor 102 can be inserted into a proximal end of the microcatheter 1910 and advanced to the distal anchoring vessel 1904 through the microcatheter 1910 lumen.

Figure 29B:
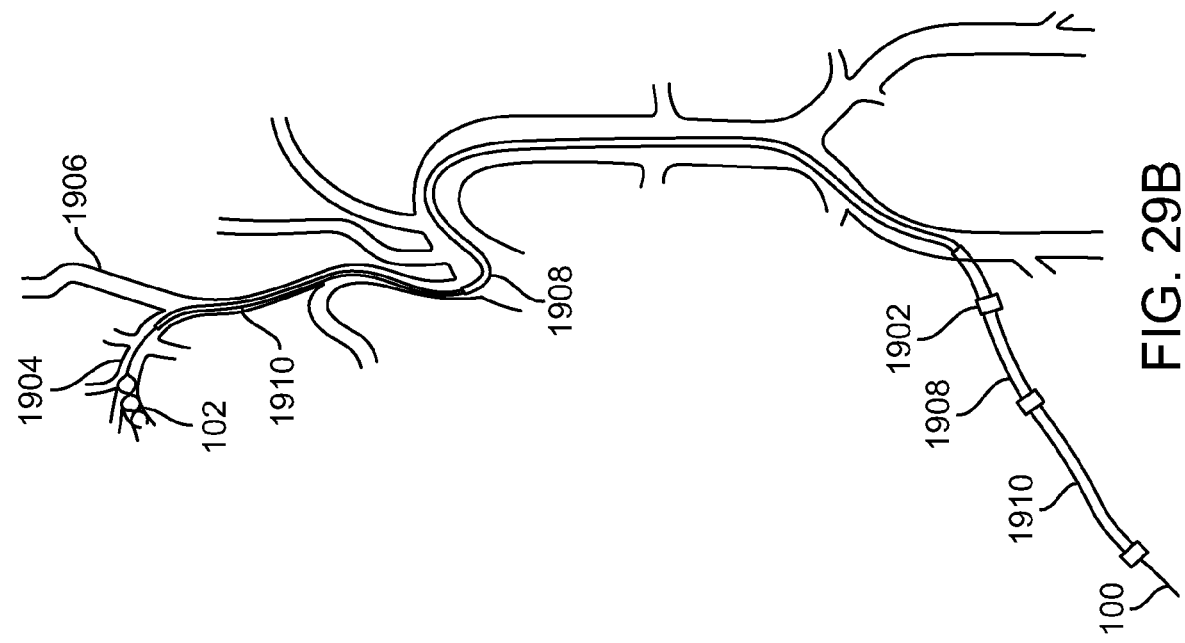
FIGS. 29A-29F illustrate operations of a method of using an anchoring delivery system to deliver a working device.
Figure 29A:
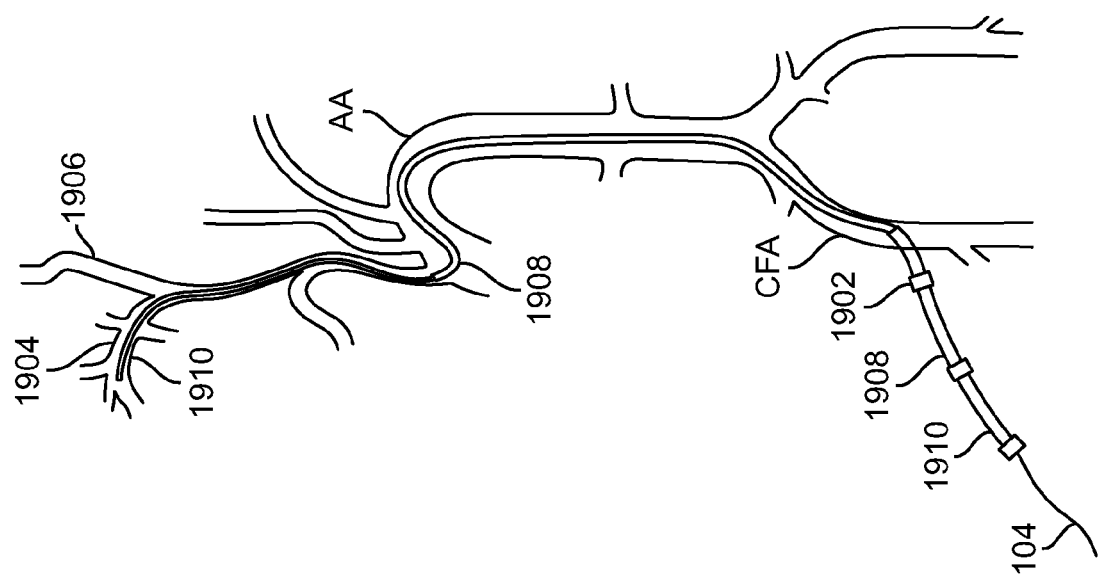

At operation 1804, the anchor 102 of the tethering device 100 can be deployed in the anchoring vessel 1904. Referring to FIG. 29B, the microcatheter 1910 can be retracted over the tethering device 100 to unsleeve and expose the anchor 102 of the tethering device 100. In the case of a self-expanding anchor 102 structure (see, e.g., FIG. 2B or 5J), the anchor 102 of the tethering device 100 can automatically deploy into the anchoring vessel 1904. Alternatively, in the case of an inflatable anchor 102 structure (see, e.g., FIG. 2C), the anchor 102 can be manipulated to deploy into the anchoring vessel 1904. More particularly, the anchor 102 can transition from the low profile, unexpanded state to the higher profile, expanded state to contact and anchor 102 at an anchoring site within the anchoring vessel 1904, e.g., distal to an entrance of the target vessel 1906.

Figure 29D:
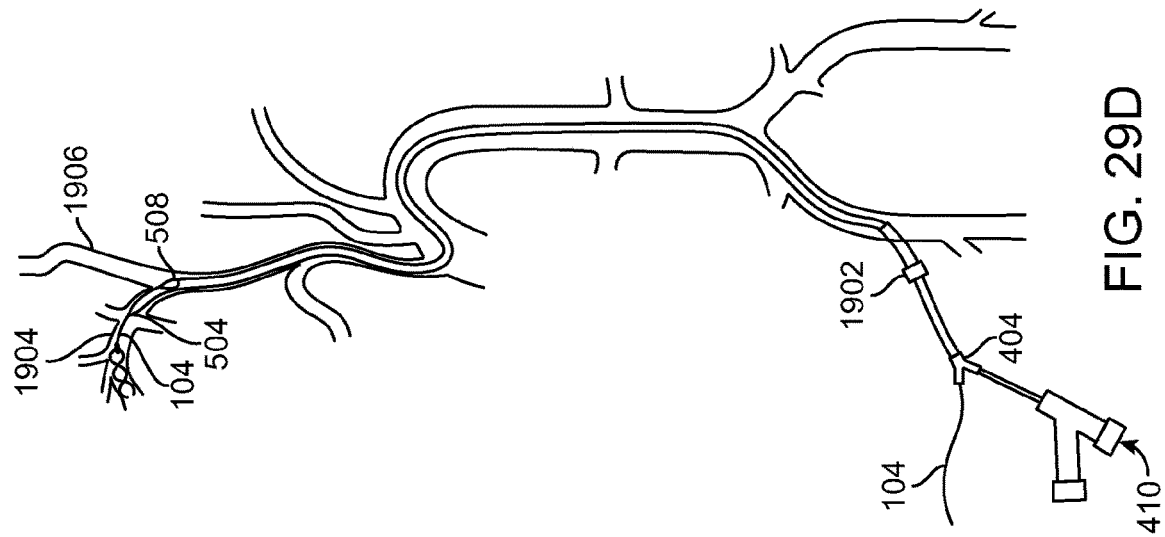
Figure 29C:
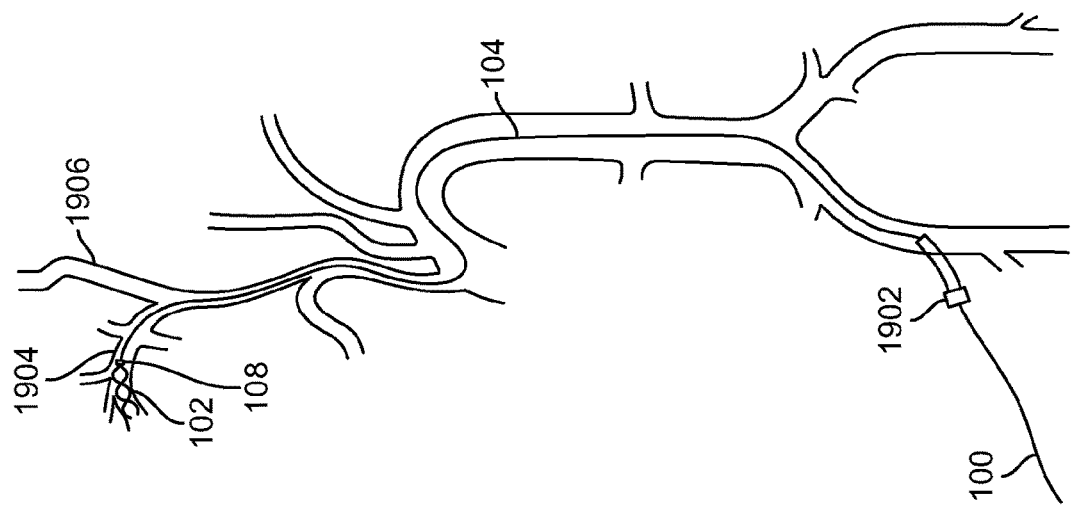

Referring to FIG. 29C, the microcatheter 1910 and/or the finder catheter 1908 can be removed through the arterial access device 1902 such that the tethering device 100 is anchored within the anchoring vessel 1904 and a proximal end of the tether 104 extends from the distal joint 108 through the arterial access device 1902. In some implementations, deployment of the anchor 102 and/or the deployed anchor 102 of the tethering device 100, e.g., expansion of a cage structure or inflation of a balloon anchor, or release of a wire device, may cause endothelial injury. Accordingly, application of tension to the tether 104 when the anchor 102 is deployed may create shear stress on the vascular tissue and/or distortion of the vascular anatomy at a location of the anchor deployment. However, minor vascular trauma in the anchoring vessel 1904 may be an acceptable tradeoff to get a supportive system in place when an aneurysm at risk for rupture or a stroke-inducing embolism or stenosis is the clinical indication for the target vessel 1906. It is also comprehended that the anchoring delivery system presented herein may also be used where the clinical syndrome is severe and the "cost" of trauma at an endothelial cell layer level in the anchoring vessel 1904 is acceptable in the judgment of the operator to achieve a desired outcome in the target vessel 1906. The anchoring delivery system may also be used for cases with or without aneurysm or stenosis where intracerebral access is needed, as compared to current transfemoral systems that simply do not allow such access.

At operation 1806, the tetherable guide-sheath 400 may be advanced over the tether 104 of the tethering device 100 to position the mouth 508 of the tetherable guide-sheath 400 near the entrance of the target vessel 1906. The tether 104 can include a length extending outside the patient. Referring to FIG. 29D, the proximal end 106 of the tether 104 (extending outside the patient) can be inserted into the tether distal port 504 of the tetherable guide-sheath 400 at a distal end of the tether lumen 408. Thus, the tether 104 can be received in the tether lumen 408. The length of the tether 104 extending outside the patient can be advanced through the tether lumen 408 until the proximal end of the tether 104 is once again available outside the proximal end of the sheath 400, for example by extending from the tether lumen 408 through the tether proximal port 414. Although the tether 104 is generally not pushable up through the vasculature without a pusher tube or some kind of delivery component, the tether 104 can have enough heft that it can be pushed through the tether lumen 408 of the sheath 400. Once the tether 104 extends out the tether proximal port of the sheath 400, the tetherable guide-sheath 400 can be advanced into the patient over the tether 104. The tethering device 100 between the anchor 102 and the proximal end of the tether 104 can be made taut such that the tether 104 of the tethering device 100 can function like a rail for advancing the tetherable guide-sheath 400 up the tether 104 until the working port 506, e.g., the mouth 508, of the tetherable guide-sheath 400 is positioned at the entrance to the target vessel 1906. The entrance to the target vessel 1906 can be, for example, a carotid bifurcation, and thus, the mouth 508 may provide access to the ICA. Thus, the tetherable guide-sheath 400 can be positioned to deliver a working device 802 toward the target vessel 1906 through the working lumen 410 in the proximal furcation 404 while the tether 104 of the tethering device 100 exits the tetherable guide-sheath 400 through the tether lumen 408 in the proximal furcation 404.

The tether 104 can provide the route for the tetherable guide-sheath 400, and the tether 104 can extend the length of the vascular path and exit near a distal end of the tetherable guide-sheath 400, e.g., through the tip 406 or a side of the tetherable guide-sheath 400 near the tip 406, leaving the working lumen 410 of the tetherable guide-sheath 400 available for petrous access. The length of the tether 104 can vary depending on the type of the tetherable guide-sheath 400. More particularly, the tetherable guide-sheath 400 can be an over-the-wire (OTW) type device, having an exit port at a proximal end, or a rapid exchange (RX) type device, having the exit port 1106 at a medial location between ends. Thus, in the case of an OTW tetherable guide-sheath 400, the tether 104 runs within the tether lumen 408 extending the length of the tetherable guide-sheath 400. Alternatively, in the case of the RX tetherable guide-sheath 400, the tether 104 runs within the tether lumen 408 extending from the tip 406 of the tetherable guide-sheath 400 to an exit port 1106 where the tether lumen 408 terminates on the outside of the tetherable guide-sheath 400. Since the length of the tether lumen 408, which receive the tether 104, can be shorter in an RX type than in an OTW type of tetherable guide-sheath 400, the length of the tether 104 of the anchoring delivery system may vary. In some implementations, an extension member having an elongated body and a distal end configured to couple with a proximal end 106 of the tether 104 can be attached and detached from the tether 104 to allow for the exchange of one type of tetherable guide-sheath 400, e.g., an RX type, for another type of tetherable guide-sheath 400, e.g., an OTW type, while maintaining the position of the tethering device 100 in the target anatomy.

Advancing the tetherable guide-sheath 400 over the tether 104 of the tethering device 100 can advance the tip 406 of the tetherable guide-sheath 400 through the entrance of the target vessel 1906 into the target vessel 1906. The tetherable guide-sheath 400 can have a stump tip. More particularly, the working port 506 can be distal to one or more tether entry ports 504 (see, e.g., FIGS. 12A and 13). The tether 104 of the tethering device 100 can be inserted through a tether distal port 504 on the side of the tetherable guide-sheath 400 proximal to the tip 406. For example, the tether 104 can be inserted into a tether distal port 504 near the tip 406 such that the portion of tetherable guide-sheath 400 distal to the utilized tether distal port 504 is short enough to be able to be advanced up the tether 104 of tethering device 100 through the arteries as well as long enough such that the keel-shaped intersection of the tetherable guide-sheath 400 and the tether 104 of the tethering device 100 exerts enough force to fix the tetherable guide-sheath 400 against the carina of the anchoring vessel/target vessel bifurcation.

In another implementation, the tether 104 of the tethering device 100 is inserted into the tether distal port 504 spaced further proximally away from the working port 506 at the tip 406. Thus, a longer portion of the tetherable guide-sheath 400 can extend into the target vessel 1906. The length of the long tip can vary depending on which tether distal port 504 the tether 104 of tethering device 100 is inserted into. That is, when the tether 104 is inserted into a more proximal tether distal port 504, then the distance between the utilized tether distal port 504 and the tip 406 of the tetherable guide-sheath 400 may be longer. In various implementations, the at least one tether distal port 504 is adjacent to one or more radiopaque markers 510 (e.g., a pair of radiopaque markers 510 may flank the utilized tether distal port 504) to indicate the location of the tether distal port 504 under fluoroscopy.

Figure 29F:
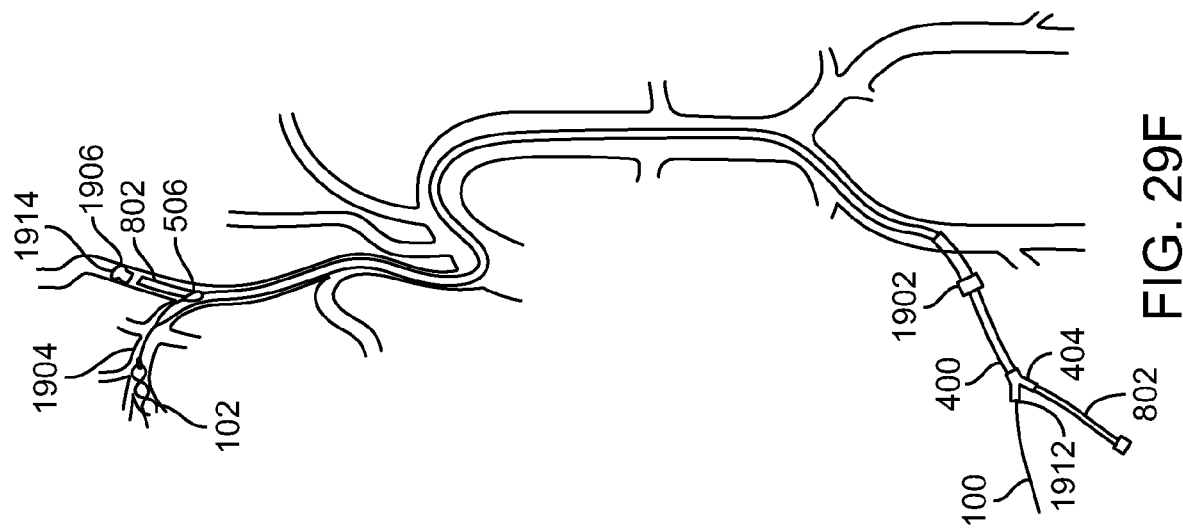
Figure 29E:
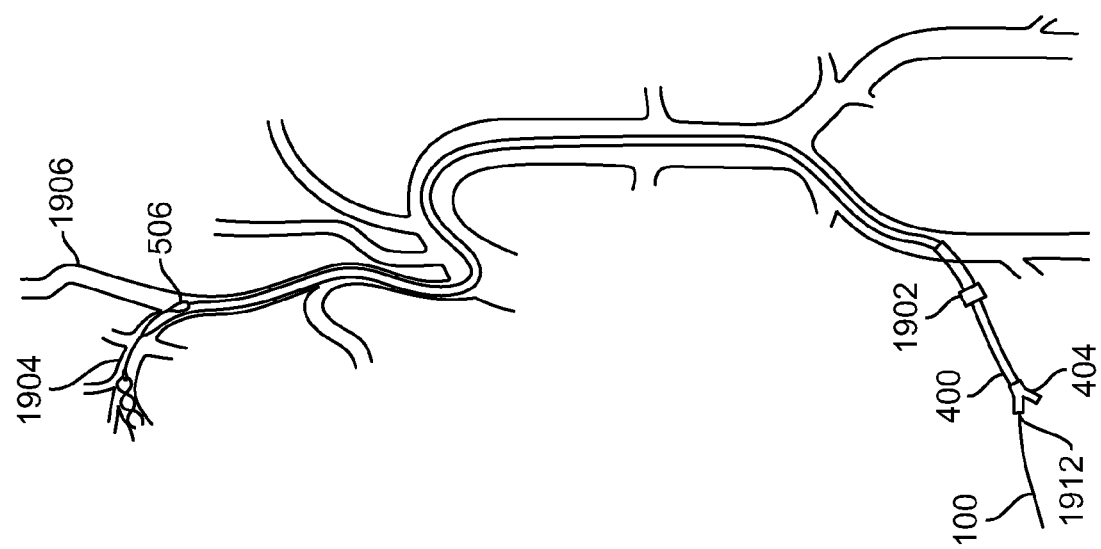

At operation 1808, the tetherable guide-sheath 400 can be attached to the tether 104 of the tethering device 100. Referring to FIG. 29E, the tether 104 can be fixed to the tetherable guide-sheath 400 at a point of fixation 1912 proximal to the entrance of the target vessel 1906. The tether 104 and the tetherable guide-sheath 400 can be fixed or locked into position relative to each other after the tetherable guide-sheath 400 is positioned at a carotid bifurcation with the mouth 508 providing access to the ICA, creating a tension in the tether 104 between the anchor 102 anchored in the target vessel 1904 distal to the target vessel 1906 takeoff and the tetherable guide-sheath 400 near the arterial access site. The tether 104 can be affixed to an outer surface or an inner surface of the tetherable guide-sheath 400 at the point of fixation 1912. The point of fixation 1912 can be outside of the patient anatomy, or in an implementation, the point of fixation 1912 can be within the patient anatomy, as may be the case when the tetherable guide-sheath 400 is an RX type device and the tether gripper 1502 is incorporated along the tethering device 100 (FIG. 19). The connection between the tetherable guide-sheath 400 and the tether 104 can be achieved using any of the fixation mechanisms described above, e.g., by the tether grippers 1502 described with respect to FIGS. 25-27. Such implementations, however, are illustrative and not limiting. For example, the tether 104 of the tethering device 100 can be attached to the tetherable guide-sheath 400 using conventional securement techniques such as by clamping, taping, or otherwise securing the tether 104 to the tetherable guide-sheath 400.

In an implementation, the tether 104 and the tetherable guide-sheath 400 are fixed by a clamp. For example, the clamp can be secured to a tab on the outside of the tetherable guide-sheath 400 or by other means of fixation. In alternative implementations, the tether 104 and the tetherable guide-sheath 400 are fixed by a hemostat, mosquito, suture, by application of a clear dressing or tape (e.g., Tegaderm™ or Opsite™), by a wire grasping element, by a closed RHV, or similar means of fixation. In additional various implementations, a non-clamping fixation technology can be used to avoid kink development of a mechanical fixation. For example, the tether 104 and the tetherable guide-sheath 400 can be fixed magnetically as described elsewhere herein. In addition, the tether 104 can be fixed within a lumen of tetherable guide-sheath 400 closer to the distal tip of tetherable guide-sheath 400 using a small interlocking detent within the tetherable guide-sheath 400. In an implementation, the tether gripper 1502 includes a balloon that is inflated within the tetherable guide-sheath 400 to pin the tether 104 within the tether lumen 408 and lock the relationship of the tether 104 to the tetherable guide-sheath 400. In some implementations, the tether 104 can be designed with at least one protrusion, e.g., a bulge formed around the tether 104, that engages with the tether lumen 408 of the tetherable guide-sheath 400. The bulge can be configured to engage the tether lumen 408 when stationary and can deflate when pushed forward. In an implementation, the tether 104 will not stretch, or may only minimally stretch, when pulled on.

At operation 1810, a working device 802 can be advanced through a working lumen 410 of the tetherable guide-sheath 400 toward the target anatomy. As described elsewhere herein, the working devices delivered through the guide sheaths described herein can vary and are not intended to be limiting. For example, the working device 802 can include a guidewire, balloon, advanced catheter, stent, flow diverter, coil, etc. as well as delivery devices configured to deliver stents, flow diverters, coils, etc. After the tetherable guide-sheath 400 is delivered to the anchoring vessel/target vessel junction, e.g., the ECA/ICA bifurcation, angiography can be performed through the tetherable guide-sheath 400 to allow full opacification of the cerebral vasculature. Referring to FIG. 29F, the operator can then deliver the working device 802 into the entrance of the target vessel 1906 and proceed with a preferred approach to the treatment site aided by the anchoring provided by the fixed tethering device 100 and tetherable guide-sheath 400, i.e., the anchoring delivery system. The support provided by the anchoring delivery system 10 can allow some approaches to be performed when they otherwise could not have been possible because of tortuous anatomy either at the great vessels and/or at the intracranial vasculature that tend to result in kinking and prolapse of typical sheaths as the working device is advanced distally. Moreover, the additional guide support can allow procedures to be completed more quickly, consistently and simply than routine interventional approaches and with greater precision and accuracy.

For example, using an approach to treat a target site that is an aneurysm or stenosis at the M1 segment (one in a main stem of middle cerebral artery), the working device 802 can be an implant delivery system delivered through the working lumen 410 of the tetherable guide-sheath 400 to a target site 1914 in the target vessel 1906. Delivery can be facilitated by the anchoring of the tethering device 100 and tethering of the tetherable guide-sheath 400, which tensions the tether 104 between the anchoring site and the point of fixation 1912 as the working device 802 advances through the mouth 508 into the distal target vessel 1906. Accordingly, commercially available 6 French intracranial catheter families which have up to 0.072 inch inner diameters for maximum diameter and stent delivery capability would be compatible with a 7 or 8 French tetherable guide-sheath 400.

In various implementations, once the working device 802, e.g., a stent delivery system, exits the mouth 508 of tetherable guide-sheath 400 and is in the ICA, the fixation of the tether 104 to the tetherable guide-sheath 400 can be relaxed. The carina formed between the working device 802 and the tetherable guide-sheath 400 can be advanced against the carina of the anchoring vessel/target vessel junction, e.g., the carotid bifurcation, to provide an additional point of securement at the bifurcation. This carina-to-carina cinching between the device junction and the anatomical junction can reestablish the fixation of the tethering device 100 and the tetherable guide-sheath 400, eliminating the possibility of both upward motion of the system and downward buckling or prolapsing of the tetherable guide-sheath 400 within the CCA or brachiocephalic artery. If a subsequent device, e.g., a balloon angioplasty device or another tethering device 100, is advanced out of the working device 802, a reaction force can be created when that device meets resistance. The reaction force can act on the working device 802 and may press against the tetherable guide-sheath 400. In the present system, however, the force should not reach the area of the aortic arch where prolapse is typical in standard systems because of the anchoring of the tethering device 100 and the fixation of the tether 104 to the tetherable guide-sheath 400 as well as the carina-to-carina cinching. The opposite reaction force can be counteracted. For example, when a stent delivery catheter is actuated to deploy the stent at the target location the pull can cause the tetherable guide-sheath 400 to ride upward in the vessel. The carina-to-carina cinching can prevent this upward motion. In essence, the tetherable guide-sheath 400 is locked into its relative position in the vasculature and provides a fulcrum for advancing subsequent devices, e.g., catheter systems and interventional devices, into the distal vessels of the neurovasculature.

In an implementation, after the target site 1914 has been successfully treated, e.g., by installing a stent, flow diverter, or stent-assisted coil, all wires, retrievable structures, and catheters can be removed from the tetherable guide-sheath 400, leaving the anchoring delivery system (the tethering device 100 and the tetherable guide-sheath 400). The fixation between the tethering device 100 and the tetherable guide-sheath 400 can be removed. For example, the tether 104 can be disengaged from the tether gripper 1502. Thus, the tetherable guide-sheath 400 can be advanced over the tether 104 to the anchor 102 deployed in the anchoring vessel 1904, e.g., the ECA. In some implementations, traction on the tether 104 can be applied to keep the tethering device 100 in position and to minimize trauma to the anchoring vessel as the tetherable guide-sheath 400 is advanced. The tetherable guide-sheath 400 can be advanced over the tether 104 to capture the anchor 102. That is, the tetherable guide-sheath 400 can be advanced to capture the anchor 102 within the tether lumen 408. Accordingly, the anchor 102 can be collapsed towards its lower profile configuration and the anchor 102 can be disengaged from the anchoring vessel 1904. The anchoring delivery system can then be retracted from the patient anatomy through the arterial access by removing tetherable guide-sheath 400 and the captured anchor 102 from the target anatomy. In an implementation, the tetherable guide-sheath 400 can be removed from the patient, leaving the deployed tethering device 100 in place, and a separate catheter, e.g., a microcatheter, can be advanced over the tether 104 to capture the anchor 102 and retrieve the tethering device 100 from the patient.

The method described with respect to FIG. 28 is illustrative, and one skilled in the art may extrapolate from this description other methods of using the anchoring delivery system to effectively deliver working device(s) to distal regions of tortuous and complex anatomies. Several such methods are described in the implementations below.

Figure 31B:
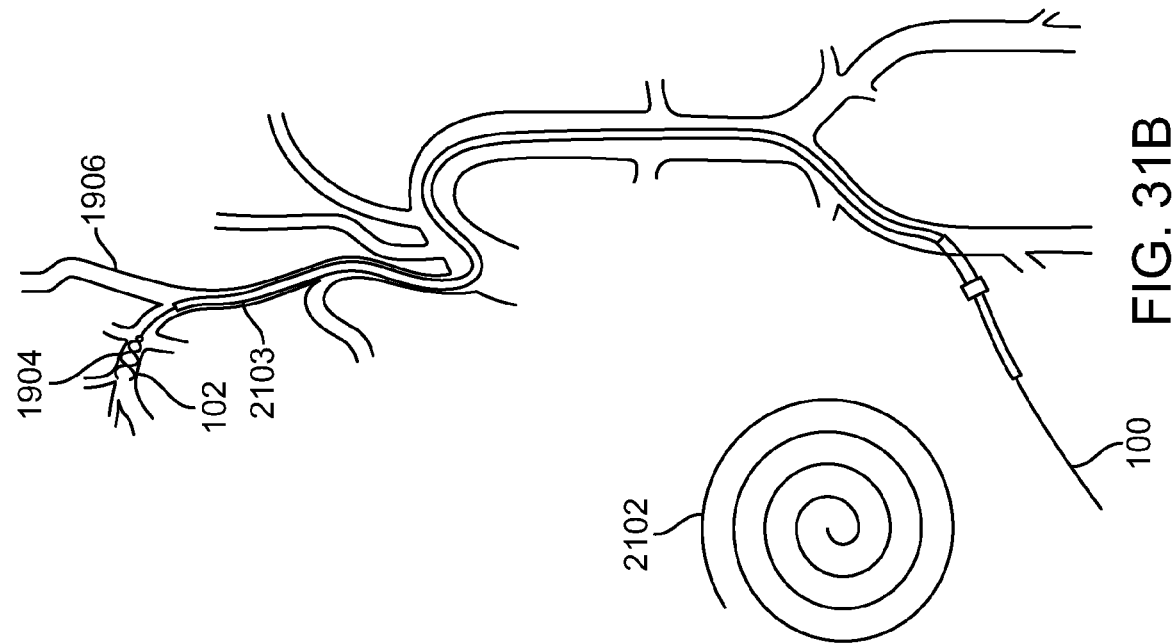
FIGS. 31A-31D illustrate operations of a method of using an anchoring delivery system to deliver a working device, in accordance with an implementation.
Figure 31A:
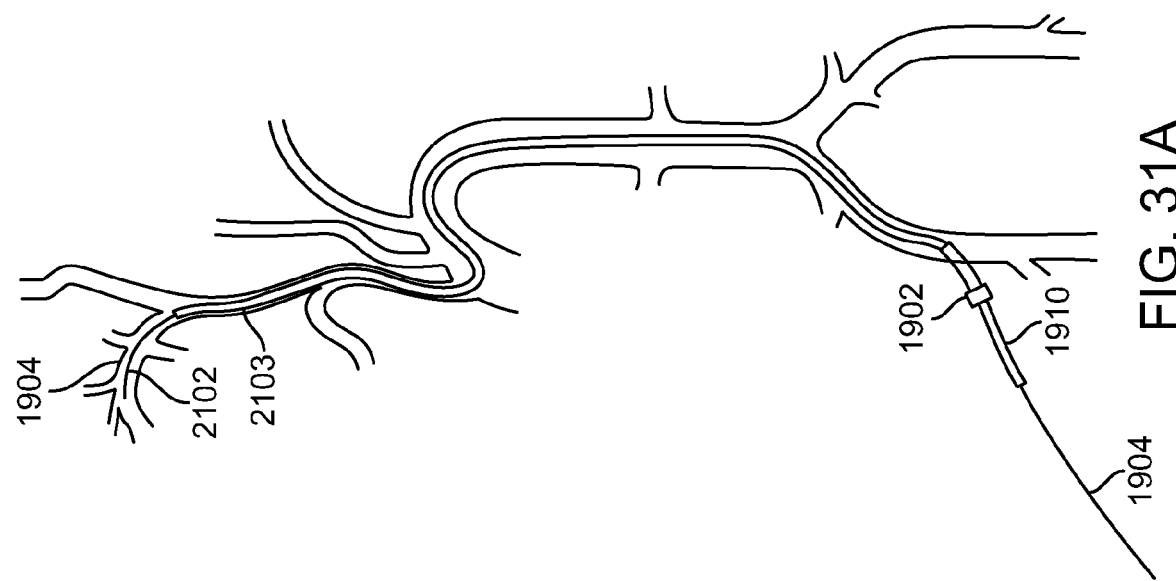

Referring to FIG. 31A, preparation of a patient may be similar to that described above. For example, an arterial access device 1902, such as a standard transfemoral sheath, can be inserted into an arterial access point such as the femoral artery. At operation 2002, a guidewire 2102 can be delivered through the arterial access device 1902 to the anchoring vessel 1904. Subsequently, at operation 2004, a catheter 2103, such as a microcatheter 1910 or a finder catheter 1908, can be delivered over the guidewire 2102 into an anchoring vessel 1904 of a target anatomy. In an implementation, the catheter 2103 can be preloaded with the guidewire 2102, and thus, the guidewire 2102 and the catheter 2103 can be advanced simultaneously. The guidewire 2102 can extend at least the length of the catheter 2103 and can be independently maneuverable within the catheter 2103 to lead the guidewire/catheter system to the anchoring vessel 1904. The coaxial system can be moved as a unit and each part can be manipulated independently depending on anatomical requirements and operator preferences. In particular implementations, a finder catheter 1908 (not shown in this figure) can also be positioned as part of the guidewire/catheter system. Thus, a route for the tethering device 100 can be established by the guidewire 2102 and one or more catheters 2103.

Referring to FIG. 31B, at operation 2006, the guidewire 2102 is exchanged for the tethering device 100. The guidewire 2102 can be removed from a lumen of the catheter 2103 and the tethering device 100 can be inserted into the catheter 2103 outside of the body 402 using an insertion tool. Insertion tools are known, for example, to insert a retrievable structure into a patient anatomy during a SMAT procedure, a stent during a balloon angioplasty procedure, or to insert a flow diverter or stent for stent-assisting coils to treat an aneurysm or stenosis. It is also possible that the tethering device 100 is already preloaded in the catheter system and the entire catheter 2103 with the tethering device 100 is inserted into the catheter 2103 instead of loading the tethering device 100 into the catheter 2103 without an outer sheath.

At operation 2008, the anchor 102 of the tethering device 100 can be deployed in the anchoring vessel 1904, e.g., the ECA. That is, the anchor 102 can be deployed at an anchoring site in the anchoring vessel 1904 distal to the entrance of the target vessel 1906. Deployment of the anchor 102 can include a standard "pin and pull" technique to keep the anchor 102 in a fixed position and prevent jumping of the device while the catheter 2103 is pulled back to unsleeve the anchor 102.

Figure 31D:
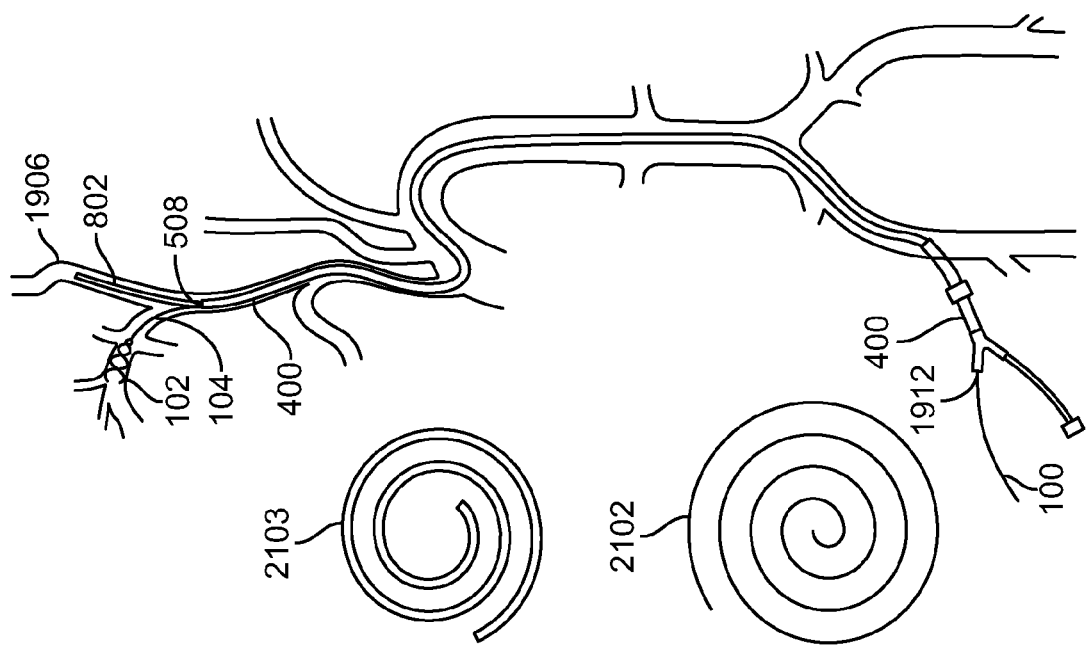
Figure 31C:
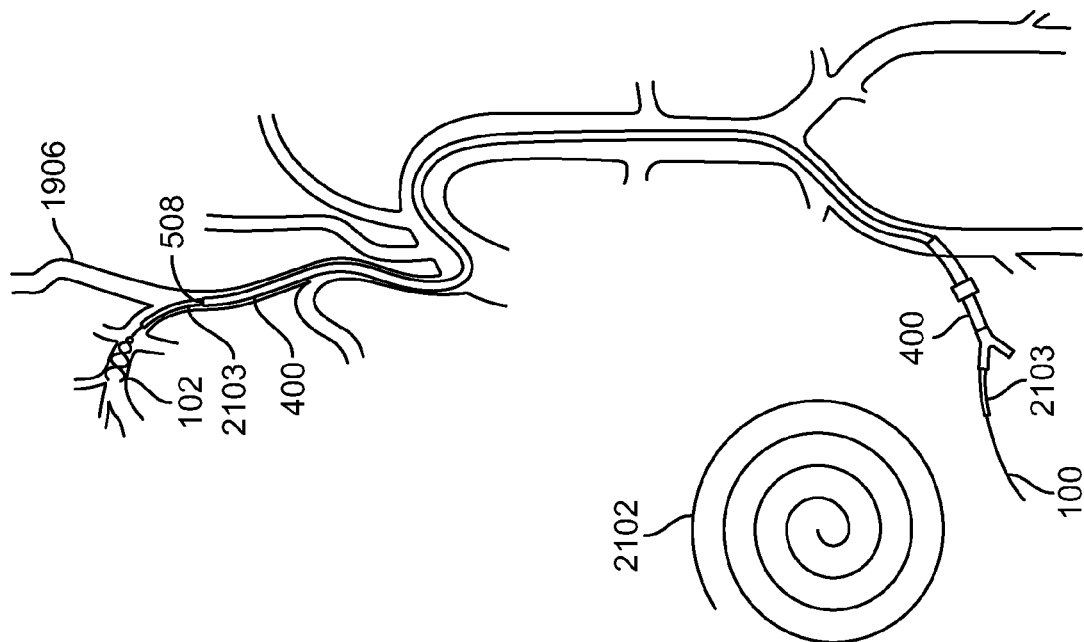

Referring to FIG. 31C, at operation 2010, the tetherable guide-sheath 400 is advanced over the catheter 2103 to position the mouth 508 of the tetherable guide-sheath 400 near an entrance of a target vessel 1906. That is, the tetherable guide-sheath 400 may include a tether lumen 408 to receive both the catheter 2103 and the tether 104 to allow the tetherable guide-sheath 400 to be tracked over an outside of the catheter 2103. Using the tethering device 100 and the catheter 2103 as support, the tetherable guide-sheath 400 can be advanced into the CCA up to the ECA/ICA bifurcation. Advancement of the tetherable guide-sheath 400 leverages the support of the tandem tether 104 and catheter 2103 combination, as well as the pulling force that the anchor 102 of the tethering device 100 provides when fully deployed in the ECA. The tetherable guide-sheath 400 can be advanced to the ECA/ICA bifurcation and a mouth 508 of the tetherable guide-sheath 400 may be directed towards the targeted vessel 1906, e.g., the ICA. The combination of the catheter 2103 and the tether 104 may provide sufficient column strength to reduce the likelihood of prolapse of the tetherable guide-sheath 400 into the ascending aorta, and to direct the tetherable guide-sheath 400 into the brachiocephalic as described in more detail above.

Referring to FIG. 31D, at operation 2012, the catheter 2103 can be removed from the tetherable guide-sheath 400. The tether 104 of the tethering device 100 can allow the catheter 2103 to be removed by pulling the catheter 2103 proximally. This differs from other techniques that require long wires and long wire exchanges. After the catheter 2103 is removed, the tetherable guide-sheath 400 can be coaxially located over the tethering device 100. The mouth 508 of the tetherable guide-sheath 400 can be adjusted, e.g., the tetherable guide-sheath 400 may be torqued, to direct the mouth 508 toward the entrance of the target vessel 1906, e.g., the ICA or another target vessel 1906.

At operation 2014, the tetherable guide-sheath 400 can be attached to the tether 104 of the tethering device 100 at a point of fixation 1912 proximal to the entrance of the target vessel 1906. For example, an RHV (not shown) connected to a connector of the proximal furcation 404 of the tetherable guide-sheath 400 can be tightened to lock the tether 104 of the tethering device 100 to the tetherable guide-sheath 400. Optionally, another securement device, e.g., a tether gripper 1502 incorporated in the tetherable guide-sheath 400 and/or the tethering device 100, a locking element, a clamp, or another clamping device, can be actuated to grip the tether 104 and lock the tether 104 to the tetherable guide-sheath 400. Thus, the tetherable guide-sheath 400 can become tethered to the deployed anchor 102 of the tethering device 100 by the tether 104.

At operation 2016, a working device 802 can be advanced through a working lumen 410 of the tetherable guide-sheath 400. For example, a delivery catheter can be advanced into the entrance of the target vessel 1906 as described above. Delivery of the working device 802 can cause a reaction force to be applied to the tetherable guide-sheath 400 between the anchoring site and the point of fixation 1912, and the reaction force may thus tension the tether 104 between the anchoring site and the point of fixation 1912. Accordingly, the anchoring delivery system can buttress the working device 802 against back-out and/or prolapse to facilitate delivery to a distal portion of the target vessel 1906. The anchoring delivery system can provide dual anchoring points, for example, at the ECA and the petrous carotid, that allows the guide-sheath to be pulled into position rather than "pushed" upstream. Further, the anchoring delivery system can allow for single operator ease of use in a rapid exchange fashion.

Figure 32:
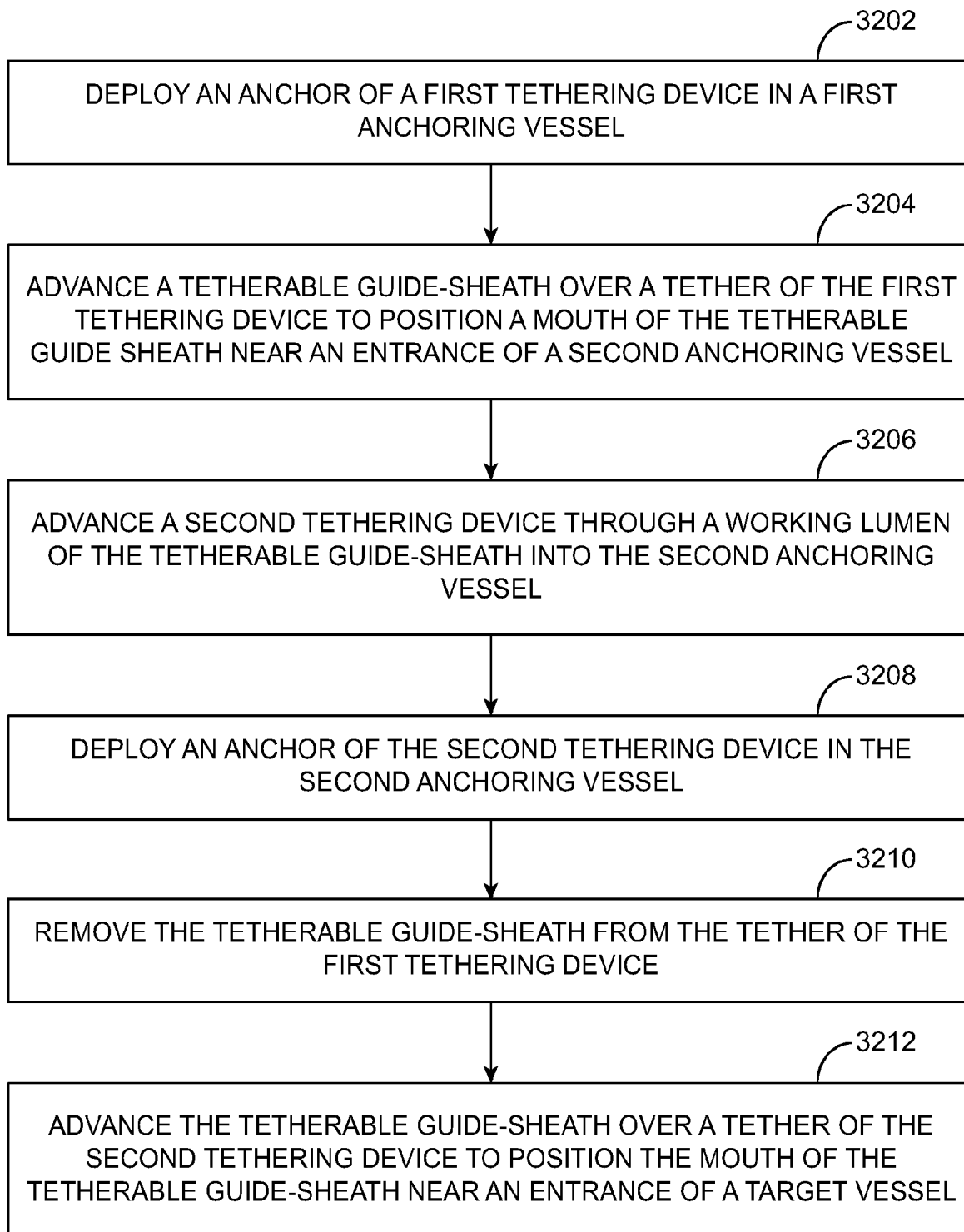
FIG. 32 illustrates a method of using several anchoring delivery systems to gain access to a target vessel, in accordance with an implementation.
Figure 33B:
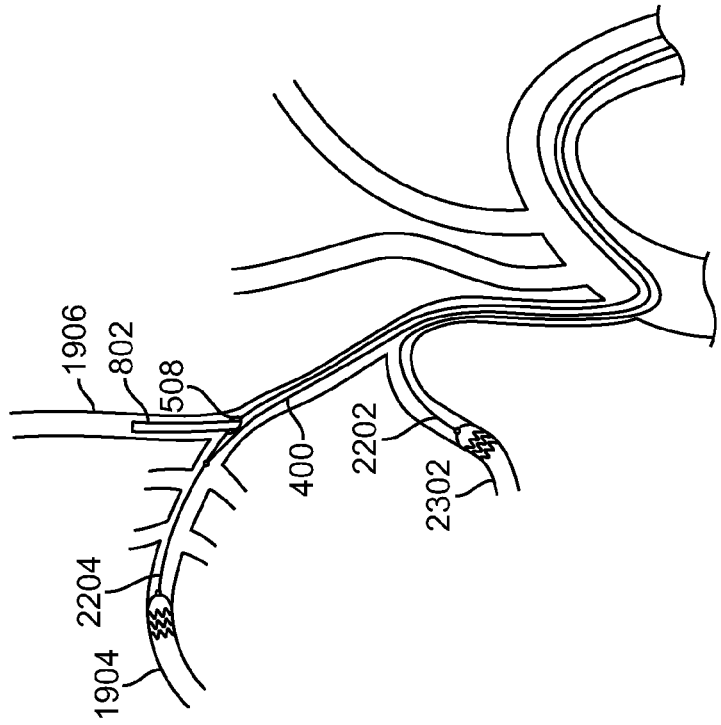
FIGS. 33A-33B illustrate operations of a method of using several anchoring delivery systems to gain access to a target vessel, in accordance with an implementation.
Figure 33A:
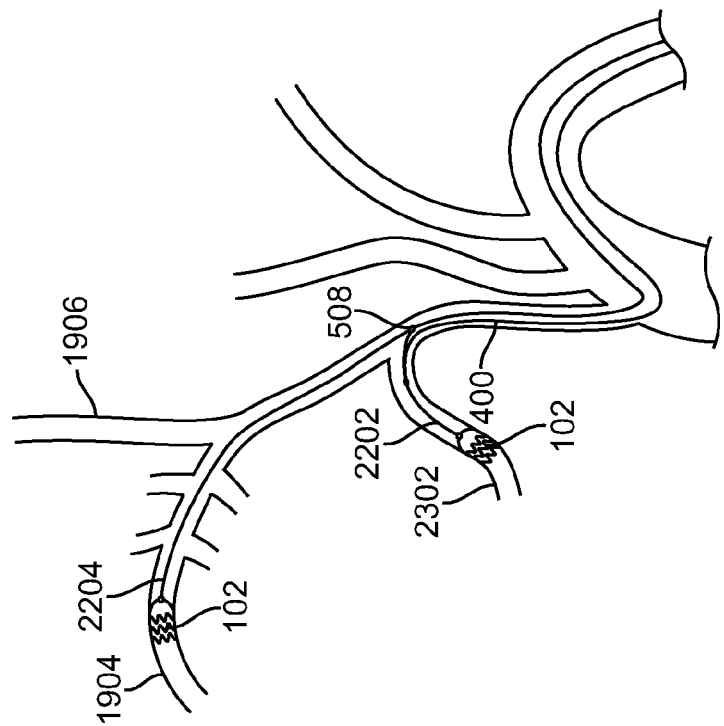

Referring to FIG. 32, a method of using several anchoring delivery systems to gain access to a target vessel is illustrated in accordance with an implementation. FIGS. 33A-33B illustrate operations of the method illustrated in FIG. 32. Accordingly, FIGS. 32-33 are described in combination below.

Figure 30:
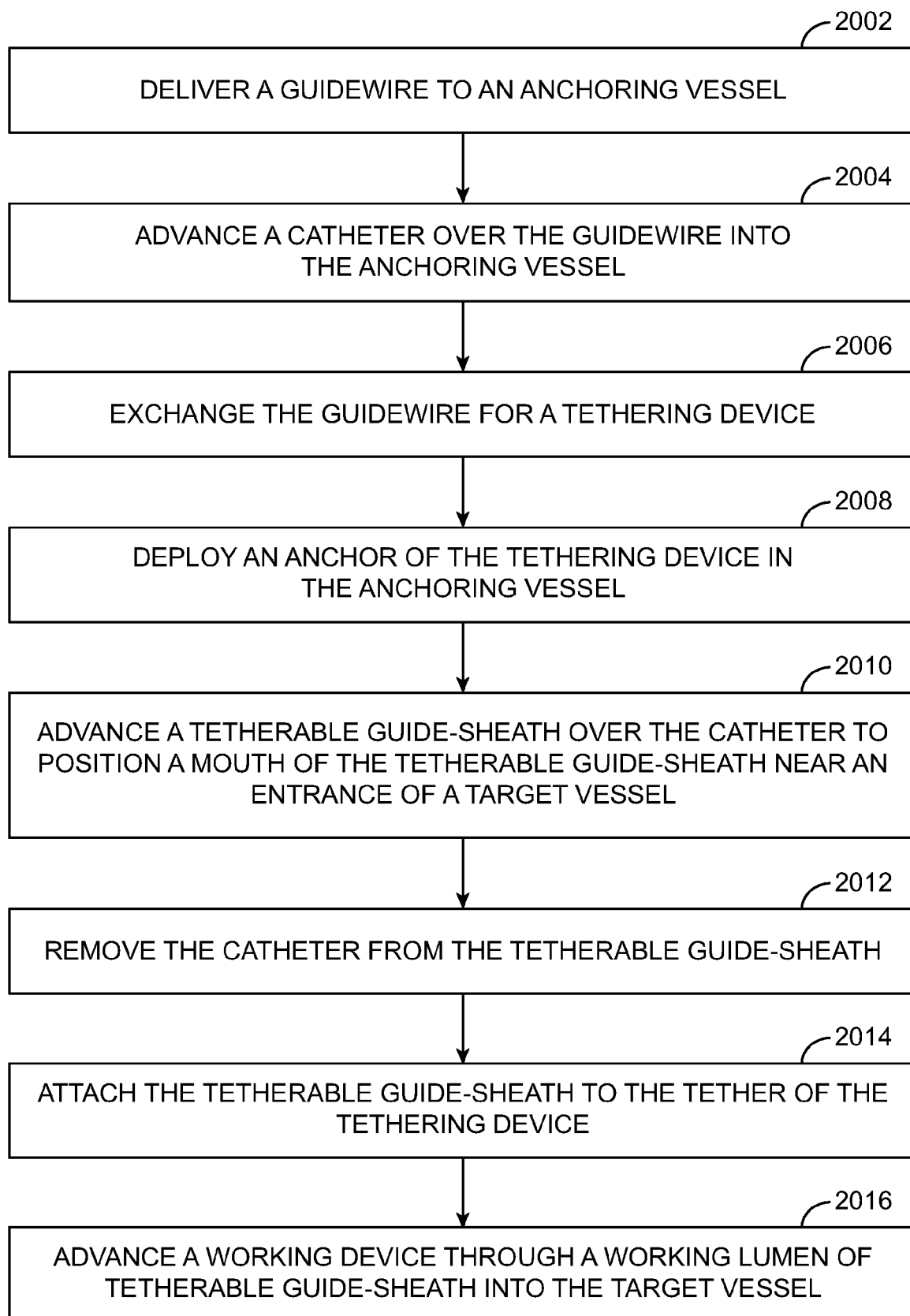
FIG. 30 illustrates a method of using an anchoring delivery system to deliver a working device, in accordance with an implementation.

The method of FIG. 32 can include operations similar to those described above. For example, at operation 3202, an anchor 102 of a first tethering device 2202 can be deployed in a first anchoring vessel 2302. Referring to FIG. 33A, the first tethering device 2202 can be comparable to the tethering device 100 described above. Thus, the operations leading up to and including operation 3202 can be similar to those leading up to and including operation 1802 of FIG. 28, or those leading up to and including operation 2008 of FIG. 30. In an implementation, the first anchoring vessel 2302 is a vessel proximal to the anchoring vessel 1904 used to reach a target vessel 1906. For example, the first anchoring vessel 2302 can be an ipsilateral subclavian and can be used as a stepping stone when an operator encounters challenging anatomies and is unable to reach the preferred anchoring vessel 1904, e.g., the ECA, with a preferred guidewire/catheter system "finder set". In the event that the operator cannot advance the finder set to the preferred anchoring vessel 1904, the finder set may instead be advanced into the first anchoring vessel 2302, where the anchor 102 of first tethering device 2202 can be deployed to provide an anchor point for the tetherable guide-sheath 400.

At operation 3204, a tetherable guide-sheath 400 can be advanced over a tether 104 of the first tethering device 2202 to position a mouth 508 of the tetherable guide-sheath 400 near an entrance of the a second anchoring vessel 1904. Thus, the operations leading up to and including operation 3204 can be similar to those leading up to and including operation 1806 of FIG. 28, or leading up to and including operation 2010 of FIG. 30.

At operation 3206, a second tethering device 2204 can be advanced through a working lumen 410 of the tetherable guide-sheath 400 into the second anchoring vessel 1904. That is, using the anchoring support of the first tethering device 2202 and the tetherable guide-sheath 400, the second tethering device 2204 can be advanced through a working lumen 410 of the tetherable guide-sheath 400 into the second anchoring vessel 1904, e.g., the ECA. The second tethering device 2204 can include a second anchor 102 attached to a second distal end of a second tether 104, and thus, can be similar in some or all respects to the first tethering device 2202. That is, the first and second tethering devices 2202, 2204 can be duplicates of the tethering device 100 described above. The second anchoring vessel 1904 can be similar to the target vessel 1906 described above, in that the second anchoring vessel 1904 can branch away from the first anchoring vessel 2302 (or vice versa) like the target vessel 1906 branches from the anchoring vessel 1904 in the above description. At operation 3208, the second anchor 102 of the second tethering device 2204 can be deployed in the second anchoring vessel 1904.

Referring to FIG. 33B, the tetherable guide-sheath 400 can be relocated to facilitate delivery of a working device 802 into a target vessel 1906. At operation 3210, the tetherable guide-sheath 400 can be removed from the tether 104 of the first tethering device 2202. At operation 3212, the tetherable guide-sheath 400 can be advanced over the second tether 104 of the second tethering device 2204 to position the mouth 508 of the tetherable guide-sheath 400 near a second entrance of a second target vessel 1906. For example, the mouth 508 can be positioned toward a target ICA branching from the second anchoring vessel 1904, e.g., the ECA. Thus, the tetherable guide-sheath 400 can be fixed to the second tether 104 of the second tethering device 2204 to provide support to the working device 802 as it is advanced into the target vessel 1906 in a manner similar to that described above. Accordingly, it is contemplated that one or more tethering devices 100 can be used to allow an operator to make his or her way up to the target anatomy in an operation using any anatomy proximal to the target anatomy as a preliminary anchoring site to advance toward a preferred anchoring site nearer to the target artery.

In some cases, the tetherable guide-sheath 400 may not be able to advance to retrieve the anchor 102 of the tethering device 100. For example, after the anchor 102 of second tethering device 2204 is anchored in the second anchoring vessel 1904, the tetherable guide-sheath 400 may be unable to advance over the tether 104 of the first tethering device 2202 to capture the first anchor 102 in the first anchoring vessel 2302. In this event, the anchor 102 of the first tethering device 2202 can be detached, as described above, and the detached anchor 102 can remain in the patient and the detached tether 104 can be pulled out of the great vessels, aorta, and out of the access sheath and/or the arteriotomy of the access site. Alternatively, a separate catheter can be advanced over the tether 104 of the first tethering device 2202 after the tetherable guide-sheath 400 is removed from the tether 104, and the separate catheter can capture and retrieve the anchor 102.

Figure 34:
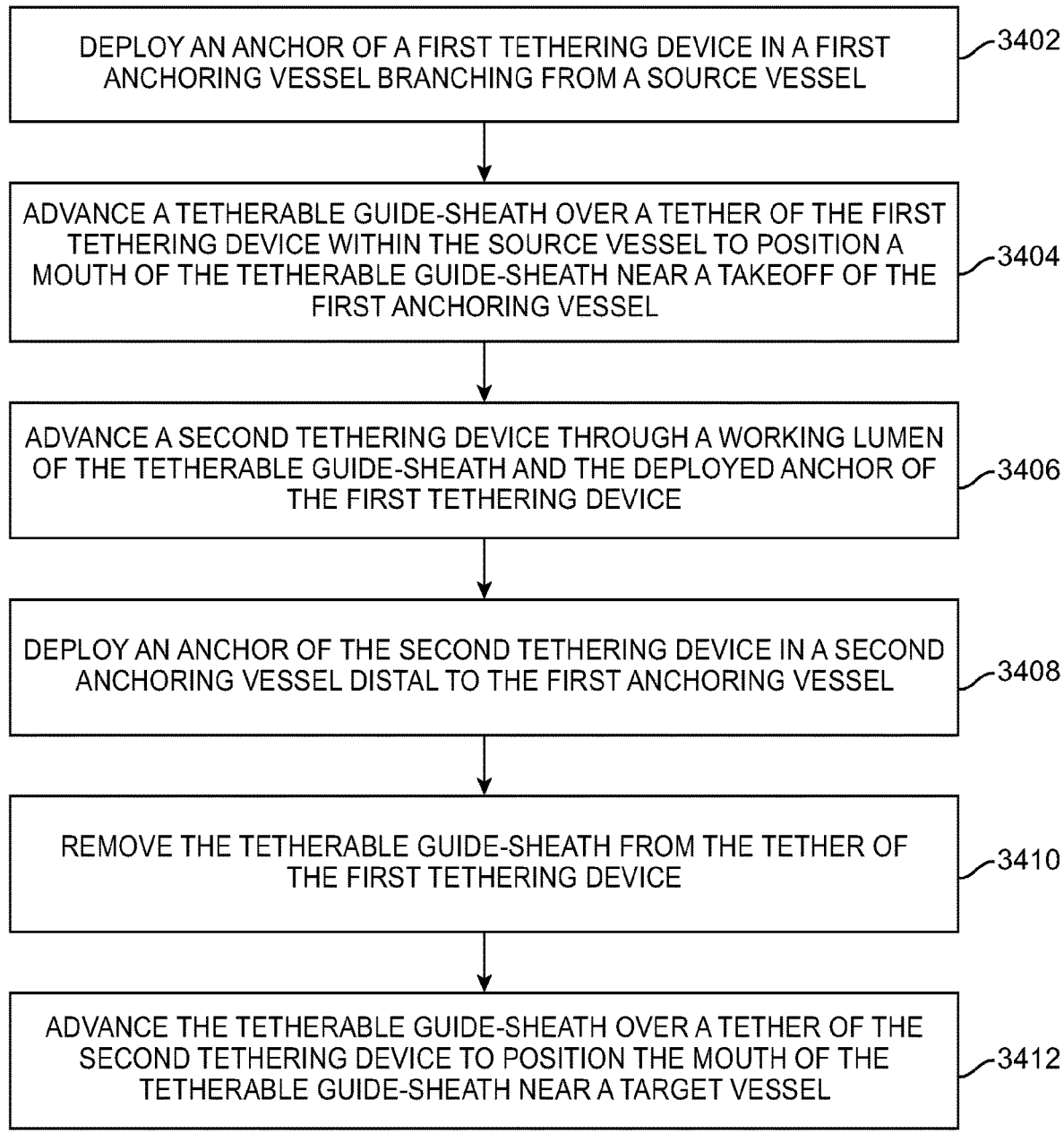
FIG. 34 illustrates a method of using several anchoring delivery systems to gain access to a target vessel, in accordance with an implementation.
Figure 35C:
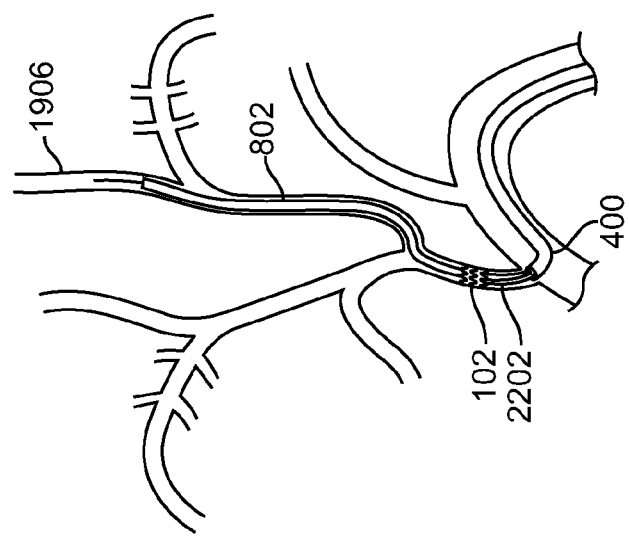
FIGS. 35A-35C illustrate operations of a method of using several anchoring delivery systems to gain access to a target vessel, in accordance with an implementation.

Referring to FIG. 34, a method of using several anchoring delivery systems to gain access to a target vessel is illustrated in accordance with an implementation. FIGS. 35A-

35C illustrate operations of the method illustrated in FIG. 34. Accordingly, FIGS. 34-35 are described in combination below.

In some anatomies, a "through-the-anchor" approach may be used to access a target vessel 1906. For example, referring to FIG. 35A, a complex anatomy includes a "bovine" arch where the left CCA takes off from the brachiocephalic artery instead of the aorta. At operation 3402, an anchor 102 of a first tethering device 2202 can be deployed in a first anchoring vessel 2302, e.g., a brachiocephalic artery proximal to a left CCA takeoff, branching from a source vessel, e.g., the AA. At operation 3404, a tetherable guide-sheath 400 can be advanced over a tether 104 of the first tethering device 2202 within the source vessel to position a mouth 508 of the tetherable guide-sheath 400 near a takeoff of the first anchoring vessel 2302. For example, the mouth 508 can be located adjacent to the takeoff of the brachiocephalic artery from the AA. At operation 3406, a second tethering device 2204 can be advanced through a working lumen 410 of the tetherable guide-sheath 400 and the deployed anchor 102 of the first tethering device 2202. For example, the anchor 102 of the first tethering device 2202 can have a central lumen, as in the case of an expandable cage, or expand in a manner that allows a second tethering device 2204 to be advanced through or along the deployed anchor 102 of the first tethering device 2202 toward a target vessel 1906. At operation 3408, an anchor 102 of the second tethering device 2204 can be deployed in a second anchoring vessel 1904 distal to the first anchoring vessel 2302. Thus, the tethers 104 of the first tethering device 2202 and the second tethering device 2204 may remain within the tetherable guide-sheath 400, e.g., in respective lumens or in a same lumen.

Figure 35B:
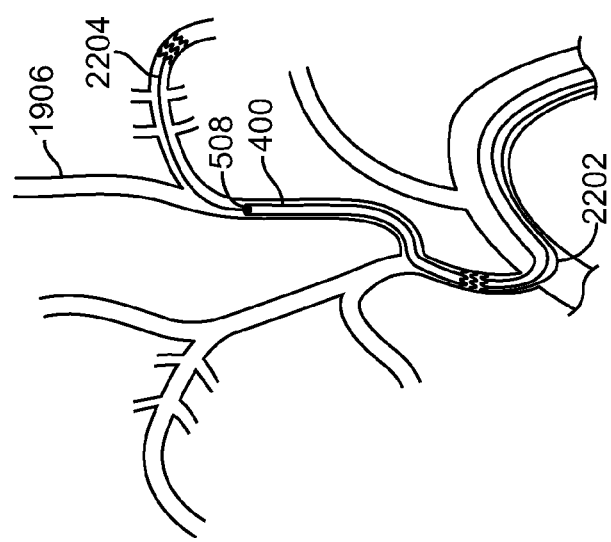
Figure 35A:
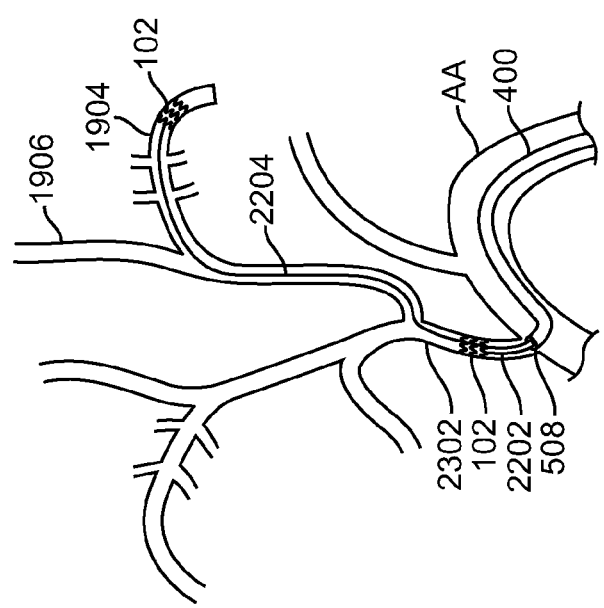

Referring to FIG. 35B, at operation 3410, the tetherable guide-sheath 400 can be removed from the tether 104 of the first tethering device 2202. Subsequently, at operation 3412, the tetherable guide-sheath 400 can be advanced over the tether 104 of the second tethering device 2204 to position the mouth 508 of the tetherable guide-sheath 400 near a target vessel 1906. The tetherable guide-sheath 400 can be advanced up the tether 104 of second tethering device 2204 to the anchoring vessel/target vessel junction, e.g., the carotid bifurcation. The mouth 508 of the tetherable guide-sheath 400 can be positioned to face the target vessel 1906, e.g., the ICA.

Referring to FIG. 35C, if the target vessel 1906 cannot be reached, the CCA can be used as an anchor point for the second tethering device 2204 to be deployed. Thus, the anchor 102 of the first tethering device 2202 can be anchored in the brachiocephalic artery, and a working device 802, such as an implant delivery system, can be delivered through a working lumen 410 of the tetherable guide-sheath 400 to traverse through the anchor 102 of the first tethering device 2202.

Figure 36:
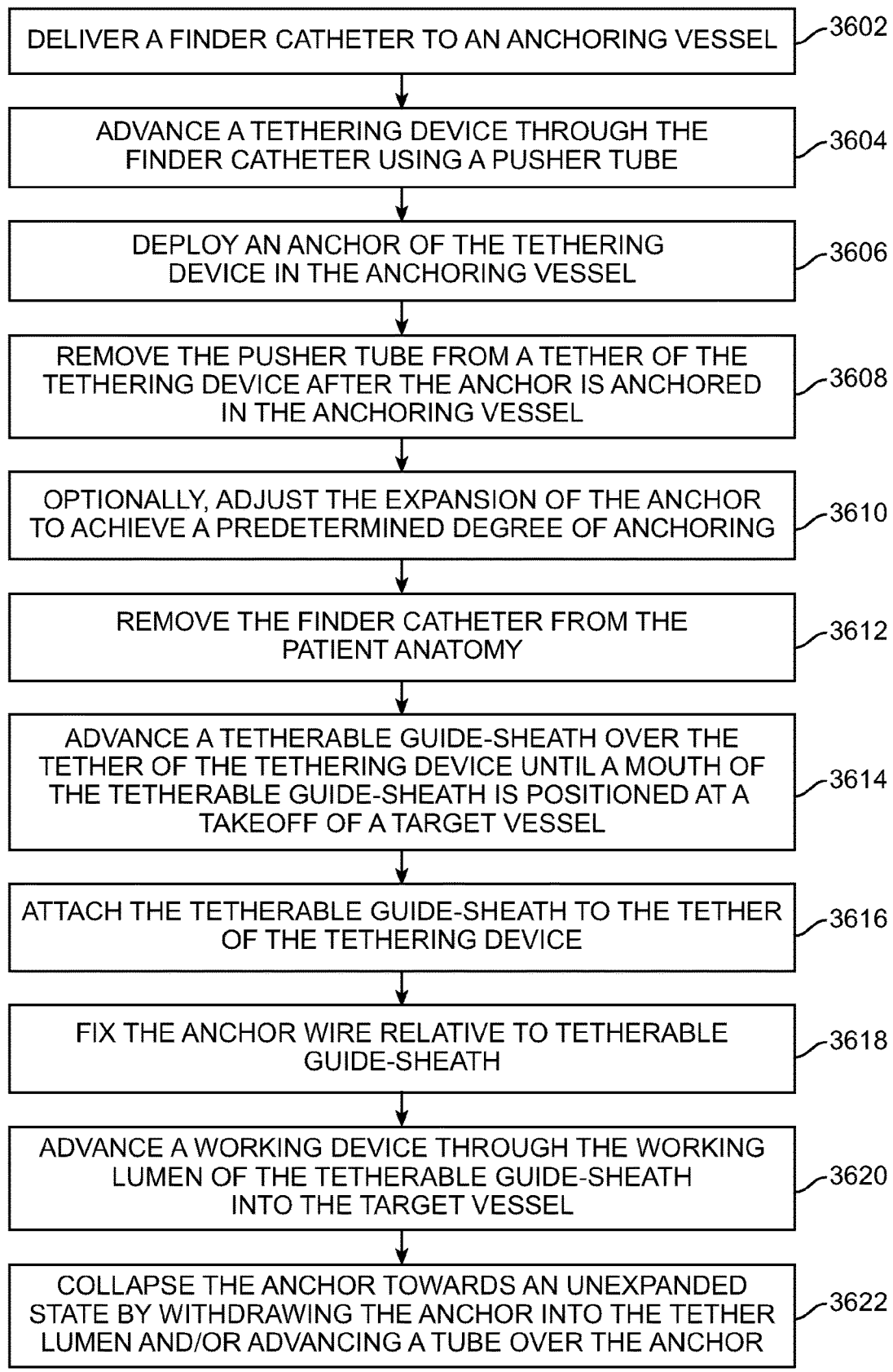
FIG. 36 illustrates a flowchart of a method of deploying an anchoring delivery system, in accordance with an implementation.

Referring to FIG. 36, a method of deploying an anchoring delivery system to gain access to a target vessel is illustrated in accordance with an implementation. At operation 3602, an operator can deliver a finder catheter (typically a 5 F guide or diagnostic catheter) to an anchoring vessel in a patient anatomy, e.g., an external carotid artery (ECA). At operation 3604, the tethering device can be advanced through the finder catheter. The tethering device 100 can have a pusher tube 109 preloaded over a runner tube 113 of the tether 104. As the tethering device 100 is advanced, the anchor 102 can slide through the finder catheter in an unexpanded state, constrained by the finder catheter. The tethering device 100 can be advanced until the anchor 102 is near a distal end of the finder catheter, and near an anchoring site in the anchoring vessel 1904. In some implementations, the distal joint 108 of the anchor 102 can move relative to the proximal joint 108 of the anchor 102, i.e., the anchoring wire can slide within the runner tube, may allow the anchor 102 to be easily loaded into a sheath or a catheter by simply pushing the anchor 102 into the sheath. More particularly, by pushing the anchor 102 into the sheath using the tether 104, the push force can be transmitted through the anchor 102 to cause the anchor 102 to elongate and/or contract such that the procedure effectively "pulls" the anchor 102 into the sheath, which may significantly simplify loading.

At operation 3606, the anchor 102 can be deployed at the anchoring site by advancing the anchor 102 out of the finder catheter, or by retracting the finder catheter over the tethering device 100 to unsleeve the anchor 102. The anchor 102 can therefore self-expand to the expanded state to press against, and anchor, within the anchoring vessel 1904. In an implementation, the anchor 102 includes a closed-cell structure, and thus, the anchor 102 can remain constricted in an unexpanded diameter as long as the anchor 102 is not full released. This may simplify the release of the anchor 102 into the anchoring anatomy.

Still with respect to FIG. 36, at operation 3608, after the anchor 102 is anchored at the anchoring site, the pusher tube 109 can be removed from the tether 104. More particularly, the pusher tube 109 can be pulled proximally to slide over the runner tube 113 and to be removed from the patient anatomy.

At operation 3610, the operator may optionally adjust the anchor 102 to achieve a predetermined degree of anchoring. For example, the anchor wire 111 can be pulled relative to the runner tube 113 to cause a desired degree of expansion of the anchor 102. It will be noted that this may cause the anchor 102 to expand from a first expanded state, e.g., a self-expanded state, to a second expanded state, e.g., an actuated state. Accordingly, the second expanded state may be greater than the first expanded state to seat the anchor 102 in the anchoring vessel 1904. The opposite can be true, and the anchor wire 102 can be advanced relative to the runner tube 113 to reduce the degree of expansion from the self-expanded state to the actuated state, e.g., if the operator assesses that the anchor 102 is oversized for the anchoring vessel 1904 and that a reduced expansion diameter will reduce the likelihood of vascular trauma while still achieving effective seating of the anchor at the anchoring site.

At operation 3612, the finder catheter can be removed from the patient anatomy with a pulling motion. In an implementation, the anchor 102 provides a resistive anchoring force greater than the friction force applied to the tether 104 by the finder catheter, and thus, the tethering device 100 remains in place during retraction of the finder catheter.

At operation 3614, the operator can advance the tetherable guide-sheath 400 over the tether 104 of the tethering device 100. For example, the anchor wire 111 can be loaded into the tether distal port 504 of the tetherable guide-sheath 400 and the tetherable guide-sheath 400 can be advanced over the runner tube 109 through the anatomy toward the target vessel 1904. More particularly, the tetherable guide-sheath 400 can be advanced until the mouth 508 is positioned at a takeoff of a target vessel 1906, e.g., an internal carotid artery (ICA) leading to a targeted treatment location such as an aneurysm or a stenosis. The tetherable guide-sheath 400 can be torqued to rotate the mouth 508 such that a working device delivered through the working lumen will be directed into an entrance of the target vessel 1906 at the anchoring vessel/target vessel junction by the deflecting surface in the working channel of the tetherable guide-sheath 400.

At operation 3616, the tetherable guide-sheath 400 can be attached to the tether 104 of the tethering device 100. For example, the tether gripper 1502, e.g., an RHV or another gripping technology (see "Dedicated Exit Lumen" and "Multi-headed RHV" implementations) can be used to affix the tetherable guide-sheath 400 to the tethering device 100 at a point of fixation 1912 proximal to the anchoring site 1904 and/or the entrance to the target vessel 1906.

At operation 3618, the anchor wire 111 of the tether 104 can be fixed by releasing an RHV 434 connected to the tether proximal port 414 and pulling relative to the tetherable guide-sheath 400 and then fixing it again in position. A locking element 130 may be added to additionally fix the anchoring wire 111 as well as given the operator an easy "handle" with which to apply push/pull on the distal anchor 102 via the anchor wire 111.

At operation 3620, a working device, e.g., an implant delivery system, may be advanced through the working lumen into the target vessel 1906 to perform a preferred treatment. As the working device is advanced into the target vessel 1906, any reaction force applied by the distal anatomy may be transmitted by the working device to the tetherable guide-sheath 400 and the tethering device 100, placing the tether 104 in tension between the anchoring site 1904 and the point of fixation 1912. Whereas such reaction force may ordinarily cause buckling of the working device, the tetherable guide-sheath 400 may be buttressed by the tensioned tether 104, and thus, may effectively support the working device to allow it to be advanced without buckling or prolapse. Once the working device is in place, e.g., at the embolus, the preferred treatment, e.g., delivery of a stent or coil, can be performed. The working device can then be removed from the anchoring delivery system and the patient anatomy.

At operation 3622, the tetherable guide-sheath 400 has a detachment point 1916 that allows the operator to manually grasp the runner tube 113 or apply a locking element 130 to the runner tube 113. Force may be applied to the runner tube 113 to move the runner tube 113 relative to the anchor wire 111 to collapse the anchor 102 from the expanded state to or towards an unexpanded state, or from the actuated state to the self-expanded state. The anchor 102 can thus be withdrawn into the tether lumen 408 and/or chamber 515 of the tetherable guide-sheath 400, or the tetherable guide-sheath 400 can be exchanged with a separate catheter, such as a guide or diagnostic catheter, that can be advanced over the anchor 102 to capture the anchor 102. The tetherable guide-sheath 400 and/or tethering device 100 can then be removed from the patient anatomy to complete the use of the anchoring delivery system and finish the intervention.

Figure 37B:
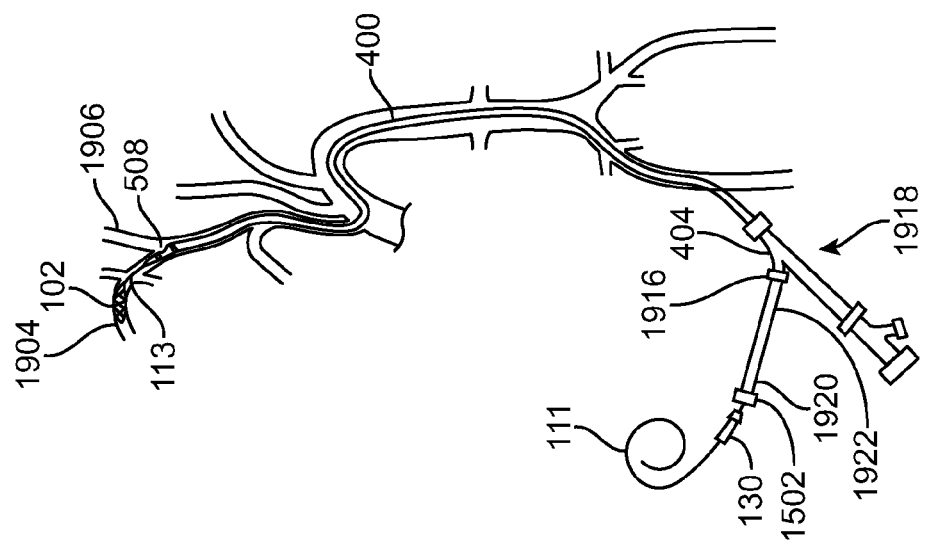
FIG. 37A-37B illustrate schematic views of an anchoring delivery system deployed in a target anatomy, in accordance with an implementation.
Figure 37A:
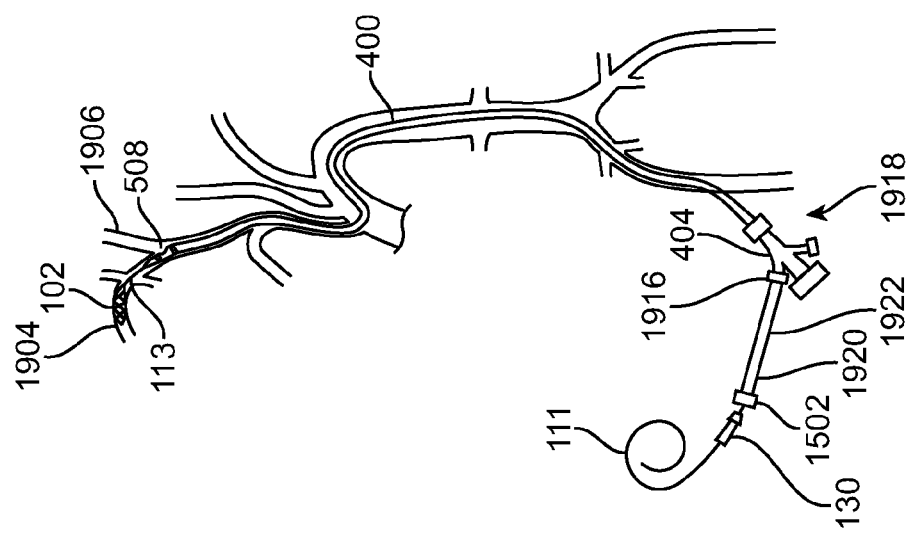

Referring to FIG. 37A, a schematic view of an anchoring delivery system deployed in a target anatomy is illustrated in accordance with an implementation. The proximal portion of the tetherable guide-sheath 400 can incorporate a multiheaded RHV 1918. The multiheaded RHV 1918 can include an elongated arm 1920 having a detachment point 1916 to expose the runner tube 113 for operator access. The elongated arm 1920 may provide an extension leading to the tether gripper 1502, which may include an anchoring RHV. For example, the anchoring RHV may include a collet, such as a brass or metal insert in the diaphragm which allows it to grasp and hold the anchoring wire, as described in more detail above.

The detachment point 1916 can include a detachable coupling, which may be formed by numerous mechanisms. For example, the elongated arm 1920 can include an external O-ring that fits within an internal groove formed in the multi-headed RHV. The elongated arm 1920 can include a rigid or semi-rigid clear extender that is of sufficient distance to reach and surpass the end of the runner tube 113. More particularly, a transition point 1922 between the anchor wire 111 and the runner tube 113, i.e., a proximal end of the runner tube 113, may occur within the elongated arm 1920 when the elongated arm 1920 is attached to the multi-headed RHV body. Accordingly, the runner tube 113 and the anchor wire 111 may be visualized, e.g., if they are of different colors or sufficient contrast to each other, in the extension tube. In an implementation, the elongated arm includes demarcations that may be used to estimate a tension applied to the tethering device 100. For example, a first distance between a point on the anchoring wire 111 and the proximal end of the transition tube may be measured when the anchor 102 is in the self-expanded state, and a second distance between those points may be measured upon actuation of the anchor wire 111. A difference in the distances may correspond to a degree of tension or an amount of anchoring provided by the tethering device 100.

The detachment point 1916 may or may not have an ability to restrain or fix the runner tube 113. In an implementation, an "in-line" RHV can be used to fix the runner tube 113 at the detachment point 1916. Alternatively, a transient fixation can be achieved using a push button, a lever, or another mechanism that can be actuated by an operator to temporarily apply pressure to the runner tube 113 when desired. Transient fixation can allow withdrawal of the anchor wire 111 relative to the runner tube 113 for adjustments during a procedure, and such adjustments may be followed by fixation of the anchor wire 111 with a separate anchoring RHV. If prolonged fixation is provided on the runner tube 113 and the anchor wire 111 simultaneously, the relative size of the anchor 102 can remain fixed by the relative positions of the tether components, and the transient increase and decrease of anchoring by loads applied to the tether 104 by the tetherable guide-sheath 400, e.g., during working device advancement, may not occur.

Reiterating the steps above with the system illustrated in FIG. 37A-37B, after the tetherable guide-sheath 400 is positioned, the tether 104 can be fed through the elongated arm 1920 of the multiheaded RHV 1918 and the anchoring RHV 1502 can fix the anchor wire 111 as it is tightened. A locking element 130, i.e., a torque device as is known in the art, can also be added to provide security of the hold on the system. If the runner tube 113 has an independent fixating technology applied to it (it is not "non-restraining"), then the relationship of the runner tube 113 and the anchor wire 111 can be stabilized to fix the tension applied to the anchor 102.

Referring to FIG. 37B, a schematic view of an anchoring delivery system deployed in a target anatomy is illustrated in accordance with an implementation. The proximal portion of the tetherable guide-sheath 400 can include a dedicated bifurcation having the multi-headed RHV 1918. For example, the working lumen may pass through an arm of the dedicated bifurcation having length of 10 to 20 mm between the working proximal port and the bifurcation point. Accordingly, standard RHVs may be connected to the tetherable guide-sheath 400. This "dedicated exit" version of the tetherable guide-sheath system may include the working lumen and the tether lumen, and the tether lumen may extend through the elongated arm and the tether gripper. More particularly, each end of the dedicated bifurcation may include a "single-headed" RHV. The arm sections of the dedicated bifurcation may be separated, e.g., by 10 to 20 mm, to avoid operator confusion during use. The working lumen portion of the dedicated bifurcation, i.e., the working lumen and RHV connected to the working lumen, may operate similar to typical neurovascular access systems. The tether lumen portion of the dedicated bifurcation may include a clear semi-rigid or rigid segment, i.e., the elongated arm, to allow visualization of the runner tube and anchoring wire for refined adjustment of the expansion of the anchor, as described above. The anchor wire may also be anchored outside the locking RHV with an anchoring locking element or other clamping device. Furthermore, the detachment point may or may not have an ability to restrain or fix the runner tube in place, as described above.

Figure 38:
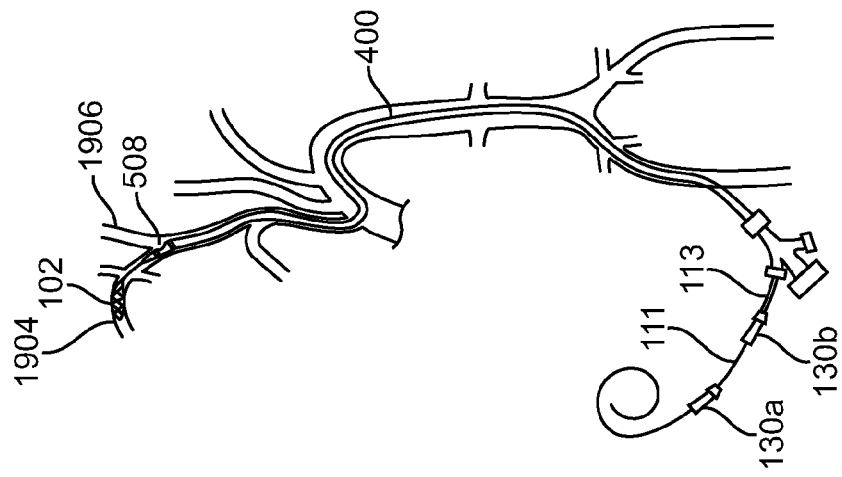
FIG. 38 illustrates a schematic view of an anchoring delivery system deployed in a target anatomy, in accordance with an implementation.

Referring to FIG. 38, a schematic view of an anchoring delivery system deployed in a target anatomy is illustrated in accordance with an implementation. The anchor 102 can be configured anchor within a vessel 1904. As previously described, anchoring can be controlled by adjusting a relative position of the anchoring wire 111 relative to the runner tube 113. In an implementation, the tethering device 100 can include a locking mechanism to fix the relative position between the anchoring wire 111 and the runner tube 113 after the desired anchor dimension or tension is achieved.

In an implementation, the locking mechanism includes a pair of clamping mechanism or devices, such as a pair of locking elements 130. Each locking element 130 can have a fitting adapted to grip one or more of the tether components (the runner tube 113 or the anchoring wire 111) securely. Thus, a predetermined tension can be applied by gripping and moving the tether components by a respective locking element 130. The pair of clamping devices can be referred to as an anchor wire locking element 130a (connected to the anchor wire 111) and the runner tube locking element 130b (connected to the runner tube 113). In an implementation, the anchor wire locking element 130a is sized to accept the anchor wire 111 diameter, but not to accept the larger diameter of the runner tube 113. For example, the anchor wire locking element 130a can incorporate a collet having a relaxed inner diameter smaller than the outer diameter of the runner tube 113. By contrast, the runner tube locking element 130b can be sized to receive the runner tube 113 in the unclamped state, but to lock down firmly on the runner tube 113 in a locked state, e.g., when the torque device is actuated by rotation of a cap component on a body component, as is known in the art.

The paradigm of a pair of locking element devices 130 to control the tethering device anchor 102 expansion can be incorporated in a "dedicated bifurcation" version of a tetherable guide-sheath 400 or in a "multiheaded RHV" version of a tetherable guide-sheath 400. In either case, respective locking elements 130 can be tightened down on a corresponding anchor wire 111 and a corresponding runner tube 113 to apply tension to expand or contract the anchor 102, e.g., between an unexpanded state and an expanded state. Furthermore, the locking element devices 130 can be gripped to advance or withdraw the tethering device 100 within the tetherable guide-sheath 400, or to advance or withdraw the combined anchoring delivery system.

In an implementation, the locking elements 130 can be used to lock the anchor 102 in position. For example, after pulling on the anchoring wire 111 relative to the runner tube 113 to expand the anchor 102, the anchoring wire locking element 130a can be repositioned to abut a proximal end of the runner tube 113. The anchoring wire locking element 130a can then be tightened and released, such that spring force retained within the anchor 102 can tension the anchoring wire 111 and the proximal end of the runner tube 113 can press against (but not move) the anchoring wire locking element 130a. The tethering device 100 can therefore be locked into position to maintain a constant size of the expanded anchor 102. Similarly, the runner tube locking element 130b, after being used to apply desired pressure and expansion to the anchor 102, can be loosened and advanced against the proximal furcation 404 or an RHV connected to the proximal furcation 404 so as to not allow any motion of the runner tube 113 relative to the tetherable guide-sheath 400.

Figure 39:
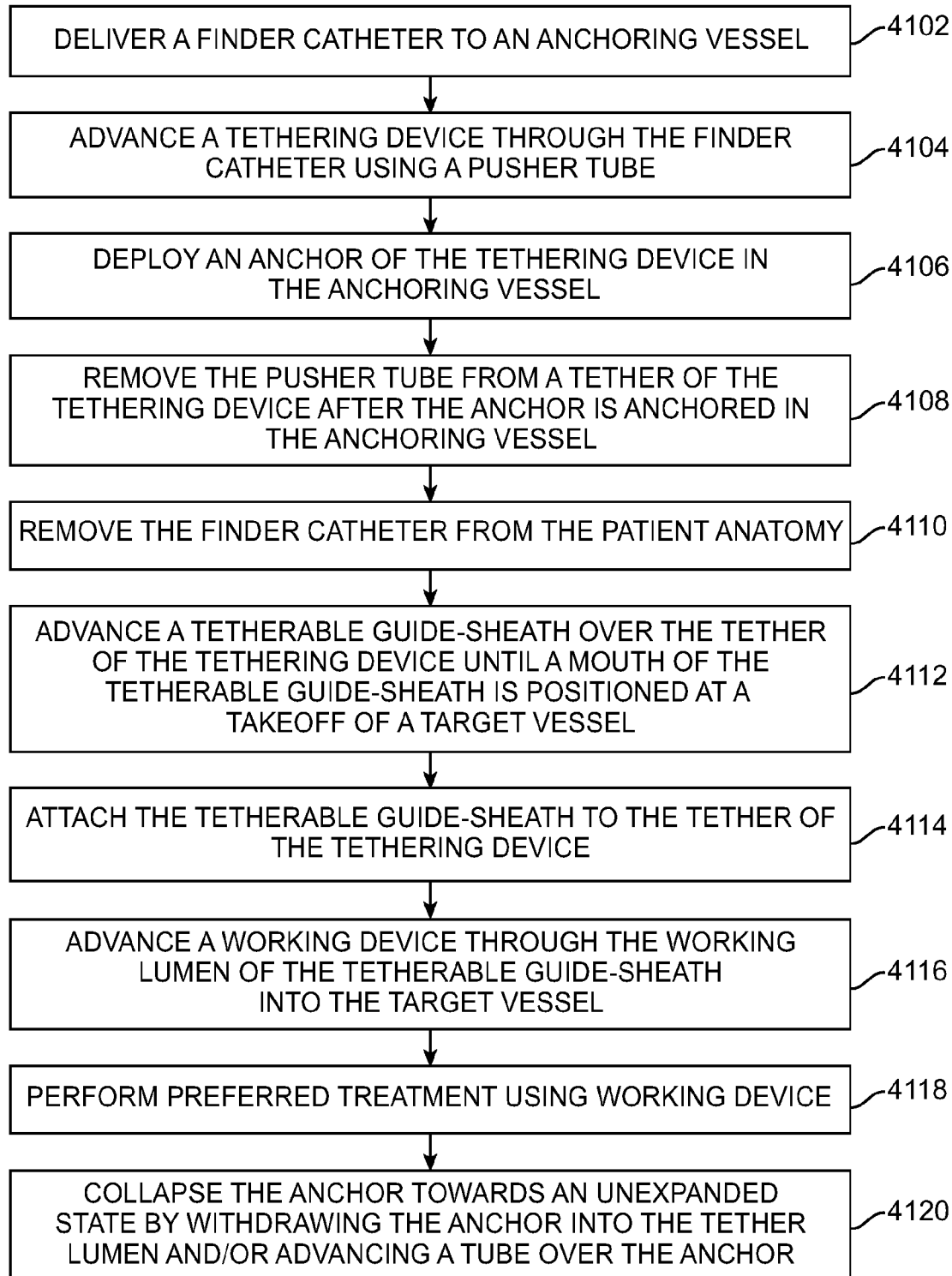
FIG. 39 illustrates a flowchart of a method of deploying an anchoring delivery system, in accordance with an implementation.

Referring to FIG. 39, a flowchart of a method of deploying an anchoring delivery system is illustrated in accordance with an implementation. The method shall be described below with reference to FIGS. 40A-40D, which illustrate schematic views of an anchoring delivery system deployed in a target anatomy, in accordance with an implementation.

Figure 40D:
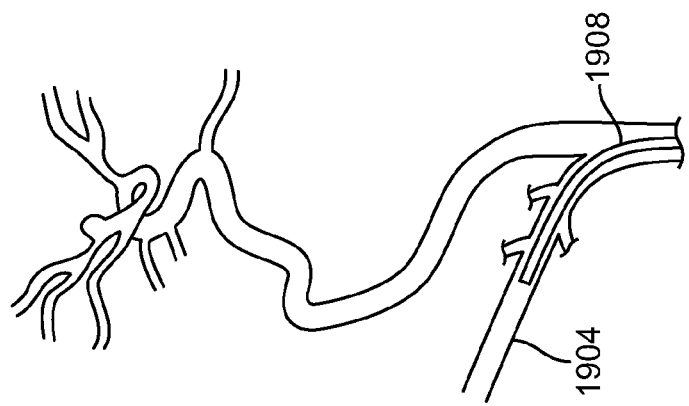
FIG. 40A-40D illustrate schematic views of an anchoring delivery system deployed in a target anatomy, in accordance with an implementation.
Figure 40C:
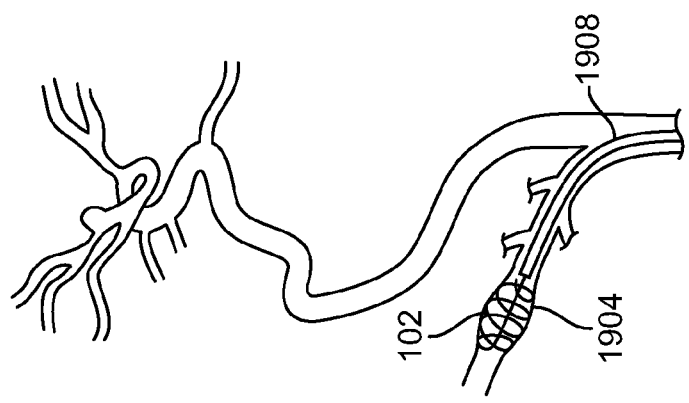
Figure 40B:
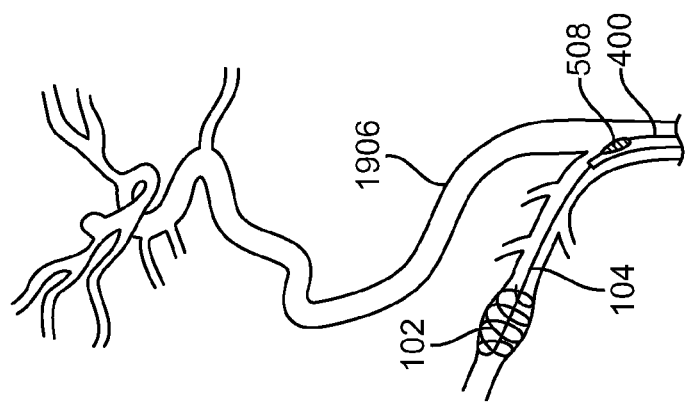
Figure 40A:
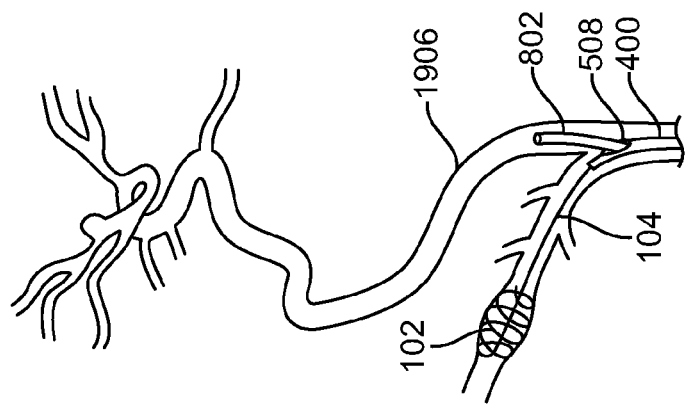

At operation 4102, referring to FIG. 40A, an operator can deliver a finder catheter 1908 (typically a 5 F guide or diagnostic catheter) to an anchoring vessel in a patient anatomy, e.g., an external carotid artery (ECA). At operation 4104, the tethering device 100 can be advanced through the finder catheter 1908. The tethering device 100 can include an anchor 102 having a pre-shaped element like a wire that can pass through the finder catheter as described elsewhere herein. As the tethering device 100 is advanced, the anchor 102 can slide through the finder catheter 1908 in an unexpanded state, e.g., the lower profile configuration shown in FIGS. 5H-5L. The tethering device 100 can be advanced until the anchor 102 is near a distal end of the finder catheter 1908, and near an anchoring site in the anchoring vessel 1904. The anchor 102 can be pushed through the finder catheter 1908 by the pusher tube 109.

At operation 4106, referring to FIG. 40B, the anchor 102 can be deployed at the anchoring site by advancing the anchor 102 out of the finder catheter 1908, by retracting a constraining element positioned over the tethering device 100 to unsleeve the anchor 102, or otherwise deploying the anchor 102 at the anchoring site. The anchor 102 can therefore self-expand, e.g., to the preformed larger profile configuration shown in FIGS. 5H-5L. In the expanded state, the anchor 102 can press against, distort, and/or anchor, within the anchoring vessel 1904. In an implementation, the anchor 102 includes a coil segment having a bulbous profile, although the anchor 102 can also include other shapes, e.g., pigtail, bulbous, hook-shaped, conical, etc., as described herein.

At operation 4108, after the anchor 102 is anchored at the anchoring site, the pusher tube 109 can be removed from the tether 104. For example, the pusher tube 109 can be retrieved from the finder catheter 1908. More particularly, the pusher tube 109 can be pulled proximally to slide over the tether 104 and to be removed from the patient anatomy.

At operation 4110, the finder catheter 1908 can be removed from the patient anatomy with a pulling motion. In an implementation, the anchor 102 can provide a resistive anchoring force greater than the friction force applied to the tether 104 by the finder catheter 1908, and thus, the tethering device 100 remains in place during retraction of the finder catheter 1908.

At operation 4112, referring to FIG. 40C, the operator can advance a tetherable guide-sheath 400 over the tether 104 of the tethering device 100. For example, the anchor wire 111 can be loaded into a tether distal port 504 of the tetherable guide-sheath 400 and the tetherable guide-sheath 400 can be advanced over the tether 104 through the anatomy toward the target vessel 1906. More particularly, the tetherable guide-sheath 400 can be advanced until a mouth 508 is positioned at or near a takeoff of a target vessel 1906, e.g., an internal carotid artery (ICA) leading to a targeted embolus. The tetherable guide-sheath 400 can be torqued to rotate the mouth 508 such that a working device 802 delivered through the working lumen will be directed into an entrance of the target vessel 1906 at the anchoring vessel/target vessel junction. It should be appreciated, however, that the mouth 508 need not be aligned with or rotated towards the entrance of the target vessel 1906 for the working device 802 to be delivered into the target vessel 1906.

At operation 4114, the tetherable guide-sheath 400 can be attached to the tether 104 of the tethering device 100. For example, a tether gripper, e.g., an RHV or another gripping technology, (not shown) can be used to affix the tetherable guide-sheath 400 to the tethering device 100 at a point of fixation 1912 proximal to the anchoring site and/or the entrance to the target vessel 1906.

At operation 4116, referring to FIG. 40D, a working device 802, e.g., an implant delivery system, can be advanced through the working lumen into the target vessel 1906 to perform a preferred treatment. As the working device 802 is advanced into the target vessel 1906, any reaction force applied by the distal anatomy may be transmitted by the working device 802 to the tetherable guide-sheath 400 and the tethering device 100, placing the tether 104 in tension between the anchoring site and the point of fixation 1912. Whereas such reaction force may ordinarily cause buckling of the working device 802, the tetherable guide-sheath 400 can be buttressed by the tensioned tether 104, and thus, may effectively support the working device 802 to allow it to be advanced without buckling or prolapse. At operation 4118, once the working device 802 is in place, e.g., at an aneurysm or stenosis, the preferred treatment, e.g., delivery of a stent, stent-assisted coil, or flow diverter, etc., can be performed. The working device 802 can then be removed from the anchoring delivery system and the patient anatomy.

At operation 4120, the tether 104 can be pulled to withdraw the anchor 102 into the tether lumen 408 of the tetherable guide-sheath 400, or the tetherable guide-sheath 400 can be exchanged with a separate catheter, such as a guide or diagnostic catheter, that can be advanced over the anchor 102 to capture the anchor 102. The tetherable guide-sheath 400 and/or tethering device 100 can then be removed from the patient anatomy to complete the use of the anchoring delivery system and finish the intervention.

Methods of Intracerebral Stent Delivery Using an Anchoring Delivery System

The anchoring delivery systems described herein can address many of the issues that standard neurovascular delivery systems for delivery of a flow diverter or a stent implant can create. The anchoring delivery systems described herein can create an anchor point at a bifurcation such as the subclavian takeoff and advancing a working device out of the sheath tip against resistance can create a downward force on the sheath, which in conventional sheaths without anchoring would result in prolapse of the sheath into the ascending aorta. The anchor point provided by the tethering device anchor prevents prolapse and provides guide support at the point of bifurcation. The anchor anchored in an anchoring vessel along with the tetherable guide-sheath fixed to the tether of the tethering device at a fixation point proximal to the anchoring site, e.g. at a locking RHV of the tetherable guide-sheath can create a cinching point at the ECA/ICA junction (or at another bifurcation point(s)) when a working device is delivered through the mouth of the tetherable guide-sheath into the target vessel thereby reducing a likelihood of prolapse into the aorta. Described below are methods of advancing an implant delivery system through an anchoring delivery system as described throughout that may replace standard approaches when the target site includes a target aneurysm or stenosis in the anterior circulation.

Figure 41A:
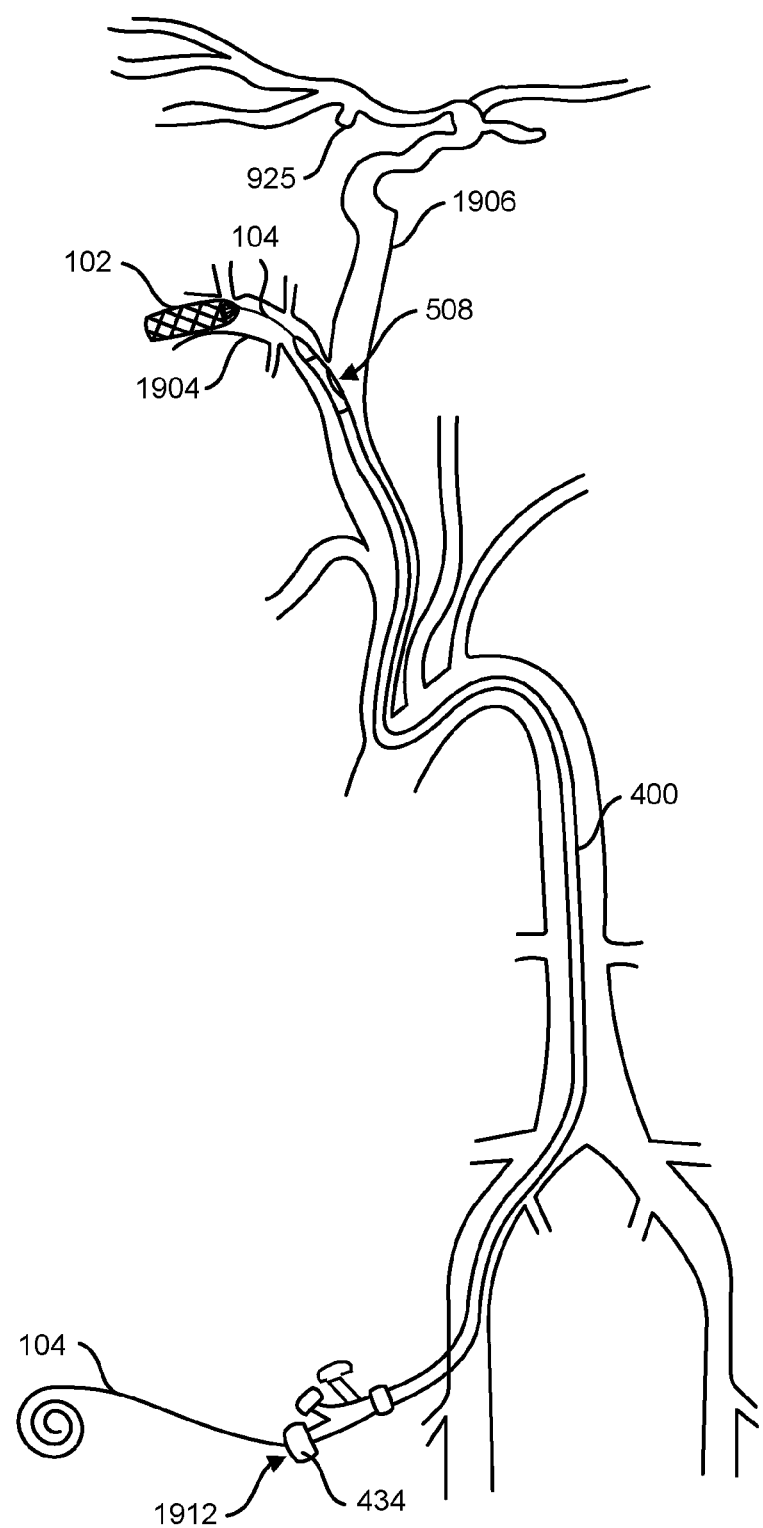
FIGS. 41A-41D illustrate schematic views of an anchoring delivery system deployed in a target anatomy for advancing an implant delivery system, in accordance with an implementation.
Figure 41B:
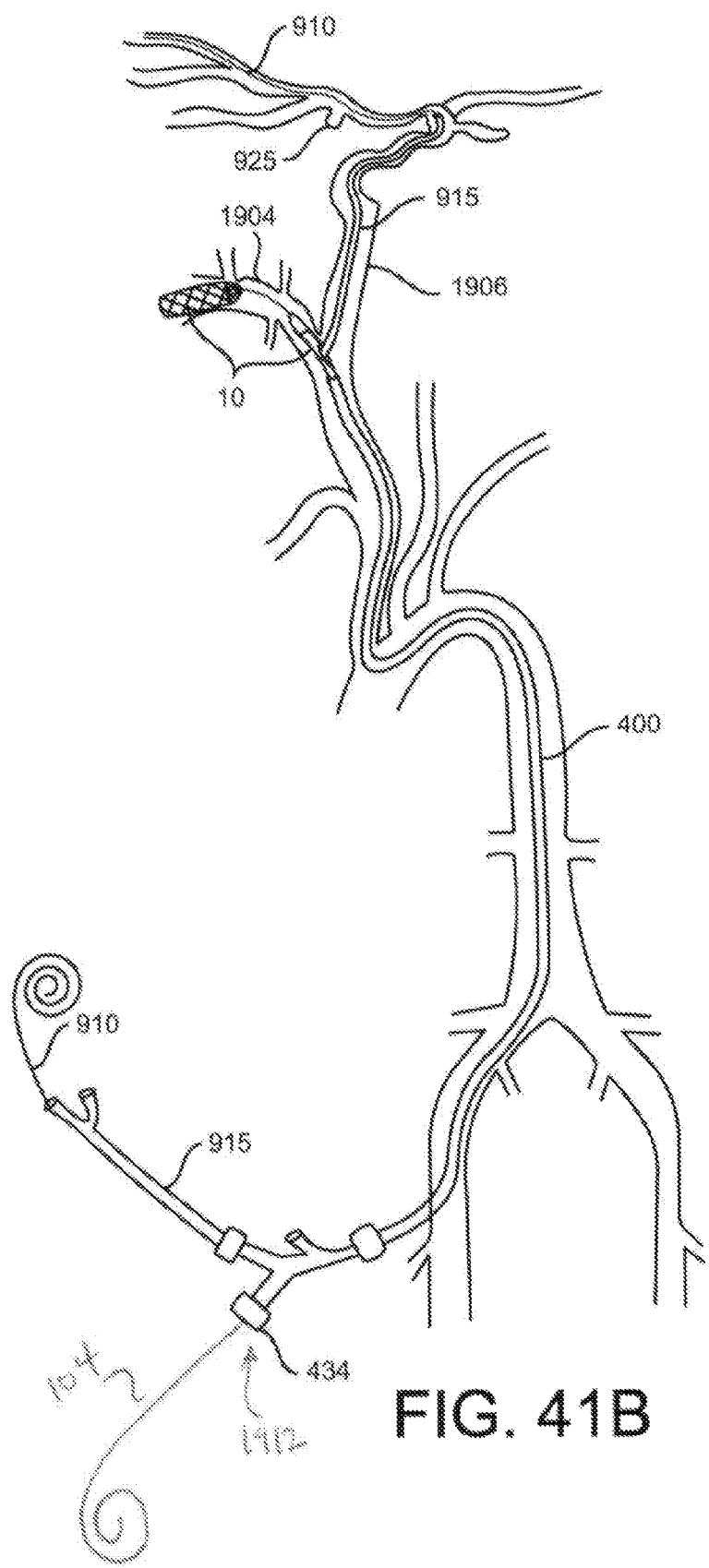

FIG. 41A shows an implementation of an anchoring delivery system 10 having a guide-sheath 400 and a tethering device 100 with a distal anchor 102 coupled to a proximal tether 104. The anchor 102 is shown deployed within an anchoring vessel 1904 and the tether 104 of the tethering device 100 is shown locked into position at a fixation point 1912 proximal to the anchoring vessel 1904 such as at a proximal hemostasis valve 434 of the tetherable guide-sheath 400. It should be appreciated that although the figures illustrate schematically the anchor 102 having a particular configuration (e.g. an expanding stent-like anchor) that the anchor configuration used in the methods described herein can vary and is not intended to be limiting. The target location 925 can be an aneurysm or an embolism or stenosis located, for example, at the M1 or M2 segments. Once deployed as shown in FIG. 41B, the anchoring delivery system 10 can provide a fixed point from which an implant delivery system 915, e.g. a SE stent delivery system, can push off into any obstruction that the implant delivery system may encounter. The implant delivery system 915 is shown as a self-expanding stent delivery system that is an over-the-wire system, although it should be appreciated that other implant delivery systems and working devices are considered herein. The implant delivery system 915 can be inserted into the guide-sheath 400 of the anchoring delivery system 10 and tracked over a procedural guidewire 910 extending through the working lumen 410 of the tetherable guide-sheath 400 to a distal vasculature in the target vessel 1906. The implant delivery system 915 can encounter severe turns, for example between the ICA/ECA takeoff from the aortic arch as well as other tortuous anatomy leading to the target site 925, e.g. the carotid siphon.

Figure 41C:
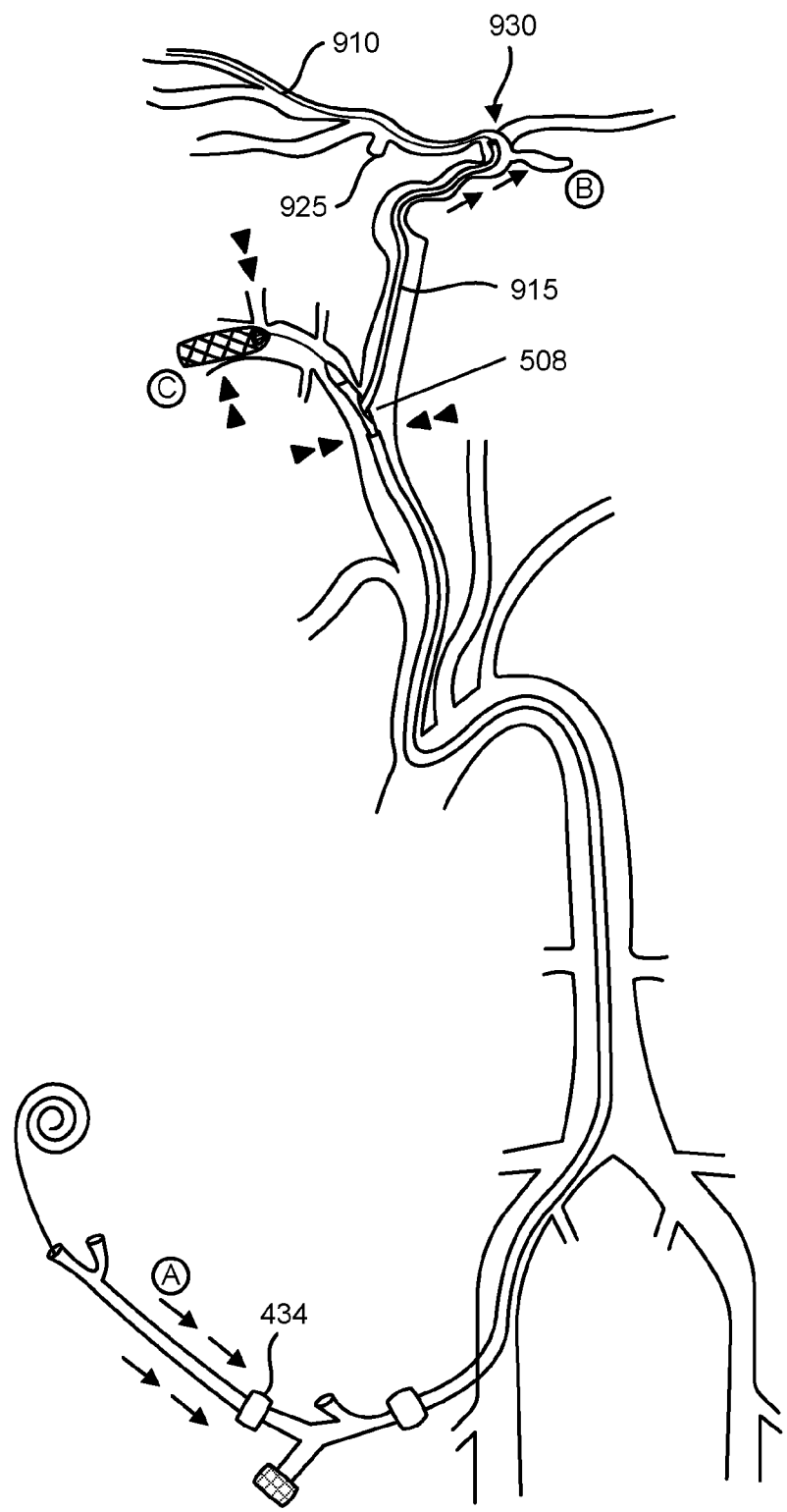

FIG. 41C shows advancement of the implant delivery system 915 with forward push at the RHV 434 (point A) through the tetherable guide-sheath 400 and out the mouth 508 near the tip 406 and advanced into the tortuous distal carotid and cerebral anatomy. A distal tip of the implant delivery system 915 can be guided by the course of a previously-positioned procedural guidewire 910 and can encounter an area of tortuosity where it meets resistance (arrows near point B) in taking the curve 930. Further advancement of the implant delivery system 915 can lead to a downward reaction force that can buckle the implant delivery system 915 if used with a standard guiding sheath without any tethering. The tetherable guide-sheath 400, however, being tensioned by the tether 104 and thus, resisting prolapse from the reaction force, may buttress the implant delivery system 915 against the reaction force to prevent such buckling. Thus, anchoring at point C prevents prolapse and buckling of the guide sheath 400 into the potential space of the ascending aorta or any of the descending aorta. The anchoring can occur both at the anchor 102 deployed in the ECA, preventing downward movement, as well as in the CCA proper, preventing lateral movement.

Figure 41D:
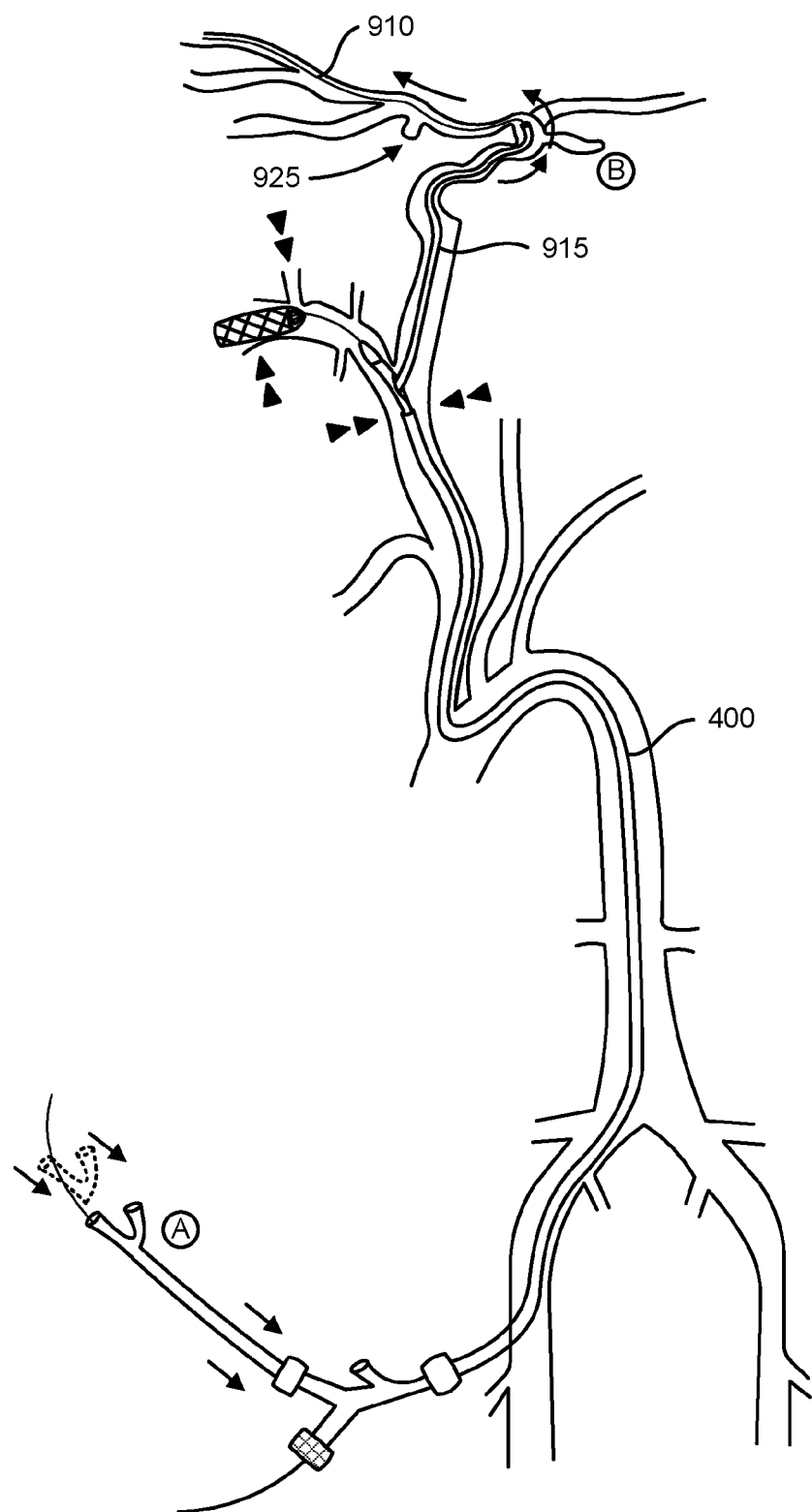

FIG. 41D shows how the anchoring provides the operator greater ability to transmit pressure to the tip of the implant delivery system 915. As described herein, pressure applied by the operator when using a conventional sheath having no anchoring to deliver the implant delivery system 915 can result in more prolapse than system advancement to the desired target 925. Continued forward advancement and ability to transmit that pressure can allow navigation of many more tortuous turns than would otherwise be possible with an unanchored sheath system increasing the likelihood of success in reaching challenging target lesions much more consistently and more quickly.

The anchoring delivery systems described herein prevents laxity in the support system below the target lesion. This allows for a very direct interaction between the push-and-pull at the hands of the operator and the fluoroscopically-guided stent placement and a more direct "one-to-one" feel. The implants are also delivered with more precision and accuracy to the target location and with less movement. For example, the "back and forth" pistoning of the working device, e.g., a delivery microcatheter, can be mitigated by the support from the anchoring delivery system 10 such that placement of Stentriever, flow diverters, stents, or other implant devices in the intracerebral anatomy is more precise and accurate. These types of implant devices typically are inserted into a microcatheter lumen and with a pushwire, each "bite" of advancement up the column of the sheath and the microcatheter can lead to a back-and-forth dislodgement and migration of the distal tip, and occasionally loss of position. The anchoring provided by the anchoring delivery systems 10 described herein helps a variety of interventions including implant delivery.

Figure 42A:
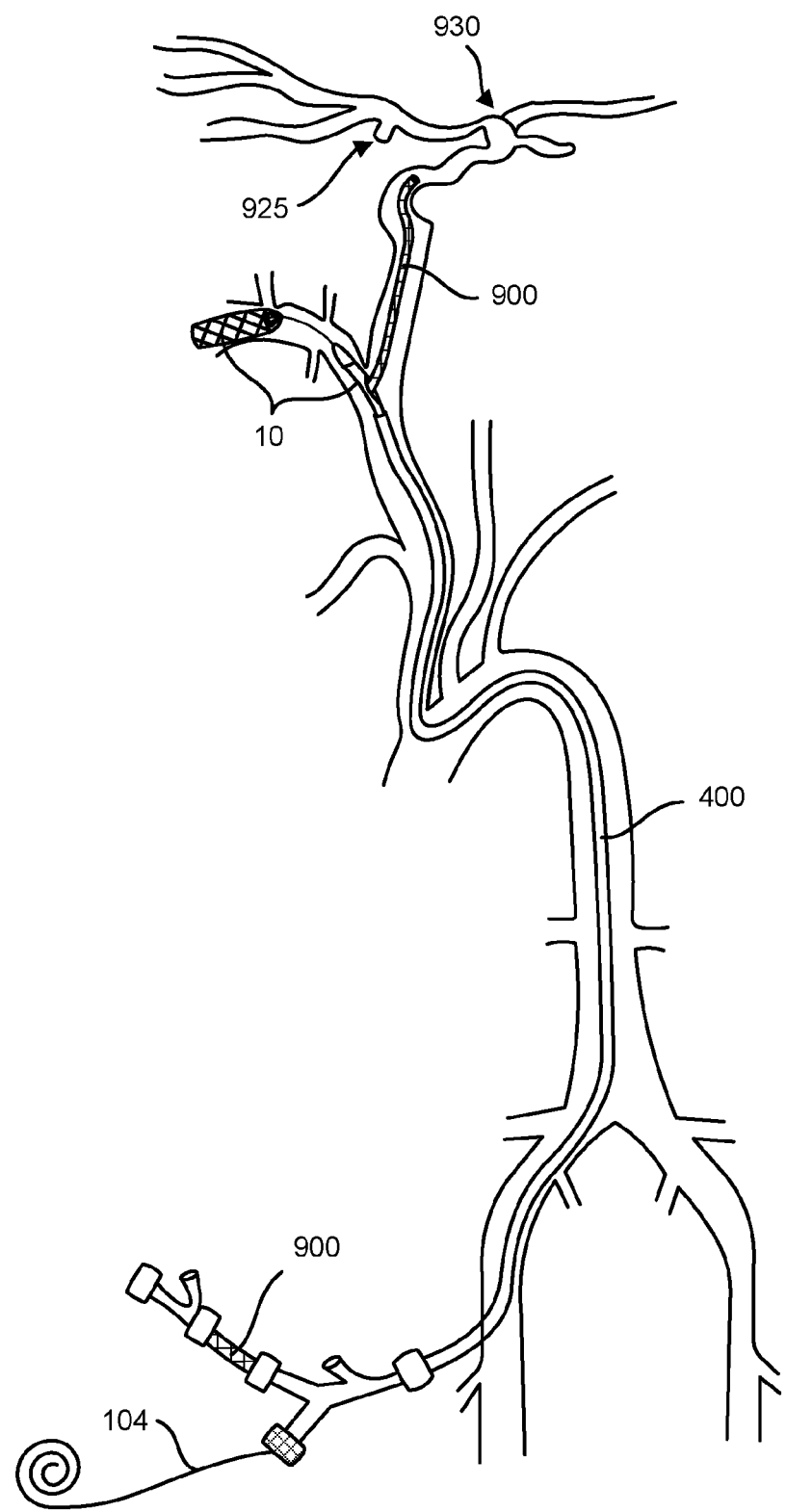
FIGS. 42A-42D illustrate schematic views of an anchoring delivery system deployed in a target anatomy for advancing an implant delivery system, in accordance with an implementation.
Figure 42B:
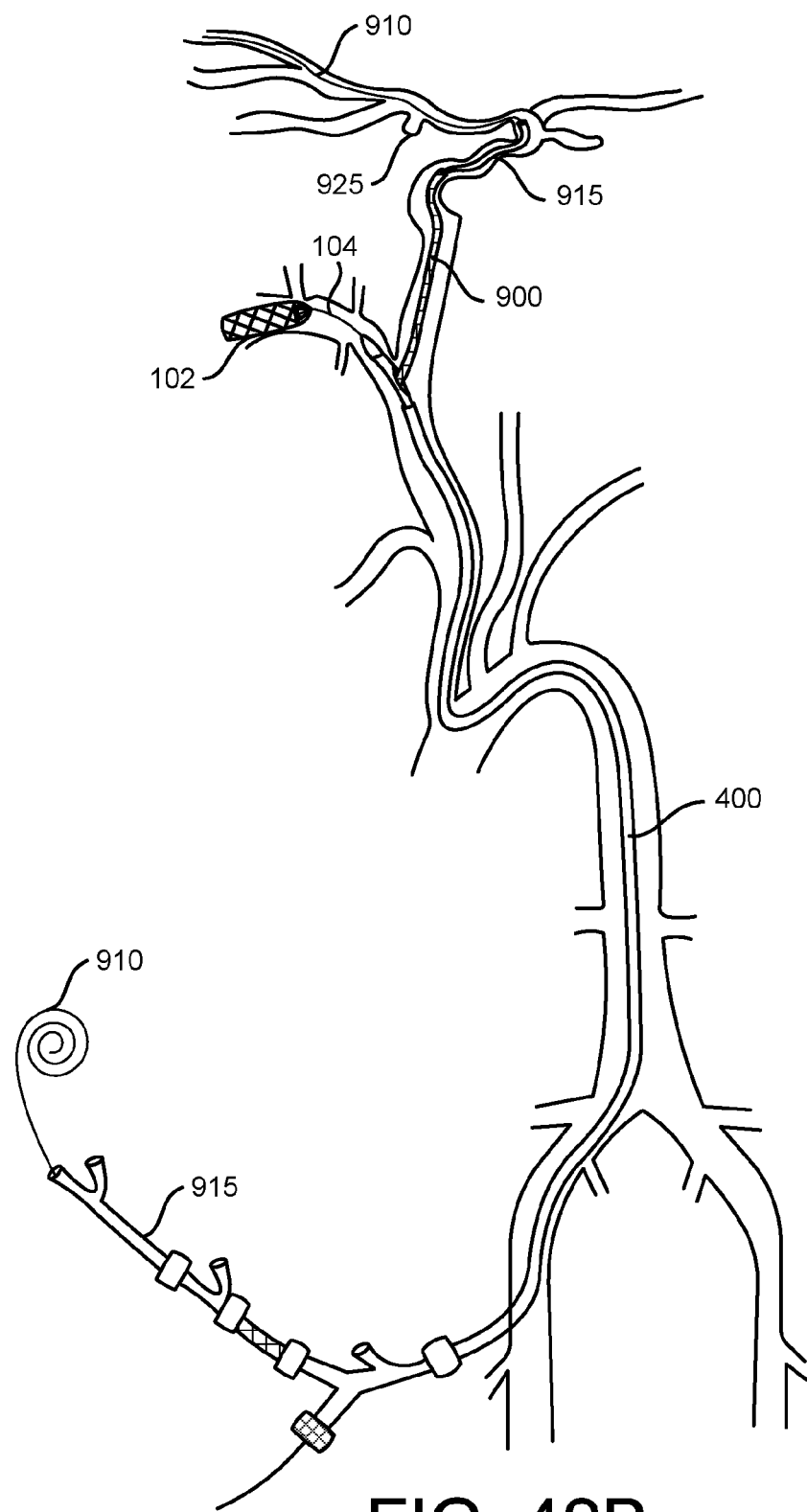
Figure 42C:
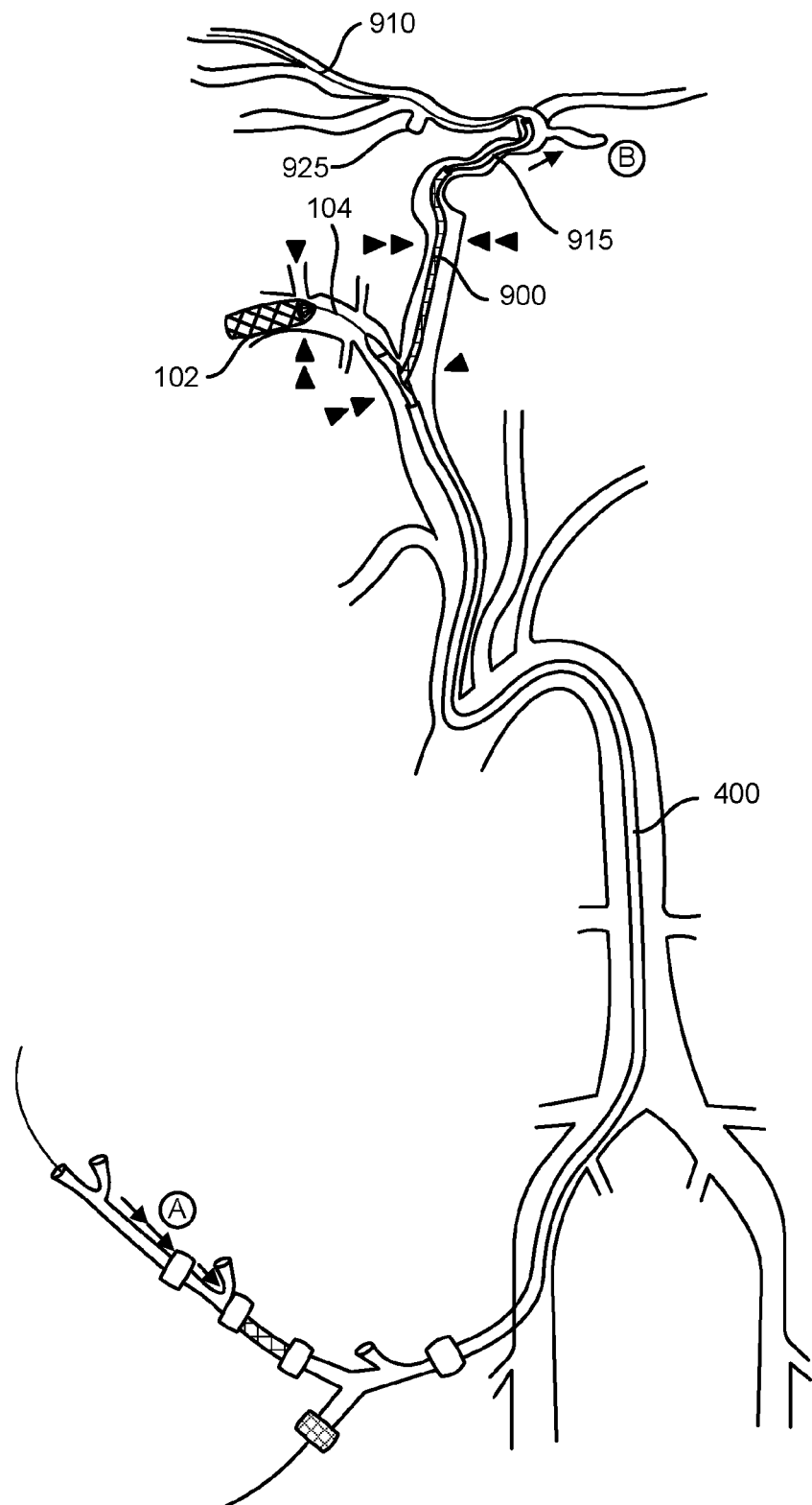
Figure 42D:
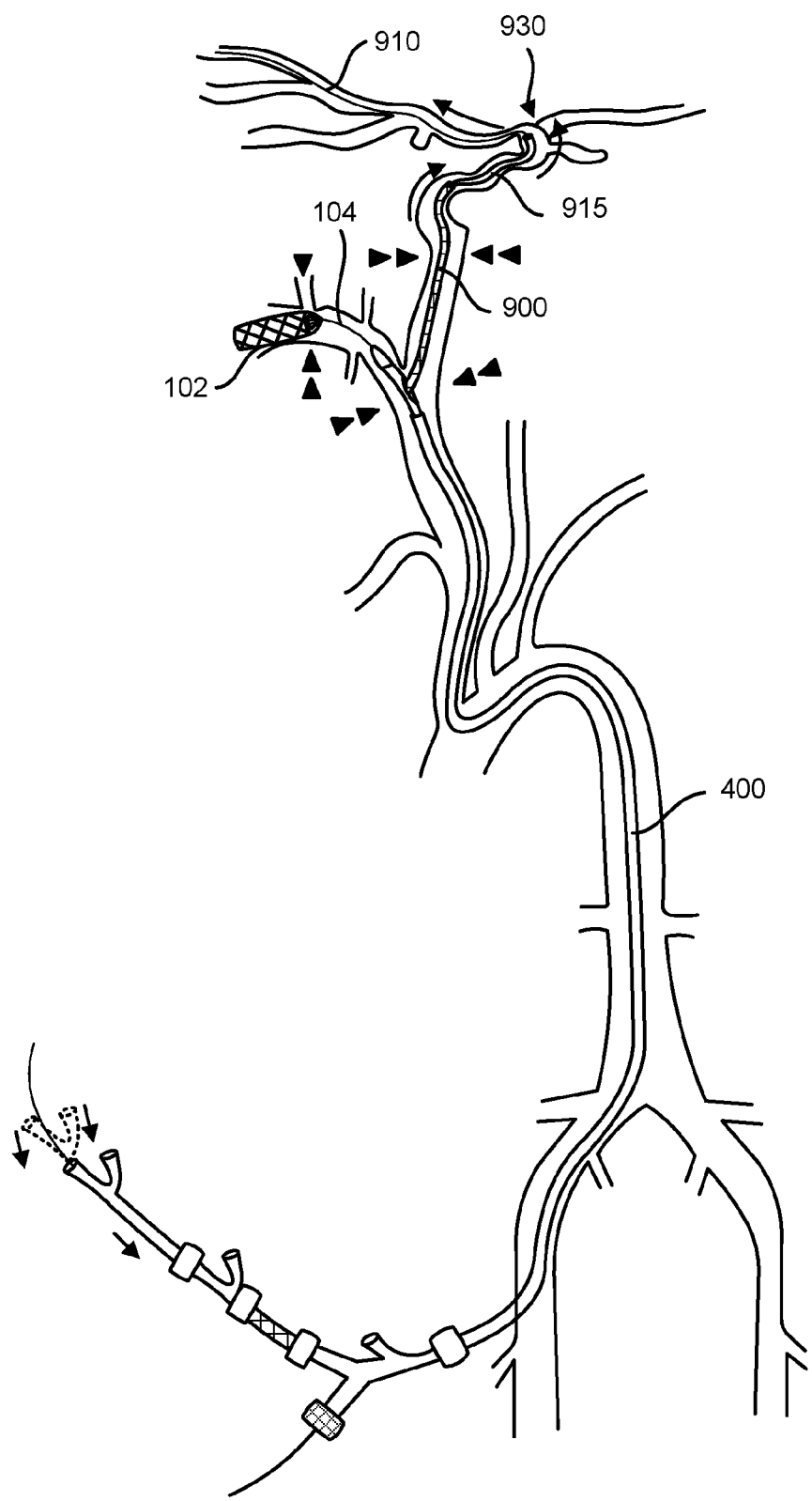

Referring now to FIG. 42A, a support catheter 900 (also referred to herein as a "guiding catheter" or a "distal access catheter") used commonly with typical sheath systems to provide support to the level of the petrous or other targets in the distal ICA and vertebral anatomy can be used in conjunction with the anchoring delivery system 10 described herein to deliver an implant 920 to an intracerebral anatomy. FIG. 42B shows the support catheter 900 extending through the mouth 508 of the tetherable guide-sheath 400 and supporting an implant delivery system 915. The implant delivery system 915 can be advanced and can encounter tortuosity that creates downward and lateral forces described elsewhere herein. The tetherable guide-sheath 400 anchored by the tethering device 100 can resist both the back-out into the ascending aorta and also lateral movement of the catheter system within the ICE and the CCA. FIGS. 42C-42D show advancement (point A of FIG. 42C) of a stent delivery system 915 into a triaxial system that includes the support guide 900 and the anchoring delivery system 10 advanced over a procedural guidewire 910. The support provided by the anchoring delivery system 10 and the support catheter 900 positioned in the body carotid can give a dramatically increased ability to deliver a force to the implant delivery system 915 at the tip to push around an obstruction and/or tortuosity (point B of FIG. 42C). Accordingly, a target site 925, e.g., an aneurysm or stenosis, can be reached in the intracerebral anatomy faster, more precisely, with improved accuracy, and with a reduced likelihood of malapposition as compared to delivery without the use of the anchoring delivery system 10.

Self-Expanding (SE) Stent Placement

The anchoring delivery systems described herein can be used to deliver a SE stent delivery system. SE stent delivery systems generally include a self-expanding stent positioned within a constraining tube that upon proximal withdrawal allow the stent to expand within the vessel. Precise and accurate delivery of an implant at distal sites within the cerebral vasculature can be impaired by release of stored tension within the system upon deployment of the implant. The anchoring delivery systems described herein can resist and/or relieve this stored tension, that together with the elimination of catheter system prolapse described elsewhere herein, ultimately increases the precision and accuracy of implant deployment at a target location.

Figure 43A:
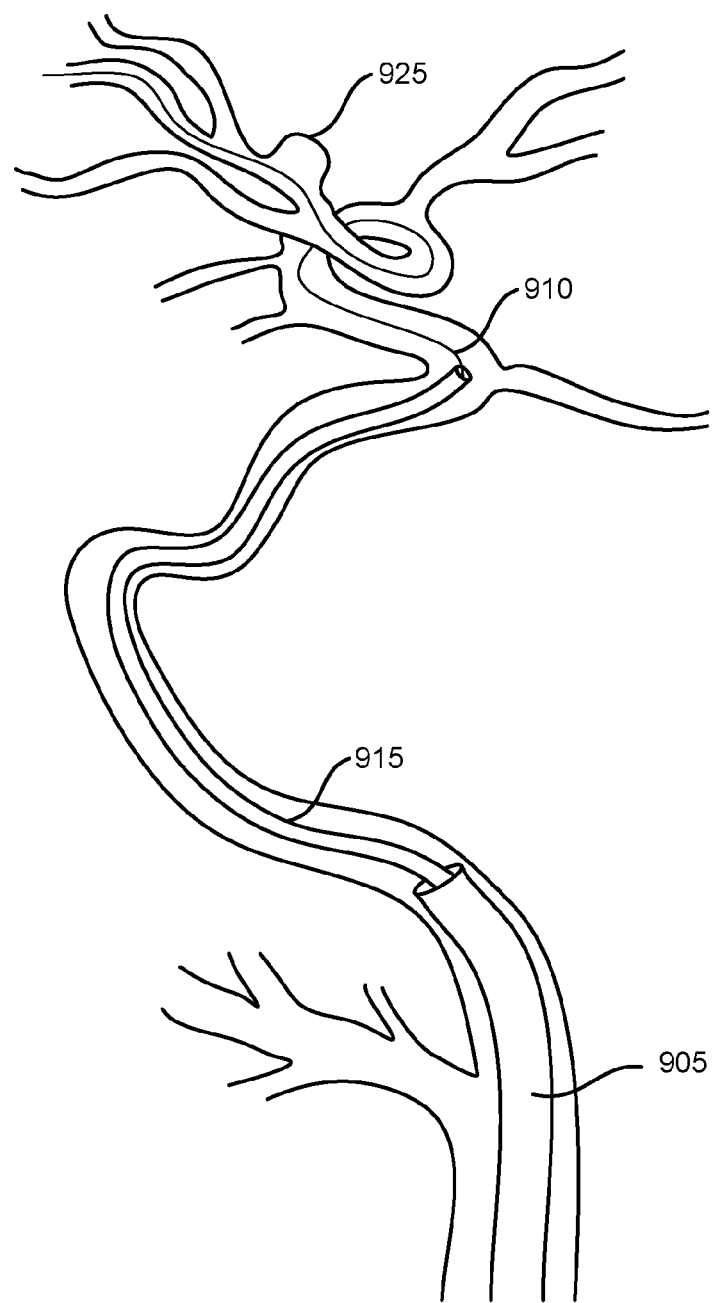
FIGS. 43A-43E illustrate schematic views of buckling and tension storage within a typical procedural guide sheath.
Figure 43B:
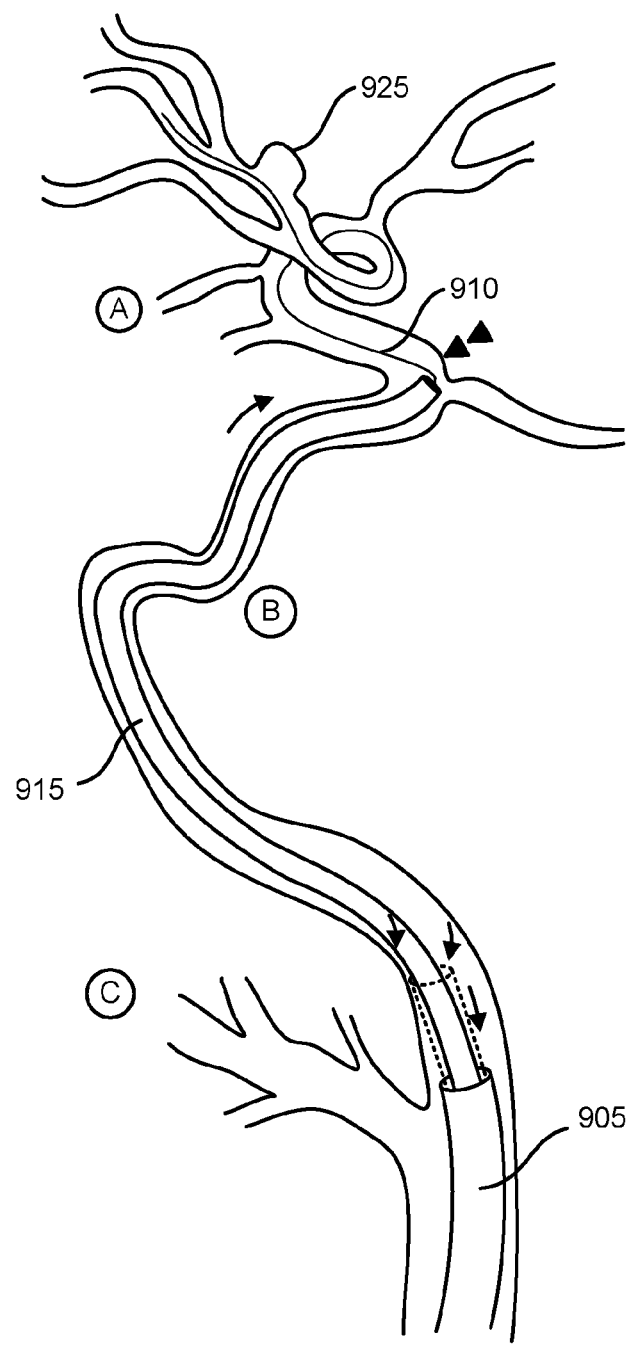

FIG. 43A shows a distal aneurysm target 925 as the target for delivery of an implant, which can include any of a variety of expanding implants such as a flow diverter, stent, or other implant. It should be appreciated that the treatment sites described herein can include, but are not limited to aneurysm, stenosis, occlusion, or other interventional treatment site where delivery of an implant is desired. A procedural guidewire 910 can be used to direct an implant delivery system 915 delivered through a standard sheath 905. The standard sheath 905 is shown placed in the CCA to provide support for the implant delivery system 915. Advancement of the implant delivery system 915 can store tension in the entire system below the tip of the implant delivery system 915 as the tip meets resistance at the points where the forces are downward and lateral to the supporting catheter system and then the tip of the implant delivery system 915 passes beyond those points of resistance. For example, as the tip navigates a straight segment of the vessel and enters a bend, an amount of tension gets stored. Upon exiting the bend and entering another straight segment, that tension can get released and propel the entire system forward creating a "jump." Referring now to FIG. 43B, the resistance can be at a tortuosity in the vessel and/or an obstruction, bifurcation, presence of a preexisting implant, etc. The least supported catheter in the system, e.g. the implant delivery system catheter 915 of FIG. 43B, will typically buckle the most and to a lower degree than, for example, the sheath 905. Generally, this sort of buckling of the implant delivery system catheter 915 can be visible to the operator and the operator can correct for this. What can be more subtle is the movement of the sheath 905. Downward forces can push the sheath 905, in some cases at least 5 cm, 10 cm, or 15 cm or more, down into the aorta, depending of course on the peculiarities of each patient and how the sheaths and catheters of the system interact with the anatomy. When movement of the sheath 905 is severe, catheters can dislodge and loop and twist creating replacement and removal issues. Tension can also be stored without a loss of position.

Figure 43C:
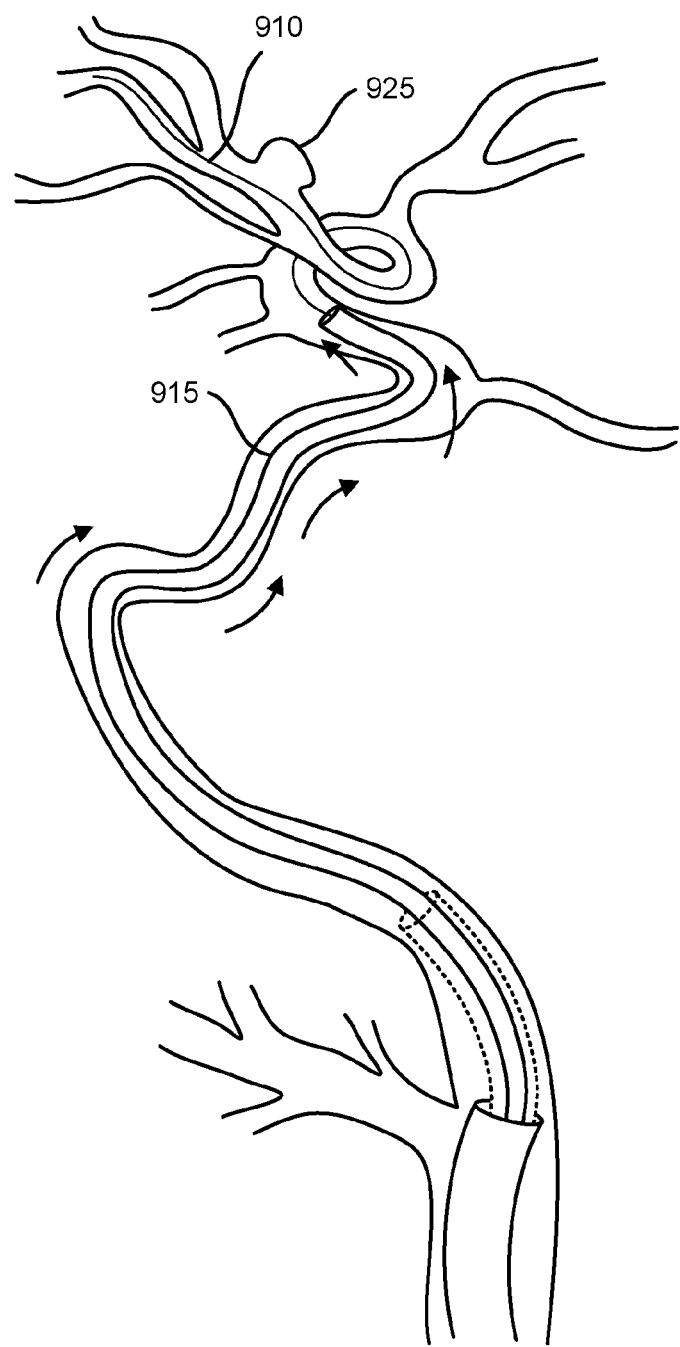

Buckling of the implant delivery system catheter can lead to loss of guidewire 910 position and backing out of the sheath 905 with prolapse of the catheter systems 915 into the ascending aorta AA as described elsewhere herein. Additionally, the sheath 905 can move proximally (or downward) due to aorta prolapse and downward pressures upon further advancement of the implant delivery system 915, despite "wanting" to be further distal (or upward) due to the stored tension (see dotted lines in FIG. 43B). The resultant effect of the stored tension, even as the implant delivery system 915 crosses and eventually reaches the target, can be a "back-and-forth" type of movement to reach the target site 925, e.g., the aneurysm or stenosis, combined with subsequent vascular trauma and risk, as well as the steady storage of tension in the sheath 905 as it is relentlessly pushed downward (see FIGS. 43C-43D). The rhythm of endovascular interventions is that there can be points of greater resistance and lesser resistance on the path to the target resulting in a "staccato" movement where there may be moments of resistance to the point of stoppage, followed by what feels like free catheter movement upon entry of open field that helps to store incremental tension above what is already stored in the sheath 905. Depending on the tortuosity, this can repeat over and over again. The latent and most problematic stored tension can be at the sheath 905. Where stored tension at the level of the implant delivery system 915 and buckling of the catheter 900 is usually visible and can be minimized by operator manipulations and equipment variations, stored tension and buckling at the level of the sheath 905 can be off the field of view under fluoroscopy. Thus, substantial movements (e.g. multi-centimeter movements) of the sheath 905 that are out of the field of view or more subtle movements that are in the field of view can be missed by the operator. Alternatively, an operator may move the patient under the image intensifier to examiner the support system at the level of ICA, CCA, or below. Extra imaging leads to extra radiation exposure for both the operator and the patient.

Figure 43D:
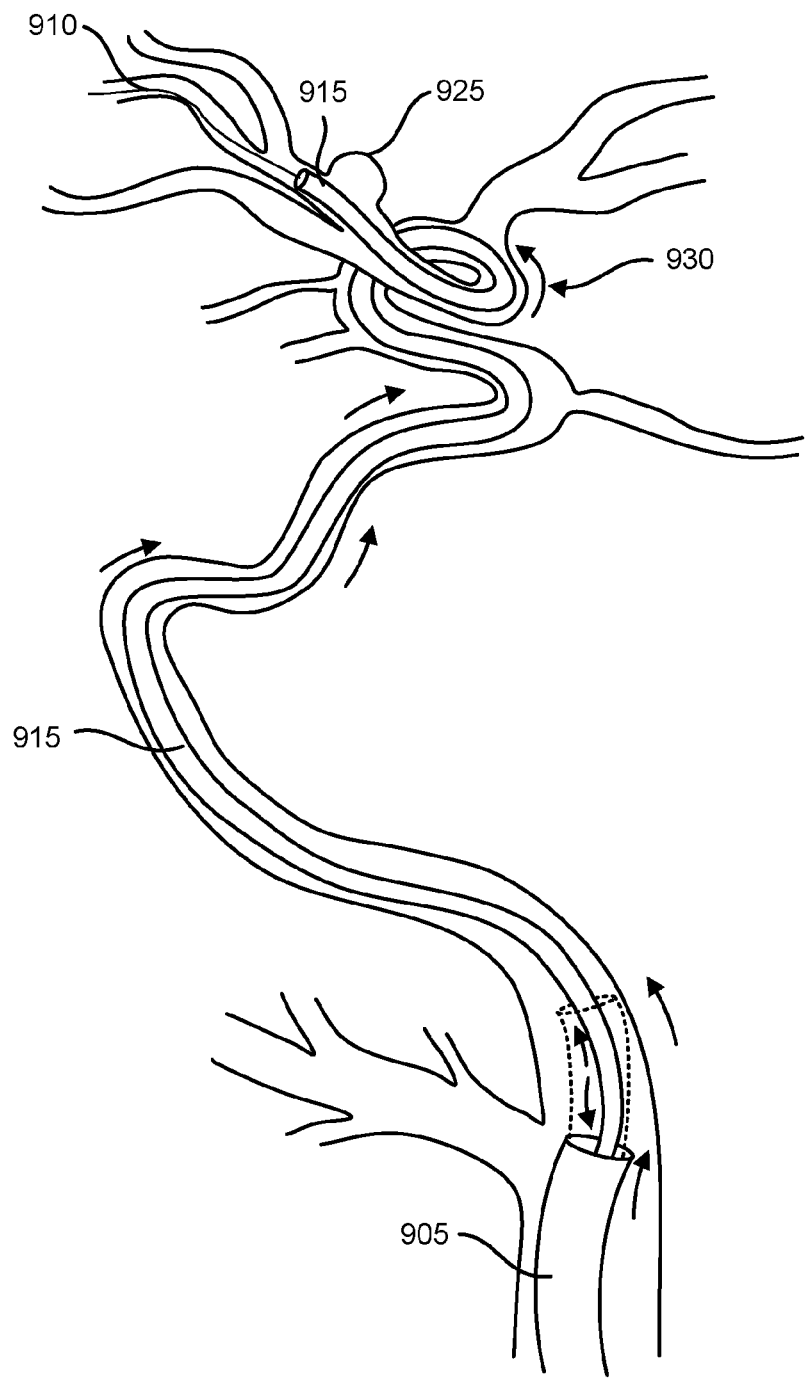
Figure 43E:
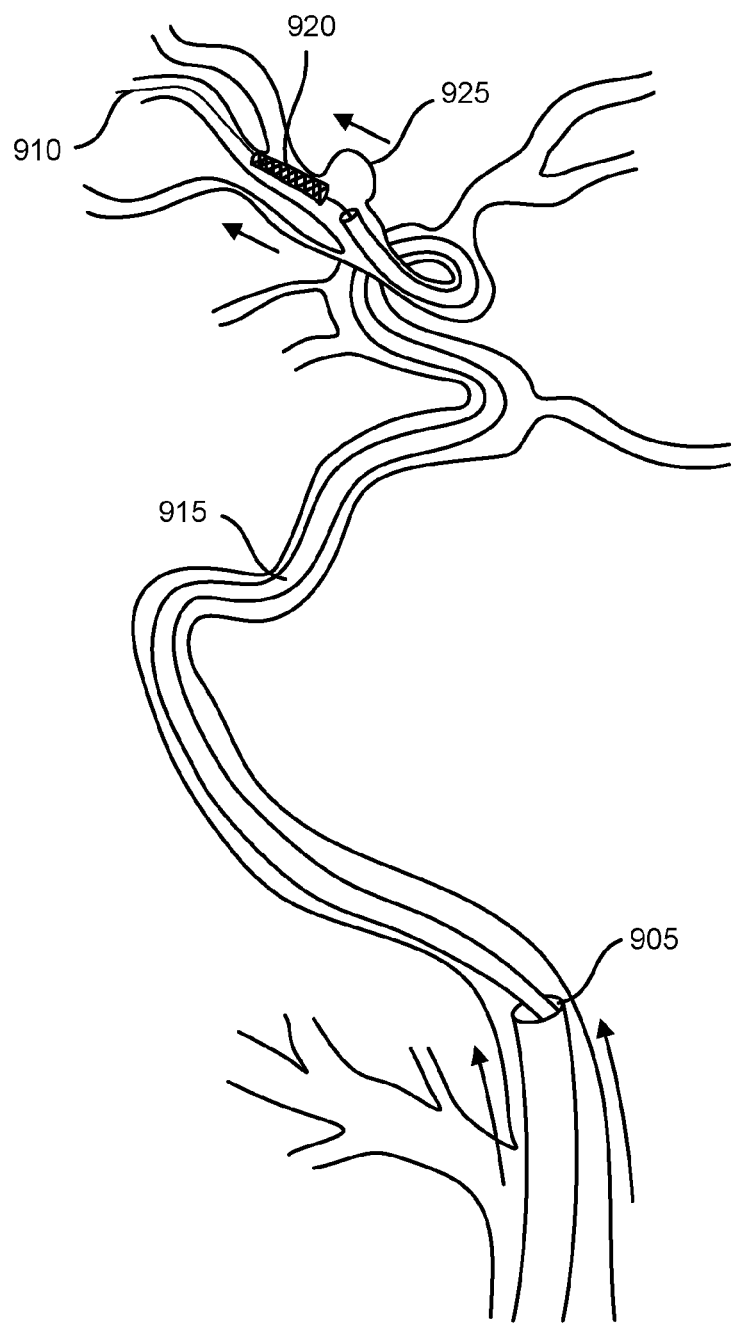
Figure 44:
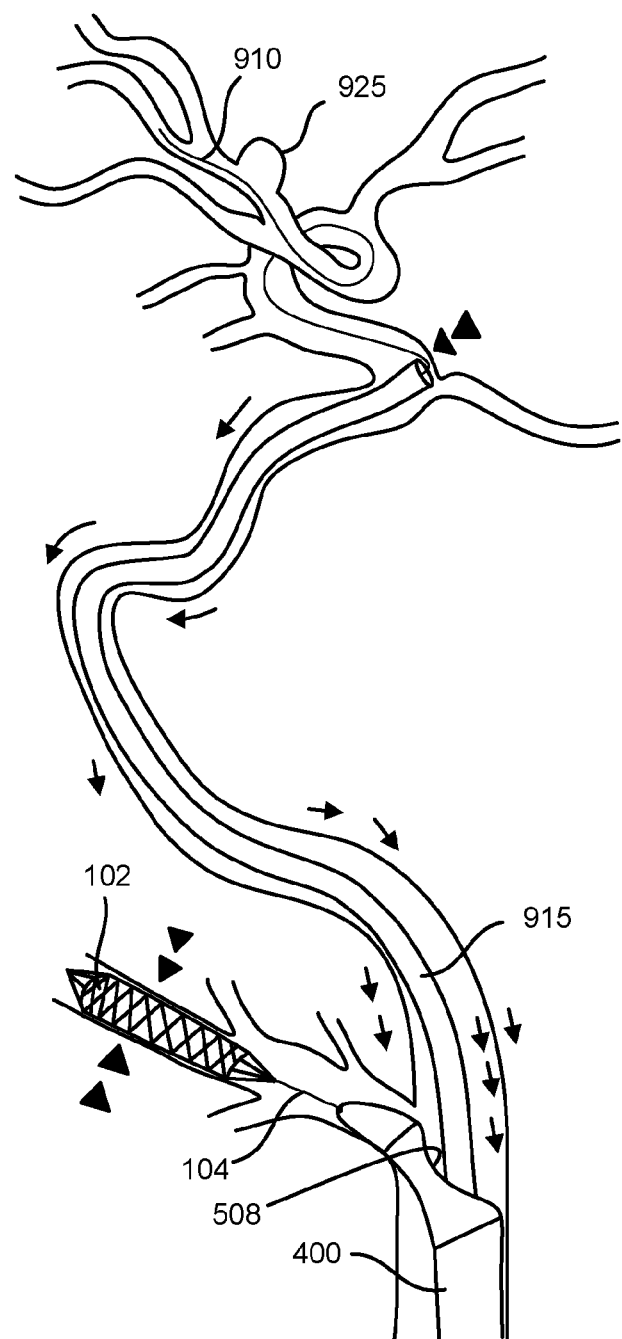
FIGS. 44A-44D illustrate schematic views of relieving tension stored during advancement of an implant delivery system through an anchoring delivery system, in accordance with an implementation.
Figure 44B:
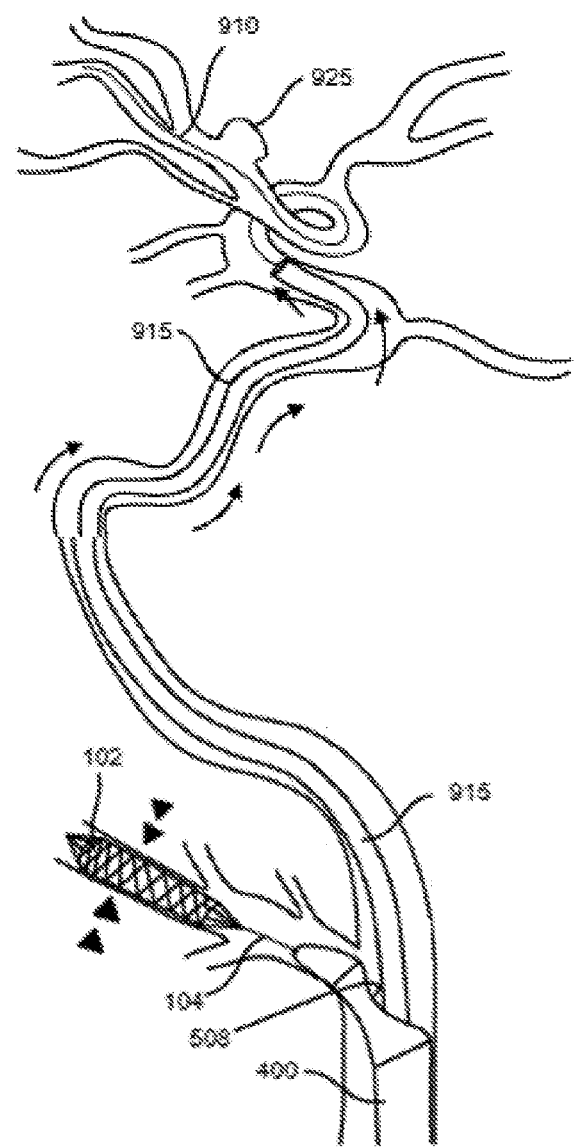
Figure 44C:
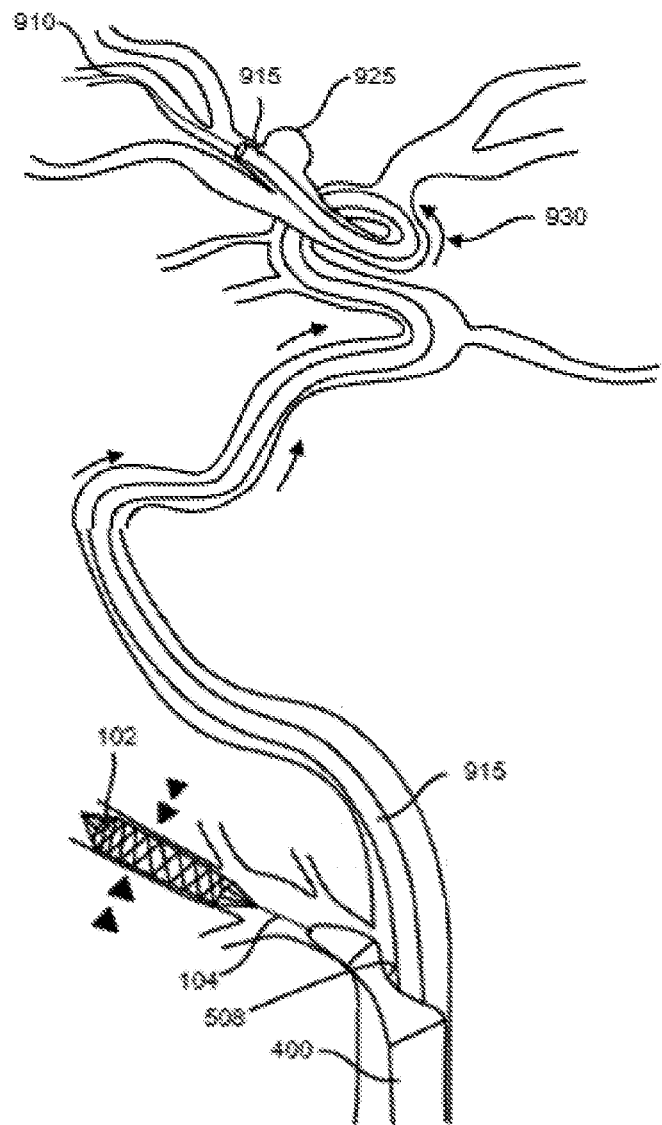
Figure 44D:
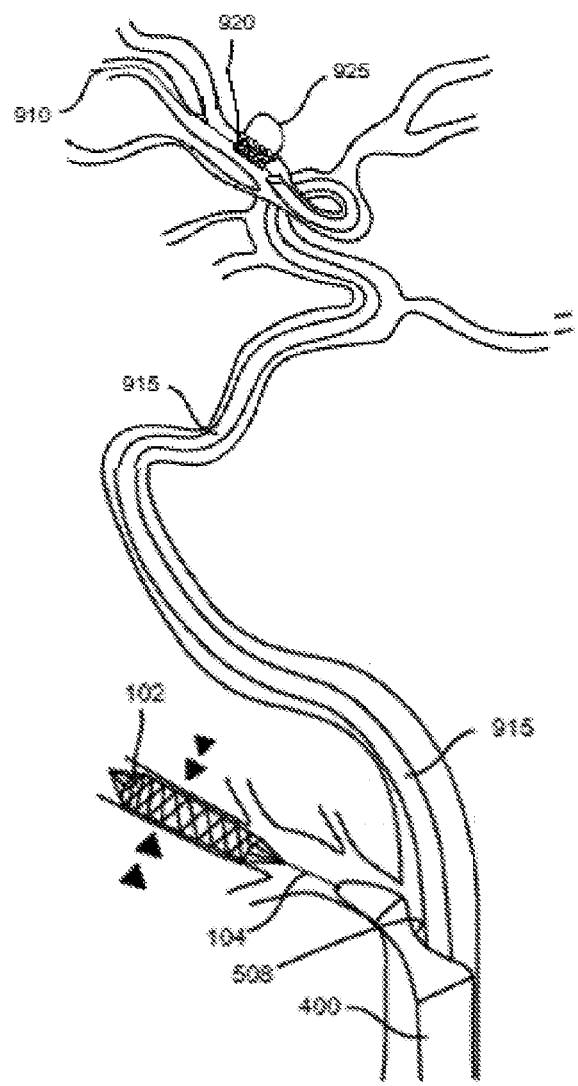

The stored tension in the sheath 905 can be particularly problematic because it can propel the entire system forward (distally) once the pressure on the implant delivery system 915 is reversed, such as when unsleeving a catheter from a self-expanding stent for deployment at the target location. FIG. 43D shows an implant delivery system 915 crossing a target 925 and ready to deploy an implant (not visible, but located inside the system 915) at the target location across the treatment site 925, such as across a neck of an aneurysm or a length of a narrowing in the vessel. Withdrawal of the implant delivery system 915 can release the self-expanding stent 920 from constraint and cause a reversal of the force exerted on the implant delivery system 915. This can relieve or release the stored tension in the sheath 905 that can cause the sheath 905 to "jump." This can cause the implant delivery system 915 and the implant 920 being deployed to miss the target site during unsheathing. This leads to inaccurate and imprecise positioning of the stent often to a point past the target location (FIG. 43E). The extreme tortuosity of the intracerebral vasculature, particularly around the bony structures of the skull that can require more severe pushes in order to cross in combination with the dramatic transition in the size between the large aorta and 1-3 mm sized target vessel can cause the stored tension and jumping effect to be even more pronounced compared to other vascular anatomies.

In contrast, the anchoring delivery systems described herein prevent this jumping effect. The anchoring delivery systems described herein provide a supportive point within the neck from which to build support for the implant delivery system 915 into distal anatomies. FIGS. 44A-44D show the tetherable guide-sheath 400 having a tethering device 100 with an anchor 102 anchored near the bifurcation in an anchoring vessel 1904, e.g. the ECA, and coupled to a tether 104 extending proximally from the anchor 102 into a distal port of the tetherable guide-sheath 400. The anchor 102 provides a first point of fixation of the system at the anchoring vessel 1904 and a second point of fixation between the guide-sheath 400 and the tether 104, such as near a proximal gripping element, creates a support system for an implant delivery system 915 advanced through the guide-sheath 400. The implant delivery system 915 is shown advanced from the mouth 508 of the tetherable guide-sheath 400 and extending towards the target anatomy. The implant delivery system 915 can encounter the same downward forces described above with respect to the untethered, conventional sheath 905. However, the forces in the tethered guide-sheath 400 can be resisted by the anchor 102 deployed in the anchoring vessel 1904 and the proximal fixation point between the tether 104 and the sheath 400. This allows for more distal tip pressure to be imparted at the tip of the implant delivery system 915 and more efficiently transmit forces delivered by the operator. The method of stent delivery using the anchoring delivery system hastens delivery and advancement of the implant, eliminates the back-and-forth motion of typical advancement, reduces pistoning during advancement of the implant, and provides more accurate and precise final implant placement. The method also provides as near a 1:1 relationship between movement applied at a proximal end of the implant delivery system by an operator and movement at the distal end of the catheter. The method and the fixation provided by the anchoring delivery system also eliminates stored tension at the sheath level, which reduces the likelihood of the jumping effect commonly experienced in stent deployment. The method and the "locked in" fixation provided by the anchoring delivery systems described herein also can reduce the need for checking for stored tension and buckling in the sheath using the image intensifier. Further, the tetherable guide-sheath 400 can be locked relative to the visible anatomy such that the operator may use buckling in the implant delivery system 915 as a guidepost for what may be occurring in the femoral sheath without needing to perform extra checks. Further, as described elsewhere herein, the anchoring delivery system provides for a single operator to deliver an implant in an easy-to-use format.

Balloon Expandable (BE) Stent Placement

The stored tension and accompanying jumping effect described above with respect to SE stent placement is markedly reduced with BE stents. For this reason, BE stents are generally preferred in non-compressible vasculature such as in the thoracic cavity and in the coronaries. BE stents are generally accepted as having a greater precision with deployment and more accurate shorter stent length requirement and ability to stay in place with deployment. However, some lesions may release embolic material during balloon inflation even with very small movements in the backward or forward direction that. Also, BE stents may be less forgiving because there is typically no adjustment that can be made in their placement once the balloon has been inflated and the stent expanded. Further, BE stents can be a challenge for use in the intracerebral circulation. BE stents tend to be more rigid and can be associated with higher complication rates, possibly because the rigidity of the BE stents provides limited access to the tortuous cerebrovasculature. BE stents are typically unsheathed such that a "hard edge" of the transition between the balloon material and the stent positioned over the balloon can lead to catching on birfurcations or diseased segments during navigation of extreme tortuosity of the cerebrovasculature. For example, to reach an M1 stenosis the bony terminal carotid segment and the "loop-the-loop" segment must be navigated.

The anchoring delivery systems described herein, at the level of the carotid bifurcation alone or in combination with a support catheter, provides a more stable platform and allows for the delivery of a BE stent system in lieu of self-expanding stent systems, which can be problematic due to their jumping distal to the target delivery site.

Implications for Better Stent Delivery and Support

Stored tension in procedural sheaths and the resultant "jump" upon deployment of a SE stent in the cerebral vasculature leads many operators to deploy SE stents having a length that far exceeds the size of the target to ensure optimum coverage, e.g. a diseased area, stenotic region, or a neck of an aneurysm. However, longer stents generally lead to poor stent apposition or malapposition that increases the likelihood of an acute thrombotic event such as acute stent thrombosis. For example, longer stents (e.g. greater than about 30 mm) are more likely to cause periprocedural embolic complications compared to shorter stents. Suboptimal stent apposition with initial deployment can occur in some instances, due to a fulcrum or another anatomic barrier that inhibit complete expansion of the stent to the vessel wall. This can leave a potential space for thrombus formation that can lead to complete thrombotic occlusion. Further, a lesion being dilated by a stent can be soft such that if the stent is not forcibly apposed to the vessel wall, the dissolution of the thrombus between the stent and the wall can also lead to high-risk malapposition. Additionally, following stent deployment the vessel can positively remodel leaving a potential space for thrombus formation.

Because of the thromboembolic risks associated with longer stents, particularly in the cerebral vasculature, due to poor stent apposition or malapposition, it would be beneficial to use shorter stents and/or stents having a length that substantially matches the length of the stenosis, embolic lesion or aneurysm being treated. For example, the anchored delivery systems described herein can allow for the delivery of an implant that when in the high-profile configuration has a longitudinal length that substantially matches a longitudinal length of the diseased region being treated, for example, a length of a stenotic region of a vessel or in the case of an aneurysm can substantially match the length of the neck. In some implementations, the longitudinal length of the implant when in the high-profile configuration can be between about 1 cm and about 4 cm, or between 4 cm and about 6 cm, or between about 4 cm and about 10 cm, or between about 4 cm and about 20 cm. Sizing precisely is critical to ensure efficacy and maximize safety. As such, the collective length the implant extends beyond the treatment target (e.g. stenotic region or the neck of the aneurysm being treated) should be no more than about 1-2 mm. Using implant delivery systems and guiding sheaths known in the art result in imprecise delivery of the stents and other implants requiring the operator to choose longer lengths than are ideal to ensure efficacious coverage at the cost of increased risk of thrombotic complications due to excess stent length and increased likelihood of poor apposition. Thus, the anchored delivery system for deployment of the treatment device allows for the length of the implant to be limited to only what is needed to bridge the treatment site (i.e., stenotic region or neck of the aneurysm) without extending substantially beyond on either side of it.

However, shorter stents, particularly those that are self-expanding, are more difficult to deliver precisely to the target location. Higher-pressure, post-dilation in BE stenting is generally thought to provide better stent apposition due to the high radial strength of this type of stent compared to the shape-memory-based SE stents. Further, BE stenting can allow for the delivery of shorter stents that can be positioned more precisely and accurately. However, as described above, BE stenting can be more difficult to deliver into the cerebral vascular compared to SE stents.

The methods described herein include using an anchoring delivery system, with or without the support of additive catheters, for the delivery of BE stents or SE stents to the cerebral anatomy. The methods allow for more precise stent placement along the longitudinal (and radial dimensions in the case of BE stenting), limiting the longitudinal length of the expanded device to substantially match the length of the target site, improve stent apposition, and subsequently reduce the risk of stent thrombosis while providing equivalent or better resolution to the hemodynamic compromise of an intracranial lesion or support for stenting, stent-assisted coiling or flow diversion. The methods also include better support delivery for stenting, stent-assisted coiling or flow diversion. The methods also provide even more precise SE stent delivery without balloon post-dilation that is enhanced due to the ability to select shorter stent products due to the more precise delivery and less "back and forth" of stent placement.

The implant delivery systems considered herein for use with the anchored delivery system can vary. In some implementations, the implant delivery system is configured to deliver a self-expanding (SE) stent. Generally, the SE system includes the stent positioned over an inner member and having an outer tubular member configured to maintain the SE stent in the low-profile configuration for delivery through the guide-sheath. Upon proximal retraction of the outer tubular member, the SE stent is released from the constraint and allowed to expand to its high-profile configuration. Upon release, the inner tubular member can be withdrawn leaving the SE stent in place within the target vessel. In another implementation, the SE stent is pushed through a catheter delivery system. In other implementations, the implant delivery system is configured to deliver a balloon-expanding (BE) stent. Generally, the BE system includes the stent positioned over an expandable balloon on the inner member. The stent can, but need not be, covered by an outer tubular member or catheter.

One or more components of the implants, working devices and anchoring delivery systems described herein may be made from a metal, metal alloy, polymer, a metal-polymer composite, ceramics, combinations thereof, and the like, or other suitable materials. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material and as described elsewhere herein.

It should be appreciated that the methods described above may be adapted to different anatomies. For example, the ipsilateral subclavian could be a point of anchoring in order to target the ipsilateral vertebral artery. Vertebral arteries are often very tortuous and benefit from support to push interventional systems through them to target anatomies at which interventions are to be performed. For example, a tethering device can be positioned distal to the takeoff of the vertebral artery with the mouth of the tetherable guide-sheath positioned at the vertebral ostium. In instances when the vertebral arteries are very tortuous, i.e., weaving in and out of the bony openings of the vertebral column, the implant delivery catheter can provide "push" to get across these turns, which is particularly beneficial for rapid access to the site of intervention. According to various implementations, the anchoring delivery system may facilitate access to all four vessels of the carotid/vertebral arterial circulation as well as anatomic variants such as the "bovine" arch discussed above. It should be appreciated that where anchoring point of fixation provided by the anchoring delivery systems described herein as being the ECA/ICA junction that other bifurcation points are considered herein.

Implementations describe anchoring delivery systems and methods of using anchoring delivery system to deliver working devices to target anatomies. However, while some implementations are described with specific regard to delivering working devices to a target vessel of a neurovascular anatomy such as a cerebral vessel, the implementations are not so limited and certain implementations may also be applicable to other uses. For example, an anchoring delivery system as described above may be used to deliver working devices to a target vessel of a coronary anatomy, to name only one possible application. It should also be appreciated that although the systems described herein are described as being useful for treating a particular condition or pathology, that the condition or pathology being treated may vary and are not intended to be limiting. For example, embodiments describe methods of intracerebral stenting. However, while some embodiments are described with specific regard to delivering a stent implant to a neurovascular anatomy, the embodiments are not so limited and certain embodiments may also be applicable to other uses. By way of example, methods may allow for the delivery of a flow diverter or embolic coil implant, and/or to deliver an implant to another anatomy, e.g., a coronary anatomy. Furthermore, the method may allow for the delivery of retrievable stents and Stentriever to target anatomies. Use of the terms "embolus," "embolic," "emboli," "thrombus," "occlusion," etc. that relate to a target for treatment using the devices described herein are not intended to be limiting. The terms may be used interchangeably and can include, but are not limited to a blood clot, air bubble, small fatty deposit, or other object carried within the bloodstream to a distant site or formed at a location in a vessel. The terms may be used interchangeably herein to refer to something that can cause a partial or full occlusion of blood flow through or within the vessel.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of an anchoring delivery system to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. A method of delivering an expandable implant in an intracranial vessel, the method comprising:
   deploying an anchor of a tethering device in an anchoring vessel forming a first fixation point, wherein the tethering device has a tether extending proximally from the anchor and wherein the anchor allows blood to flow past the anchor in the anchoring vessel when deployed;
   advancing a guide-sheath to a location near the first fixation point in the anchoring vessel, the guide-sheath having at least one lumen;
   attaching the guide-sheath to the tether of the tethering device forming a second fixation point proximal to the first fixation point;
   delivering the implant through the at least one lumen of the guide-sheath towards a treatment site distal to the first fixation point and located within an intracranial vessel, wherein delivering the implant through the at least one lumen tensions the tether between the first fixation point and the second fixation point; and deploying the implant at the treatment site.

2. The method of claim 1, wherein the implant is a balloon-expandable stent, a self-expanding stent, or a flow diverter.

3. The method of claim 1, wherein the treatment site is an aneurysm or a stenosis.

4. The method of claim 1, wherein the first fixation point is formed in the anchoring vessel near a bifurcation between the anchoring vessel and a vessel leading to the treatment site.

5. The method of claim 1, wherein deploying the anchor comprises deploying the anchor from a low profile configuration to a higher profile configuration.

6. The method of claim 1, wherein advancing the guide-sheath comprises advancing the guide-sheath over the tether such that the tether extends at least in part through the at least one lumen of the guide-sheath.

7. The method of claim 1, wherein the guide-sheath comprises at least a second lumen, and the tether extends through at least a portion of the second lumen.

8. The method of claim 1, wherein attaching the guide-sheath to the tether comprises using a tether gripper at the second point of fixation to attach the guide-sheath to the tether of the tethering device.

9. The method of claim 8, wherein the tether gripper is on one or both of the tethering device and the guide-sheath.

10. The method of claim 1, further comprising preventing prolapse of the guide-sheath during delivery of the implant.

11. The method of claim 1, further comprising resisting tension stored in the guide-sheath during delivery of the implant.

12. The method of claim 1, wherein the implant is a self-expanding stent and deploying the implant at the treatment site comprises unsheathing the self-expanding stent by withdrawing proximally a constraint.

13. The method of claim 12, further comprising preventing the self-expanding stent from missing the treatment site during unsheathing.

14. The method of claim 1, further comprising removing the anchor from the anchoring vessel; and removing the guide-sheath.

15. A method of delivering an expandable implant in an intracranial vessel, the method comprising:

delivering a tethering device to an anchoring vessel, wherein the tethering device includes a tether extending proximally from an anchor;

deploying the anchor of the tethering device in the anchoring vessel forming a first fixation point, the anchor configured to allow at least partial blood flow through the anchoring vessel when deployed;

advancing a guide-sheath over the tether of the tethering device to position an opening from the guide-sheath near an entrance of a target vessel bifurcating from the anchoring vessel;

forming a second fixation point proximal to the anchoring vessel by attaching the guide-sheath to the tether; and delivering the implant through the guide-sheath to a treatment site distal to the anchoring vessel, wherein delivering the implant through the guide-sheath tensions the tether between the anchor deployed in the anchoring vessel and the second fixation point.

16. The method of claim 15, wherein the tethering device fixes and supports the guide-sheath for delivering the implant through the guide-sheath.

17. The method of claim 15, wherein the anchor is deployed at an anchoring site in the anchoring vessel.

18. The method of claim 15, wherein the guide-sheath includes a lumen to receive at least a portion of the tether.

19. The method of claim 18, wherein the implant is delivered through a first lumen of the guide-sheath and the tether extends at least in part through the first lumen.

20. The method of claim 18, wherein the implant is delivered through a first lumen of the guide-sheath and the tether extends at least in part through a second lumen separate from the first lumen.

21. The method of claim 15, wherein the implant is a balloon-expandable stent, a self-expanding stent, or a flow diverter.

22. The method of claim 15, wherein the treatment site is an aneurysm or a stenosis.

23. The method of claim 15, further comprising preventing prolapse of the guide-sheath during delivery of the implant.

24. The method of claim 15, further comprising resisting tension stored in the guide-sheath during delivery of the implant.

25. The method of claim 15, wherein the implant is a self-expanding stent and deploying the implant at the treatment site comprises unsheathing the self-expanding stent by withdrawing proximally a constraint.

26. The method of claim 25, further comprising preventing the self-expanding stent from missing the treatment site during unsheathing.

27. The method of claim 15, further comprising removing the anchor from the anchoring vessel; and removing the guide-sheath.

* * * * *